(12) United States Patent
Dunn et al.

(10) Patent No.: US 11,083,631 B2
(45) Date of Patent: Aug. 10, 2021

(54) NEGATIVE PRESSURE WOUND CLOSURE DEVICE

(71) Applicants: Smith & Nephew, Inc., Memphis, TN (US); University of Massachusetts, Boston, MA (US)

(72) Inventors: Raymond M. Dunn, Shrewsbury, MA (US); Victoria Jody Hammond, Hull (GB); Edward Yerbury Hartwell, Hull (GB); John Kenneth Hicks, Pocklington (GB); Elizabeth Mary Huddleston, Copmanthorpe (GB); Andrew Kelly, Hitchin (GB); Andrew Linton, Woodthorpe (GB); Mark Richardson, Grimsby (GB); Carl Saxby, Brough (GB); Tim Stern, Belper (GB)

(73) Assignees: University of Massachusetts, Boston, MA (US); Smith & Nephew, Inc., Memphis, TN (US)

(*) Notice: Subject to any disclaimer, the term of this patent is extended or adjusted under 35 U.S.C. 154(b) by 21 days.

(21) Appl. No.: 16/191,237

(22) Filed: Nov. 14, 2018

(65) Prior Publication Data
US 2019/0290495 A1 Sep. 26, 2019

Related U.S. Application Data

(62) Division of application No. 14/415,470, filed as application No. PCT/US2013/050698 on Jul. 16, 2013, now Pat. No. 1,030,520.
(Continued)

(51) Int. Cl.
*A61M 35/00* (2006.01)
*A61M 1/00* (2006.01)
(Continued)

(52) U.S. Cl.
CPC ..... *A61F 13/00068* (2013.01); *A61M 1/0088* (2013.01); *A61F 2013/00178* (2013.01); *A61F 2013/00536* (2013.01)

(58) Field of Classification Search
CPC ........ A61M 35/00; A61M 1/00; A61M 27/00; A61F 13/00; A61F 13/02
See application file for complete search history.

(56) References Cited

U.S. PATENT DOCUMENTS

| 1,006,716 A | 10/1911 | Bloomer |
| 3,014,483 A | 12/1961 | Frank et al. |

(Continued)

FOREIGN PATENT DOCUMENTS

| AU | 2012261793 | 11/2014 |
| AU | 2013206230 B2 | 5/2016 |

(Continued)

OTHER PUBLICATIONS

"Definition of Oculiform," Webster's Revised Unabridged Dictionary, accessed from The Free Dictionary on May 30, 2018 from URL: https://www.thefreedictionary.com/Oculiform, 1913, 1 page.
(Continued)

*Primary Examiner* — Tatyana Zalukaeva
*Assistant Examiner* — Ilya Y Treyger
(74) *Attorney, Agent, or Firm* — McCarter & English, LLP

(57) ABSTRACT

The present invention relates to a negative pressure wound closure system and methods for using such a system. Preferred embodiments of the invention facilitate closure of the wound by preferentially contracting to provide for movement of the tissue. Preferred embodiments can utilize tissue grasping elements to apply a wound closing force to the tissue.

22 Claims, 86 Drawing Sheets

Related U.S. Application Data

(60) Provisional application No. 61/672,225, filed on Jul. 16, 2012, provisional application No. 61/771,732, filed on Mar. 1, 2013, provisional application No. 61/780,629, filed on Mar. 13, 2013.

(51) Int. Cl.
  *A61F 13/00* (2006.01)
  *A61M 27/00* (2006.01)
  *A61F 13/02* (2006.01)

(56) References Cited

U.S. PATENT DOCUMENTS

| | | | |
|---|---|---|---|
| 3,194,239 A | 7/1965 | Sullivan |
| 3,578,003 A | 5/1971 | Everett |
| 3,789,851 A | 2/1974 | Leveen |
| 3,812,616 A | 5/1974 | Koziol |
| 3,952,633 A | 4/1976 | Nakai |
| 4,000,845 A | 1/1977 | Zeller |
| 4,467,805 A | 8/1984 | Fukuda |
| 4,608,041 A | 8/1986 | Nielsen |
| 4,637,819 A | 1/1987 | Ouellette et al. |
| 4,699,134 A | 10/1987 | Samuelsen |
| 4,771,482 A | 9/1988 | Shlenker |
| 4,815,468 A | 3/1989 | Annand |
| 5,176,663 A | 1/1993 | Svedman et al. |
| 5,264,218 A | 11/1993 | Rogozinski |
| 5,332,149 A | 7/1994 | Gepfer |
| 5,368,910 A | 11/1994 | Langdon |
| 5,368,930 A | 11/1994 | Samples |
| 5,376,067 A | 12/1994 | Daneshvar |
| 5,409,472 A | 4/1995 | Rawlings et al. |
| 5,415,715 A | 5/1995 | Delage et al. |
| 5,423,857 A | 6/1995 | Rosenman et al. |
| 5,512,041 A | 4/1996 | Bogart |
| 5,514,105 A | 5/1996 | Goodman, Jr. et al. |
| 5,562,107 A | 10/1996 | Lavender et al. |
| 5,584,859 A | 12/1996 | Brotz |
| 5,636,643 A | 6/1997 | Argenta et al. |
| 5,695,777 A | 12/1997 | Donovan et al. |
| 5,853,863 A | 12/1998 | Kim |
| 5,928,210 A | 7/1999 | Ouellette et al. |
| 5,960,497 A | 10/1999 | Castellino et al. |
| 6,080,168 A | 6/2000 | Levin et al. |
| 6,086,591 A | 7/2000 | Bojarski |
| 6,142,982 A | 11/2000 | Hunt et al. |
| 6,176,868 B1 | 1/2001 | Detour |
| 6,291,050 B1 | 9/2001 | Cree et al. |
| 6,471,715 B1 | 10/2002 | Weiss |
| 6,500,112 B1 | 12/2002 | Khouri |
| 6,503,208 B1 | 1/2003 | Skovlund |
| 6,530,941 B1 | 3/2003 | Muller et al. |
| 6,548,727 B1 | 4/2003 | Swenson |
| 6,553,998 B2 | 4/2003 | Heaton et al. |
| 6,566,575 B1 | 5/2003 | Stickels et al. |
| 6,641,575 B1 | 11/2003 | Lonky |
| 6,685,681 B2 | 2/2004 | Lockwood et al. |
| 6,695,823 B1 | 2/2004 | Lina et al. |
| 6,712,830 B2 | 3/2004 | Esplin |
| 6,712,839 B1 | 3/2004 | Lonne |
| 6,767,334 B1 | 7/2004 | Randolph |
| 6,770,794 B2 | 8/2004 | Fleischmann |
| 6,776,769 B2 | 8/2004 | Smith |
| 6,787,682 B2 | 9/2004 | Gilman |
| 6,814,079 B2 | 11/2004 | Heaton et al. |
| 6,883,531 B1 | 4/2005 | Perttu |
| 6,893,452 B2 | 5/2005 | Jacobs |
| 6,936,037 B2 | 8/2005 | Bubb et al. |
| 6,951,553 B2 | 10/2005 | Bubb et al. |
| 6,977,323 B1 | 12/2005 | Swenson |
| 6,994,702 B1 | 2/2006 | Johnson |
| 7,004,915 B2 | 2/2006 | Boynton et al. |
| 7,025,755 B2 | 4/2006 | Epstein et al. |
| 7,070,584 B2 | 7/2006 | Johnson et al. |
| 7,117,869 B2 | 10/2006 | Heaton et al. |
| 7,128,735 B2 | 10/2006 | Weston et al. |
| 7,144,390 B1 | 12/2006 | Hannigan et al. |
| 7,153,312 B1 | 12/2006 | Torrie et al. |
| 7,156,862 B2 | 1/2007 | Jacobs et al. |
| 7,172,615 B2 | 2/2007 | Morriss et al. |
| 7,189,238 B2 | 3/2007 | Lombardo et al. |
| 7,196,054 B1 | 3/2007 | Drohan et al. |
| 7,198,046 B1 | 4/2007 | Argenta et al. |
| 7,216,651 B2 | 5/2007 | Argenta et al. |
| D544,092 S | 6/2007 | Lewis |
| 7,262,174 B2 | 8/2007 | Jiang et al. |
| 7,279,612 B1 | 10/2007 | Heaton et al. |
| 7,315,183 B2 | 1/2008 | Hinterscher |
| 7,351,250 B2 | 4/2008 | Zamierowski |
| 7,361,184 B2 | 4/2008 | Joshi |
| 7,367,342 B2 | 5/2008 | Butler |
| 7,381,211 B2 | 6/2008 | Zamierowski |
| 7,381,859 B2 | 6/2008 | Hunt et al. |
| 7,413,571 B2 | 8/2008 | Zamierowski |
| 7,438,705 B2 | 10/2008 | Karpowicz et al. |
| 7,494,482 B2 | 2/2009 | Orgill et al. |
| 7,524,315 B2 | 4/2009 | Blott et al. |
| 7,534,240 B1 | 5/2009 | Johnson |
| 7,540,848 B2 | 6/2009 | Hannigan et al. |
| 7,553,306 B1 | 6/2009 | Hunt et al. |
| 7,553,923 B2 | 6/2009 | Williams et al. |
| 7,569,742 B2 | 8/2009 | Haggstrom et al. |
| 7,578,532 B2 | 8/2009 | Schiebler |
| D602,583 S | 10/2009 | Pidgeon et al. |
| 7,611,500 B1 | 11/2009 | Lina et al. |
| 7,612,248 B2 | 11/2009 | Burton et al. |
| 7,615,036 B2 | 11/2009 | Joshi et al. |
| 7,617,762 B1 | 11/2009 | Ragner |
| 7,618,382 B2 | 11/2009 | Vogel et al. |
| 7,622,629 B2 | 11/2009 | Aali |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,683,667 B2 | 3/2010 | Kim et al. |
| 7,699,823 B2 | 4/2010 | Haggstrom et al. |
| 7,699,830 B2 | 4/2010 | Martin et al. |
| 7,699,831 B2 | 4/2010 | Bengtson et al. |
| 7,700,819 B2 | 4/2010 | Ambrosio et al. |
| 7,708,724 B2 | 5/2010 | Weston et al. |
| 7,713,743 B2 | 5/2010 | Villanueva et al. |
| 7,722,528 B2 | 5/2010 | Arnal et al. |
| 7,723,560 B2 | 5/2010 | Lockwood et al. |
| 7,753,894 B2 | 7/2010 | Blott et al. |
| 7,754,937 B2 | 7/2010 | Boehringer et al. |
| 7,776,028 B2 | 8/2010 | Miller et al. |
| 7,777,522 B2 | 8/2010 | Yang et al. |
| 7,779,625 B2 | 8/2010 | Joshi et al. |
| D625,801 S | 10/2010 | Pidgeon et al. |
| 7,811,269 B2 | 10/2010 | Boynton et al. |
| 7,815,616 B2 | 10/2010 | Boehringer et al. |
| 7,820,453 B2 | 10/2010 | Heylen et al. |
| 7,846,141 B2 | 12/2010 | Weston |
| 7,857,806 B2 | 12/2010 | Karpowicz et al. |
| 7,863,495 B2 | 1/2011 | Aali |
| 7,892,181 B2 | 2/2011 | Christensen et al. |
| 7,896,856 B2 | 3/2011 | Petrosenko et al. |
| 7,909,805 B2 | 3/2011 | Weston et al. |
| 7,910,789 B2 | 3/2011 | Sinyagin |
| 7,931,774 B2 | 4/2011 | Hall et al. |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,519 B2 | 7/2011 | Bubb et al. |
| 7,976,524 B2 | 7/2011 | Kudo et al. |
| 7,981,098 B2 | 7/2011 | Boehringer et al. |
| 8,030,534 B2 | 10/2011 | Radl et al. |
| 8,057,447 B2 | 11/2011 | Olson et al. |
| 8,062,272 B2 | 11/2011 | Weston et al. |
| 8,062,295 B2 | 11/2011 | McDevitt et al. |
| 8,062,331 B2 | 11/2011 | Zamierowski |
| 8,067,662 B2 | 11/2011 | Aali et al. |

(56) References Cited

U.S. PATENT DOCUMENTS

| | | |
|---|---|---|
| 8,070,773 B2 | 12/2011 | Zamierowski |
| 8,080,702 B2 | 12/2011 | Blott et al. |
| 8,100,887 B2 | 1/2012 | Weston et al. |
| 8,114,126 B2 | 2/2012 | Heaton et al. |
| 8,123,781 B2 | 2/2012 | Zamierowski |
| 8,128,615 B2 | 3/2012 | Blott et al. |
| 8,129,580 B2 | 3/2012 | Wilkes et al. |
| 8,142,419 B2 | 3/2012 | Heaton et al. |
| 8,162,909 B2 | 4/2012 | Blott et al. |
| 8,172,816 B2 | 5/2012 | Kazala, Jr. et al. |
| 8,182,413 B2 | 5/2012 | Browning |
| 8,187,237 B2 | 5/2012 | Seegert |
| 8,188,331 B2 | 5/2012 | Barta et al. |
| 8,192,409 B2 | 6/2012 | Hardman et al. |
| 8,197,467 B2 | 6/2012 | Heaton et al. |
| 8,207,392 B2 | 6/2012 | Haggstrom et al. |
| 8,215,929 B2 | 7/2012 | Shen et al. |
| 8,235,955 B2 | 8/2012 | Blott et al. |
| 8,235,972 B2 | 8/2012 | Adahan |
| 8,246,590 B2 | 8/2012 | Hu et al. |
| 8,246,606 B2 | 8/2012 | Stevenson et al. |
| 8,246,607 B2 | 8/2012 | Karpowicz et al. |
| 8,257,328 B2 | 9/2012 | Augustine et al. |
| 8,273,105 B2 | 9/2012 | Cohen et al. |
| 8,298,200 B2 | 10/2012 | Vess et al. |
| 8,328,776 B2 | 12/2012 | Kelch et al. |
| 8,337,411 B2 | 12/2012 | Nishtala et al. |
| 8,353,931 B2 | 1/2013 | Stopek et al. |
| 8,357,131 B2 | 1/2013 | Olson |
| 8,362,315 B2 | 1/2013 | Aali |
| 8,376,972 B2 | 2/2013 | Fleischmann |
| 8,399,730 B2 | 3/2013 | Kazala, Jr. et al. |
| 8,430,867 B2 | 4/2013 | Robinson et al. |
| 8,439,882 B2 | 5/2013 | Kelch |
| 8,444,392 B2 | 5/2013 | Turner et al. |
| 8,444,611 B2 | 5/2013 | Wilkes et al. |
| 8,447,375 B2 | 5/2013 | Shuler |
| 8,454,990 B2 | 6/2013 | Canada et al. |
| 8,460,255 B2 | 6/2013 | Joshi et al. |
| 8,460,257 B2 | 6/2013 | Locke et al. |
| 8,481,804 B2 | 7/2013 | Timothy |
| 8,486,032 B2 | 7/2013 | Seegert et al. |
| 8,500,704 B2 | 8/2013 | Boehringer et al. |
| 8,500,776 B2 | 8/2013 | Ebner |
| 8,523,832 B2 | 9/2013 | Seegert |
| 8,535,296 B2 | 9/2013 | Blott et al. |
| 8,562,576 B2 | 10/2013 | Hu et al. |
| 8,608,776 B2 | 12/2013 | Coward et al. |
| 8,622,981 B2 | 1/2014 | Hartwell et al. |
| 8,628,505 B2 | 1/2014 | Weston |
| 8,632,523 B2 | 1/2014 | Eriksson et al. |
| 8,673,992 B2 | 3/2014 | Eckstein et al. |
| 8,679,080 B2 | 3/2014 | Kazala, Jr. et al. |
| 8,679,153 B2 | 3/2014 | Dennis |
| 8,680,360 B2 | 3/2014 | Greener et al. |
| 8,708,984 B2 | 4/2014 | Robinson et al. |
| 8,715,256 B2 | 5/2014 | Greener |
| 8,721,629 B2 | 5/2014 | Hardman et al. |
| 8,746,662 B2 | 6/2014 | Poppe |
| 8,747,375 B2 | 6/2014 | Barta et al. |
| 8,764,732 B2 | 7/2014 | Hartwell |
| 8,784,392 B2 | 7/2014 | Vess et al. |
| 8,791,315 B2 | 7/2014 | Lattimore et al. |
| 8,791,316 B2 | 7/2014 | Greener |
| 8,801,685 B2 | 8/2014 | Armstrong et al. |
| 8,802,916 B2 | 8/2014 | Edward et al. |
| 8,814,842 B2 | 8/2014 | Coulthard et al. |
| 8,821,535 B2 | 9/2014 | Greener |
| 8,843,327 B2 | 9/2014 | Vernon-Harcourt et al. |
| 8,853,486 B2 | 10/2014 | Wild et al. |
| 8,882,730 B2 | 11/2014 | Zimnitsky et al. |
| 8,936,618 B2 | 1/2015 | Sealy et al. |
| 8,945,030 B2 | 2/2015 | Weston et al. |
| 8,951,235 B2 | 2/2015 | Allen et al. |
| 8,956,336 B2 | 2/2015 | Haggstrom et al. |
| 9,044,579 B2 | 6/2015 | Blott et al. |
| 9,050,398 B2 | 6/2015 | Armstrong et al. |
| 9,061,095 B2 | 6/2015 | Adie et al. |
| 9,084,845 B2 | 7/2015 | Adie et al. |
| 9,180,231 B2 | 11/2015 | Greener |
| 9,204,801 B2 | 12/2015 | Locke et al. |
| 9,220,822 B2 | 12/2015 | Hartwell |
| 9,226,737 B2 | 1/2016 | Dunn |
| 9,301,742 B2 | 4/2016 | Dunn |
| 9,339,248 B2 | 5/2016 | Tout et al. |
| 9,352,076 B2 | 5/2016 | Boynton et al. |
| 9,408,755 B2 | 8/2016 | Larsson et al. |
| 9,421,132 B2 | 8/2016 | Dunn et al. |
| 9,555,170 B2 | 1/2017 | Fleischmann |
| 9,597,484 B2 | 3/2017 | Dunn |
| 9,655,807 B2 | 5/2017 | Locke et al. |
| 9,737,649 B2 | 8/2017 | Begin et al. |
| 9,757,500 B2 | 9/2017 | Locke et al. |
| 9,770,368 B2 | 9/2017 | Robinson et al. |
| 9,801,986 B2 | 10/2017 | Greener |
| 9,820,888 B2 | 11/2017 | Greener et al. |
| D805,039 S | 12/2017 | Dejanovic et al. |
| 9,844,472 B2 | 12/2017 | Hammond et al. |
| 9,849,023 B2 | 12/2017 | Hall et al. |
| 9,895,270 B2 | 2/2018 | Coward et al. |
| 9,962,295 B2 | 5/2018 | Dunn et al. |
| 10,070,994 B2 | 9/2018 | Dodd et al. |
| 10,117,782 B2 | 11/2018 | Dagger et al. |
| 10,124,098 B2 | 11/2018 | Dunn et al. |
| 10,130,520 B2 | 11/2018 | Dunn et al. |
| 10,143,485 B2 | 12/2018 | Locke et al. |
| 10,179,073 B2 | 1/2019 | Hartwell et al. |
| 10,201,642 B2 | 2/2019 | Hartwell et al. |
| 10,245,185 B2 | 4/2019 | Hicks et al. |
| 10,405,861 B2 | 9/2019 | Dunn |
| 10,537,657 B2 | 1/2020 | Phillips et al. |
| 10,575,991 B2 | 3/2020 | Dunn |
| 10,660,992 B2 | 5/2020 | Canner et al. |
| 10,814,049 B2 | 10/2020 | Dunn |
| 2001/0029956 A1 | 10/2001 | Argenta et al. |
| 2001/0034499 A1 | 10/2001 | Sessions et al. |
| 2002/0022861 A1 | 2/2002 | Jacobs et al. |
| 2002/0077661 A1 | 6/2002 | Saadat |
| 2002/0161346 A1 | 10/2002 | Lockwood et al. |
| 2003/0065360 A1 | 4/2003 | Jacobs et al. |
| 2003/0108587 A1 | 6/2003 | Orgill et al. |
| 2003/0114816 A1 | 6/2003 | Underhill et al. |
| 2003/0114818 A1 | 6/2003 | Benecke et al. |
| 2003/0114821 A1 | 6/2003 | Underhill et al. |
| 2003/0120249 A1 | 6/2003 | Wulz et al. |
| 2003/0121588 A1 | 7/2003 | Pargass et al. |
| 2003/0178274 A1 | 9/2003 | Chi |
| 2003/0220660 A1 | 11/2003 | Kortenbach et al. |
| 2004/0006319 A1 | 1/2004 | Lina et al. |
| 2004/0010275 A1 | 1/2004 | Jacobs et al. |
| 2004/0054346 A1 | 3/2004 | Zhu et al. |
| 2004/0064132 A1 | 4/2004 | Boehringer et al. |
| 2004/0147465 A1 | 7/2004 | Jiang et al. |
| 2004/0162512 A1 | 8/2004 | Liedtke et al. |
| 2004/0243073 A1 | 12/2004 | Lockwood et al. |
| 2004/0267312 A1 | 12/2004 | Kanner et al. |
| 2005/0107731 A1 | 5/2005 | Sessions |
| 2005/0119694 A1 | 6/2005 | Jacobs, I et al. |
| 2005/0131414 A1 | 6/2005 | Chana |
| 2005/0142331 A1 | 6/2005 | Anderson et al. |
| 2005/0182445 A1 | 8/2005 | Zamierowski |
| 2005/0209574 A1 | 9/2005 | Boehringer et al. |
| 2005/0222544 A1 | 10/2005 | Weston |
| 2005/0222613 A1 | 10/2005 | Ryan |
| 2005/0240220 A1 | 10/2005 | Zamierowski |
| 2005/0258887 A1 | 11/2005 | Ito et al. |
| 2005/0267424 A1 | 12/2005 | Eriksson et al. |
| 2006/0020269 A1 | 1/2006 | Cheng |
| 2006/0058842 A1 | 3/2006 | Wilke et al. |
| 2006/0064124 A1 | 3/2006 | Zhu et al. |
| 2006/0069357 A1 | 3/2006 | Marasco |
| 2006/0079599 A1 | 4/2006 | Arthur et al. |
| 2006/0135921 A1 | 6/2006 | Wiercinski et al. |
| 2006/0213527 A1 | 9/2006 | Argenta et al. |

(56) References Cited

U.S. PATENT DOCUMENTS

| | | |
|---|---|---|
| 2006/0217795 A1 | 9/2006 | Besselink et al. |
| 2006/0257457 A1 | 11/2006 | Gorman et al. |
| 2006/0259074 A1 | 11/2006 | Kelleher et al. |
| 2006/0271018 A1 | 11/2006 | Korf |
| 2007/0027414 A1 | 2/2007 | Hoffman et al. |
| 2007/0027475 A1 | 2/2007 | Pagedas |
| 2007/0032755 A1 | 2/2007 | Walsh |
| 2007/0032763 A1 | 2/2007 | Vogel |
| 2007/0038172 A1 | 2/2007 | Zamierowski |
| 2007/0052144 A1 | 3/2007 | Knirck et al. |
| 2007/0055209 A1 | 3/2007 | Patel |
| 2007/0104941 A1 | 5/2007 | Kameda et al. |
| 2007/0118096 A1 | 5/2007 | Smith et al. |
| 2007/0123816 A1 | 5/2007 | Zhu et al. |
| 2007/0123973 A1 | 5/2007 | Roth et al. |
| 2007/0129660 A1 | 6/2007 | McLeod et al. |
| 2007/0149910 A1 | 6/2007 | Zocher |
| 2007/0161937 A1 | 7/2007 | Aali |
| 2007/0179421 A1 | 8/2007 | Farrow |
| 2007/0185463 A1 | 8/2007 | Mulligan |
| 2007/0213597 A1 | 9/2007 | Wooster |
| 2007/0219513 A1 | 9/2007 | Lina et al. |
| 2007/0265585 A1 | 11/2007 | Joshi et al. |
| 2007/0282309 A1 | 12/2007 | Bengtson et al. |
| 2007/0282374 A1 | 12/2007 | Sogard et al. |
| 2007/0299541 A1 | 12/2007 | Chernomorsky et al. |
| 2008/0041401 A1 | 2/2008 | Casola et al. |
| 2008/0103462 A1 | 5/2008 | Wenzel et al. |
| 2008/0108977 A1 | 5/2008 | Heaton et al. |
| 2008/0167593 A1 | 7/2008 | Fleischmann |
| 2008/0177253 A1 | 7/2008 | Boehringer et al. |
| 2008/0243096 A1 | 10/2008 | Svedman et al. |
| 2008/0275409 A1 | 11/2008 | Kane et al. |
| 2008/0287973 A1 | 11/2008 | Aster et al. |
| 2008/0306456 A1 | 12/2008 | Riesinger |
| 2009/0005716 A1 | 1/2009 | Abuzaina et al. |
| 2009/0005744 A1 | 1/2009 | Karpowicz et al. |
| 2009/0018578 A1 | 1/2009 | Wilke et al. |
| 2009/0018579 A1 | 1/2009 | Wilke et al. |
| 2009/0043268 A1 | 2/2009 | Eddy et al. |
| 2009/0069760 A1 | 3/2009 | Finklestein |
| 2009/0069904 A1 | 3/2009 | Picha |
| 2009/0093550 A1 | 4/2009 | Rolfes et al. |
| 2009/0099519 A1 | 4/2009 | Kaplan |
| 2009/0105670 A1 | 4/2009 | Bentley et al. |
| 2009/0131888 A1 | 5/2009 | Joshi |
| 2009/0137973 A1 | 5/2009 | Karpowicz et al. |
| 2009/0204423 A1 | 8/2009 | Degheest et al. |
| 2009/0227938 A1 | 9/2009 | Fasching et al. |
| 2009/0227969 A1 | 9/2009 | Jaeb et al. |
| 2009/0246238 A1 | 10/2009 | Gorman et al. |
| 2009/0259203 A1 | 10/2009 | Hu et al. |
| 2009/0299255 A1 | 12/2009 | Kazala, Jr. et al. |
| 2009/0299256 A1 | 12/2009 | Barta et al. |
| 2009/0299303 A1 | 12/2009 | Seegert |
| 2009/0299307 A1 | 12/2009 | Barta et al. |
| 2009/0299341 A1 | 12/2009 | Kazala, Jr. et al. |
| 2009/0299342 A1 | 12/2009 | Cavanaugh, II et al. |
| 2009/0312685 A1 | 12/2009 | Olsen et al. |
| 2010/0022972 A1 | 1/2010 | Lina et al. |
| 2010/0022990 A1 | 1/2010 | Karpowicz et al. |
| 2010/0028407 A1 | 2/2010 | Del et al. |
| 2010/0030132 A1 | 2/2010 | Niezgoda et al. |
| 2010/0036333 A1 | 2/2010 | Schenk, III et al. |
| 2010/0047324 A1 | 2/2010 | Fritz et al. |
| 2010/0081983 A1 | 4/2010 | Zocher et al. |
| 2010/0087854 A1 | 4/2010 | Stopek et al. |
| 2010/0100022 A1 | 4/2010 | Greener et al. |
| 2010/0100063 A1 | 4/2010 | Joshi et al. |
| 2010/0106106 A1 | 4/2010 | Heaton et al. |
| 2010/0106184 A1 | 4/2010 | Coward et al. |
| 2010/0106188 A1 | 4/2010 | Heaton et al. |
| 2010/0121286 A1 | 5/2010 | Locke et al. |
| 2010/0121287 A1 | 5/2010 | Smith et al. |
| 2010/0125233 A1 | 5/2010 | Edward S. et al. |
| 2010/0137775 A1 | 6/2010 | Hu et al. |
| 2010/0137890 A1 | 6/2010 | Martinez et al. |
| 2010/0150991 A1 | 6/2010 | Bernstein |
| 2010/0160874 A1 | 6/2010 | Robinson et al. |
| 2010/0160876 A1 | 6/2010 | Robinson et al. |
| 2010/0160901 A1 | 6/2010 | Hu et al. |
| 2010/0179515 A1 | 7/2010 | Swain et al. |
| 2010/0198128 A1 | 8/2010 | Turnlund et al. |
| 2010/0211030 A1 | 8/2010 | Turner et al. |
| 2010/0256672 A1 | 10/2010 | Weinberg et al. |
| 2010/0262092 A1 | 10/2010 | Hartwell |
| 2010/0262106 A1 | 10/2010 | Hartwell |
| 2010/0262126 A1 | 10/2010 | Hu et al. |
| 2010/0280468 A1 | 11/2010 | Haggstrom et al. |
| 2010/0292717 A1 | 11/2010 | Petter-Puchner et al. |
| 2010/0305490 A1 | 12/2010 | Coulthard et al. |
| 2010/0312159 A1 | 12/2010 | Aali et al. |
| 2010/0318046 A1 | 12/2010 | Boehringer et al. |
| 2011/0004173 A1 | 1/2011 | Hu et al. |
| 2011/0009838 A1 | 1/2011 | Greener |
| 2011/0015594 A1 | 1/2011 | Hu et al. |
| 2011/0015595 A1 | 1/2011 | Robinson et al. |
| 2011/0021965 A1 | 1/2011 | Karp et al. |
| 2011/0022082 A1 | 1/2011 | Burke et al. |
| 2011/0054283 A1 | 3/2011 | Shuler |
| 2011/0054365 A1 | 3/2011 | Greener |
| 2011/0059291 A1 | 3/2011 | Boyce et al. |
| 2011/0060204 A1 | 3/2011 | Weston |
| 2011/0066096 A1 | 3/2011 | Svedman |
| 2011/0077605 A1 | 3/2011 | Karpowicz et al. |
| 2011/0082480 A1 | 4/2011 | Viola |
| 2011/0105963 A1 | 5/2011 | Hu et al. |
| 2011/0106026 A1 | 5/2011 | Wu et al. |
| 2011/0110996 A1 | 5/2011 | Schoenberger et al. |
| 2011/0112458 A1 | 5/2011 | Holm et al. |
| 2011/0113559 A1 | 5/2011 | Dodd |
| 2011/0130774 A1 | 6/2011 | Criscuolo et al. |
| 2011/0152800 A1 | 6/2011 | Eckstein et al. |
| 2011/0172760 A1 | 7/2011 | Anderson |
| 2011/0178451 A1 | 7/2011 | Robinson et al. |
| 2011/0196420 A1 | 8/2011 | Ebner |
| 2011/0213287 A1 | 9/2011 | Lattimore et al. |
| 2011/0213319 A1 | 9/2011 | Blott et al. |
| 2011/0224631 A1 | 9/2011 | Simmons et al. |
| 2011/0224632 A1 | 9/2011 | Zimnitsky et al. |
| 2011/0224634 A1 | 9/2011 | Locke et al. |
| 2011/0236460 A1 | 9/2011 | Stopek et al. |
| 2011/0238026 A1 | 9/2011 | Zhang et al. |
| 2011/0238095 A1 | 9/2011 | Browning |
| 2011/0238110 A1 | 9/2011 | Wilke et al. |
| 2011/0245682 A1 | 10/2011 | Robinson et al. |
| 2011/0245788 A1 | 10/2011 | Marquez |
| 2011/0264138 A1 | 10/2011 | Avelar et al. |
| 2011/0270201 A1 | 11/2011 | Bubb et al. |
| 2011/0270301 A1 | 11/2011 | Cornet et al. |
| 2011/0275964 A1 | 11/2011 | Greener |
| 2011/0282136 A1 | 11/2011 | Browning |
| 2011/0282309 A1 | 11/2011 | Adie et al. |
| 2011/0282310 A1 | 11/2011 | Boehringer et al. |
| 2011/0305736 A1 | 12/2011 | Wieland et al. |
| 2011/0313374 A1 | 12/2011 | Lockwood et al. |
| 2011/0319804 A1 | 12/2011 | Greener |
| 2012/0004631 A9 | 1/2012 | Hartwell |
| 2012/0010637 A1 | 1/2012 | Stopek et al. |
| 2012/0016321 A1 | 1/2012 | Wu et al. |
| 2012/0016322 A1 | 1/2012 | Coulthard et al. |
| 2012/0029449 A1 | 2/2012 | Khosrowshahi |
| 2012/0029455 A1 | 2/2012 | Perez-Foullerat et al. |
| 2012/0035560 A1 | 2/2012 | Eddy et al. |
| 2012/0041402 A1 | 2/2012 | Greener |
| 2012/0059399 A1 | 3/2012 | Hoke et al. |
| 2012/0059412 A1 | 3/2012 | Fleischmann |
| 2012/0065664 A1 | 3/2012 | Avitable et al. |
| 2012/0071841 A1 | 3/2012 | Bengtson |
| 2012/0073736 A1 | 3/2012 | O'Connor et al. |
| 2012/0083755 A1 | 4/2012 | Lina et al. |
| 2012/0095426 A1 | 4/2012 | Visscher et al. |
| 2012/0109188 A1 | 5/2012 | Viola |
| 2012/0121556 A1 | 5/2012 | Fraser et al. |

(56) References Cited

U.S. PATENT DOCUMENTS

| | | |
|---|---|---|
| 2012/0123358 A1 | 5/2012 | Hall et al. |
| 2012/0130327 A1 | 5/2012 | Marquez |
| 2012/0136326 A1 | 5/2012 | Croizat et al. |
| 2012/0136328 A1 | 5/2012 | Johannison et al. |
| 2012/0143113 A1 | 6/2012 | Robinson et al. |
| 2012/0143158 A1 | 6/2012 | Yang et al. |
| 2012/0144989 A1 | 6/2012 | Du et al. |
| 2012/0150078 A1 | 6/2012 | Chen et al. |
| 2012/0150133 A1 | 6/2012 | Heaton et al. |
| 2012/0157942 A1 | 6/2012 | Weston |
| 2012/0165764 A1 | 6/2012 | Allen et al. |
| 2012/0172778 A1 | 7/2012 | Rastegar et al. |
| 2012/0172926 A1 | 7/2012 | Hotter |
| 2012/0191054 A1 | 7/2012 | Kazala, Jr. et al. |
| 2012/0191132 A1 | 7/2012 | Sargeant |
| 2012/0197415 A1 | 8/2012 | Montanari et al. |
| 2012/0203189 A1 | 8/2012 | Barta et al. |
| 2012/0209226 A1 | 8/2012 | Simmons et al. |
| 2012/0209227 A1 | 8/2012 | Dunn |
| 2012/0220968 A1 | 8/2012 | Confalone et al. |
| 2012/0222687 A1 | 9/2012 | Czajka, Jr. et al. |
| 2012/0238931 A1 | 9/2012 | Rastegar et al. |
| 2012/0253302 A1 | 10/2012 | Corley |
| 2012/0277773 A1 | 11/2012 | Sargeant et al. |
| 2012/0302440 A1 | 11/2012 | Theliander et al. |
| 2013/0012891 A1 | 1/2013 | Gross et al. |
| 2013/0023842 A1 | 1/2013 | Song |
| 2013/0066365 A1 | 3/2013 | Belson et al. |
| 2013/0096518 A1 | 4/2013 | Hall et al. |
| 2013/0110058 A1 | 5/2013 | Adie et al. |
| 2013/0110066 A1 | 5/2013 | Sharma et al. |
| 2013/0131564 A1 | 5/2013 | Locke et al. |
| 2013/0138054 A1 | 5/2013 | Fleischmann |
| 2013/0150813 A1 | 6/2013 | Gordon et al. |
| 2013/0150814 A1 | 6/2013 | Buan |
| 2013/0190705 A1 | 7/2013 | Vess et al. |
| 2013/0197457 A1 | 8/2013 | Kazala, Jr. et al. |
| 2013/0204213 A1 | 8/2013 | Heagle et al. |
| 2013/0245527 A1 | 9/2013 | Croizat et al. |
| 2013/0253401 A1 | 9/2013 | Locke et al. |
| 2013/0274717 A1 | 10/2013 | Dunn |
| 2013/0310781 A1 | 11/2013 | Phillips et al. |
| 2013/0317465 A1 | 11/2013 | Seegert |
| 2013/0325142 A1 | 12/2013 | Hunter et al. |
| 2013/0331757 A1 | 12/2013 | Belson |
| 2014/0066868 A1 | 3/2014 | Freedman et al. |
| 2014/0068914 A1 | 3/2014 | Coward et al. |
| 2014/0088455 A1 | 3/2014 | Christensen et al. |
| 2014/0094730 A1 | 4/2014 | Greener et al. |
| 2014/0109560 A1 | 4/2014 | Ilievski et al. |
| 2014/0163415 A1 | 6/2014 | Zaiken et al. |
| 2014/0180225 A1 | 6/2014 | Dunn |
| 2014/0180229 A1 | 6/2014 | Fuller et al. |
| 2014/0194836 A1 | 7/2014 | Kazala, Jr. et al. |
| 2014/0194837 A1 | 7/2014 | Robinson et al. |
| 2014/0195004 A9 | 7/2014 | Engqvist et al. |
| 2014/0213994 A1 | 7/2014 | Hardman et al. |
| 2014/0228789 A1 | 8/2014 | Wilkes et al. |
| 2014/0249495 A1 | 9/2014 | Mumby et al. |
| 2014/0316359 A1 | 10/2014 | Collinson et al. |
| 2014/0336602 A1 | 11/2014 | Karpowicz et al. |
| 2014/0343517 A1 | 11/2014 | Jameson |
| 2014/0343518 A1 | 11/2014 | Riesinger |
| 2015/0000018 A1 | 1/2015 | Brandt |
| 2015/0005722 A1 | 1/2015 | Hu et al. |
| 2015/0025484 A1 | 1/2015 | Simmons et al. |
| 2015/0030806 A1 | 1/2015 | Fink |
| 2015/0057762 A1 | 2/2015 | Harms et al. |
| 2015/0065805 A1 | 3/2015 | Edmondson et al. |
| 2015/0065968 A1 | 3/2015 | Sealy et al. |
| 2015/0075697 A1 | 3/2015 | Gildersleeve |
| 2015/0080947 A1 | 3/2015 | Greener |
| 2015/0100008 A1 | 4/2015 | Chatterjee |
| 2015/0112290 A1 | 4/2015 | Dunn |
| 2015/0112311 A1 | 4/2015 | Hammond et al. |
| 2015/0119837 A1 | 4/2015 | Thompson, Jr. et al. |
| 2015/0119865 A1 | 4/2015 | Barta et al. |
| 2015/0148760 A1 | 5/2015 | Dodd et al. |
| 2015/0150729 A1 | 6/2015 | Dagger et al. |
| 2015/0157758 A1 | 6/2015 | Blücher et al. |
| 2015/0159066 A1 | 6/2015 | Hartwell et al. |
| 2015/0164174 A1 | 6/2015 | West |
| 2015/0174304 A1 | 6/2015 | Askem et al. |
| 2015/0190288 A1 | 7/2015 | Dunn et al. |
| 2015/0196431 A1 | 7/2015 | Dunn et al. |
| 2015/0216732 A1 | 8/2015 | Hartwell et al. |
| 2015/0320434 A1 | 11/2015 | Ingram et al. |
| 2015/0320602 A1 | 11/2015 | Locke et al. |
| 2015/0374561 A1 | 12/2015 | Hubbard, Jr. et al. |
| 2016/0022885 A1 | 1/2016 | Dunn et al. |
| 2016/0030646 A1 | 2/2016 | Hartwell et al. |
| 2016/0067939 A1 | 3/2016 | Liebe et al. |
| 2016/0144085 A1 | 5/2016 | Melin et al. |
| 2016/0166744 A1 | 6/2016 | Hartwell |
| 2016/0184496 A1 | 6/2016 | Jaecklein et al. |
| 2016/0235897 A1 | 8/2016 | Boynton et al. |
| 2016/0354086 A1 | 12/2016 | Dunn |
| 2017/0007462 A1 | 1/2017 | Hartwell et al. |
| 2017/0007751 A1 | 1/2017 | Hartwell et al. |
| 2017/0065751 A1 | 3/2017 | Toth et al. |
| 2017/0156611 A1 | 6/2017 | Burnett et al. |
| 2017/0281838 A1 | 10/2017 | Dunn |
| 2018/0140465 A1 | 5/2018 | Dunn et al. |
| 2019/0105202 A1 | 4/2019 | Dunn et al. |
| 2019/0231599 A1 | 8/2019 | Dagger et al. |
| 2019/0231944 A1 | 8/2019 | Dunn et al. |
| 2019/0262182 A1 | 8/2019 | Collinson et al. |
| 2020/0038023 A1 | 2/2020 | Dunn |
| 2020/0188564 A1 | 6/2020 | Dunn |
| 2020/0268562 A1 | 8/2020 | Dunn |

FOREIGN PATENT DOCUMENTS

| | | |
|---|---|---|
| CN | 1438904 A | 8/2003 |
| CN | 101112326 A | 1/2008 |
| CN | 101123930 A | 2/2008 |
| CN | 101208115 A | 6/2008 |
| CN | 101257938 A | 9/2008 |
| CN | 101588836 A | 11/2009 |
| CN | 201519362 U | 4/2010 |
| CN | 101744688 A | 6/2010 |
| CN | 202568632 U | 7/2010 |
| CN | 102038575 A | 5/2011 |
| CN | 102046117 A | 5/2011 |
| CN | 102196830 A | 9/2011 |
| CN | 102256637 A | 11/2011 |
| CN | 102781380 A | 11/2012 |
| CN | 103071197 A | 5/2013 |
| CN | 103405846 A | 11/2013 |
| CN | 103501709 A | 1/2014 |
| CN | 203408163 U | 1/2014 |
| CN | 104736110 A | 6/2015 |
| CN | 104768474 A | 7/2015 |
| CN | 104812343 A | 7/2015 |
| DE | 2949920 A1 | 3/1981 |
| DE | 102005007016 A1 | 8/2006 |
| DE | 102012001752 A1 | 8/2013 |
| EP | 1320342 A1 | 6/2003 |
| EP | 2094211 A1 | 9/2009 |
| EP | 2279016 A1 | 2/2011 |
| EP | 2341955 A1 | 7/2011 |
| EP | 2366721 A1 | 9/2011 |
| EP | 2367517 A2 | 9/2011 |
| EP | 2368523 A1 | 9/2011 |
| EP | 2404571 A1 | 1/2012 |
| EP | 2404626 A2 | 1/2012 |
| EP | 2529767 A2 | 12/2012 |
| EP | 2547375 A1 | 1/2013 |
| EP | 2563421 A1 | 3/2013 |
| EP | 2567682 A1 | 3/2013 |
| EP | 2567717 A1 | 3/2013 |
| EP | 2594299 A2 | 5/2013 |
| EP | 2601984 A2 | 6/2013 |
| EP | 2623137 A2 | 8/2013 |

(56) References Cited

FOREIGN PATENT DOCUMENTS

| | | | |
|---|---|---|---|
| EP | 2759265 A2 | 7/2014 |
| EP | 2829287 A1 | 1/2015 |
| EP | 2852419 A2 | 4/2015 |
| EP | 2872085 A1 | 5/2015 |
| EP | 3225261 A1 | 10/2017 |
| GB | 2378392 A | 2/2003 |
| GB | 2389794 A | 12/2003 |
| GB | 2423019 A | 8/2006 |
| GB | 2489947 A | 10/2012 |
| GB | 2496310 A | 5/2013 |
| IE | 20140129 A1 | 3/2016 |
| JP | S6257560 A | 3/1987 |
| JP | H0341952 A | 2/1991 |
| JP | 109-503923 A | 4/1997 |
| JP | 2006528038 A | 12/2006 |
| JP | 2007-505678 A | 3/2007 |
| JP | 2007-531567 A | 11/2007 |
| JP | 2008-529618 A | 8/2008 |
| JP | 2009525087 A | 7/2009 |
| JP | 2009-536851 A | 10/2009 |
| JP | 2010-526597 A | 8/2010 |
| JP | 2011-500170 A | 1/2011 |
| JP | 2011521740 A | 7/2011 |
| JP | 2011-523575 A | 8/2011 |
| JP | 2011-526798 A | 10/2011 |
| JP | 2012-504460 A | 2/2012 |
| JP | 2012-105840 A | 6/2012 |
| JP | 2012-513826 A | 6/2012 |
| JP | 2012529974 A | 11/2012 |
| JP | 2013-526938 A | 6/2013 |
| JP | 2014168573 A | 9/2014 |
| RU | 62504 | 4/2007 |
| SU | 1818103 | 5/1993 |
| WO | 1994/20041 A1 | 9/1994 |
| WO | 2000/59424 A1 | 10/2000 |
| WO | 2001/34223 A1 | 5/2001 |
| WO | 2001/085248 A1 | 11/2001 |
| WO | 2001/89392 A2 | 11/2001 |
| WO | 0205737 A1 | 1/2002 |
| WO | 03003948 A1 | 1/2003 |
| WO | WO-03049598 A2 | 6/2003 |
| WO | 2004/018020 A1 | 3/2004 |
| WO | 2004/037334 A1 | 5/2004 |
| WO | 2005046761 A1 | 5/2005 |
| WO | WO 2005/105174 | 11/2005 |
| WO | 2006041496 A1 | 4/2006 |
| WO | 2006/046060 A2 | 5/2006 |
| WO | 2006/087021 A1 | 8/2006 |
| WO | 2006/100053 A2 | 9/2006 |
| WO | 2007/030601 A2 | 3/2007 |
| WO | 2007/120138 A2 | 10/2007 |
| WO | 2007/133618 A2 | 11/2007 |
| WO | 2008/005532 A2 | 1/2008 |
| WO | WO 2008/027449 A2 | 3/2008 |
| WO | 2008/039223 A1 | 4/2008 |
| WO | 2008/039839 A2 | 4/2008 |
| WO | 2008064502 A1 | 6/2008 |
| WO | 2008/091521 A2 | 7/2008 |
| WO | 2008104609 A1 | 9/2008 |
| WO | 2009019495 A1 | 2/2009 |
| WO | 2009071926 A1 | 6/2009 |
| WO | 2009071933 A2 | 6/2009 |
| WO | 2009/093116 A1 | 7/2009 |
| WO | 2009/112848 A1 | 9/2009 |
| WO | 2009/114624 A2 | 9/2009 |
| WO | 2009112062 A1 | 9/2009 |
| WO | 2009/158125 A1 | 12/2009 |
| WO | 2009/158132 A1 | 12/2009 |
| WO | 2009156709 A1 | 12/2009 |
| WO | 2010/033725 A2 | 3/2010 |
| WO | 2010/051073 A1 | 5/2010 |
| WO | 2010/059612 A2 | 5/2010 |
| WO | 2010/075178 A2 | 7/2010 |
| WO | 2010/075180 A2 | 7/2010 |
| WO | 2010/078349 A2 | 7/2010 |
| WO | 2010/079359 A1 | 7/2010 |
| WO | 2010/092334 A1 | 8/2010 |
| WO | 2010/097570 A1 | 9/2010 |
| WO | 2010/147535 A1 | 12/2010 |
| WO | 2011023384 A1 | 3/2011 |
| WO | 2011087871 A2 | 7/2011 |
| WO | 2011091169 A1 | 7/2011 |
| WO | 2011/106722 A1 | 9/2011 |
| WO | 2011/115908 A1 | 9/2011 |
| WO | 2011/116691 A1 | 9/2011 |
| WO | 2011/135284 A1 | 11/2011 |
| WO | 2011/135286 A1 | 11/2011 |
| WO | 2011/135287 A1 | 11/2011 |
| WO | 2011/144888 A1 | 11/2011 |
| WO | 2011137230 A1 | 11/2011 |
| WO | 2012/021553 A1 | 2/2012 |
| WO | 2012038727 A2 | 3/2012 |
| WO | 2012/069793 A1 | 5/2012 |
| WO | 2012/069794 A1 | 5/2012 |
| WO | 2012082716 A2 | 6/2012 |
| WO | 2012082876 A1 | 6/2012 |
| WO | 2012087376 A1 | 6/2012 |
| WO | 2012/106590 A2 | 8/2012 |
| WO | 2012/112204 A1 | 8/2012 |
| WO | 2012136707 A1 | 10/2012 |
| WO | 2012142473 A1 | 10/2012 |
| WO | 2012156655 A1 | 11/2012 |
| WO | 2012168678 A1 | 12/2012 |
| WO | 2013/007973 A2 | 1/2013 |
| WO | 2013012381 A1 | 1/2013 |
| WO | 2013043258 A1 | 3/2013 |
| WO | 2013/074829 A1 | 5/2013 |
| WO | 2013/076450 A1 | 5/2013 |
| WO | 2013071243 A2 | 5/2013 |
| WO | 2013079947 A1 | 6/2013 |
| WO | WO-2013079447 A1 | 6/2013 |
| WO | 2013/175309 A1 | 11/2013 |
| WO | 2013/175310 A2 | 11/2013 |
| WO | 2013136181 A3 | 11/2013 |
| WO | 2014/013348 A2 | 1/2014 |
| WO | 2014/014842 A1 | 1/2014 |
| WO | 2014/014871 A1 | 1/2014 |
| WO | 2014/014922 A1 | 1/2014 |
| WO | 2014/024048 A1 | 2/2014 |
| WO | 2014/140578 A1 | 9/2014 |
| WO | 2014/158526 A1 | 10/2014 |
| WO | 2014/165275 A1 | 10/2014 |
| WO | 2014/178945 A1 | 11/2014 |
| WO | 2014/194786 A1 | 12/2014 |
| WO | 2015/008054 A1 | 1/2015 |
| WO | 2015/061352 A2 | 4/2015 |
| WO | 2015/109359 A1 | 7/2015 |
| WO | 2015/110409 A1 | 7/2015 |
| WO | 2015/110410 A1 | 7/2015 |
| WO | 2015/169637 A1 | 11/2015 |
| WO | 2015/172108 A1 | 11/2015 |
| WO | 2015/193257 A1 | 12/2015 |
| WO | 2016/018448 A1 | 2/2016 |
| WO | 2016/176513 A1 | 11/2016 |
| WO | 2016/179245 A1 | 11/2016 |
| WO | 2016/184913 A1 | 11/2016 |
| WO | 2017/063036 A1 | 4/2017 |
| WO | 2017/106576 A1 | 6/2017 |
| WO | 2018/038665 A1 | 3/2018 |
| WO | 2018/041805 A1 | 3/2018 |
| WO | 2018/044944 A1 | 3/2018 |
| WO | 2018/044949 A1 | 3/2018 |
| WO | 2018/237206 A2 | 12/2018 |

OTHER PUBLICATIONS

Bengezi et al., Elevation as a treatment for fasciotomy wound closure. Can J Plast Surg. 2013 Fall;21(3):192-4.
Epstein et al., Lipoabdominoplasty Without Drains or Progressive Tension Sutures: An Analysis of 100 Consecutive Patients. Aesthetic Surgery Journal. Apr. 2015;35(4):434-440.
Jauregui et al., Fasciotomy closure techniques. J Orthop Surg (Hong Kong). Jan. 2017;25(1):2309499016684724. 8 pages.

(56) References Cited

OTHER PUBLICATIONS

Macias et al., Decrease in Seroma Rate After Adopting Progressive Tension Sutures Without Drains: A Single Surgery Center Experience of 451 Abdominoplasties over 7 Years. Aesthetic Surgery Journal. Mar. 2016;36(9):1029-1035.
Pollock et al., Progressive Tension Sutures in Abdominoplasty: A Review of 597 Consecutive Cases. Aesthetic Surgery Journal. Aug. 2012;32(6):729-742.
Quaba et al., The no-drain, no-quilt abdominoplasty: a single-surgeon series of 271 patients. Plast Reconstr Surg. Mar. 2015;135(3):751-60.
Rothenberg et al., Emerging Insights on Closed Incision NPWT and Transmetatarsal Amputations. http://www.podiatrytoday.com/emerging-insights-closed-incision-npwt-and-transmetatarsal-amputations. Apr. 2015;28(4):1-5.
"Definition of Adhere," The Free Dictionary, accessed on Mar. 23, 2017 from http://www.thefreedictionary.com/adhere, 6 pages.
"Definition of Throughout," Merriam-Webster Dictionary, accessed on Aug. 29, 2017 from https://www.merriam-webster.com/dictionary/throughout, 11 pages.
Hougaard, et al., "The Open Abdomen: Temporary Closure with a Modified Negative Pressure Therapy Technique," International Wound Journal, ISSN 1742-4801, 2014, pp. 13-16.
International Preliminary Report on Patentability and Written Opinion for Application No. PCT/US2013/050619, dated Jan. 20, 2015, 9 pages.
International Preliminary Report on Patentability and Written Opinion for Application No. PCT/US2013/050698, dated Jan. 20, 2015, 9 pages.
International Search Report and Written Opinion for Application No. PCT/US2013/050619, dated Oct. 14, 2013, 14 pages.
International Search Report and Written Opinion for Application No. PCT/US2013/050698, dated Oct. 14, 2013, 14 pages.
Kapischke M., et al., "Self-Fixating Mesh for the Lichtenstein Procedure—a Prestudy," Langenbecks Arch Surg, 2010, vol. 395, pp. 317-322.

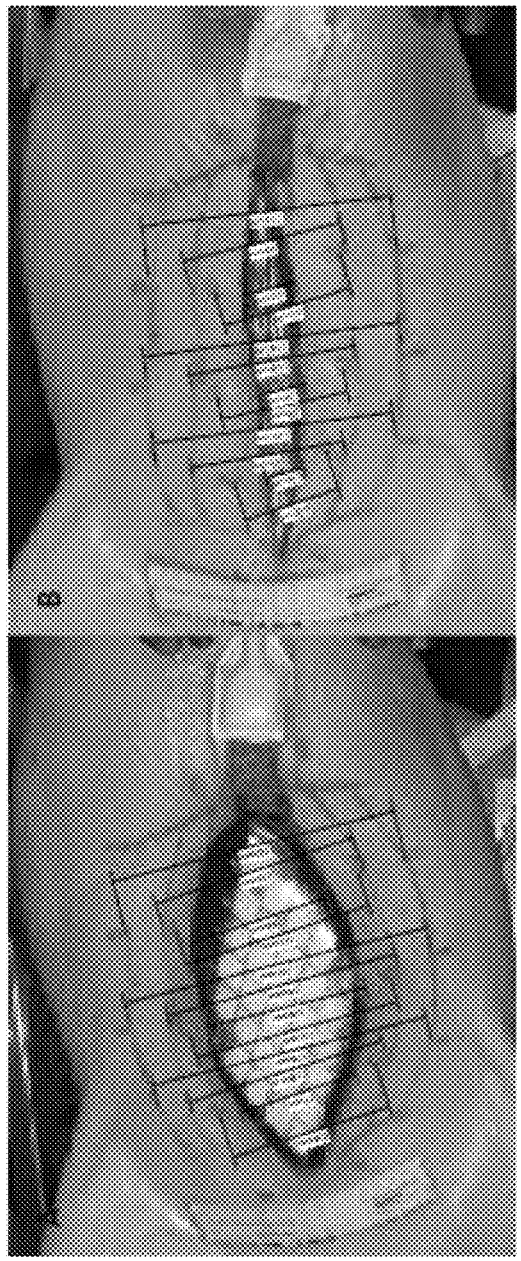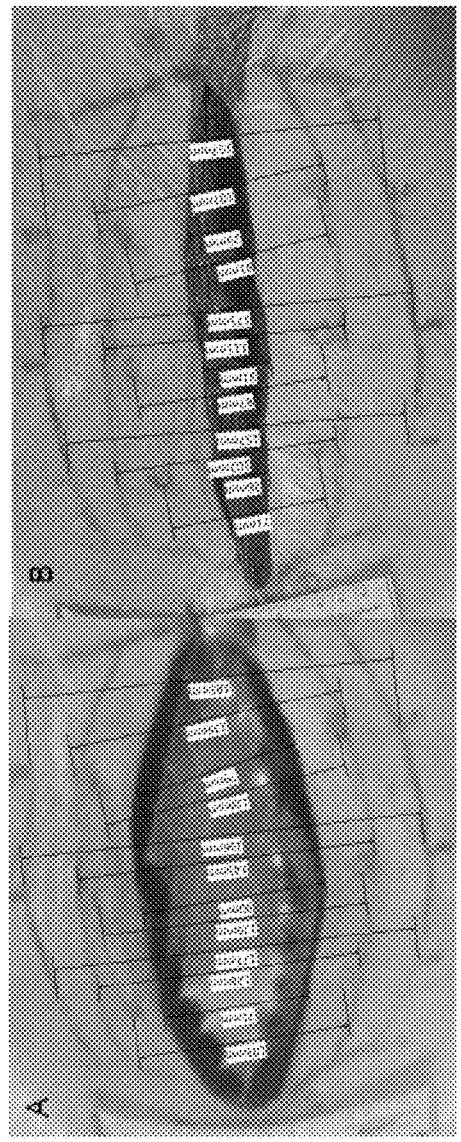
FIG. 17A  FIG. 17B  FIG. 18A  FIG. 18B

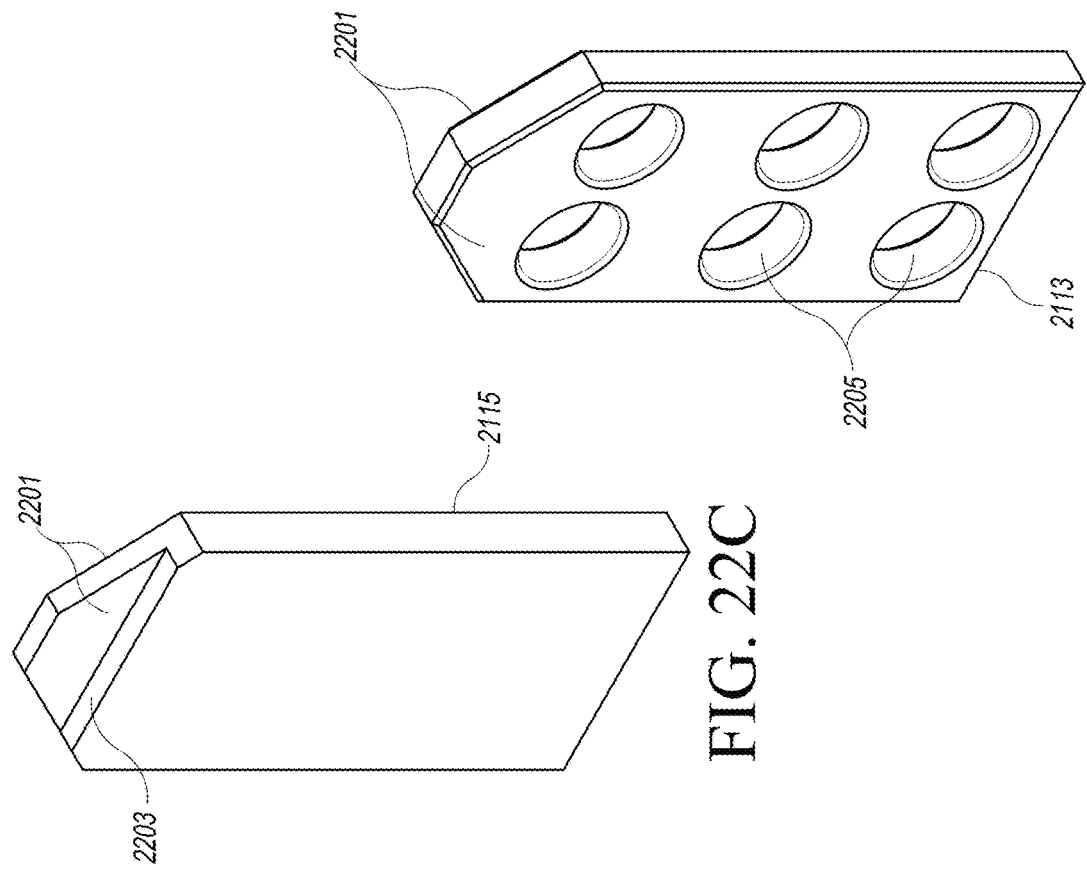
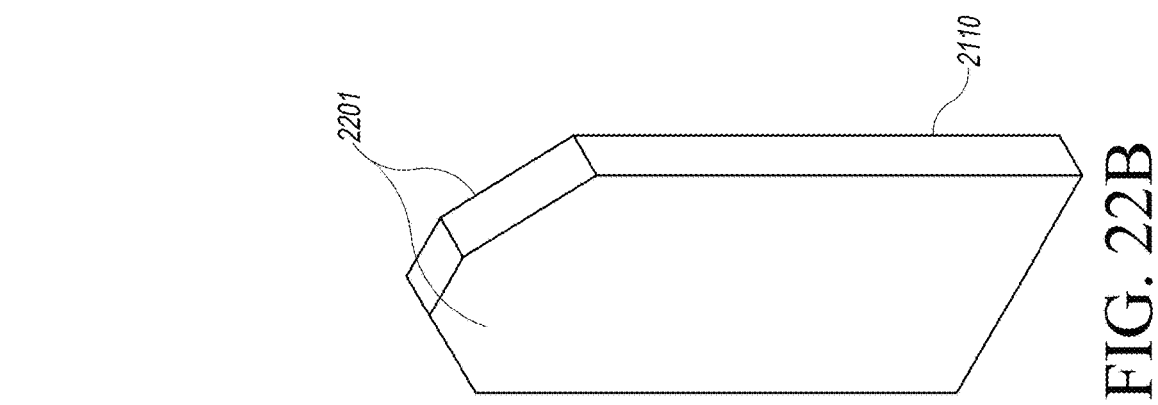
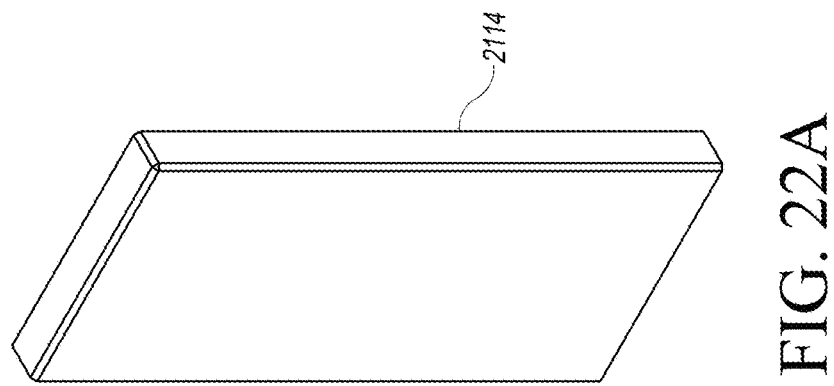

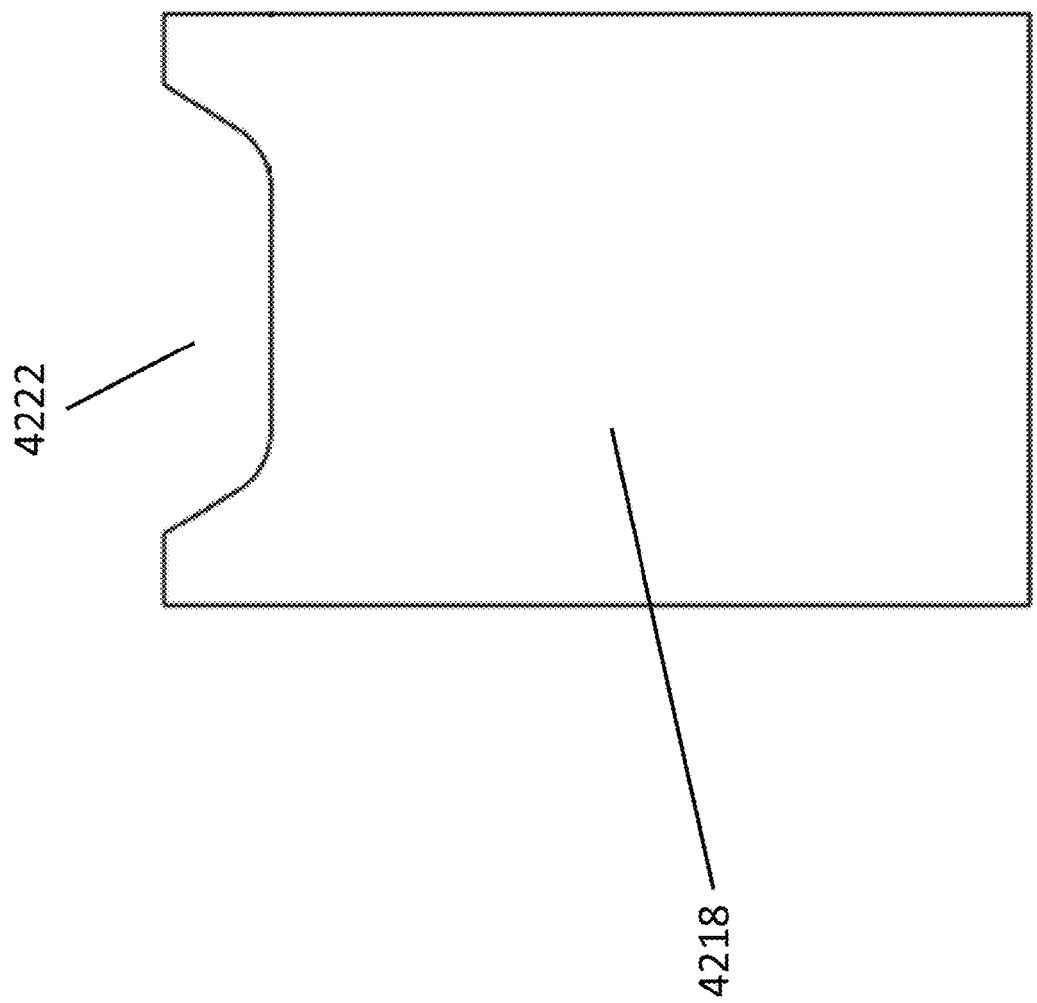

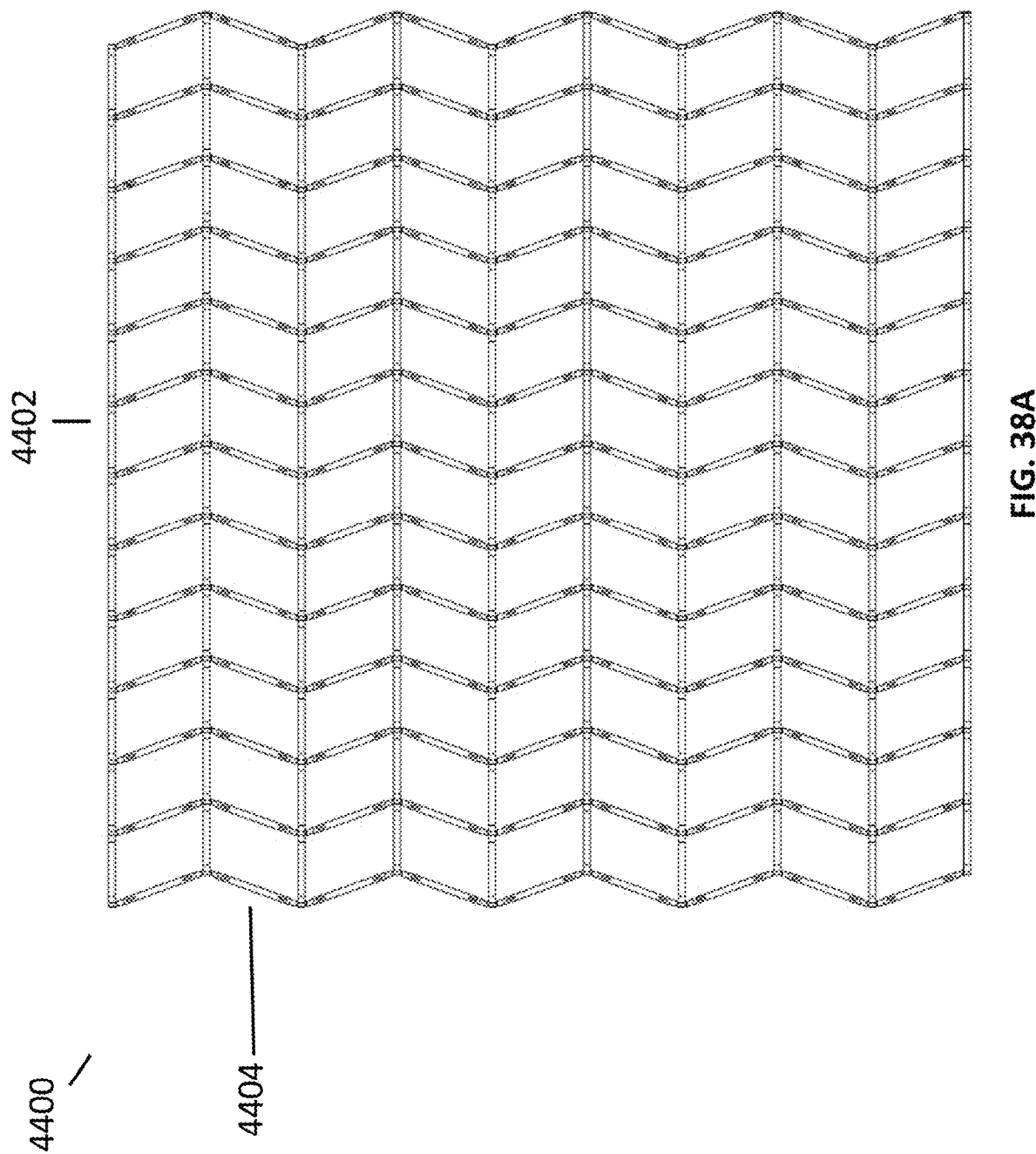

NEGATIVE PRESSURE WOUND CLOSURE DEVICE

CROSS-REFERENCE TO RELATED APPLICATIONS

This application is a divisional of U.S. application Ser. No. 14/415,470, filed Jan. 16, 2015, which is a National Stage Application of International Patent Application No. PCT/US2013/050698, filed Jul. 16, 2013, which claims the benefit of U.S. Provisional Application No. 61/672,225, filed Jul. 16, 2012, entitled NEGATIVE PRESSURE WOUND CLOSURE DEVICE, U.S. Provisional Application No. 61/771,732, filed Mar. 1, 2013, entitled NEGATIVE PRESSURE WOUND CLOSURE DEVICE, and U.S. Provisional Application No. 61/780,629, filed Mar. 13, 2013, entitled NEGATIVE PRESSURE WOUND CLOSURE DEVICE. The contents of the aforementioned applications are hereby incorporated by reference in their entireties as if fully set forth in this specification. The benefit of priority to the foregoing applications is claimed under the appropriate legal basis, including, without limitation, under 35 U.S.C. § 119(e).

BACKGROUND OF THE INVENTION

Field of the Invention

This application describes embodiments of apparatuses, methods, and systems for the treatment of wounds, specifically to aid in the closure of large wounds, in conjunction with the administration of negative pressure.

Description of the Related Art

Negative pressure wound therapy has been used in the treatment of wounds, and in many cases can improve the rate of healing while also removing exudates and other deleterious substances from the wound site.

Abdominal compartment syndrome is caused by fluid accumulation in the peritoneal space due to edema and other such causes, and results in greatly increased intra-abdominal pressure that may cause organ failure eventually resulting in death. Causes may include sepsis or severe trauma. Treatment of abdominal compartment syndrome may require an abdominal incision to permit decompression of the abdominal space, and as such, a large wound may be created onto the patient. Closure of this wound, while minimizing the risk of secondary infections and other complications, and after the underlying edema has subsided, then becomes a priority.

Other large or incisional wounds, either as a result of surgery, trauma, or other conditions, may also require closure. For example, wound resulting from sterniotomies, fasciotomies, and other abdominal wounds may require closure. Wound dehiscence of existing wounds is another complication that may arise, possibly due to incomplete underlying fascial closure, or secondary factors such as infection.

Existing negative pressure treatment systems, while permitting eventual wound closure, still require lengthy closure times. Although these may be combined with other tissue securement means, such as sutures, there is also a risk that underlying muscular and fascial tissue is not appropriately reapproximated so as to permit complete wound closure. Further, when foam or other wound fillers are inserted into the wound, the application of negative pressure to the wound and the foam may cause atmospheric pressure to bear down onto the wound, compressing the foam downward and outward against the margins of the wound. This downward compression of the wound filler slows the healing process and slows or prevents the joining of wound margins. Additionally, inflammation of the fascia in the form of certain types of fasciitis can lead to rapid and excessive tissue loss, potentially meriting the need for more advanced negative pressure treatment systems. Accordingly, there is a need to provide for an improved apparatus, method, and system for the treatment and closure of wounds.

SUMMARY OF THE INVENTION

Embodiments of the present invention relate to negative pressure wound closure devices, methods, and systems that facilitate closure of a wound. The devices, methods, and systems may operate to reduce the need for repetitive replacement of wound filler material currently employed and can advance the rate of healing. The devices, methods, and systems may be simultaneously used with negative pressure to remove wound fluids.

In one embodiment, a wound closure device comprises: a stabilizing structure comprising a plurality of planar support structures, each planar support structure comprising a first plurality of beams intersecting with a second plurality of beams, the plurality of planar support structures being arranged parallel to one another; a plurality of spring elements joining adjacent planar support structures, the plurality of spring elements providing for compression of the stabilizing structure so that the planar support structures come closer to one another.

In some embodiments, the beams are rigid. In some embodiments, the first plurality of beams intersects with the second plurality of beams at a right angle. Some embodiments may provide for each planar support structure to be substantially rigid within the plane of the support structure. In further embodiments, the planar support structure comprises one or more standoffs located on an outer plane or perimeter. In further embodiments, the standoffs are provided with one or more tissue anchors configured to engage tissue placed into contact with the device. In some embodiments, a first plurality of spring elements is located in a first plane perpendicular to the planar support structures, and a second plurality of spring elements is located in a second plane perpendicular to both the first plane and to the planar support structures. Some embodiments may provide for the first plurality of spring elements being located in a first plurality of parallel planes, the first plurality of parallel planes including the first plurality of rigid beams, and wherein the second plurality of spring elements are located in a second plurality of parallel planes, the second plurality of parallel planes including the second plurality of rigid beams. Some embodiments may provide spring elements comprising V-shaped members. In some embodiments, each planar support structure is identical. In some embodiments, a porous material such as foam surrounds one or more of the planar support structures. In further embodiments, the porous material surrounds the entire device. In some embodiments, the stabilizing structure comprises 2, 3, 4, 5 or more parallel planar support structures, with spring elements provided between each. In some embodiments, there may be an identical arrangement of spring elements between each of the planar support structures.

Another embodiment provides for a stabilizing structure comprising a plurality of cells provided side-by-side in a plane, each cell defined by one or more walls, each cell having a top end and a bottom end with an opening extending through the top and bottom ends in the direction perpendicular to the plane; wherein the stabilizing structure is configured to collapse significantly more within the plane than along the direction perpendicular to the plane.

In some embodiments, the stabilizing structure is constructed from a material selected from the group consisting of silicone, polyurethanes, flexible plastics, rigid plastics, and foam. In some embodiments, the cells are identical; in other embodiments, one or more of the cells are differently shaped from the remaining ones. The plane may extend in a horizontal direction. In some embodiments the walls may extend in a vertical direction. In some embodiments, the walls adjoin to adjacent cells. In some embodiments, the shape of each cell is selected from the group consisting of square, diamond, oblong, oval, and parallelepiped. In some embodiments, at least one wall of each cell includes a notch or a hole. In some embodiments, at least one wall of each cell is configured to fold against another wall of the cell. Further embodiments may provide for each cell to be connected to an adjacent cell by a joint, wherein the joints are more flexible than the walls. Some joints may be more flexible than other joints in the same cell. The stabilizing structure may comprise cells that are more collapsible in a first direction along the plane than in a second direction at an angle to the first direction along the same plane. Sometimes the second direction may be perpendicular to the first direction. The stabilizing structure may comprise a plurality of first strips extending in a first direction, and a plurality of intersecting strips extending in a second direction perpendicular to the first direction, wherein the structure is collapsible in the first and second directions.

In some embodiments, the one or more walls further comprise an insert disposed therein. The insert may be more rigid than the one or more walls, and may be insertable into a preformed pocket within the one or more walls. In some embodiments, the stabilizing structure comprises one or more inserts, and wherein each of the one or more walls are molded around an individual insert. The insert may have a rectangular configuration. The insert may have a rectangular configuration with two notches formed thereupon. In some embodiments, the insert comprises one or more longitudinal grooves extending in the direction of the plane. The insert may further comprise one or more holes disposed therethrough. In some embodiments, the holes are arranged in a 6×6 pattern. In certain embodiments, the holes are arranged in a 2×3 pattern or any other pattern. The one or more holes may be disposed on an edge of the insert.

Embodiments of the wound closure device disclosed in this section or elsewhere in this specification may also comprise a porous material surrounding or within each cell of the stabilizing structures described both above and below. In some embodiments, a porous material may surround the entire stabilizing structure, or may surround only a perimeter of the stabilizing structure. The porous material may be foam. In some embodiments, porous materials may surround or be within each cell, quadrilateral space or other interior portions of the stabilizing structure. In some embodiments, the stabilizing structure may be insertable into a sock or enclosure formed of porous material such that the porous material covers at least a portion of an outer perimeter of the stabilizing structure. In some embodiments, separate porous material layers may be provided above, below, or on both upper and lower layers of the stabilizing structure. In certain embodiments, the entire wound closure device or the entire stabilizing structure is surrounded by foam. In some embodiments, the cells of the wound closure device may comprise foam or other porous material inserts. In certain embodiments, foam surrounds the perimeter of the stabilizing structure or wound closure device.

In other embodiments, a stabilizing structure sized to be inserted into a wound, comprises:
  at least one top strip extending in a first direction, the top strip comprising at least one notch extending partly therethrough and opening on a bottom side of the top strip;
  at least one bottom strip extending in a second direction, the bottom strip comprising at least one notch extending partly therethrough and opening on a top side of the bottom strip;
  wherein the at least one top strip and bottom strip are configured to be movably interlocked together by placing the notch on the top strip over the notch on the bottom strip, and
  wherein the at least one top strip and the at least one bottom strip are configured to preferentially collapse along a first plane defined by the first and second directions, while remaining movably interlocked and substantially not collapsing along a third direction perpendicular to the first plane.

Additional embodiments provide for the at least one notch on the top strip and the at least one notch on the bottom strip to be dimensioned such that, when movably interlocked together, the top strip does not extend substantially above the bottom strip in the third direction. In further embodiments, the stabilizing structure comprises at least two top strips and at least two bottom strips so as to form at least one quadrilateral space bounded by two top strips and two bottom strips.

In other embodiments, a stabilizing structure for insertion into a wound comprises:
  at least one top strip extending in a first direction;
  at least one bottom strip extending in a second direction;
  wherein the at least one top strip and bottom strip are configured to be movably interlocked using an interlock mechanism, and
  wherein the at least one top strip and the at least one bottom strip are configured to preferentially collapse along a first plane defined by the first and second directions, while remaining movably interlocked and substantially not collapsing along a third direction perpendicular to the first plane.

In some embodiments, the interlock mechanism comprises: one of the at least one top strip or bottom strip comprising two parallel clasps extending in the third direction; the other of the at least one top strip or bottom strip comprising a projection extending in the third direction; and wherein the two parallel clasps rotatably engage with the projection so as to rotate about the projection in the first plane while remaining substantially fixed in the third direction. In some embodiments, the interlock mechanism comprises: one of the top strip or the bottom strip comprising a projection with an enlarged distal end, the other of the top strip or bottom strip comprising a cup-shaped member configured to receive the enlarged distal end of the projection therein; and wherein the top strip and bottom strips are rotatably engaged so as to rotate about the projection in the first plane without disengaging in the third direction. In some embodiments, the interlock mechanism comprises: one of the at least one top strip or bottom strip comprising four clasps disposed at perpendicular angles to each other extending in the third direction; the other of the at least one top strip or bottom strip comprises a projection extending in the third direction; and wherein the two parallel clasps rotatably engage with the projection so as to rotate about the projection in the first plane while remaining substantially fixed in the third direction. Some embodiments may also comprise an uncompressed volume defined by the height of the stabilizing structure and the area of the stabilizing structure in the first plane when the first and second directions defined by the at least one top strip and bottom strip are at perpendicular angles to each other, and wherein the stabilizing structure, when compressed, defines a compressed volume that is at least 15% smaller than the uncompressed area.

Additional embodiments provide for the top strip comprising at least one notch extending partly therethrough and opening on a bottom side of the top strip, and the bottom strip comprising at least one notch extending partly therethrough and opening on a top side of the bottom strip. In such an embodiment, the interlock mechanism places the notch on the top strip over the notch on the bottom strip. In some embodiments, the at least one notch on the top strip and the at least one notch on the bottom strip to be dimensioned such that, when movably interlocked together, the top strip does not extend substantially above the bottom strip in the third direction. In further embodiments, the stabilizing structure comprises at least two top strips and at least two bottom strips so as to form at least one quadrilateral space bounded by two top strips and two bottom strips.

In some embodiments, a stabilizing structure is provided for insertion into a wound, comprising a plurality of elongate strips arranged in parallel (or generally in parallel), and a plurality of intervening members connecting the elongate strips, wherein the plurality of intervening members are configured to pivot relative to the strips to allow the plurality of elongate strips to collapse relative to one another; wherein the intervening members between a first strip and a second strip are configured to pivot independently of the intervening members between a second strip and a third strip.

In certain embodiments, the intervening members are connected to the elongate strips via at least one joint. In particular embodiments, the joint is a hinge. In some embodiments, the hinges are configured to collapse in one direction. In particular embodiments, the joints are configured to restrict the movement of the intervening members. In certain embodiments, the elongate strips are rigid. In certain embodiments, the elongate strips are configured to bend along their length. In some embodiments, the elongate strips can be constructed from a material selected from the group consisting of silicone, polyurethane, rigid plastics, semi-rigid plastics, biocompatible materials, flexible plastic materials, composite materials, and foam. In some embodiments, the intervening members are constructed from a material selected from the group consisting of silicone, polyurethane rigid plastics, semi-rigid plastics, biocompatible materials, flexible plastic materials, composite materials, and foam.

In some embodiments, the stabilizing structure comprises a plurality of intervening members between adjacent elongate strips to define a row of cells between each pair of adjacent elongate strips. In some embodiments, the cells are in the shape of a diamond. In particular embodiments, the cells in a row between adjacent elongate strips are configured to collapse together as the adjacent strips collapse relative to one another. In some embodiments, the rows of cells between adjacent strips are configured to collapse in a first direction, and one or more rows of cells between adjacent strips are configured to collapse in a second direction opposite the first direction. In some embodiments, all of the rows of cells of the stabilizing structure are configured to collapse in the same direction.

In some embodiments, the intervening members between the first strip and the second strip are offset relative to intervening members between the second strip and the third strip. In certain embodiments, foam surrounds the elongate strips and the intervening members. In some embodiments, foam is contained between adjacent elongate strips.

In certain embodiments, the intervening members comprise panels. In other embodiments, the intervening members comprise a plurality of bars configured to pivot relative to the elongate strips, and a plurality of pins connecting the elongate strips to the bars. In some embodiments, a plurality of stops is configured to restrict the rotational movement of the pins.

In further embodiments, the intervening members of the stabilizing structures described above may further comprise one or more sleeves and one or more inserts, wherein the sleeves are configured to receive one or more inserts. In certain embodiments, the inserts may be constructed from rigid or semi-rigid materials such as polyvinyl chloride. In some embodiments, the sleeves can be constructed from flexible or semi-flexible materials such as silicone or polyurethane. In other embodiments, the inserts may further comprise one or more indents.

In some embodiments, the elongate strips of the stabilizing structures described above can comprise one or more flexing segments and one or more supporting segments. The flexing segments may be constructed from flexible or semi-flexible materials such as silicone or polyurethane, while the supporting segments may be constructed from rigid or semi-rigid material such as polyvinyl chloride. In certain embodiments, the length of the supporting segments is greater than the length of the flexing segments.

In some embodiments, the elongate strips of the stabilizing structures described above can comprise holes configured to allow the passage of fluid. In additional embodiments, the elongate strips may further comprise one or more gaps that extend along at least a portion of the elongate strip. In further embodiments, the intervening members of the stabilizing structures described above can comprise one or more windows configured to allow the passage of fluid. Further embodiments may provide for windows that further comprise a bar.

In certain embodiments, the stabilizing structures as described above may be configured such that 90% of the total collapse of any dimension occurs within one hour. In other embodiments, the stabilizing structures are configured such that 90% of the total collapse of any dimension occurs within five minutes.

Further embodiments may provide for the use of separate foam layers above, below, or on both upper and lower layers of the stabilizing structure. In certain embodiments, the foam layers further comprise fingers that extend into or around the stabilizing structure. In some embodiments the stabilizing structure is surrounded by foam in the form of a ribbon or ring.

The embodiments disclosed in this section or elsewhere in this specification may also comprise a drape configured to be placed over the wound closure device or stabilizing structure once inserted into a wound so as to create a fluid-tight seal on the skin surrounding the wound. Embodiments may also comprise a source of negative pressure configured to be connected to the wound, and other associated apparatuses.

Further embodiments provide for methods of closing a wound, comprising:
    placing a wound closure device or stabilizing structure such as described in this section or elsewhere in this specification within a wound;

sealing the wound with a fluid-tight drape;
fluidically connecting the wound to a source of negative pressure; and applying negative pressure to the wound via the source of negative pressure.

Further embodiments may provide for removing fluid from the wound site. In some embodiments, the wound closure device or stabilizing structure is placed into the wound such that the direction of collapse or compression of the wound closure device or stabilizing structure is parallel or substantially parallel with the surface of the skin. In some embodiments, the application of negative pressure causes the wound closure device or stabilizing structure to at least partly collapse. Further, the wound closure device or stabilizing structure may be at least partly collapsed or compressed prior to inserting the stabilizing structure into the wound. In some embodiments, the wound closure device or stabilizing structure is capable of collapse or compression to 40% or less, 30% or less, 20% or less, 10% or less or even 5% or less of one of its original dimensions (e.g., along one of its lengths). Some embodiments provide for reducing the wound area by at least 50% upon the application of negative pressure.

Additional embodiments of a negative pressure wound closure system may comprise:
 a stabilizing structure such as described in this section or elsewhere in this specification;
 a drape sized and configured to be placed over the stabilizing structure and to form a substantially fluid-tight seal against a region of skin surrounding the wound; and
 a source of negative pressure in fluid communication with the wound.

In certain embodiments, a method of closing a wound may comprise:
 placing a wound closure device into a wound, the wound closure device configured to removably received one or more inserts, wherein the wound closure device is configured to collapse under negative pressure;
 sealing the wound with a fluid-tight drape;
 fluidically connecting the wound to a source of negative pressure;
 applying negative pressure to the wound via the source of negative pressure; and
 removing one or more inserts from the stabilizing structure and/or inserting one or more inserts into the stabilizing structure to dynamically control collapse of the wound closure device.

Further embodiments of the above method may provide a wound closure device comprising a stabilizing structure as described in this section or elsewhere in this specification, such as a stabilizing structure comprising intervening members which further comprise one or more sleeves and one or more inserts, wherein the sleeves are configured to receive one or more inserts.

Other embodiments of wound closure devices, stabilizing structures and associated apparatuses are described below.

BRIEF DESCRIPTION OF THE DRAWINGS

Other features and advantages of the present invention will be apparent from the following detailed description of the invention, taken in conjunction with the accompanying drawings of which:

FIGS. 17A-B, 18A-B are before and after photographs of experiments performed to determine the efficacy of certain embodiments of wound closure devices.

FIGS. 22A-F illustrate various embodiments of inserts that may be used in stabilizing structures.

FIG. 36A-F illustrate multiple views of an embodiment of a stabilizing structure.

FIG. 38A-C illustrate multiple embodiments of a stabilizing structure.

DETAILED DESCRIPTION OF THE PREFERRED EMBODIMENTS

Figure 1:
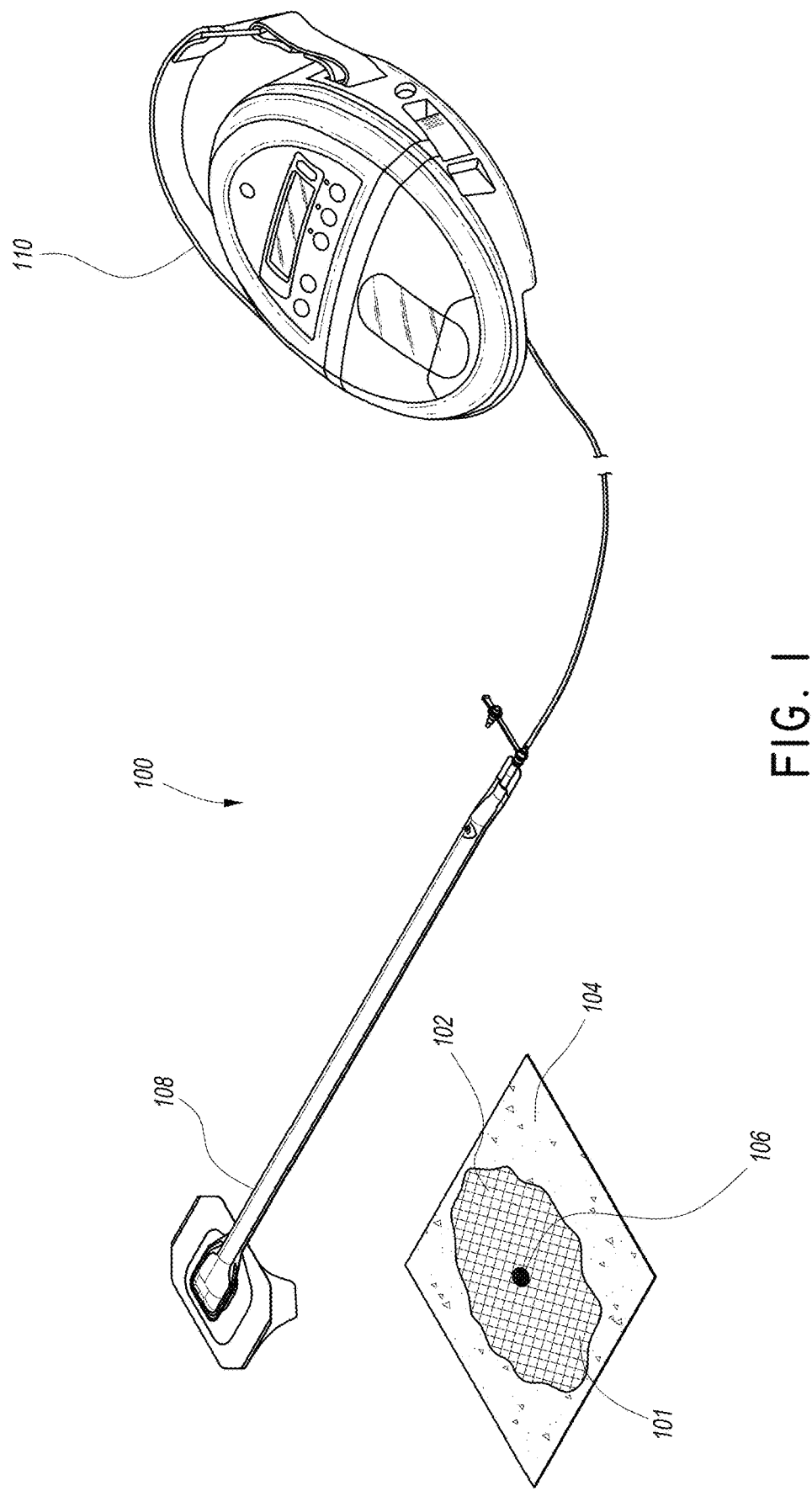
FIG. 1 illustrates an embodiment of a negative pressure treatment system.

Embodiments disclosed in this section or elsewhere in this specification relate to apparatuses and methods of treating a wound with reduced pressure, including pump and wound dressing components and apparatuses. The apparatuses and components comprising the wound overlay and packing materials, if any, are sometimes collectively referred to in this section or elsewhere in this specification as dressings.

It will be appreciated that throughout this specification reference is made to a wound. It is to be understood that the term wound is to be broadly construed and encompasses open and closed wounds in which skin is torn, cut or punctured or where trauma causes a contusion, or any other superficial or other conditions or imperfections on the skin of a patient or otherwise that benefit from reduced pressure treatment. A wound is thus broadly defined as any damaged region of tissue where fluid may or may not be produced. Examples of such wounds include, but are not limited to, abdominal wounds or other large or incisional wounds, either as a result of surgery, trauma, sterniotomies, fasciotomies, or other conditions, dehisced wounds, acute wounds, chronic wounds, subacute and dehisced wounds, traumatic wounds, flaps and skin grafts, lacerations, abrasions, contusions, burns, electrical burns, diabetic ulcers, pressure ulcers, stoma, surgical wounds, trauma and venous ulcers or the like.

As is used in this section or elsewhere in this specification, reduced or negative pressure levels, such as $-X$ mmHg, represent pressure levels that are below standard atmospheric pressure, which corresponds to 760 mmHg (or 1 atm, 29.93 inHg, 101.325 kPa, 14.696 psi, etc.). Accordingly, a negative pressure value of $-X$ mmHg reflects absolute pressure that is X mmHg below 760 mmHg or, in other words, an absolute pressure of (760-X) mmHg. In addition, negative pressure that is "less" or "smaller" than X mmHg corresponds to pressure that is closer to atmospheric pressure (e.g., -40 mmHg is less than -60 mmHg). Negative pressure that is "more" or "greater" than $-X$ mmHg corresponds to pressure that is further from atmospheric pressure (e.g., -80 mmHg is more than -60 mmHg).

The negative pressure range for some embodiments of the present disclosure can be approximately -80 mmHg, or between about -10 mmHg and -200 mmHg. Note that these pressures are relative to normal ambient atmospheric pressure. Thus, -200 mmHg would be about 560 mmHg in practical terms. In some embodiments, the pressure range can be between about -40 mmHg and -150 mmHg. Alternatively a pressure range of up to -75 mmHg, up to -80 mmHg or over -80 mmHg can be used. Also in other embodiments a pressure range of below -75 mmHg can be used. Alternatively, a pressure range of over approximately -100 mmHg, or even -150 mmHg, can be supplied by the negative pressure apparatus. In some embodiments, the negative pressure range can be as small as about -20 mmHg or about -25 mmHg, which may be useful to reduce fistulas. In some embodiments of wound closure devices described here, increased wound contraction can lead to increased tissue expansion in the surrounding wound tissue. This effect may be increased by varying the force applied to the tissue, for example by varying the negative pressure applied to the wound over time, possibly in conjunction with increased tensile forces applied to the wound via embodiments of the wound closure devices. In some embodiments, negative pressure may be varied over time for example using a sinusoidal wave, square wave, and/or in synchronization with one or more patient physiological indices (e.g., heartbeat). Examples of such applications where additional disclosure relating to the preceding may be found include application Ser. No. 11/919,355, titled "Wound treatment apparatus and method," filed Oct. 26, 2007, published as US 2009/0306609; and U.S. Pat. No. 7,753,894, titled "Wound cleansing apparatus with stress," issued Jul. 13, 2010. Both applications are hereby incorporated by reference in their entirety. Other applications that may contain teachings relevant for use with the embodiments described in this section or elsewhere in this specification may include application Ser. No. 12/886,088, titled "Systems And Methods For Using Negative Pressure Wound Therapy To Manage Open Abdominal Wounds," filed Sep. 20, 2010, published as US 2011/0213287; application Ser. No. 13/092,042, titled "Wound Dressing And Method Of Use," filed Apr. 21, 2011, published as US 2011/0282309; and application Ser. No. 13/365,615, titled "Negative Pressure Wound Closure Device," filed Feb. 3, 2012, published as US 2012/0209227.

It will be understood that throughout this specification in some embodiments reference is made to an elongate, elongated or longitudinal strip or strips. It is to be understood that these terms are to be broadly construed and refer in some embodiments to an elongate material having two parallel or substantially parallel faces, where in cross-section a thickness of the material as measured perpendicular to the faces is relatively smaller than a height of the material measured parallel to the faces. While in some embodiments the strips may be constructed from discrete lengths of material, in other embodiments the strips may simply refer to elongate portions of an overall structure having two parallel or substantially parallel faces. The strips in some embodiments have a rectangular or generally rectangular-shaped faces, wherein a length of the face is longer than the height of the face. In some embodiments, the length of the face may be more than 2 times, 4 times, 6 times, 8 times or 10 times greater than the height of the face.

As used in this section or elsewhere in this specification, the term "horizontal," when referring to a wound, indicates a direction or plane generally parallel to the skin surrounding the wound. The term "vertical," when referring to a wound, generally refers to a direction extending perpendicular to the horizontal plane. The term "longitudinal," when referring to a wound, generally refers to a direction in the horizontal plane taken in a direction along which the wound is longest. The term "lateral," when referring to a wound, generally refers to a direction in the horizontal plane perpendicular to the longitudinal direction. The terms "horizontal," "vertical," "longitudinal," and "lateral" may also be used to describe the stabilizing structures and wound closure devices described throughout this specification. When describing these structures or devices, these terms should not be construed to require that the structures or devices necessarily be placed into a wound in a certain orientation, though in certain embodiments, it may be preferable to do so.

FIG. 1 illustrates an embodiment of a negative pressure treatment system 100 that comprises a wound packer 102 inserted into a wound 101. The wound packer 102 may comprise porous materials such as foam, and in some embodiments may comprise one or more embodiments of wound closure devices described in further detail in this section or elsewhere in this specification. In some embodiments, the perimeter or top of any wound closure device inserted into the wound 101 may also be covered with foam or other porous materials. A single drape 104 or multiple drapes may be placed over the wound 101, and is preferably adhered or sealed to the skin on the periphery of the wound 101 so as to create a fluid-tight seal. An aperture 106 may be made through the drape 104 which can be manually made or preformed into the drape 104 so as to provide a fluidic connection from the wound 101 to a source of negative pressure such as a pump 110. Preferably, the fluidic connection between the aperture 106 and the pump 110 is made via a conduit 108. In some embodiments, the conduit 108 may comprise a RENASYS® Soft Port™, manufactured by Smith & Nephew. Of course, in some embodiments, the drape 104 may not necessarily comprise an aperture 106, and the fluidic connection to the pump 110 may be made by placing the conduit 108 below the drape. In some wounds, particularly larger wounds, multiple conduits 108 may be used, fluidically connected via one or more apertures 106.

In some embodiments, the drape 104 may be provided with one or more corrugations or folds. Preferably, the corrugations are aligned along the longitudinal axis of the wound, and as such may support closure of the wound by preferentially collapsing in a direction perpendicular to the longitudinal axis of the wound. Such corrugations may aid in the application of contractile forces parallel to the wound surface and in the direction of wound closure. Examples of such drapes may be found in application Ser. No. 12/922, 118, titled "Vacuum Closure Device," filed Nov. 17, 2010 (published as US 2011/0054365), which is hereby incorporated by reference in its entirety.

In use, the wound 101 is prepared and cleaned. In some cases, such as abdominal wounds, a non- or minimally-adherent organ protection layer (not illustrated) may be applied over any exposed viscera. The wound packer 102 is then inserted into the wound, and is covered with the drape 104 so as to form a fluid-tight seal. A first end of the conduit 108 is then placed in fluidic communication with the wound, for example via the aperture 106. The second end of the conduit 108 is connected to the pump 110. The pump 110 may then be activated so as to supply negative pressure to the wound 101 and evacuate wound exudate from the wound 101. As will be described in additional detail below and in relation to the embodiments of the foregoing wound closure devices, negative pressure may also aid in promoting closure of the wound 101, for example by approximating opposing wound margins.

EXAMPLE 1

By means of a non-limiting example, an experiment was conducted to determine the effectiveness of an embodiment of the wound closure devices described above, with testing being performed on a cadaveric model. A midline incision was made through the peritoneum and into the abdominal cavity of the cadaver, which was then filled with two saline bags with a total capacity of approximately 2 L so as to provide upward tension to simulate the effects of abdominal edema and organ swelling that may be seen, for example, in abdominal compartment syndrome. These bags, together with the intestines, were placed into the wound cavity underneath an organ protection layer, as provided in the Renasys® A/B treatment kit (Smith & Nephew).

Figures 2A, 2B:
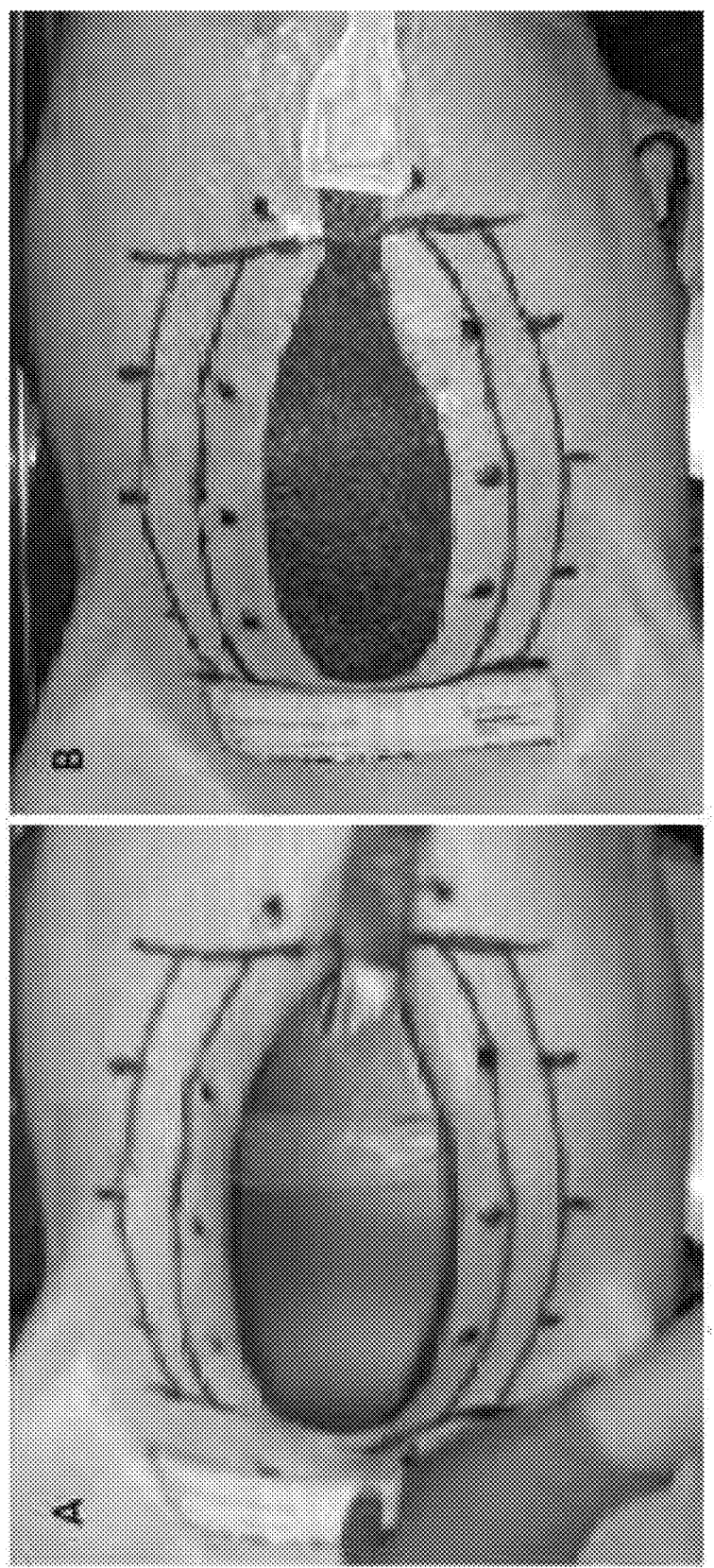
FIGS. 2A-B are before and after photographs of experiments performed to determine the efficacy of embodiments of wound closure devices.

With reference to FIG. 2A, a piece of black foam was inserted into the abdominal incision, sealed with a drape, and connected to a source of negative pressure via a fluidic connection (here, a Soft Port™ suction port assembly manufactured by Smith & Nephew). FIG. 2B illustrates the area of the wound after activation of the source of negative pressure. Negative pressure was then applied at 80, 120, and 180mmHg. With all three of these negative pressure levels, there was no significant difference to the amount of wound margin contraction achieved, although vacuum levels below 80 mmHg did not appear to contract the wound margins as much. This was true in all of the other subsequent experiments described in this section or elsewhere in this specification.

Wound area measurements were taken before and after activation of the negative pressure source. In this example, the size of the wound area before and after application of negative pressure decreased from 167mm$^2$ to 126mm$^2$. This is a difference of 25%.

Stabilizing Structures and Wound Closure Devices of FIGS. 3A-4E

FIGS. 3A-D illustrate different views of an embodiment of a wound closure device comprising a stabilizing structure 1701. Here, the stabilizing structure 1701 comprises a first set of beams 1703 that are rigidly or semi-rigidly attached or bonded to a second set of intersecting beams 1705. These beams 1703, 1705 form a planar support structure 1702 that is preferably substantially rigid within a plane. The beams 1703, 1705 may meet at right angles to each other (although other configurations, e.g., honeycombs are possible). Two or more planar support structures 1702 may be joined together to form the stabilizing structure 1701, and each planar support structure 1702 is preferably separated from the other by spring elements 1711 and 1713, described in further detail below. The number of planar support structures 1702 used in the stabilizing structure may be tailored in relation to the size of the wound. For example, there may be 2, 3, 4, 5 or more planar support structures 1702 arranged parallel or substantially parallel to one another. The spring elements 1711, 1713 are preferably arranged so as to allow for compression of the stabilizing structure 1701 in one direction so as to bring the planar support structures 1702 closer together. In a preferred embodiment, the stabilizing structure 1701 may collapse to 40% or less of its original size, preferably 30% or less of its original size; more preferably, 20% or less of its original size; even more preferably, 10% or less of its original size. In some embodiments, the stabilizing structure 1701 may collapse to 5% or less of its original size.

The spring elements 1711, 1713 are preferably resiliently flexible and biased to be resiliently collapsible along a direction perpendicular to the plane defined by the planar support structure 1702. In some embodiments, the elements 1711, 1713 may be inelastic, and retain their shape when collapsed. In such embodiments, the spring elements or the stabilizing structure may be constructed with a ratchet mechanism that maintains the spring elements 1711, 1713 in their collapsed configuration.

Figure 3A:
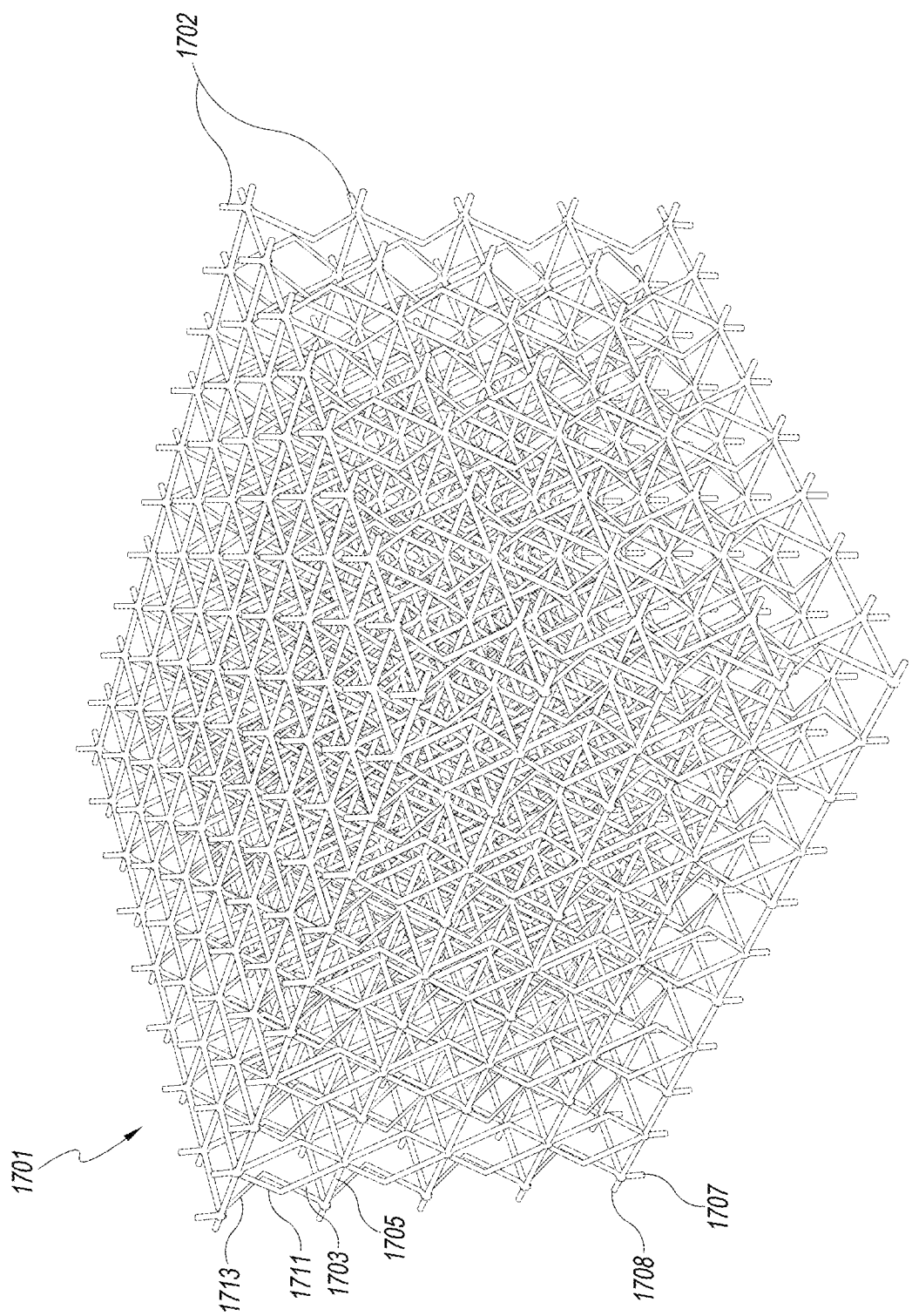
FIGS. 3A-D illustrate different views of embodiments of a wound closure device comprising a stabilizing structure.
Figure 3B:
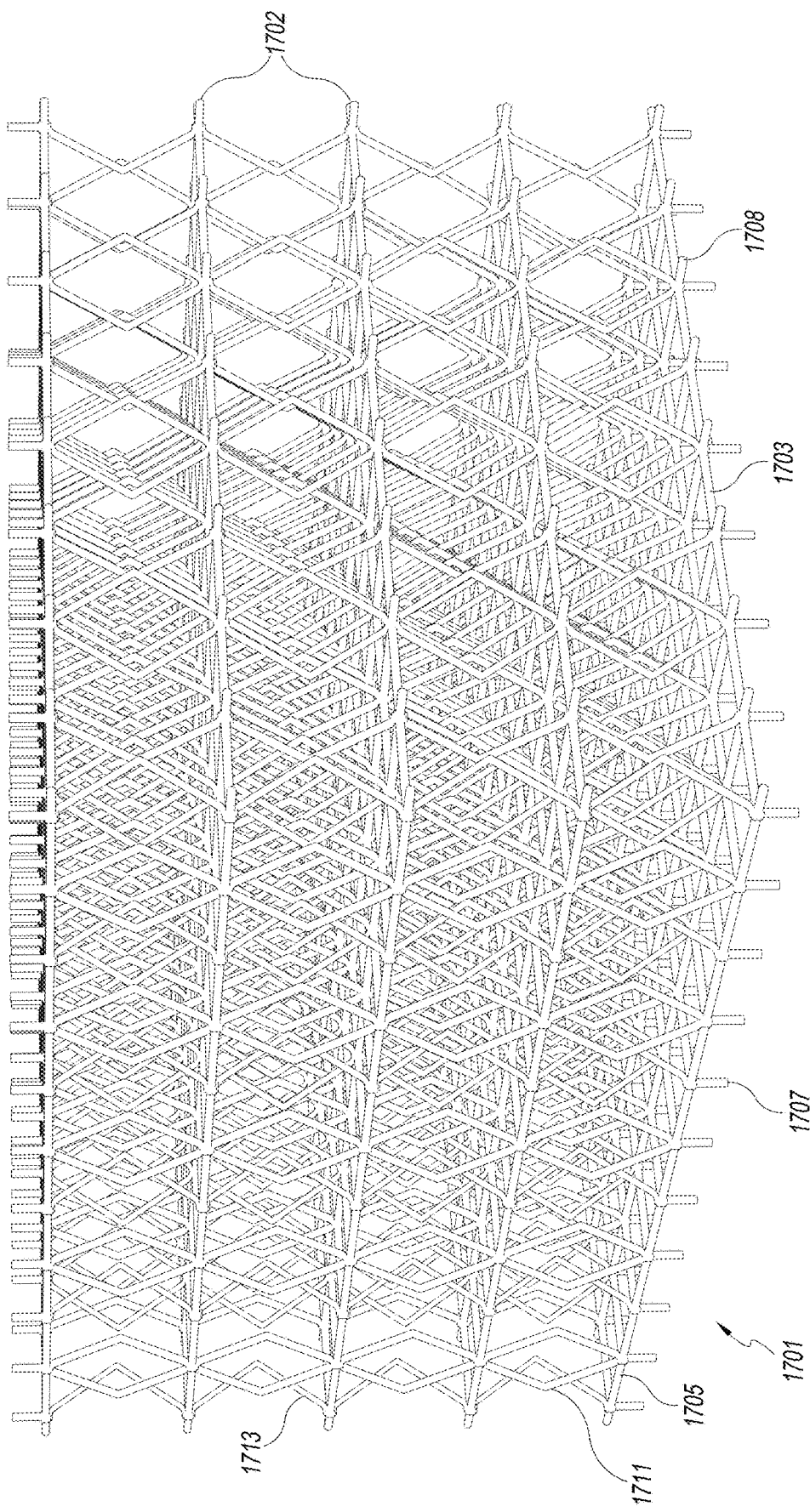
Figure 3C:
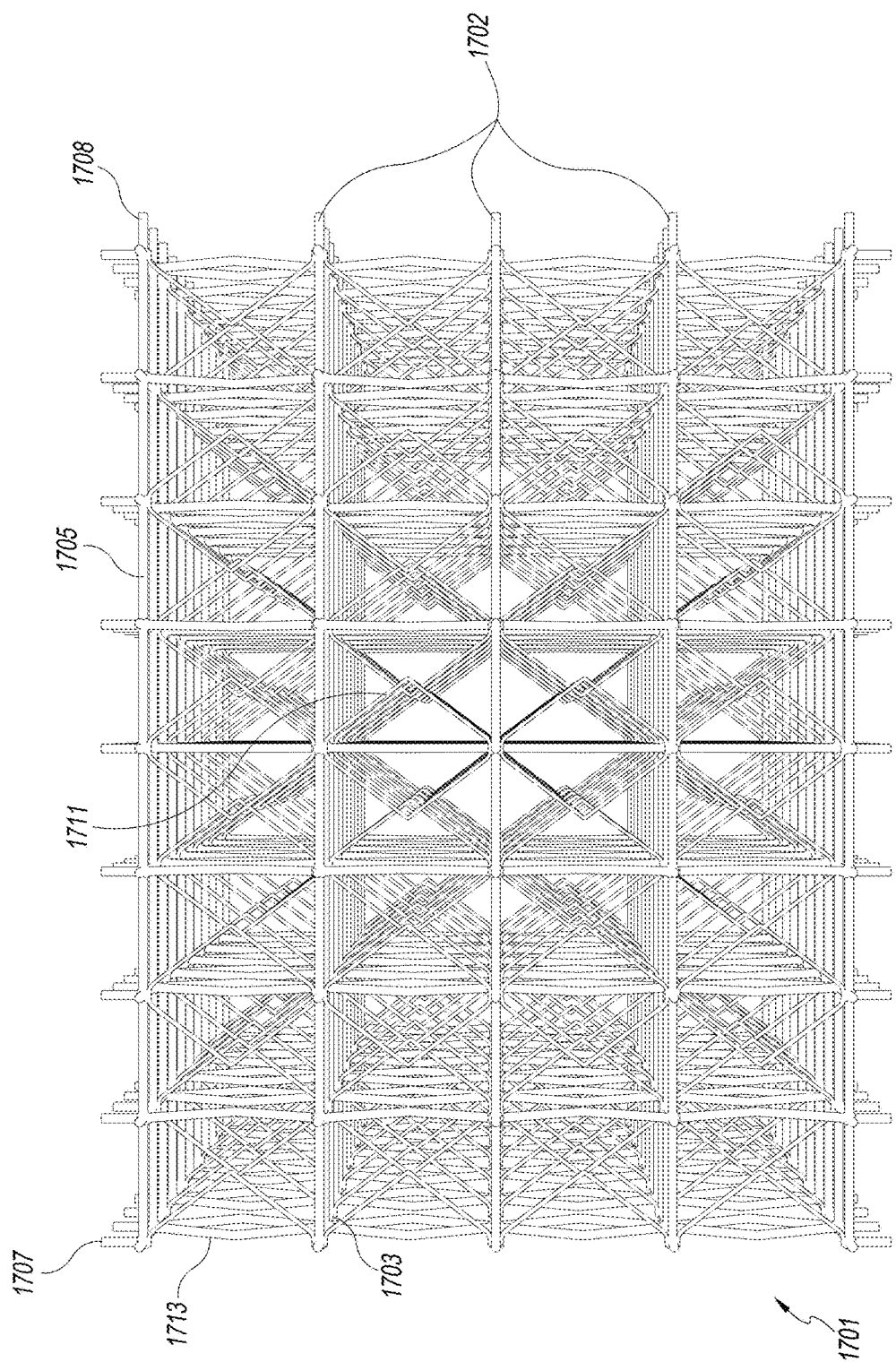
Figure 3D:
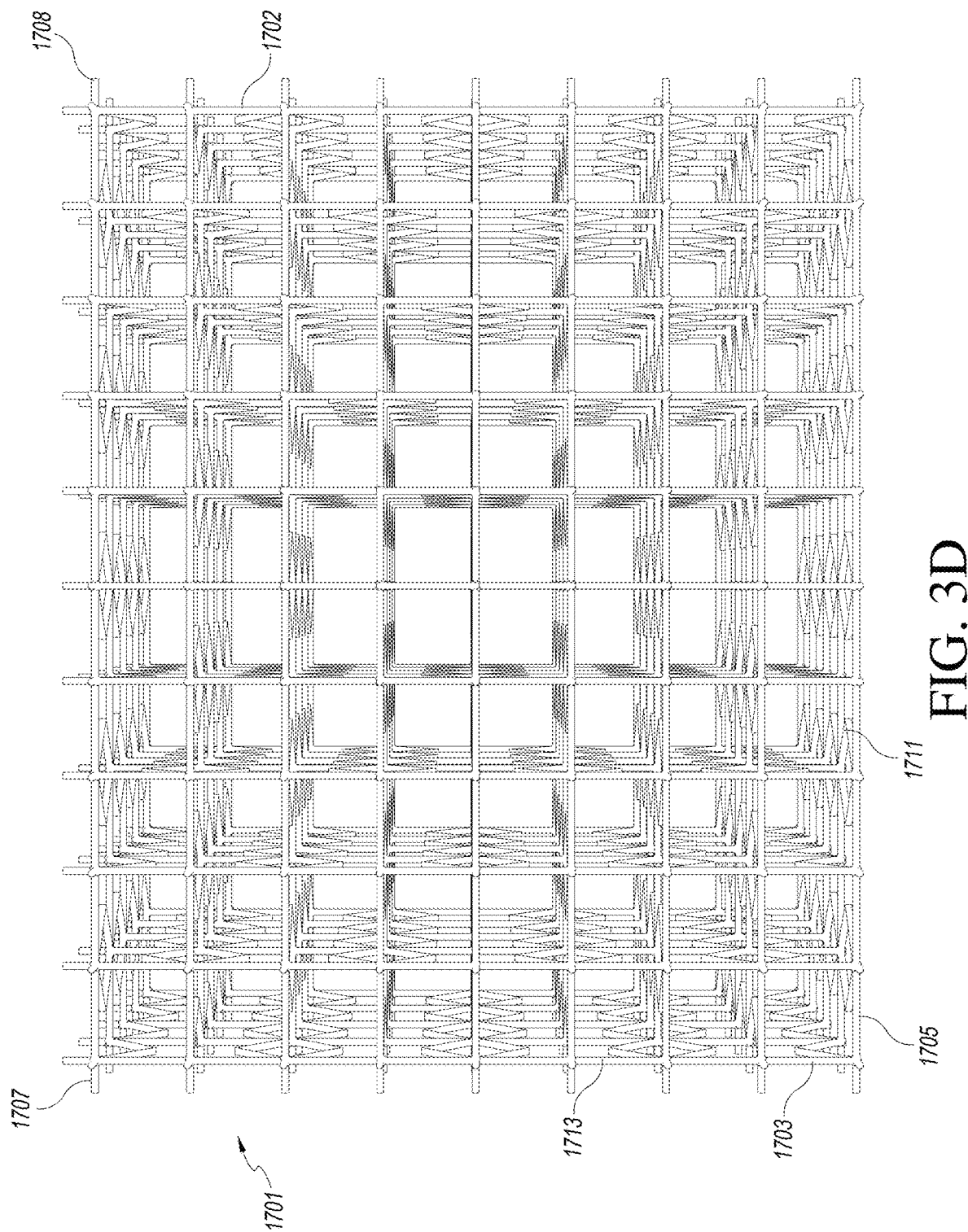
Figure 4A:
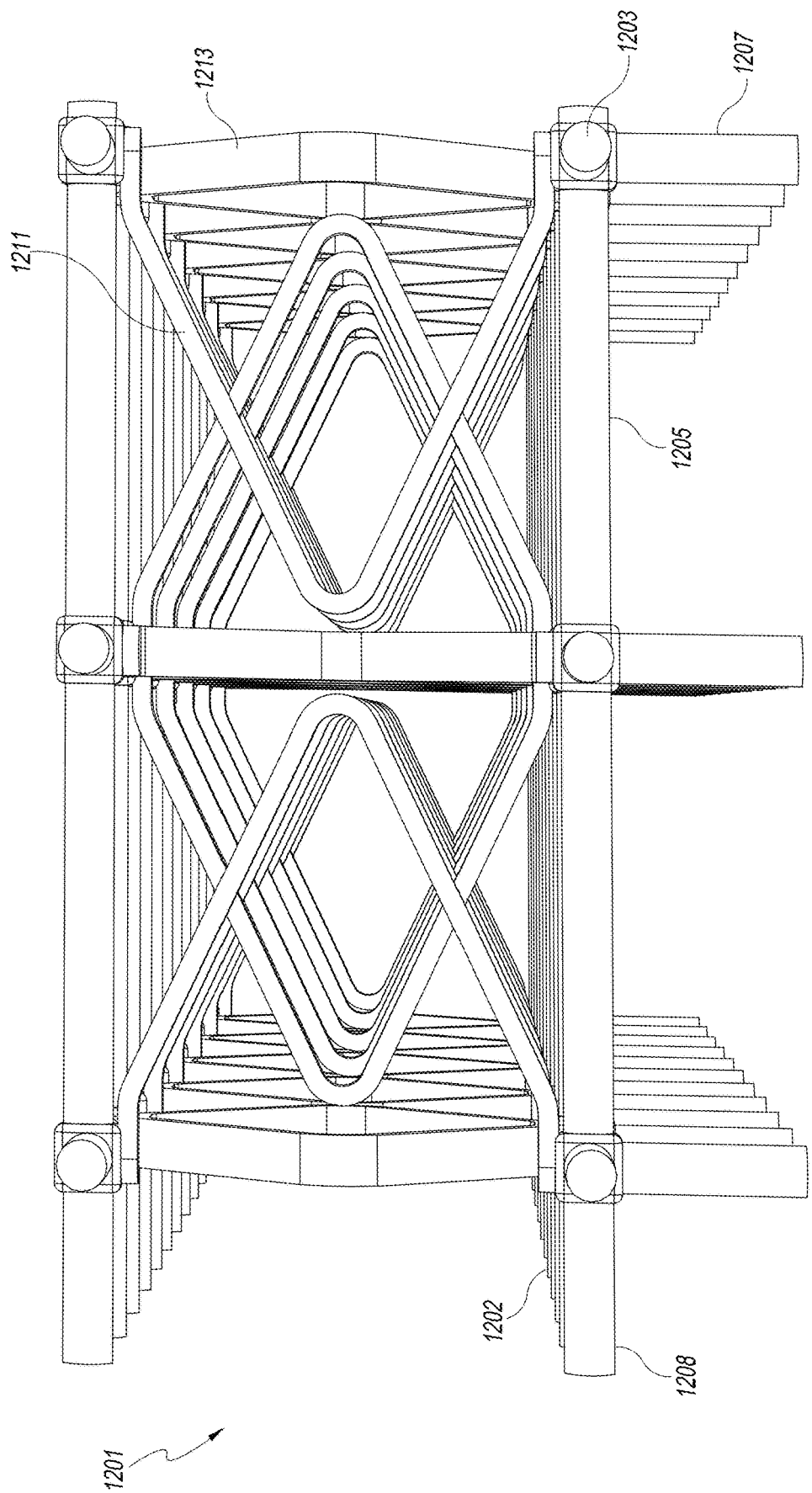
FIGS. 4A-E illustrate different views and photographs of embodiments of a wound closure device comprising a stabilizing structure.
Figure 4B:
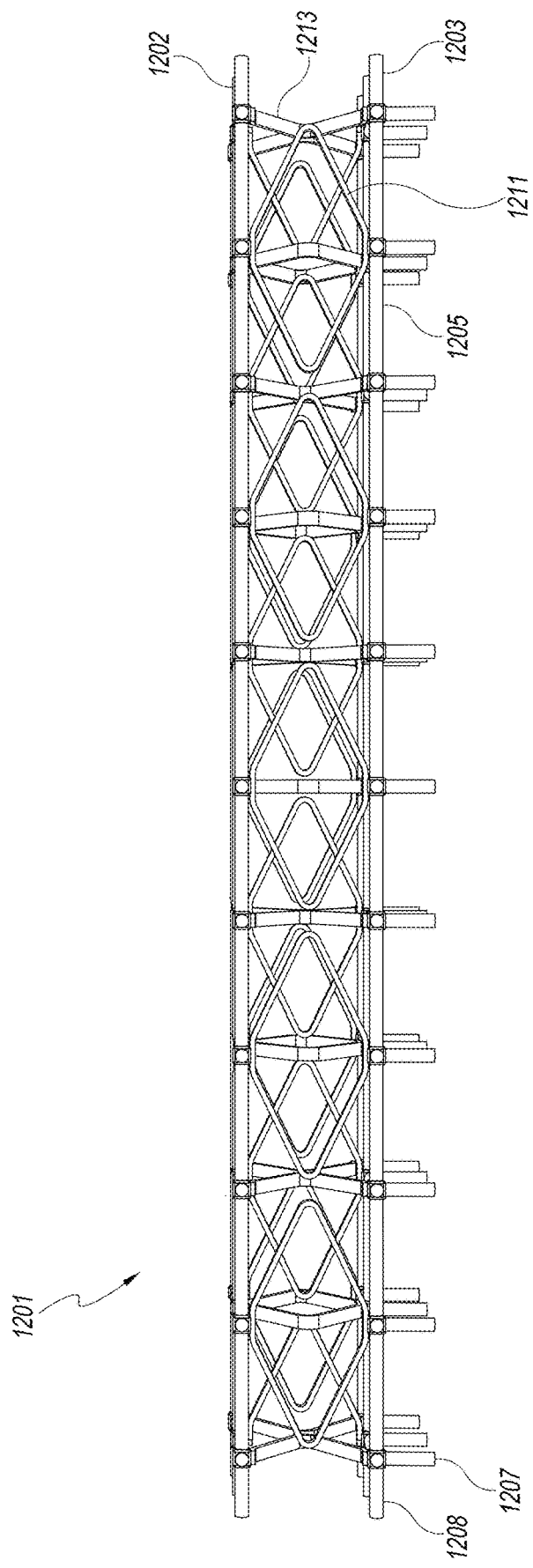
Figure 4C:
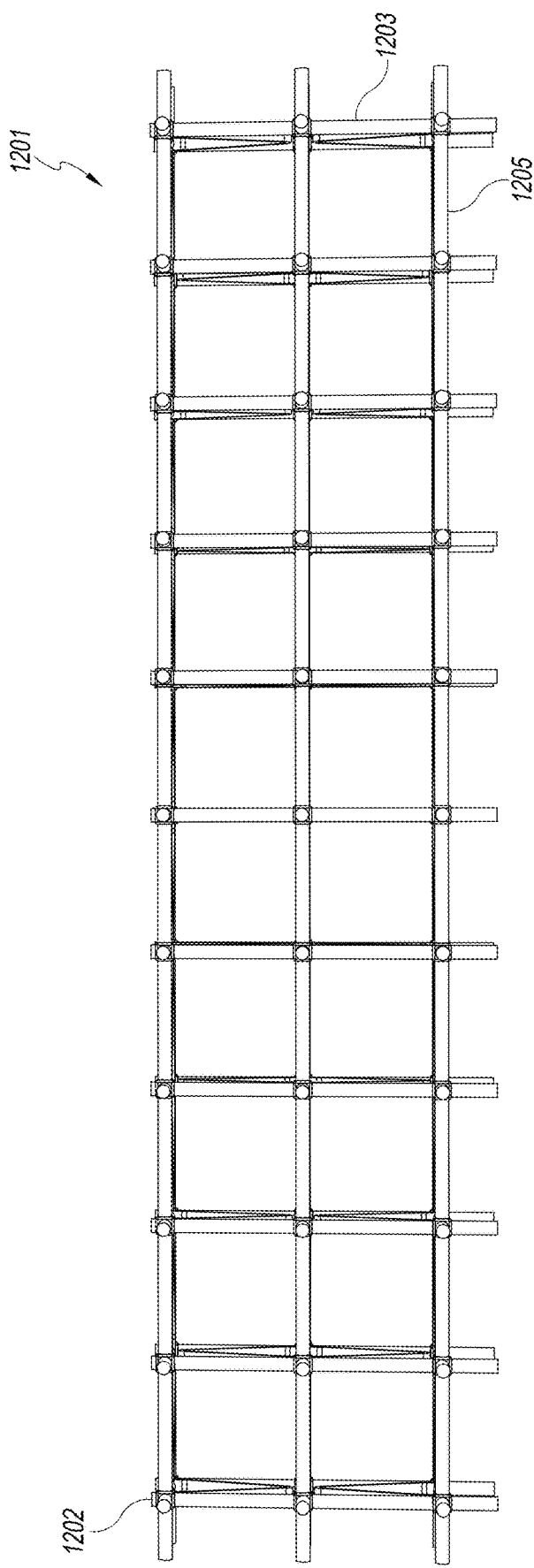
Figure 4D:
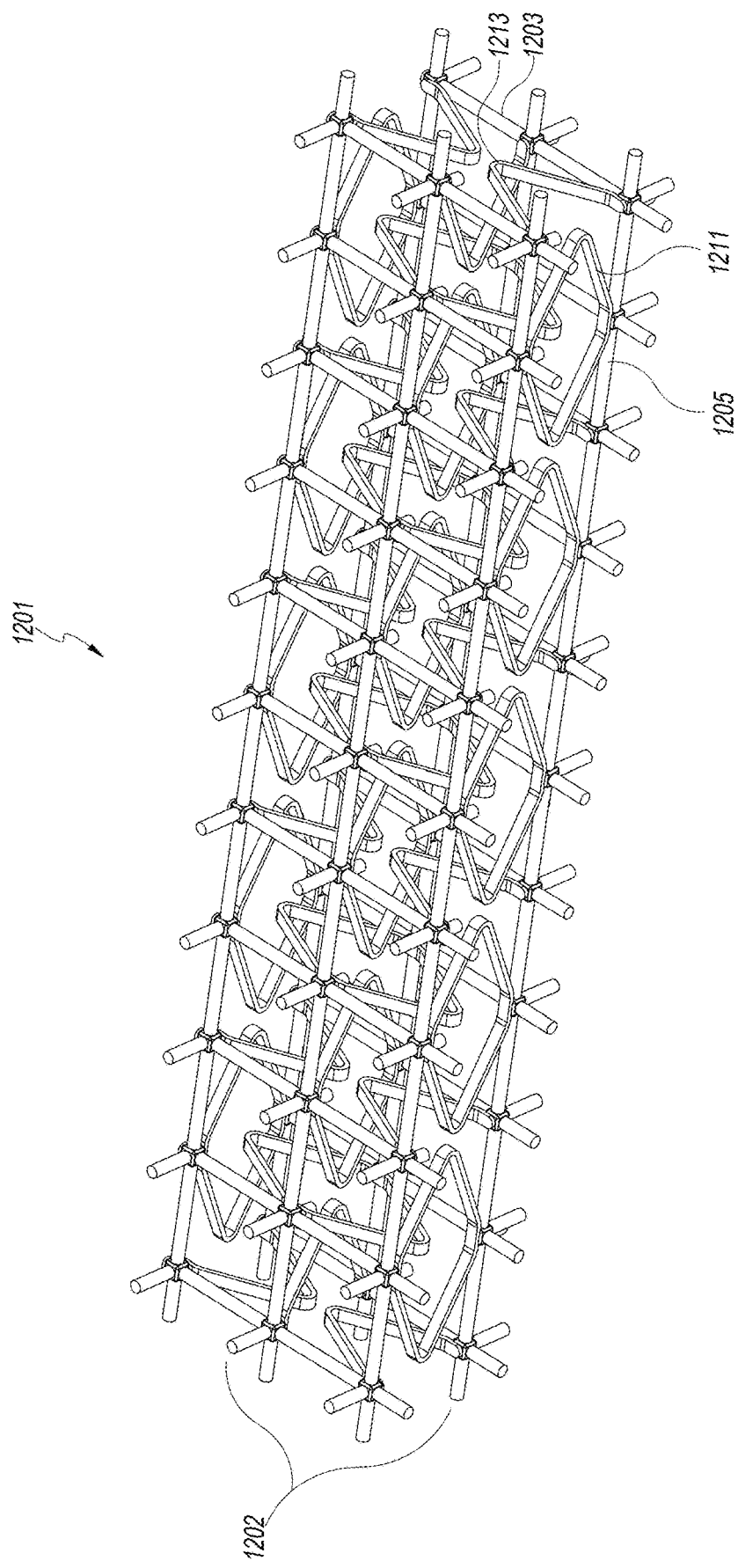
Figure 4E:
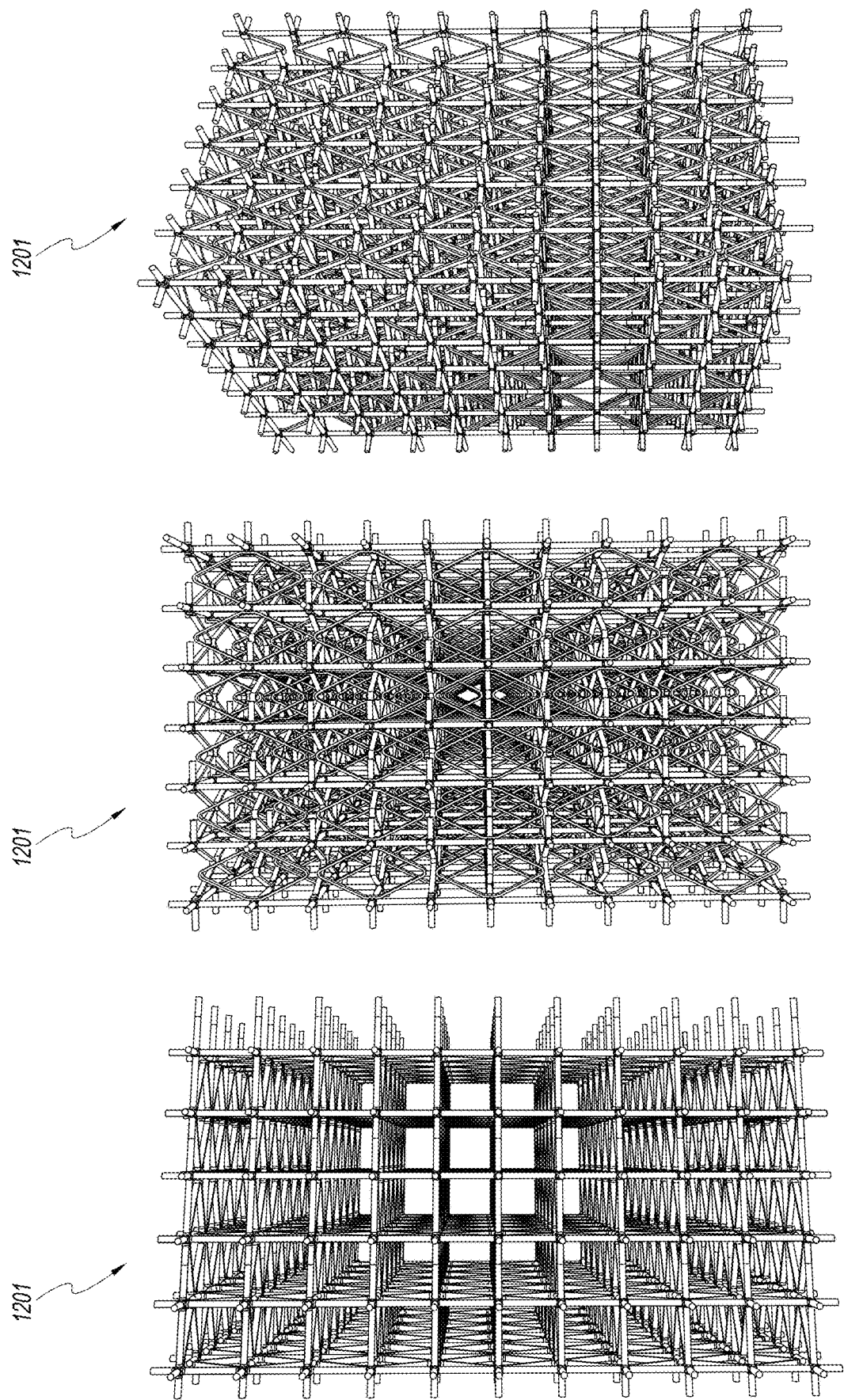

In a preferred embodiment, these spring elements 1711, 1713 may be V- or U-shaped. Each spring element may comprise two elongated portions that are bent relative to each other and form an obtuse angle (as shown in FIGS. 3A-3C), or an acute angle (as shown in FIG. 4A). Spring elements 1711 preferably run in a plane parallel to beam 1705, and may be attached to either the beam 1703 or 1705. Similarly, spring elements 1713 preferably run in a plane parallel to beam 1703, and may be attached to either the beam 1703 or 1705. For both spring elements 1711, 1713, a preferred attachment point is at the junction between beams 1703 and 1705. Preferably, the spring elements 1711 are arranged in a first plurality of parallel planes, which run parallel to the direction of the beam 1705, and the spring elements 1713 are arranged in a second plurality of parallel planes which run parallel to the direction of the beam 1703. The spring elements 1711 located between two adjacent planar support structures 1702 may be arranged in a repeating pattern within the first plurality of parallel planes. The spring elements 1713 located between two adjacent planar support structures 1702 may be arranged in a repeating pattern within the second plurality of parallel planes. In one embodiment as illustrated in FIGS. 3A and 3C, adjacent spring elements 1711 and 1713 form a diamond shape. However, different patterns, arrangements and numbers of spring elements may be employed. In some embodiments, the spring elements 1711, 1713 may have a spring constant ranging between 10 and 30 N/m, more preferably between 15 and 25 N/m, and even more preferably 23 N/m. In some preferred embodiments, the force required to compress seven spring elements by 15mm equals 250g. In some embodiments, the force required to compress the same seven springs by the same distance ranges between 180 and 230g. In some embodiments, there are a total of four spring elements 1711, 1713 per 10 cm$^3$. Of course, one will recognize that factors such as the spring constants and/or number of springs may be tailored to the particular tissue type and wound closure desired, and that higher or lower spring constants or numbers of springs may be used.

Standoffs 1707 and 1708 may be provided at the edges or along the outer faces of the structure 1701, and which may be configured to contact the wound. In some embodiments, the standoffs 1707, 1708 may be extensions of the beams 1703, 1705, or may be provided separately. In some embodiments, the standoffs 1707, 1708 may be provided with hook or anchor elements configured to anchor tissue placed into contact with them. Additionally or alternatively, hook or anchor elements attached to the structure 1701 may be provided separately from or instead of the standoffs 1707, 1708. Such hook or anchor elements may be useful to enhance fascial tissue closure by ensuring that different tissue layers (e.g., muscle tissue, fat tissue) are closed at approximately the same rate. Preferably, the hook or anchor elements are configured so as to be have a release force (once engaged into tissue) that causes no or minimal pain to the patient while permitting sufficient pulling force to be applied thereto so as to allow for wound closure. In some embodiments, different anchor elements may be used to engage different types of tissue. For example, the release force to release an anchor element from subcutaneous fatty tissue may be lower than the force needed to release another anchor element from muscle tissue.

Further, the anchor elements, by virtue of their attachment to the surrounding tissue, may be useful in helping prevent a drape or other materials placed over the wound from going into the edges between the skin and the structure 1701. In some embodiments, the anchor elements may be broken off, which may aid in sizing the device as described below so as to fit into a wound. Additionally, all or part of the structure 1701 may be covered or embedded within a porous wound filler material. In such configurations, the standoffs 1707, 1708 may be used to provide additional securement to any such wound filler material.

In use, the stabilizing structure 1701 may be cut to size as appropriate to fit the wound. Optionally, a porous material such as foam may be placed around the perimeter of the structure 1701, and may be secured using one or more of the standoffs 1707, 1708. The porous material may also surround or envelop the entire device, for example by using a foam enclosure. Foam may also be added into the entire structure 1701, including its interior portions, and if this is done during manufacturing, the structure 1701 is preferably capable of withstanding a reticulation process. Such a device comprising foam will have composite tensile structures that are to be considered when inserting the device into the wound. When inserting the device into the wound, the stabilizing structure 1701 is preferably oriented such that the planar support structures 1702 are aligned such that they are perpendicular or substantially perpendicular to the general direction of wound closure, or perpendicular or substantially perpendicular to the patient's skin. Optionally, an organ protection layer, which may comprise a polymer sheet or other flexible material, optionally provided with apertures, may be placed into contact with at least the bottom portion of the wound. A drape may be sealed over the skin surrounding the wound, and a source of negative pressure may be placed into fluid communication with the wound so as to effectuate wound closure. Further details regarding the drape, the application of negative pressure, and other apparatuses and methods that may be used with these stabilizing structures, are described below with respect to other embodiments.

FIGS. 4A-E illustrate different views and photographs of embodiments of a wound closure device comprising a stabilizing structure 1201. This embodiment is similar in some respects and in function to the embodiment described above in relation to FIGS. 3A-D, and share similar elements. The device comprises beams 1203 and 1205 that form a planar support structure 1202 separated by spring elements 1211 and 1213. Standoffs 1207 and 1208 may also be provided. Here, however, the spring elements 1211 and 1213 are thicker and have portions that are bent relative to each other at acute angles. Additionally, compared to FIGS. 3A-D, the structure 1201 has a greater volume and greater number of spring elements 1211, 1213. As illustrated best in FIG. 4D, the spring elements 1211 form a repeating diamond pattern within a first plurality of parallel planes, with the diamond location being staggered between adjacent parallel planes. A corresponding pattern is employed for spring elements 1213 with a second plurality of parallel planes. A similar configuration may be seen in FIGS. 3A-3D.

EXAMPLE 2

Figures 5A, 5B:
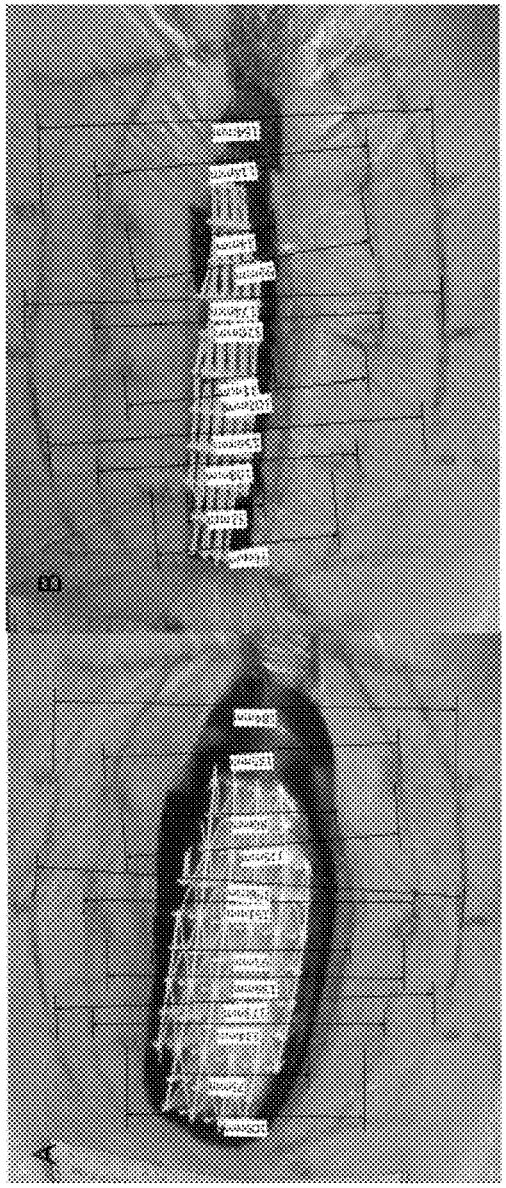
FIGS. 5A-B, 6A-B, and 7A-B are before and after photographs of experiments performed to determine the efficacy of certain embodiments of wound closure devices.

By means of a non-limiting example, an experiment was conducted to determine the effectiveness of an embodiment of the wound closure devices described above, with testing being performed on a cadaveric model. FIGS. 5A-B illustrate the results where a structure with foam, similar to the embodiments of FIGS. 4A-E, was placed into a wound. The perimeter of the structure was wrapped in a layer of foam.

Wound area measurements before and after application of negative pressure indicated that the wound area decreased by 64%, from 152mm$^2$ to 55mm$^2$.

EXAMPLE 3

Figures 6A, 6B:
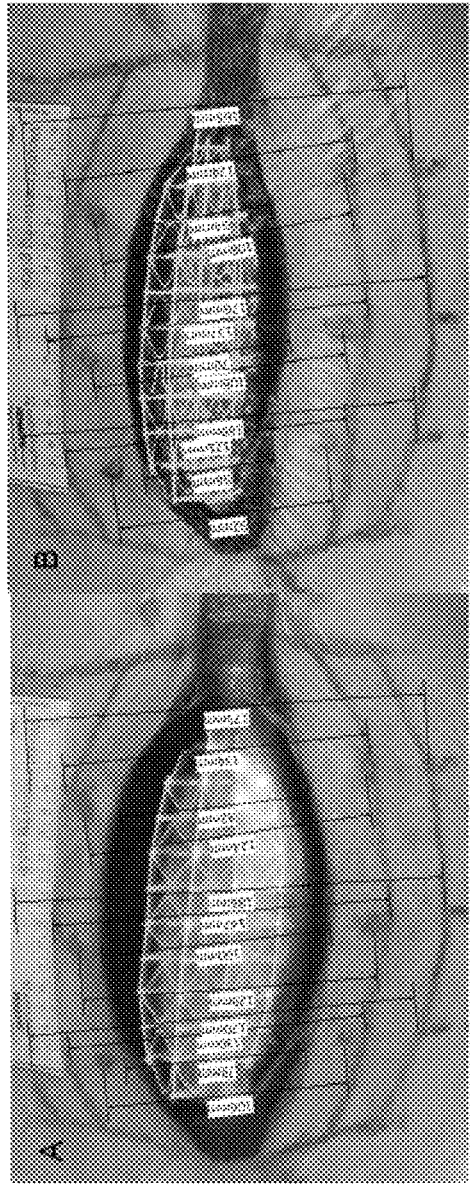

This non-limiting experiment tested a structure wrapped in foam and prestretched along its width and held in place by bendable plastic strips, but otherwise similar to the embodiments of FIGS. 4A-E. FIGS. 6A-B illustrate the wound size before and after application of negative pressure. Here, the wound area measured 154mm² before the application of negative pressure, and 101mm² afterwards, for a 34% reduction in wound area.

EXAMPLE 4

Figures 7A, 7B:
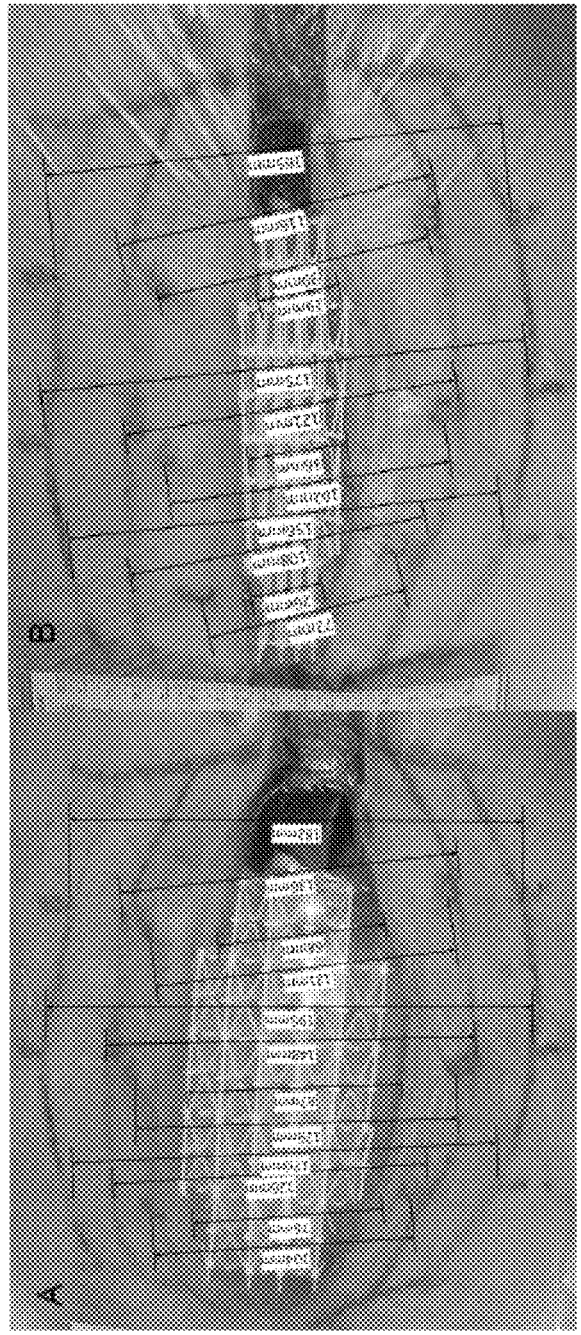

FIGS. 7A-B illustrate the non-limiting results of an experiment where a structure similar to the embodiment of FIGS. 4A-E was placed into a wound without any foam wrapping. The experiment was performed similarly to the other examples described in this section or elsewhere in this specification, and here, the wound area measured 126mm² before application of negative pressure, and 53mm² afterwards, for a 58% reduction in wound area.

Stabilizing Structures and Wound Closure Devices of FIGS. 8A-16B, 19-20B and 32

Figure 8A:
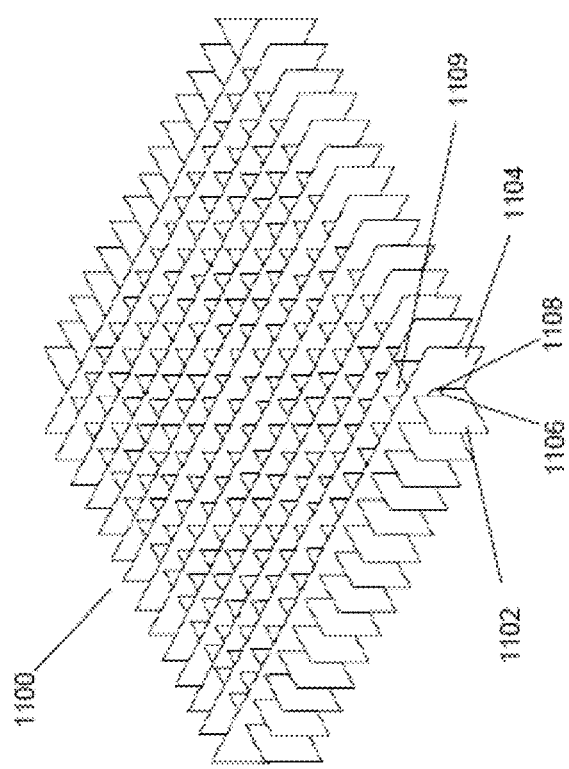
FIGS. 8A-E illustrate additional embodiments of a wound closure device comprising a stabilizing structure.

FIGS. 8A-E illustrate additional embodiments of a wound closure device comprising a stabilizing structure 1100. FIG. 8A shows a perspective view of an embodiment of a stabilizing structure 1100. Here, the stabilizing structure 1100 is preferably comprised of two or more interlocking strips (described below in more detail with relation to FIG. 8B) that extend in directions approximately perpendicular to each other when in a substantially uncollapsed configuration. The stabilizing structure is preferably configured to collapse in one direction or along a first plane while remaining relatively rigid and collapse-resistant in a direction perpendicular to the first direction or plane.

Figure 8B:
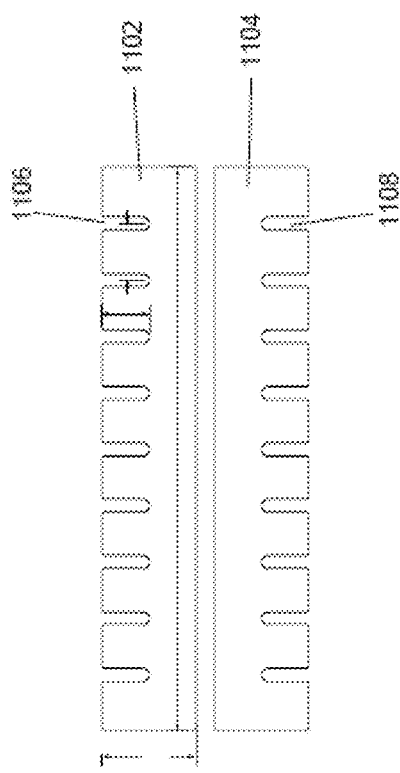

FIG. 8B illustrates side views of a bottom strip 1102 and a top strip 1104 that may be used to make a stabilizing structure 1100 such as the embodiment illustrated in FIG. 8A. Each of the top and bottom strips 1102, 1104 are preferably configured to movably interlock with each other, for example via matching notches 1106 and 1108. One or more notches 1106 may be provided on a top side of bottom strip 1102, and similarly, one or more notches 1108 may be provided on a bottom side of top strip 1104. When assembled together, the one or more top and bottom strips 1102, 1104 may be positioned so that the notches 1106, 1108 line up. Preferably, the top and bottom strips 1102, 1104 are positioned at substantially perpendicular angles to each other, thereby permitting the notches 1106, 1108 to slot together so as to create a movably interlocking structure. Typically, the number of notches 1106 on the bottom strip 1102 will equal the number of top strips 1108 that will form the stabilizing structure 1100, and vice versa. The notches 1106, 1108 are preferably shaped with a width that permits the strips 1102, 1104 to move from approximately perpendicular angles to angles far from perpendicular (i.e., close to parallel) to each other, thus permitting the stabilizing structure 1100 to articulate and collapse along one direction or plane.

In a preferred embodiment, the strips 1102, 1104 are constructed from a rigid or semi-rigid material, such as a polymer. Examples of suitable polymers include polyethylene, polypropylene, polyurethane, polyvinyl chloride, polystyrene, polyacrylate, polymethyl methacrylate, PEEK, silicone, polyurethane, polycarbonate, composites and laminates, or combinations thereof. In some embodiments, the material may include compressed or "felted" reticulated foam. Of course, other materials, such as cardboard or metal may be used. Preferably, the materials may be at least partially porous so as to permit fluid to flow through the material. Further, such properties may aid in distributing negative pressure through the device and to the wound, and may aid in removing fluid from the wound dressing. Such materials may include, for example, low density polypropylene, foamed material, or sintered material. The material used does not necessarily need to be strong along the length of the strips 1102, 1104, but should preferably be able to withstand pressure applied to a top or bottom edge. Preferably, the material is capable of withstanding the pressure from atmospheric pressure exerted on a drape when up to 200mmHg negative pressure is applied to the wound. In some embodiments, the material can withstand a force of 5 psi applied to a top or bottom edge.

In a preferred embodiment, each strip 1102, 1104 measures 180 mm long by 30mm high. The thickness of the strips 1102, 1104 may range, for example, between 1.50 to 2.40mm, although the thickness will be selected at least partly based on the ability of the material to withstand pressure being applied along its edge. The thickness is preferably balanced between keeping the material thin enough to minimize the compressed thickness of the stabilizing structure 1000, while keeping the material thick enough to avoid causing excessive localized pressure upon the wound bed. The notches 1106, 1108 may measure approximately 15mm in height, and may be spaced apart from other notches by 18 mm. Although the notches 1106, 1108 are shown with rounded bottoms, these may also be cut with squared-off or triangular bottoms. In some embodiments, the rounded edges reduce stresses onto the strips 1102, 1104 so as to prevent fracture and crack propagation, and may also increase the springiness of the stabilizing structure 1100.

It will be understood that the interlocking strips 1102, 1104 may not necessarily need to be joined together via notches. Hinges or other devices could be used to provide the articulation or movable interlocking ability illustrated above. In some embodiments, hinges may be constructed from thinner areas of the same material used to construct the strips 1102, 1104, and are configured to flex or bend to a predetermined position. The stabilizing structure 1100 could also be molded as a single piece such that the interlocking strips 1102, 1104 form a single unit.

Returning to FIG. 8A, the perspective view illustrates an example of a stabilizing structure 1100 configuration with multiple interlocking top and bottom strips 1102, 1104 movably interlocked via multiple notches 1106, 1108. The intersections of two top strips 1102 and two bottom strips 1104 form a quadrilateral-shaped boundary space 1109. When the top and bottom strips 1102, 1104 are at perpendicular angles to each other, the space 1109 will be square or rectangular. However, as the stabilizing structure 1100 collapses along a direction or plane, the space 1109 will become more diamond- or parallelogram-shaped. The stabilizing structure 1100 will preferably comprise multiple spaces 1109, which form cells defined by the walls of the top and bottom strips and with openings on top and bottom ends.

Figure 8C:
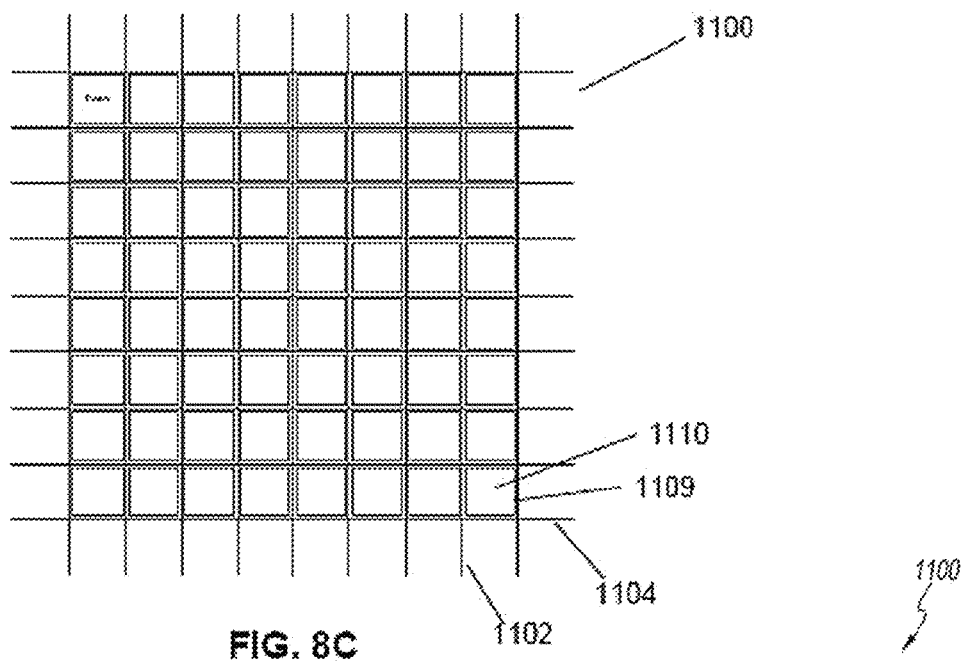

FIG. 8C illustrates a top view of an embodiment of the stabilizing structure 1100 where a porous wound filler material 1110 has been placed into the quadrilateral-shaped boundary space 1109. Here, the porous wound filler material 1110 used is preferably soft and conformable so as to be able to adapt to the any change in the configuration of the stabilizing structure 1100 if it collapses. Preferably, the porous wound filler material is a foam, such as a polyurethane foam. This porous wound filler material may be cast around the stabilizing structure 1100 so as to completely encapsulate it. When used, the resulting stabilizing structure 1100 may be cut to size so as to fit into a wound. Such porous wound filler material 1110 may be used to aid in the fluid transmission or wicking of fluid from within a wound, and may also, when in contact with the wound (e.g., when used in negative pressure wound therapy), aid in the healing of the wound.

Figure 8D:
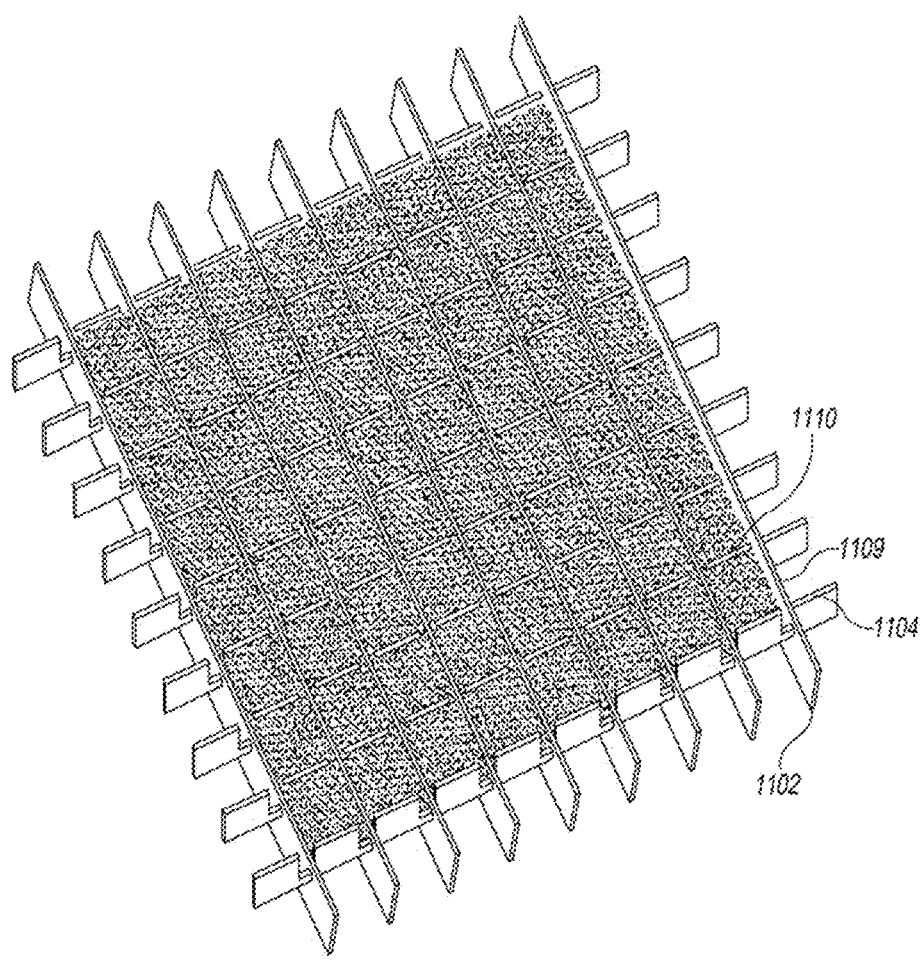

FIG. 8D illustrates a perspective photograph of an embodiment of the stabilizing structure 1100 with a porous wound filler material 1110 inserted into the spaces 1109. In some embodiments, additional porous wound filler material may also be used to encapsulate or surround the structure 1100. For example, a sock or wrap may be fitted around the structure 1100, and may for example be constructed from foam or gauze. When inserted into a wound, the stabilizing structure 1100 may be preferably oriented so as to collapse in a direction generally parallel with the orientation of collagen and other fibrous tissue fibers in the body. This orientation is sometimes referred to as Langer's lines or Kraissl's lines, and closing a wound in a direction coinciding with (and preferably parallel to) these lines may heal faster and more easily than attempting to close a wound in a direction perpendicular or opposed to these lines. It will be appreciated that the other embodiments of stabilizing structures described in this specification may also be oriented in the same manner with respect to Langer's lines or Kraissl's lines, or other landmarks.

Advantageously for some types of wounds, the stabilizing structure of FIG. 8A may elongate in a direction perpendicular to the primary direction of closure, but still within the horizontal plane. Such elongation can be beneficial to wound healing as the physiology of the wound may dictate that it should lengthen as it closes.

In use, the stabilizing structure 1100 may be placed into a wound such that the upward facing portion of the structure 1100 is substantially rigid and resists collapse in the vertical direction once negative pressure is applied to the wound (e.g., once covered by a drape as described previously). A porous material such as foam may be placed around, into, and/or so as to surround or encapsulate the stabilizing structure 1100. In some embodiments, an organ protection layer as described previously may be placed into contact with at least the bottom portion of the wound. As negative pressure is applied, the structure 1100 will then preferably collapse in the plane perpendicular to the vertical direction, aiding in wound closure. Due to the relative incompressibility of the vertical dimension of the device, the pressure on the drape transmitted from the greater atmospheric pressure onto the wound will reduce the pressure applied to the stabilizing structure 1100 onto the wound margins in comparison to existing prior art devices (such as those illustrated in FIGS. 2A-B). Optionally, in this and other embodiments described in this section or elsewhere in this specification, negative pressure may be applied so as to increase transmission of negative pressure to the sides of the wound rather than the bottom portions thereof. This may be accomplished, for example, by providing an organ protection layer that at least partially shields the bottom of the wound from negative pressure. In a preferred embodiment, the sides of the wound would be provided with negative pressure of at least 100 mmHg, preferably 120mmHg, 140mmHg, 180mmHg, or 200mmHg, while the bottom of the wound would be provided with at most 120mmHg, more preferably 80mmHg, 40mmHg, 20mmHg, or 10mmHg.

Figure 8E:
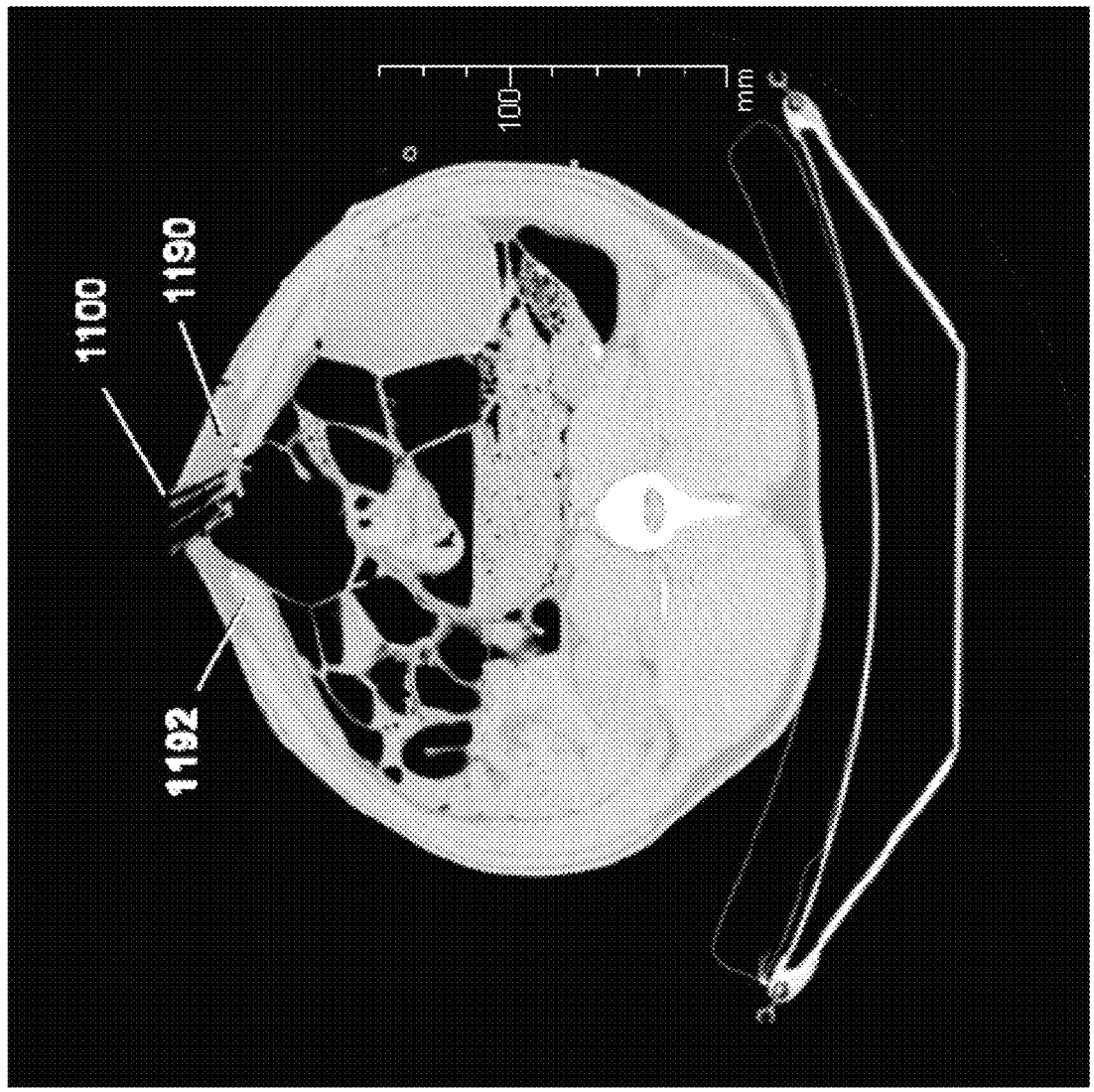

FIG. 8E illustrates a CT image of an embodiment of a stabilizing structure 1100 described in FIGS. 8A-D inserted into an abdominal wound. The tissue fascia layers are also visible, with a subcutaneous fat layer 1190 above a layer of muscle tissue 1192. With the application of negative pressure (as illustrated), improved fascial reapproximation and wound closure may be observed. In particular, the muscle tissue layers 1192 on opposite sides of the wound have been moved much closer together, while remaining attached to the other fascial layers. In measurements, the width of the wound along the view illustrated reduced from approximately 82mm to 28 mm, a reduction of 65%.

Figure 9A:
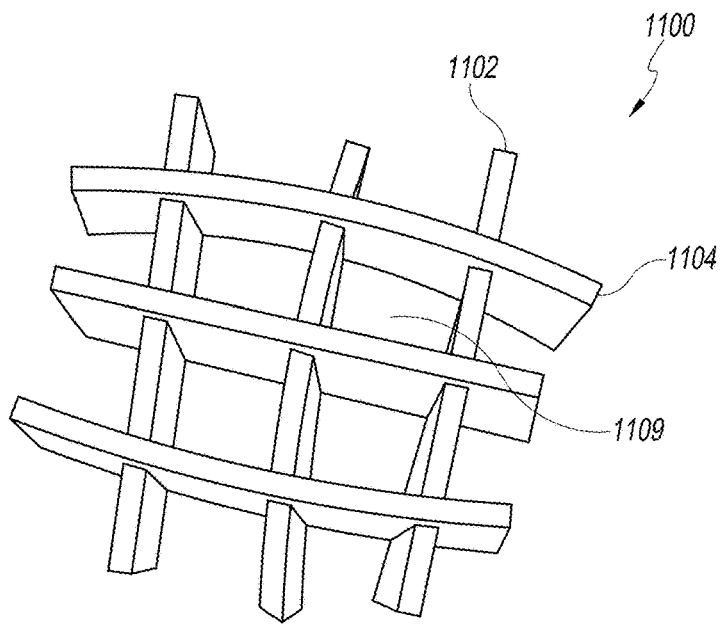
FIGS. 9A-C illustrate an embodiment of a stabilizing structure manufactured from felted foam.
Figure 9B:
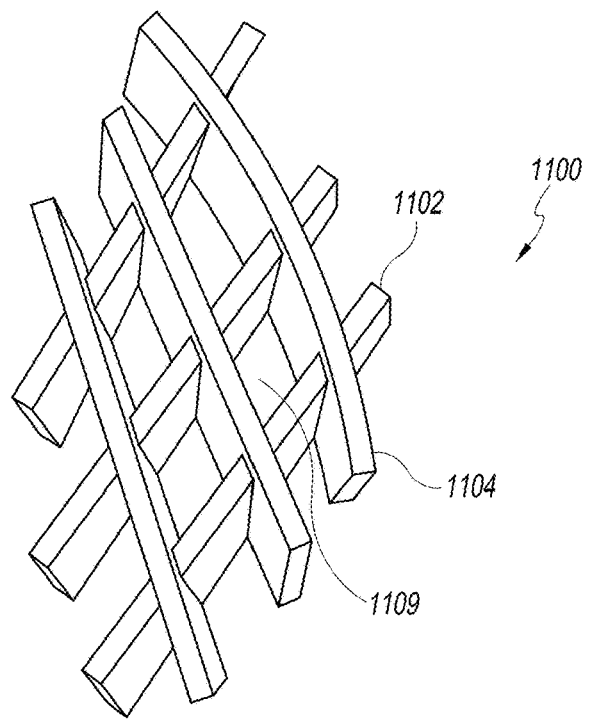
Figure 9C:
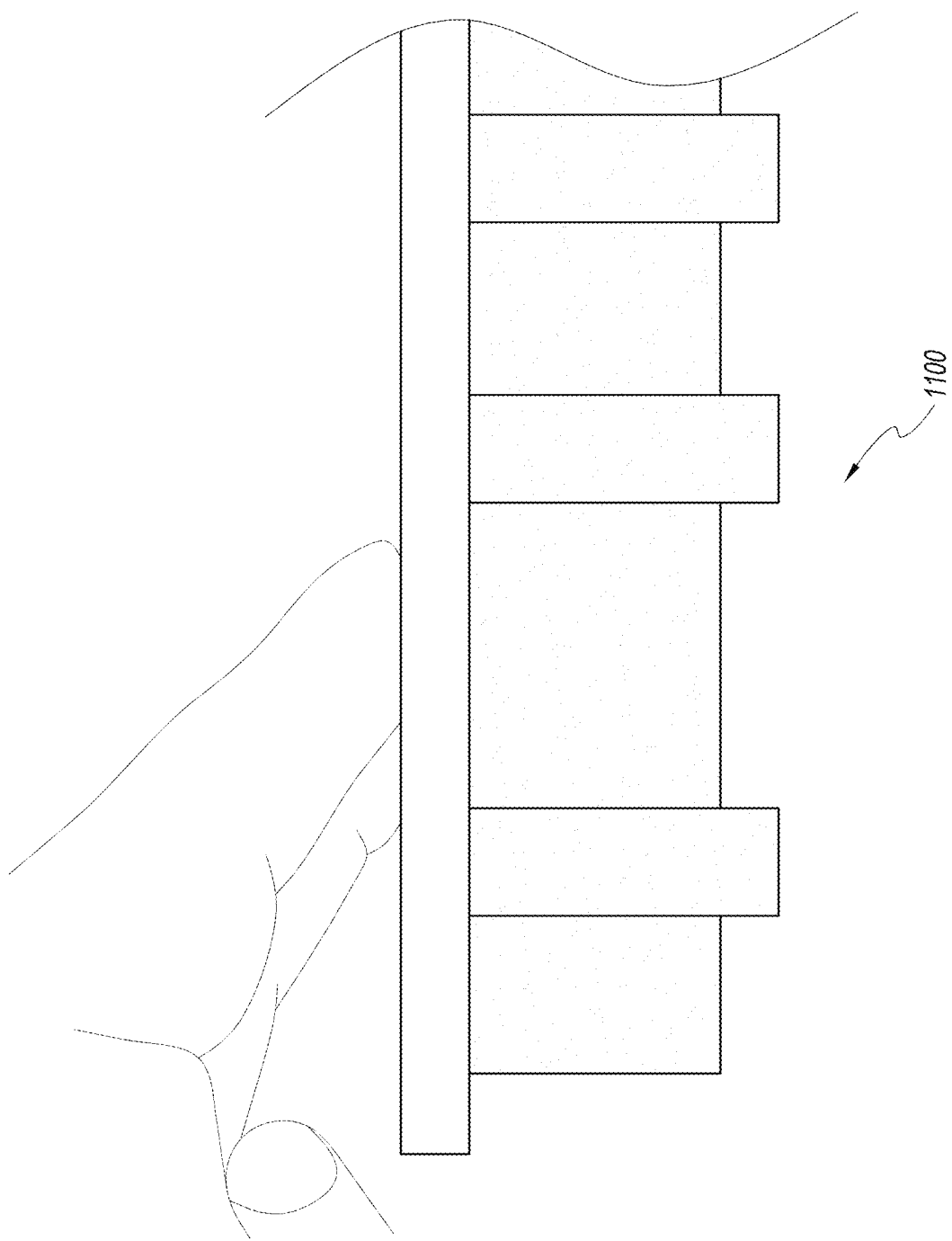

FIGS. 9A-C illustrate an embodiment of a wound closure device comprising a stabilizing structure 1100 similar to that described above in relation to FIGS. 8A-E. Here, the stabilizing structure 1100 is constructed from interlocking strips constructed from felted foam. The physical relationship between and the mechanism for the interlocking top and bottom strips 1102 and 1104 are substantially similar to what was discussed previously above, and will not be repeated here. Felted foam, however, is foam (e.g., polyurethane foam) that has been heated and compressed. After this procedure, the foam will be stiffer and less compressible, while still remaining porous. Such a material may be advantageously used in a stabilizing structure 1100 used for a wound closure device, as the material may be compressible in a plane defined by the top and bottom strips 1102, 1104, as shown in FIG. 9B. However, the material is substantially rigid in the vertical direction, as illustrated in FIG. 9C, where a weight has been placed over the foam without substantial buckling. Here, the foam can support approximately 6 kg of weight, and embodiments of the device have been measured to support at least 3 psi of applied pressure without collapse. Further, while such material is substantially rigid, the porous nature of the material permits negative pressure to be transmitted to the wound and for wound exudate to be removed.

Figure 10A:
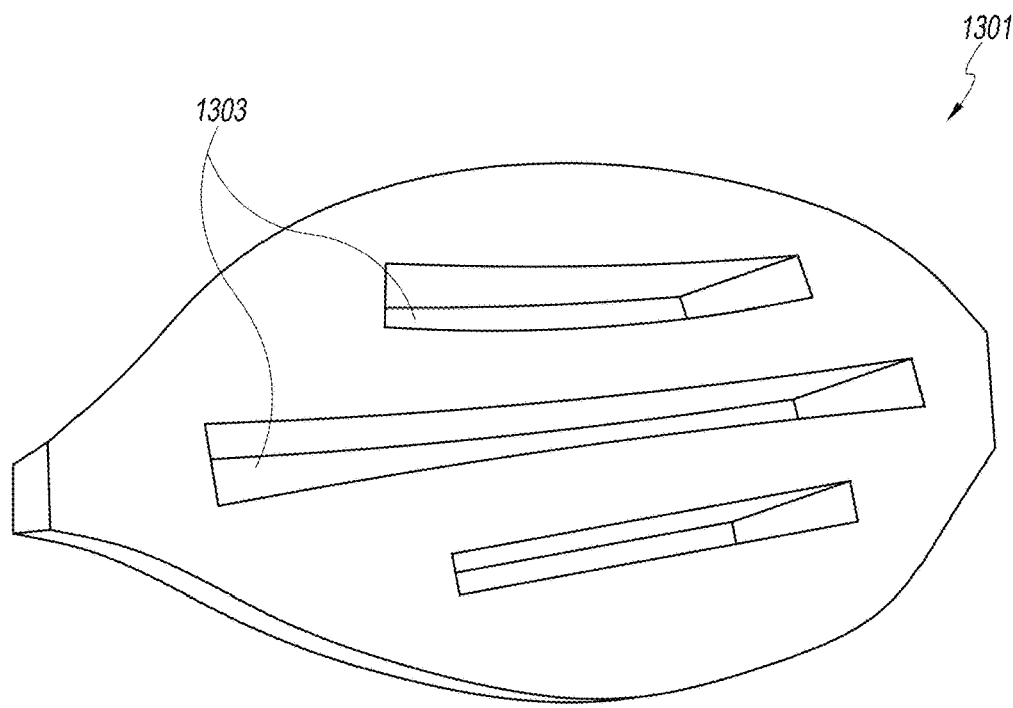
FIGS. 10A-B are photographs of further embodiments of wound closure devices comprising a porous wound filler material.
Figure 10B:
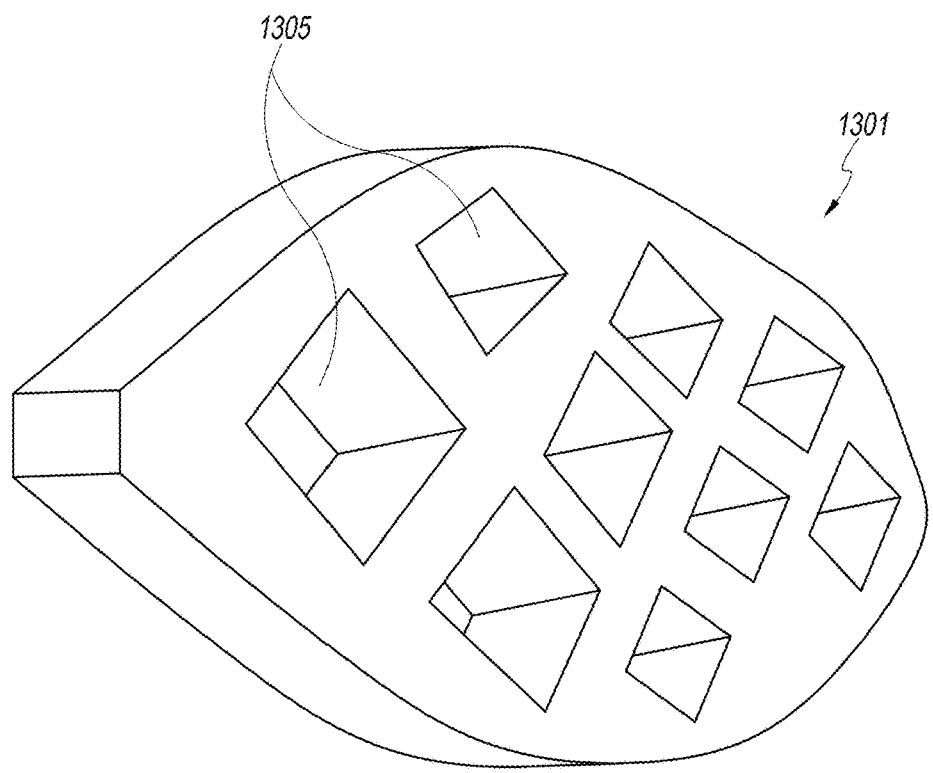

FIGS. 10A-B are photographs of further embodiments of wound closure devices. FIG. 10A illustrates an embodiment of a wound closure device 1301 that preferentially collapses along one direction. Here, the wound closure device 1301 comprises a porous wound filler material (e.g., foam) into which one or more slots 1303 have been cut. These slots 1303 preferably extend longitudinally through the thickness of the wound closure device 1301. Accordingly, the empty space will permit the wound closure device to preferentially collapse in a direction when a force is applied in a direction perpendicular to the slots 1303. Because the empty space is easier to compress than the remainder of the foam, the width and thickness of the foam will preferably not (or minimally) compress compared to the resulting compression perpendicular to the length of the wound closure device 1301.

As illustrated in FIG. 10B, the wound closure device 1301 may also be provided with holes or cells 1305 in other configurations, such as diamond-shaped holes forming a lattice. This configuration permits compression along the length and width of the wound closure device due to the compressible holes 1305, while the comparatively more rigid thickness of the foam resists compression to a greater extent.

In some embodiments, stabilizing structures similar to those illustrated above in FIGS. 8A-E may be constructed as a single unit, for example by molding, rather than from multiple parts. As with the previously-described embodiments, the stabilizing structures are configured to form an array of one or more cells defined by one or more walls and forming a plane, with each cell having a top and bottom end with an opening extending through the top and bottom ends in a direction perpendicular to the plane. In some embodiments, the stabilizing structures may have cells that are square, diamond, oblong, oval, lozenge, and/or parallelepiped, and non-limiting examples of the same are illustrated in FIGS. 11-20. While some embodiments may have cells that are all the same shape, the cells may also be tailored to be larger, smaller, or differently-shaped than other cells in the structure. The shape and size of the cells may be tailored to the desired characteristics (e.g., resilience and ease of collapse) for optimal wound closure and healing.

Construction of a single unit stabilizing structure may be advantageous in terms of ease of use and cost. For example, single unit stabilizing structures may be trimmed as necessary to fit into a wound site. The material used is preferably biocompatible, and even more preferably nonadherent to the wound site. Suitable materials are preferably chosen to be soft while remaining sufficiently strong to resist collapse in a vertical direction, and may include polymers, such as polyethylene, polypropylene, polyurethane, silicone (including siloxanes), ethyl vinyl acetate, and copolymers and blends thereof. The hardness of the material may affect the thickness of the resulting stabilizing structure, and may be selected based upon the desired thickness of the stabilizing structure components (including hinges and other joints thereof) and the ability of the stabilizing structure to resist collapse, e.g., due to the atmospheric pressure acting upon a drape placed over the stabilizing structure. Suitable durometer hardnesses of materials used range from about 30 shore to 120 shore (as measured on the Shore durometer type A scale), preferably from about 40 shore to 60 shore, and even more preferably about 42 shore. Generally, the material chosen is preferably softer (while still satisfactorily meeting other material requirements), as harder materials may provide reduced levels of closure as the hardness increases.

Figure 19:
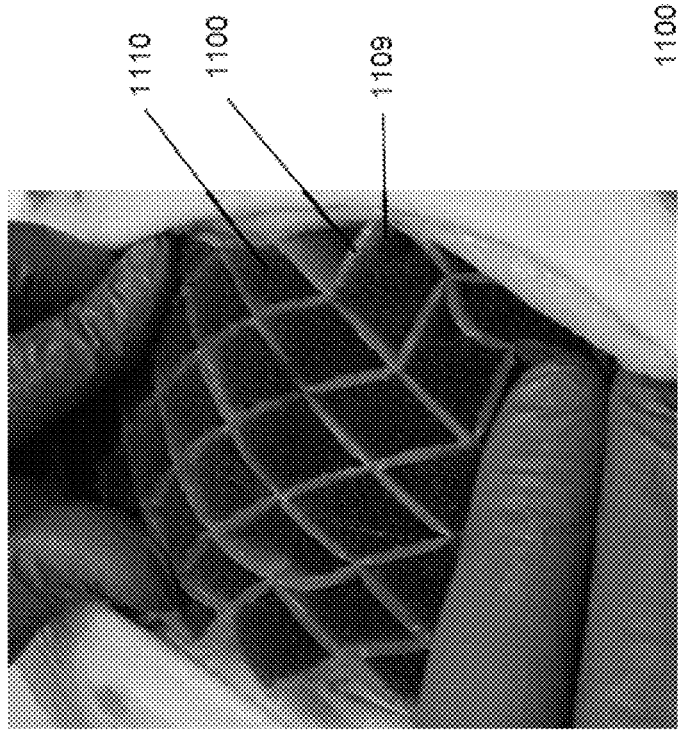
FIG. 19 is a photograph of an experiment performed to determine the efficacy of certain embodiments of wound closure devices.

FIG. 19 is a photograph of an embodiment of such device 1100 constructed as a single unit. The apertures 1109 are filled with a porous material 1110, which in some embodiments may comprise foam. Here, the device 1100 is inserted into a wound.

Figure 11A:
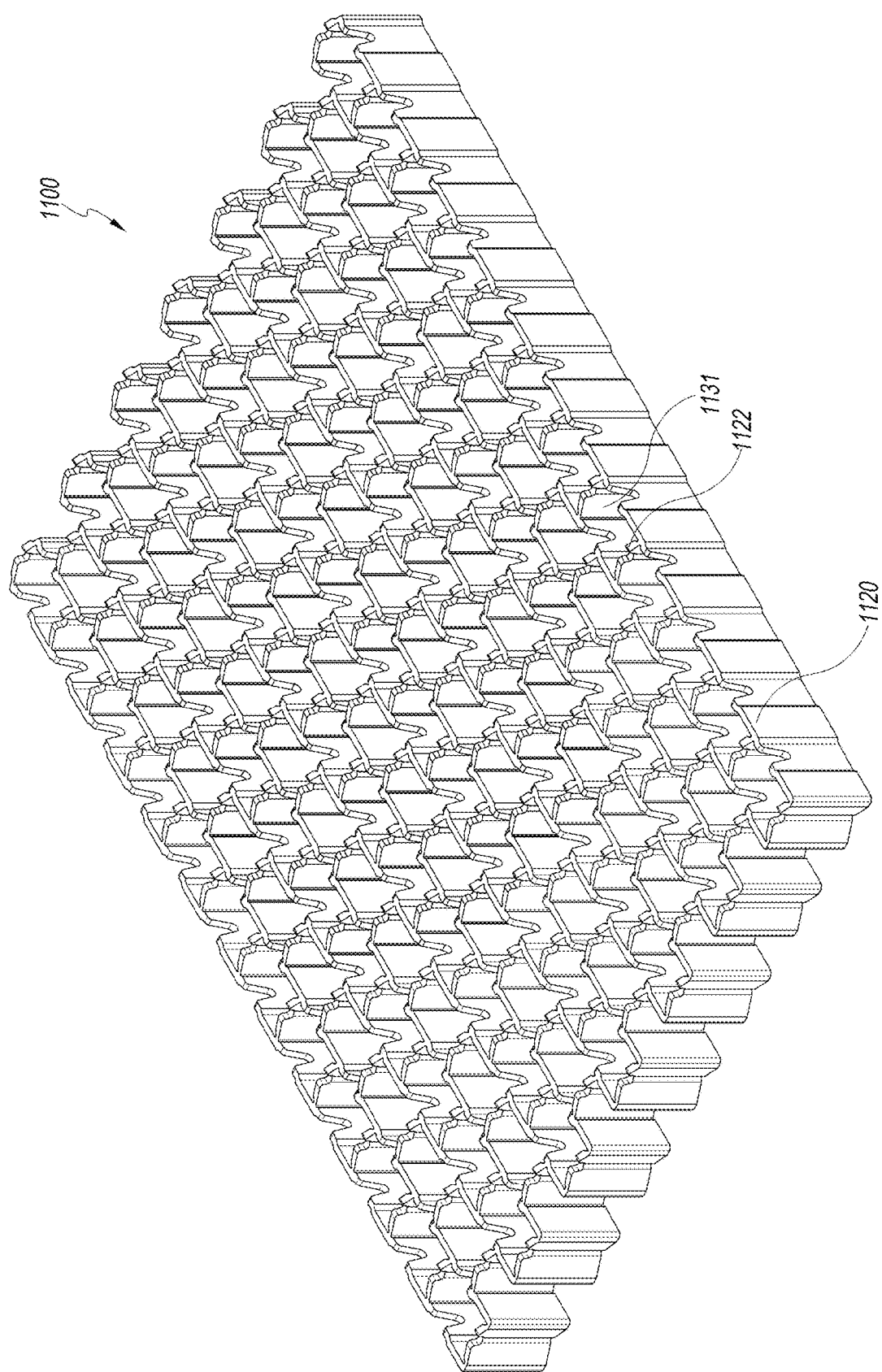
FIGS. 11A-B, 12, 13, 14, 15, and 16A-B illustrate additional embodiments of wound closure devices comprising a stabilizing structure.
Figure 11B:
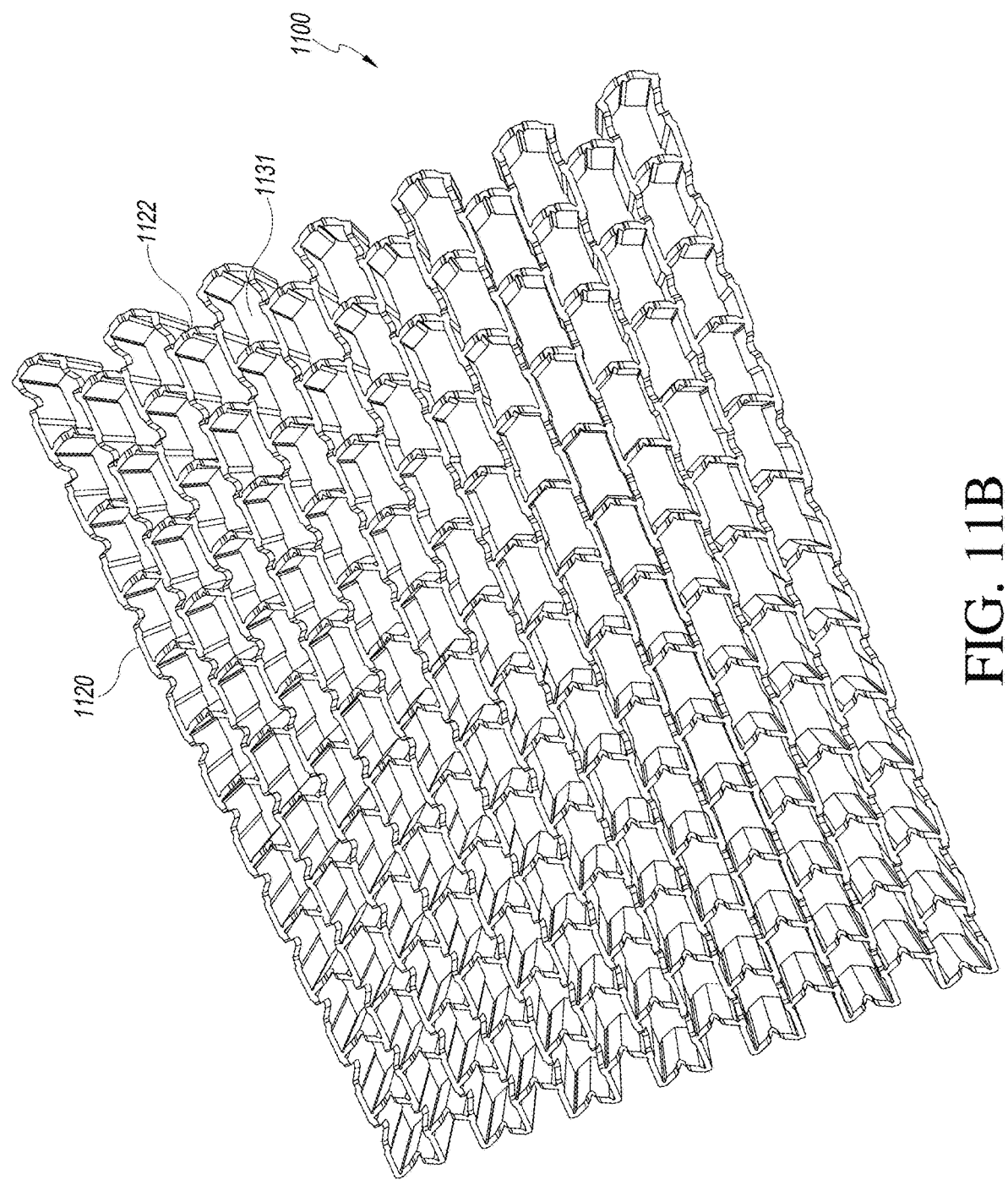

FIGS. 11A-B illustrate an embodiment of a stabilizing structure 1100 configured to preferentially collapse in only one horizontal direction while remaining substantially rigid or uncollapsed when force is applied in a vertical direction. Preferably, the stabilizing structure 1100 is constructed as a single unit as illustrated so as to form one or more cells 1131. Here, two or more longitudinal strips 1120 (which form the walls of the cells) may have relatively straight configurations, and are connected together via one or more collapsible cross strips 1122. It will be appreciated that in a single unit embodiment, the strips are merely portions of the same material that may have been formed together to form the entire single unit structure. The collapsible cross strips 1122 may be angled or indented so as to make them more likely to collapse in a direction generally parallel to their length. In this embodiment illustrated in this section or elsewhere in this specification, the collapsible cross strip 1122 is more likely to collapse at the apex of the angled portion and at the junctions to the longitudinal strips 1120 when a force is applied in a direction approximately parallel to the general length of the collapsible cross strip 1122. In some embodiments, the collapsible cross strip is configured to fold into a portion (which may be thinner) of the longitudinal cross strip 1120.

In some configurations, one or both of the longitudinal strips 1120 and/or collapsible cross strips 1122 may comprise one or more notches positioned along a length thereof. These notches promote fluid transfer across the structure, and aid in distributing negative pressure. In some embodiments, notches may be used in conjunction with a porous material so as to enhance fluid transfer. In relation to the longitudinal strips 1120, the collapsible cross strips 1122 may be positioned alternately along the length of the longitudinal strips 1120, as best illustrated in FIG. 11B, to form a configuration somewhat analogous to a "stretcher bond" used in bricklaying. Of course, other configurations are possible. Further, although this embodiment is illustrated as being formed as a single unit, those of skill in the art will recognize that this embodiment (and the others described below) may be constructed from multiple pieces joined or connected together.

Figure 20A:
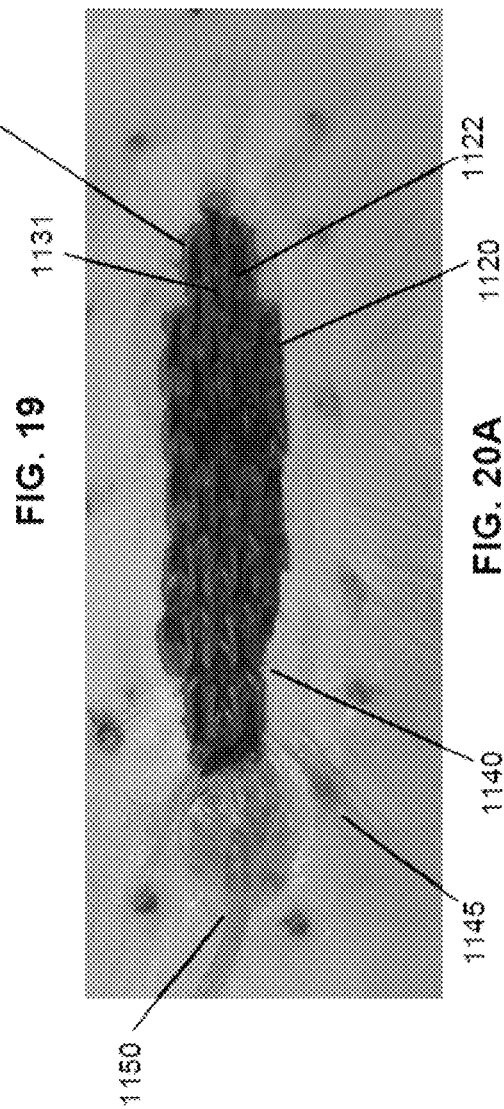
FIGS. 20A-B are photographs of experiments performed to determine the efficacy of certain embodiments of wound closure devices.
Figure 20B:
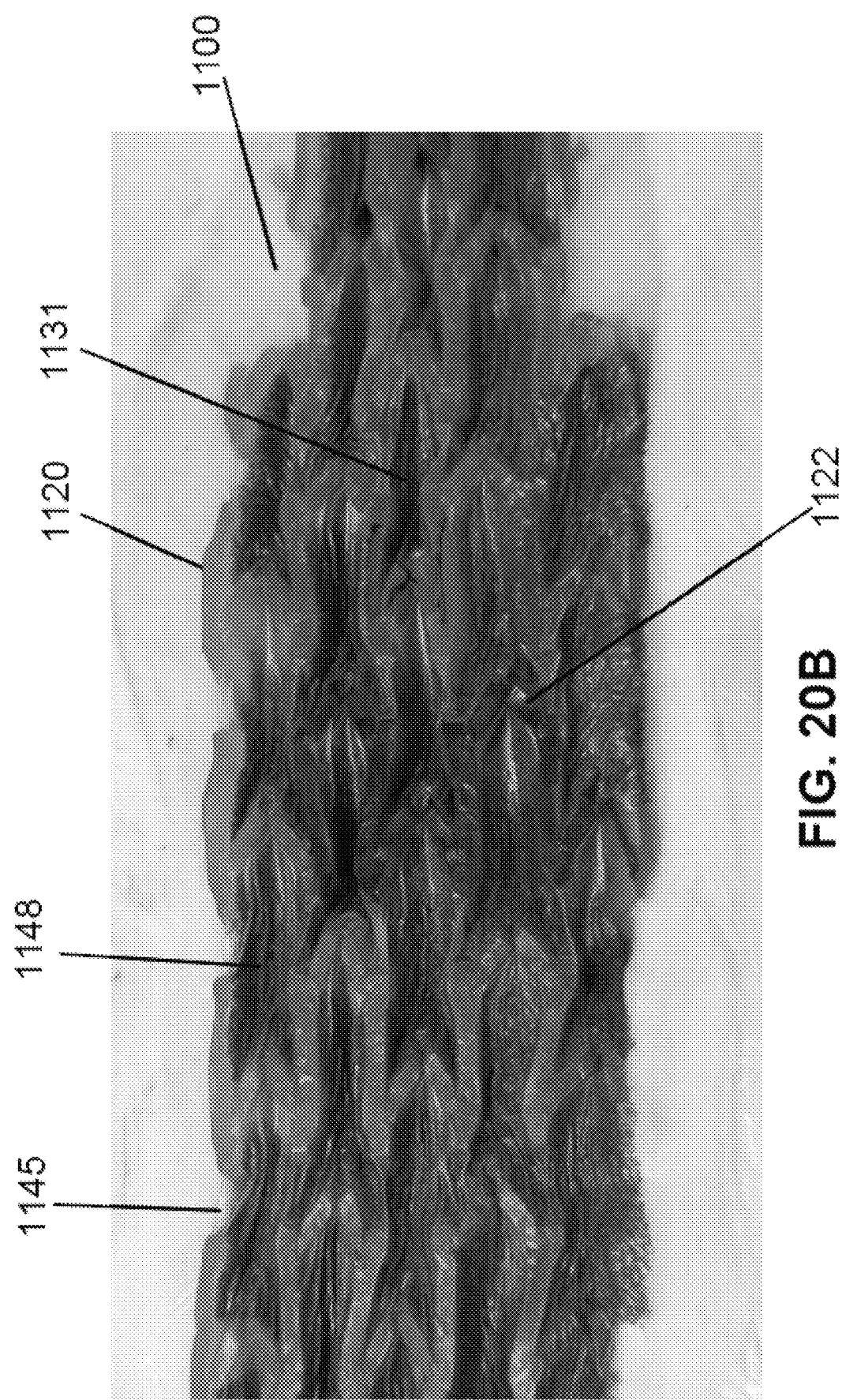

FIGS. 20A-B are photographs of an embodiment of a stabilizing structure 1100 similar to the one described above in relation to FIGS. 11A-B. Here, the structure 1100 is inserted into a wound 1140 and placed under a drape 1145. A source of negative pressure is connected via a fluidic connector 1150. FIG. 20B is a closeup view of the stabilizing structure 1100 photographed in FIG. 20A, which illustrates how the cells 1131 collapse upon the application of negative pressure while under the drape 1145. An optional porous wound filler 1148 is also illustrated.

Figure 12:
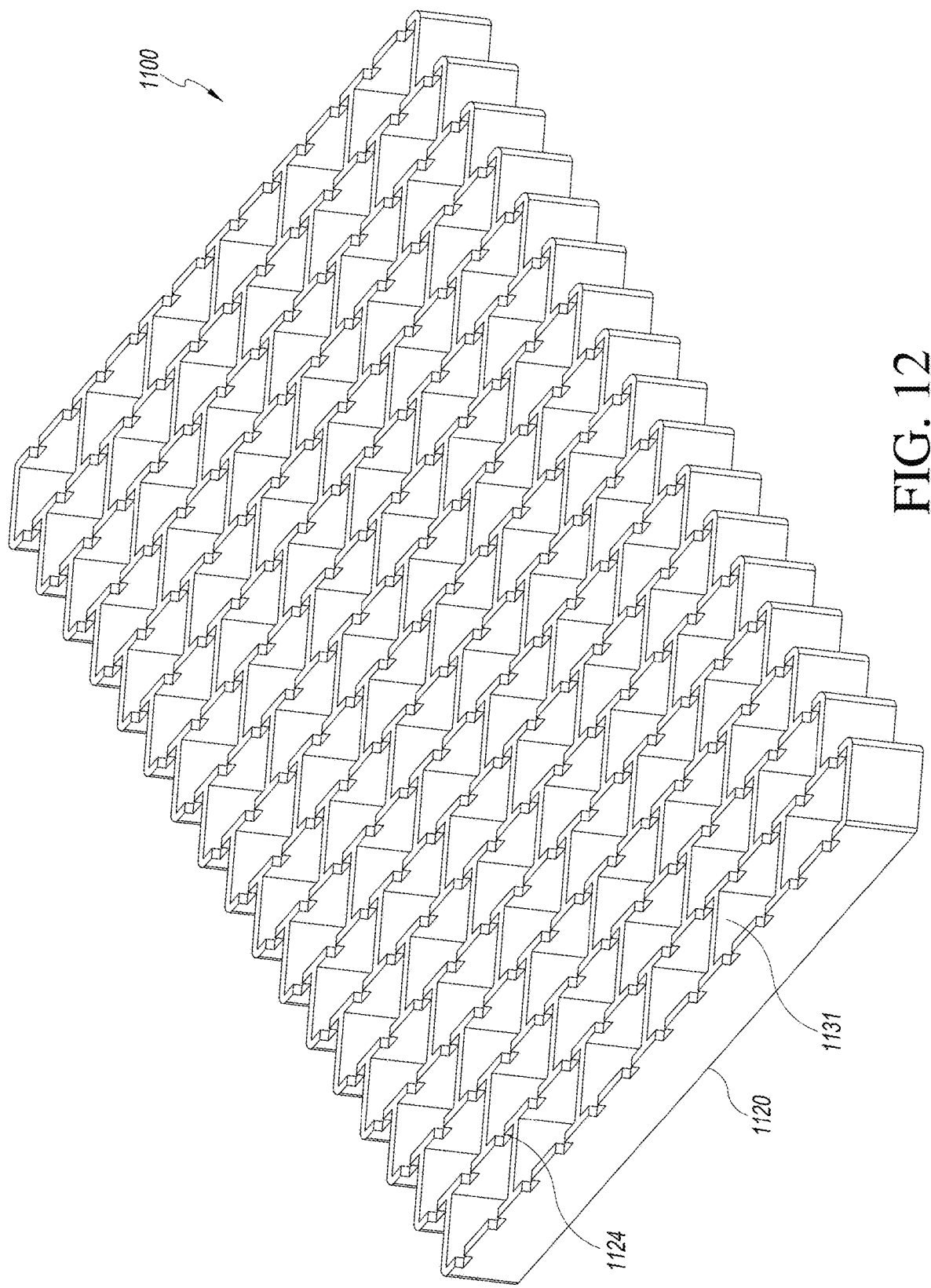

FIG. 12 illustrates another embodiment of a stabilizing structure 1100, here comprising two or more longitudinal strips 1120 attached to each other via one or more angled cross strips 1124 so as to form cells 1131. As with the embodiment illustrated in the preceding figure, the stabilizing structure 1100 is configured to collapse when pushed in a direction perpendicular to the length of the longitudinal strips 1120, while remaining substantially rigid or uncollapsed when force is applied in a vertical direction. The angled cross strips 1124 are preferably attached to the longitudinal strips 1120 so as to form a non-perpendicular angle so as to promote collapse of the stabilizing structure 1100 in the direction perpendicular to the length of the longitudinal strips 1120. As with FIGS. 8A-B, one or more notches may be formed on either or both of the longitudinal strips 1120 and/or angled cross strips 1124.

Figure 13:
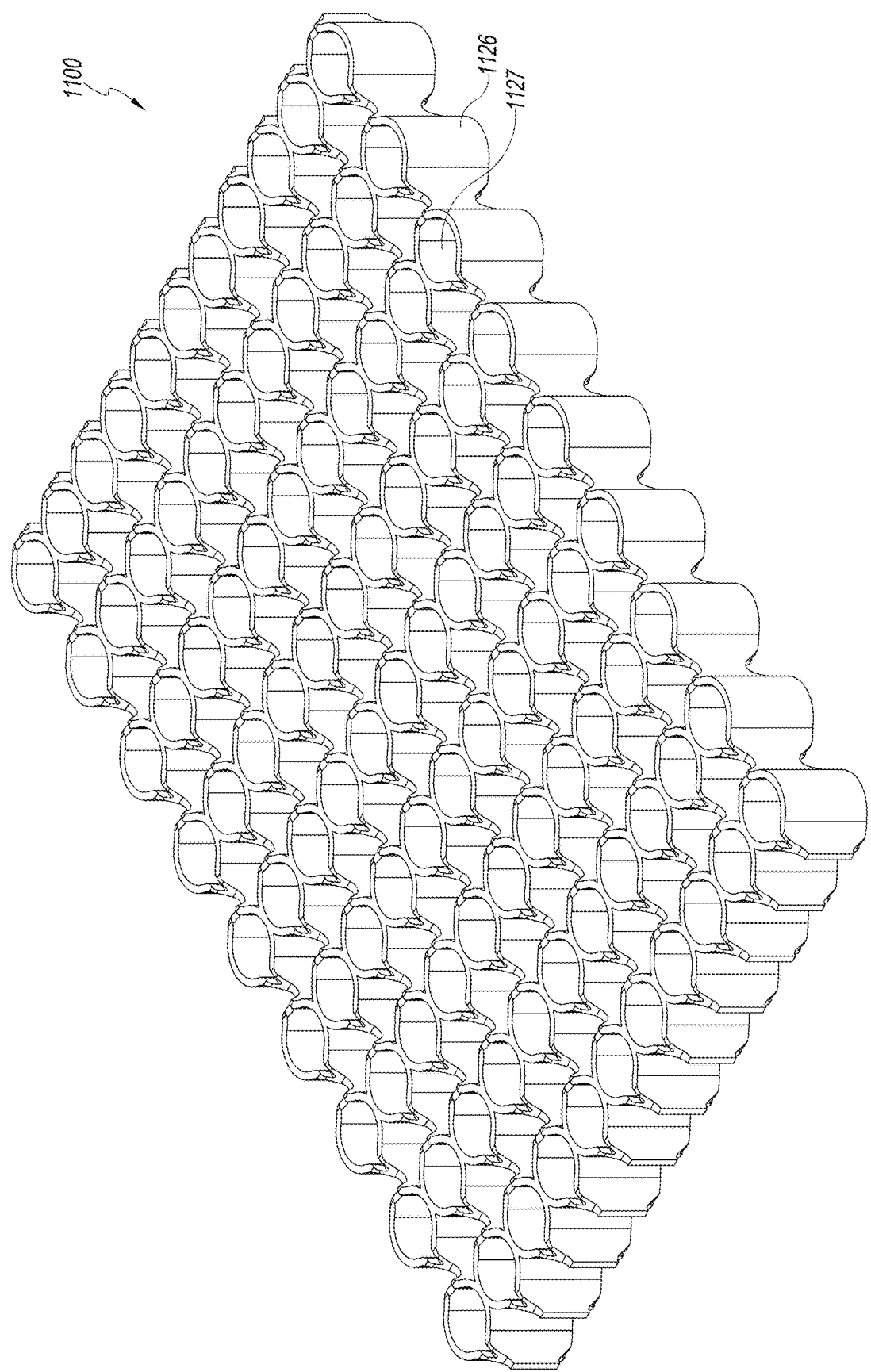

FIG. 13 illustrates a single unit stabilizing structure 1100 comprising one or more pairs of curved longitudinal strips 1126. Each individual longitudinal strip 1126 may be formed as a "wavy" strip (when seen from a vertical orientation) that, when joined face-to-face, form a one or more circular or ovoid cells 1127. As with the other stabilizing structures illustrated in this section or elsewhere in this specification, this structure 1100 is configured to preferably collapse along a horizontal plane or direction while remaining substantially rigid or uncollapsed when force is applied in a vertical direction. Although the structure 1100 is illustrated here as being formed from a single unit, the structure may be constructed from two or more curved longitudinal strips 1126 welded or attached together at the points shown. As with several other embodiments described in this section or elsewhere in this specification, one or more notches may be made onto the walls so as to aid in fluid transfer across and through the structure 1100.

Figure 14:
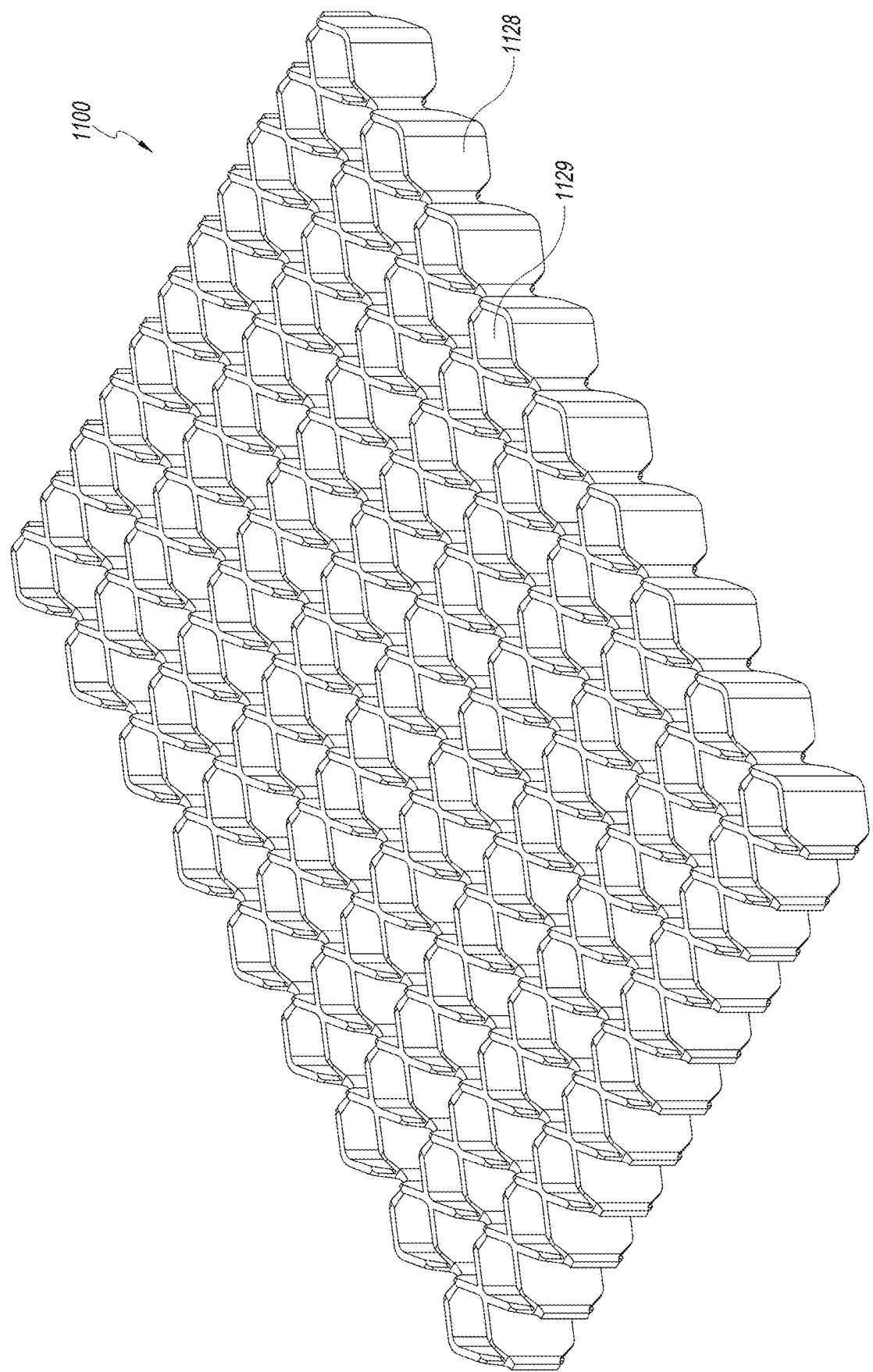

FIG. 14 illustrates a stabilizing structure 1100 similar to the one illustrated in FIG. 13. Here, however, zigzag longitudinal strips 1128 are joined to form diamond-shaped (rather than circular or ovoid) cells 1129. It will be of course appreciated that this embodiment may also be manufactured using substantially straight strips in a style similar to the embodiments illustrated in FIGS. 8A-D.

Figure 15:
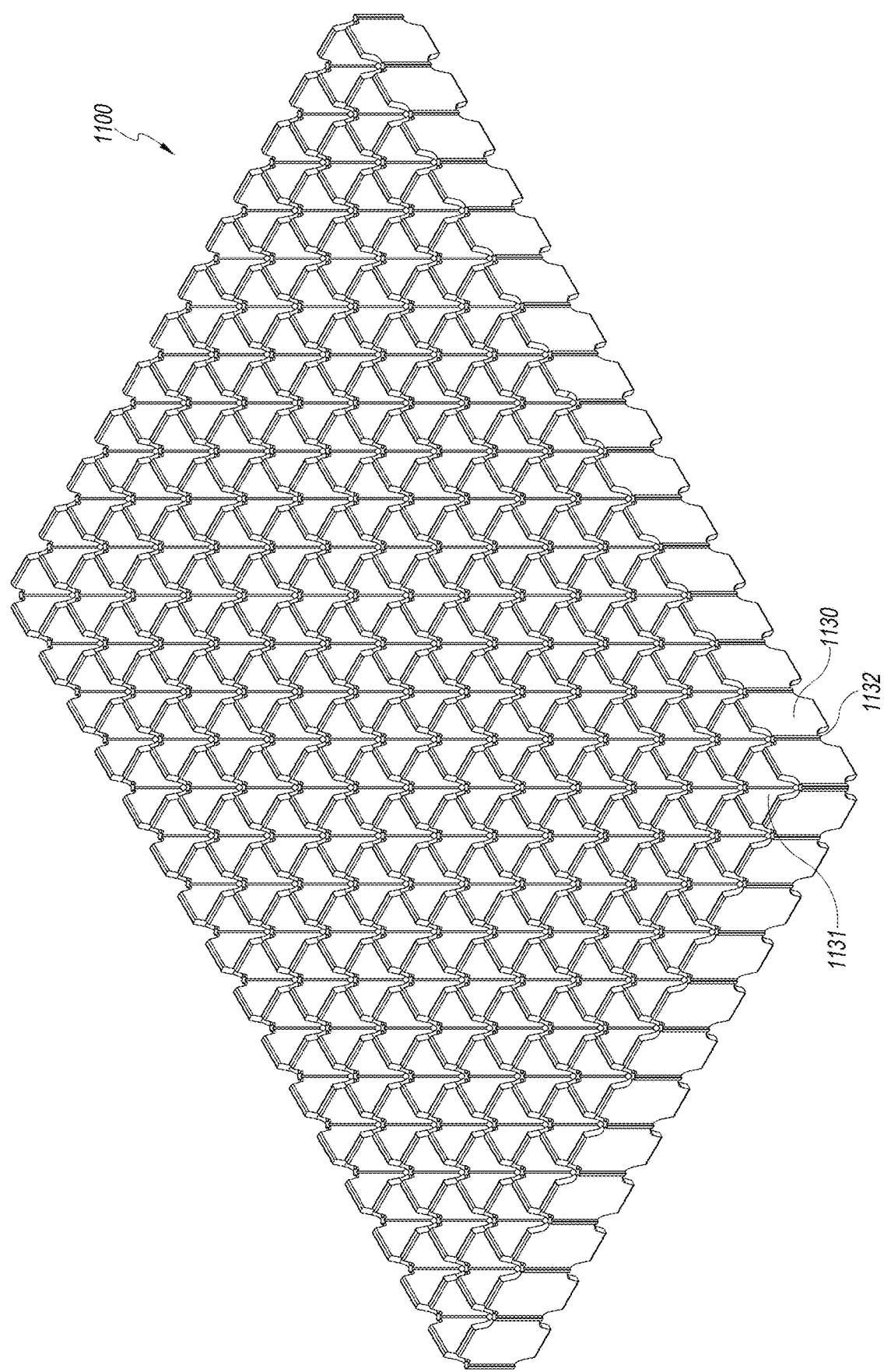

FIG. 15 illustrates a stabilizing structure 1100 comprising vertical segments 1130 joined together at approximately perpendicular angles so as to form quadrilateral or square cells 1131. Preferably, the vertical segments 1130 are of a square or rectangular shape, with tapers 1132 that join the segments together in a movable and flexible configuration. As with the other embodiments described in this section or elsewhere in this specification, this stabilizing structure 1100 may be manufactured as a single unit, and is preferably configured to collapse in a horizontal plane or direction while remaining substantially uncollapsed in a vertical direction.

Figure 16A:
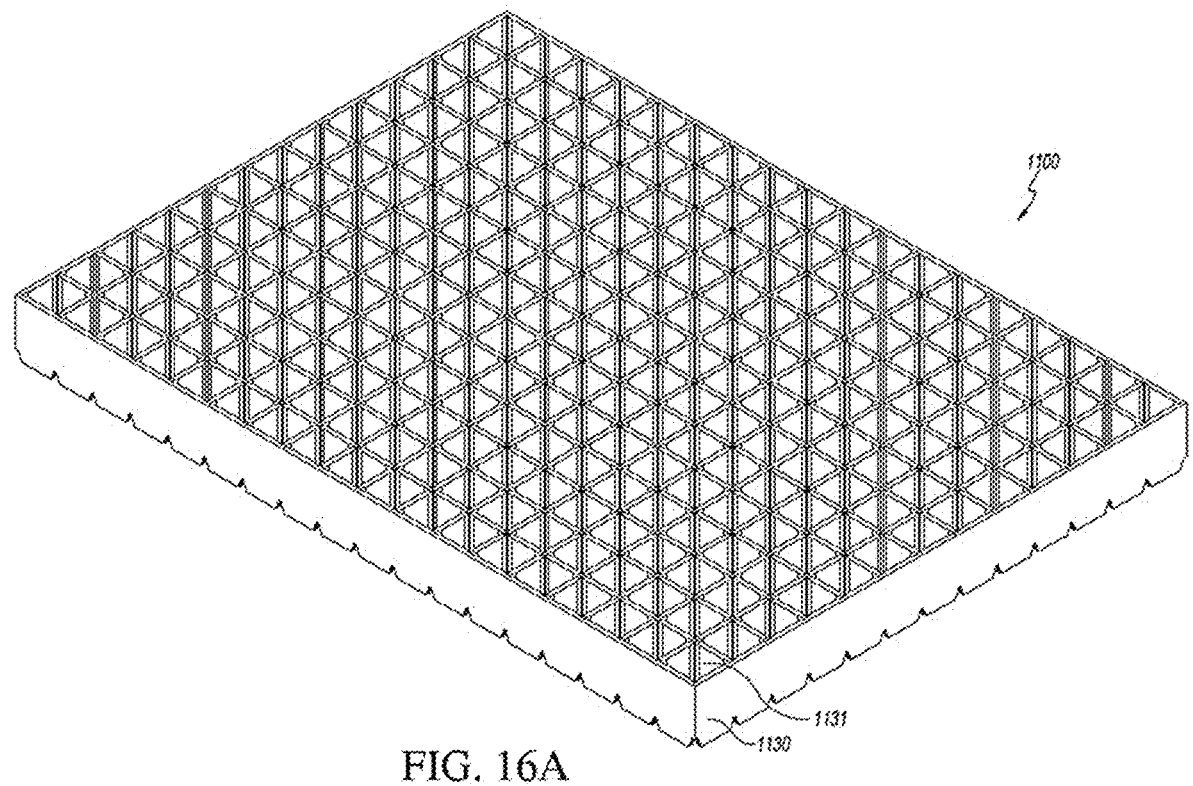
Figure 16B:
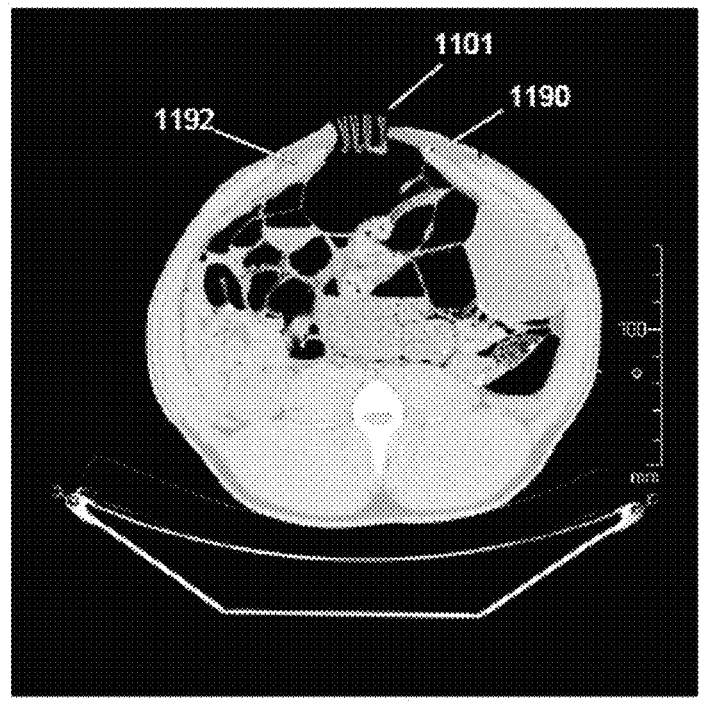

FIG. 16A-B illustrates another stabilizing structure 1100 similar to the embodiment illustrated above in FIG. 15. The vertical segments 1130 are preferably joined together so as to form one or more quadrilateral or square cells 1131. Here, however, the vertical segments 1130 do not comprise a tapered portion 1132. However, one or more notches may be present on the underside (wound-facing side) of the structure 1100, and which function as described in preceding embodiments. Although this embodiment may be manufactured from multiple vertical segments 1130, it is preferably molded as a single unit.

FIG. 16B illustrates a CT image of an embodiment of a stabilizing structure 1100 as described above in relation to FIG. 16A, and which has been inserted into an abdominal wound. Subcutaneous fat layers 1190 are bilateral and present over muscle tissue layer 1192. Upon application of negative pressure (as illustrated), improved fascial re-approximation and wound closure may be observed. Here, the width of the wound along the view illustrated reduced from approximately 82mm to 52mm, a reduction of 37%.

In some embodiments, the stabilizing structures described in this section or elsewhere in this specification (such as those described in FIGS. 11A-16B) may be entirely molded from a single type of material, such as a plastic. In other embodiments, the stabilizing structures described in this section or elsewhere in this specification may be constructed via an overmolding process whereby the more rigid portions of the structure are molded first and the hinges or flexible portions are molded second. In further embodiments of the stabilizing structure described in this section or elsewhere in this specification, a soft polymer could be molded over the entire structure to soften the feel of the device, thereby protecting the surrounding organs and/or other tissues. In other embodiments, the soft polymer could be molded only over the bottom portion of the stabilizing device, while in some embodiments the softer polymer can be molded over the top and/or the sides of the device. In some embodiments, the soft polymer could be molded over particular edges of the stabilizing structure, such as those on the bottom, sides, and/or top. In certain embodiments, the soft polymer could be molded over any side or combination of sides of the stabilizing device. The soft polymer may act like a softened rim surrounding the hard edges of the stabilizing structure.

Figure 32:
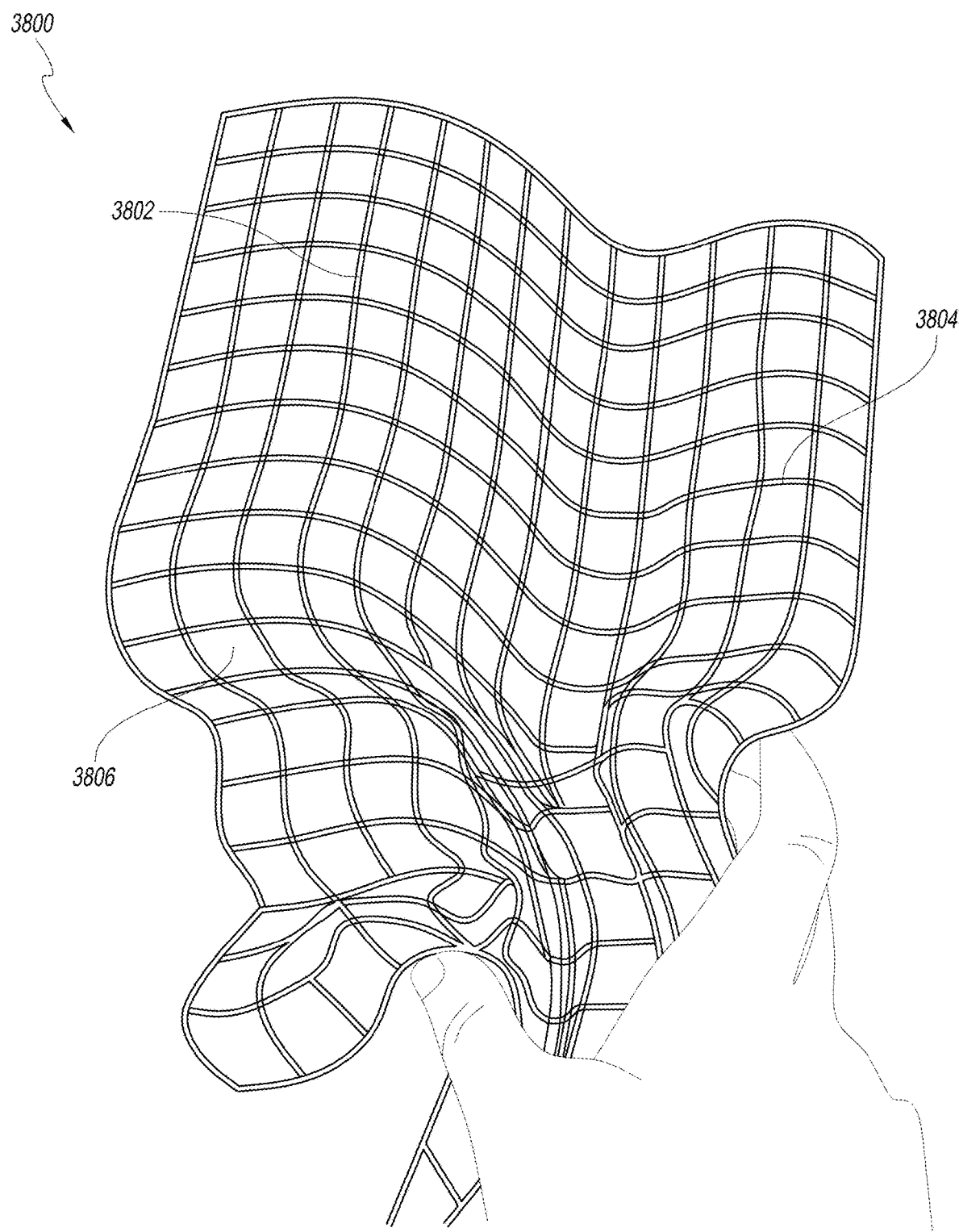
FIG. 32 illustrates an embodiment of a fully flexible stabilizing structure.

FIG. 32 illustrates an embodiment of a stabilizing structure 3800 similar to the structures described in FIGS. 11-16A. In this embodiment, the longitudinal strips 3802 and cross strips 3804 are formed from a single piece of material and form rows of flexible cells 3806 that are configured to collapse in a horizontal plane. Because each of the longitudinal and cross strips are formed from the same flexible material, applying a lateral force to the structure causes the cells to collapse generally independently of each other. In other words, the collapse of one or more cells in a row does not necessarily cause the collapse of other cells in the same row.

EXAMPLE 5

In this next non-limiting experiment, the wound described in the preceding examples had an embodiment of the stabilizing structure device described above in relation to FIGS. 8A-E inserted into the abdominal cavity. In this experiment, and as illustrated in FIG. 17A, white foam inserts were placed into the quadrilateral openings of the stabilizing structure, and the outer edges (in contact with the wound) were wrapped in black foam. The wound and stabilizing structure were then sealed with a drape and connected to a source of negative pressure as described previously.

Wound area measurements were taken before and after activation of the negative pressure source. Here, the size of the wound before application of negative pressure was measured as 171mm$^2$. Upon the application of negative pressure, as illustrated in FIG. 17B, the area of the wound was greatly reduced to 55mm$^2$, a reduction of 68%. It is noted that here and in the following examples, as the wound area contracts along its width, the length of the wound increases slightly, indicating that the tissue margins are returning to their original anatomical position.

EXAMPLE 6

FIGS. 18A-B illustrate the results of a non-limiting experiment similar to those illustrated above, where a stabilizing structure similar to the embodiments of FIGS. 8A-E was inserted into the abdominal cavity. Here, the spaces in the quadrilateral openings of the stabilizing structure were empty, and a layer of foam was wrapped around the outer edges of the structure.

Wound area measurements before and after application of negative pressure indicated that the wound area decreased by 63%, from 155mm$^2$ to 58mm$^2$.

Without wishing to be bound by theory, the greater reduction in wound area in the preceding examples, as compared to the black foam control of Example 1, is believed to be due to the fact that the wound devices used therein do not significantly compress in a vertical direction when negative pressure is applied. This is different from traditional foam dressings, where the application of negative pressure causes downward pressure on the foam due to the air pressure pressing onto the drape, [thus causing the foam to collapse towards the wound bed, creating a concave shape to the drape. The atmosphere acts predominantly in a perpendicular direction to the surface of the drape. Thus, on the periphery of the concave shape, closest to the wound edge or where the drape approaches an angle perpendicular to the plane of the wound, the atmosphere now creates a force in a direction that pushes the wound apart.] Similarly, pressure is transmitted along the foam dressing into a horizontal force that pushes the wound margins outward. With the use of a stabilizing structure as used in the various examples illustrated here, the foam and other dressing components are not pushed outward, and thus the wound margins may be approximated more easily so as to achieve faster wound closure. In fact, in some experiments, certain embodiments of the wound devices projected upward over the wound margins, and these vertical surfaces may therefore allow for atmospheric pressure to produce contractile forces onto the devices and/or the wound margins.

Traditional negative pressure wound treatment typically uses foam (or other porous materials) placed into a wound underneath a drape, to which negative pressure is applied to the wound. In such situations, the application of negative pressure may cause downward pressure on the foam due to the air pressure pressing onto the drape, which is then transmitted along the foam dressing into a horizontal force that pushes the wound margins outward. Without wishing to be bound by theory, it is believed that some of the embodiments of stabilizing structures, wound closure devices, and wound treatment devices, methods, and systems described below are able to cause a greater reduction in wound area as compared to traditional negative pressure treatment. One of these factors is believed to be because embodiments of the stabilizing structures and wound closure devices described in this section or elsewhere in this specification do not significantly compress in a vertical direction when negative pressure is applied. With the use of certain embodiments described in this section or elsewhere in this specification, foam and other dressing components are not pushed outward due to negative pressure, and thus the wound margins may be approximated more easily so as to achieve faster wound closure and better wound healing.

Stabilizing Structures and Wound Closure Devices of FIGS. 21A-27B

Figure 21A:
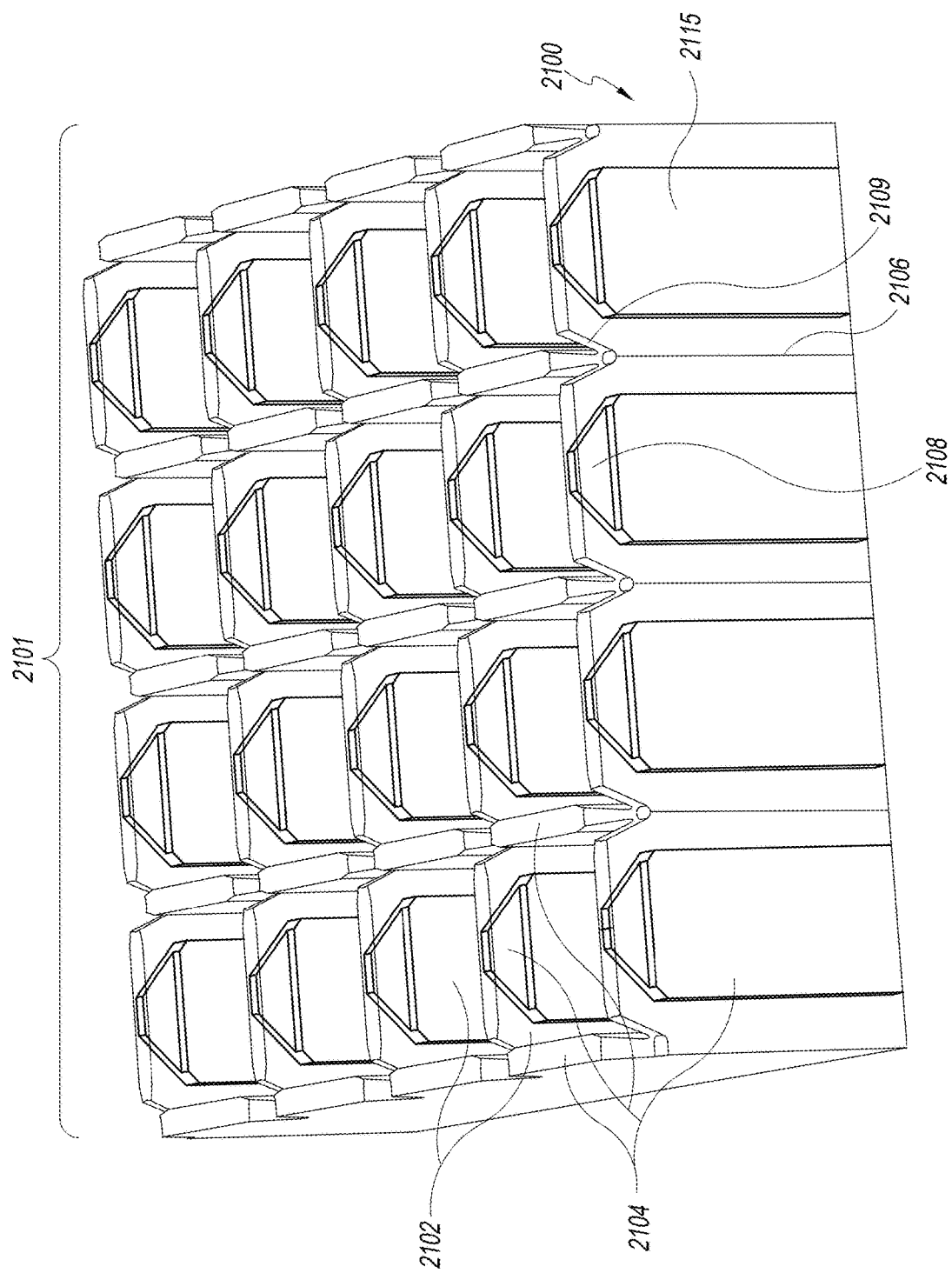
FIGS. 21A-E are photographs of various embodiments of stabilizing structures comprising inserts disposed therein.

FIG. 21A is a photograph of an embodiment of a wound closure device comprising a stabilizing structure 2100 that may be placed or inserted into a wound. Here, the device comprises a plurality of cells 2102 provided side-by-side in a generally planar configuration. Preferably, the stabilizing structure 2100 is configured to collapse in a direction along a plane 2101 defined by the width of the device, without significantly collapsing in a direction perpendicular to the plane 2101. That is, when viewed in the figure, the stabilizing structure 2100 will collapse in the horizontal direction, but will not compress in the vertical direction. In some embodiments, the stabilizing structure collapses in conjunction with the movement of tissue. Here, the cells 2102 are preferably open at both ends in a direction perpendicular to the plane 2101.

Each of the cells 2102 is preferably formed with four walls 2104, each wall 2104 being joined to the next by a flexible joint 2106. The joints 2106 are preferably designed so as to be more flexible than the walls 2104, and promote collapse of the stabilizing structure 2100 in the direction of the plane. Of course, it will be understood that other configurations are possible, and in some embodiments each cell 2102 may be defined by less than or greater than four walls 2104, for example five walls or six walls, thus forming pentagonal or hexagonal cells. The cells 2102 may not necessarily be symmetric, and can form rectangular, diamond, rhomboidal, trapezoidal, parallelepiped, oblong, oval, lozenge and other such shapes in addition to the square-walled embodiment illustrated in this section or elsewhere in this specification.

One or more of the walls 2104 defining the one or more cells 2102 may further comprise an insert 2115 disposed therein, and described in greater detail below in FIGS. 22A-F. Preferably, the insert 2115 will be constructed from a material more rigid than the material used to construct the remainder of the wall 2104. Some suitable materials may include metals such as titanium, stainless steel, and largely inert alloys (such as monel and hastelloy), and/or polymers such as polyurethane, silicone, rubber, isoprene, polyethylene, polypropylene, nylon, polyacrylate, polycarbonate, and PEEK. Some embodiments may also comprise composite materials, including resin-reinforced fiber composites where the resin may be, for example, various types of epoxies. Suitable fibers may include glass, carbon, carbon nanotubes, graphene, and aramids (e.g., Kevlar). Preferably, the material chosen for the insert 2115 is not only sufficiently rigid, but also able to adhere to the material used in the wall 2104. For example, the insert material is preferably able to adhere to softer polymers such as silicones or polyurethanes used in the wall 2104. The more rigid materials used in the insert 2115 may provide for additional collapse resistance in the direction perpendicular to the plane for the stabilizing structure 2100.

In some embodiments, one or more notches 2109 may be provided between multiple walls 2104, and which may further aid in permitting the flexible joints 2106 to move. Without wishing to be bound by theory, the notches 2109 may also aid in distributing negative pressure and transmitting fluid throughout the stabilizing structure 2100 when negative pressure is applied, for example in a clinical care setting. Some embodiments may also comprises holes in the walls 2104 or joints 2106, or be constructed from porous materials.

Preferably, a cavity 2108 is provided within each wall 2104 for the insert 2110 to be disposed therein. The walls 2104 may be molded around each insert 2115. An insert 2115 may also be inserted into the cavity 2108 after the wall 2104 is manufactured. While the embodiment illustrated here and in the subsequent images shows a single insert 2115 in each wall 2104, some embodiments may be provided with one or more inserts 2115 disposed therein.

Figure 21B:
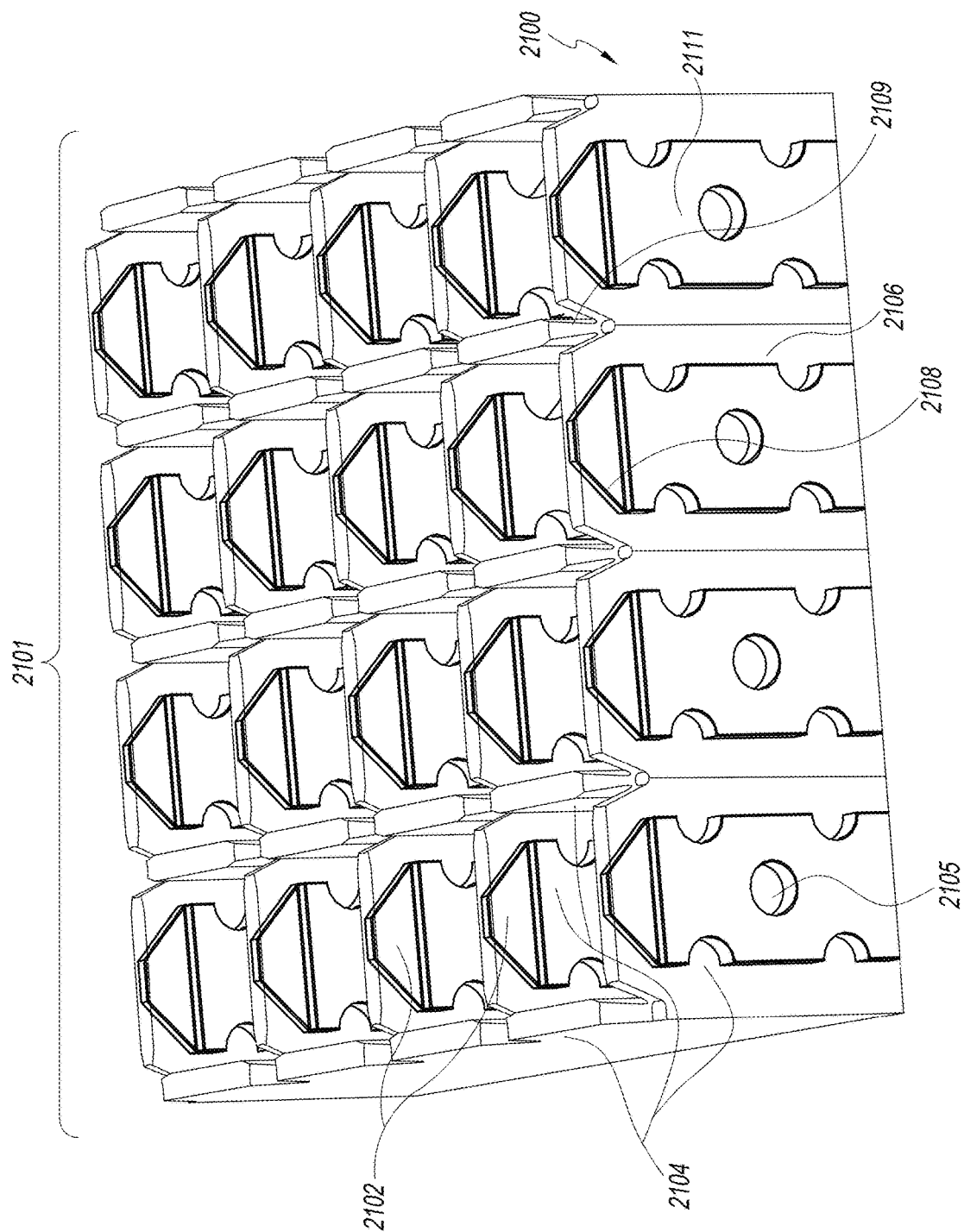

FIG. 21B illustrates an embodiment of a stabilizing structure 2100 with many similar features to FIG. 21A. Here, an insert 2111 comprises structural differences compared to the insert 2110, and is discussed in more detail below in relation to FIG. 22E. When inserted or placed within the cavity 2108, one or more of the walls 2104 may comprise a hole 2105 communicating through at least one aperture in the insert 2111. In addition to any notches 2109, the one or more holes 2105 may permit additional displacement of wound exudate and distribution of negative pressure within the stabilizing structure 2100.

Figure 21C:
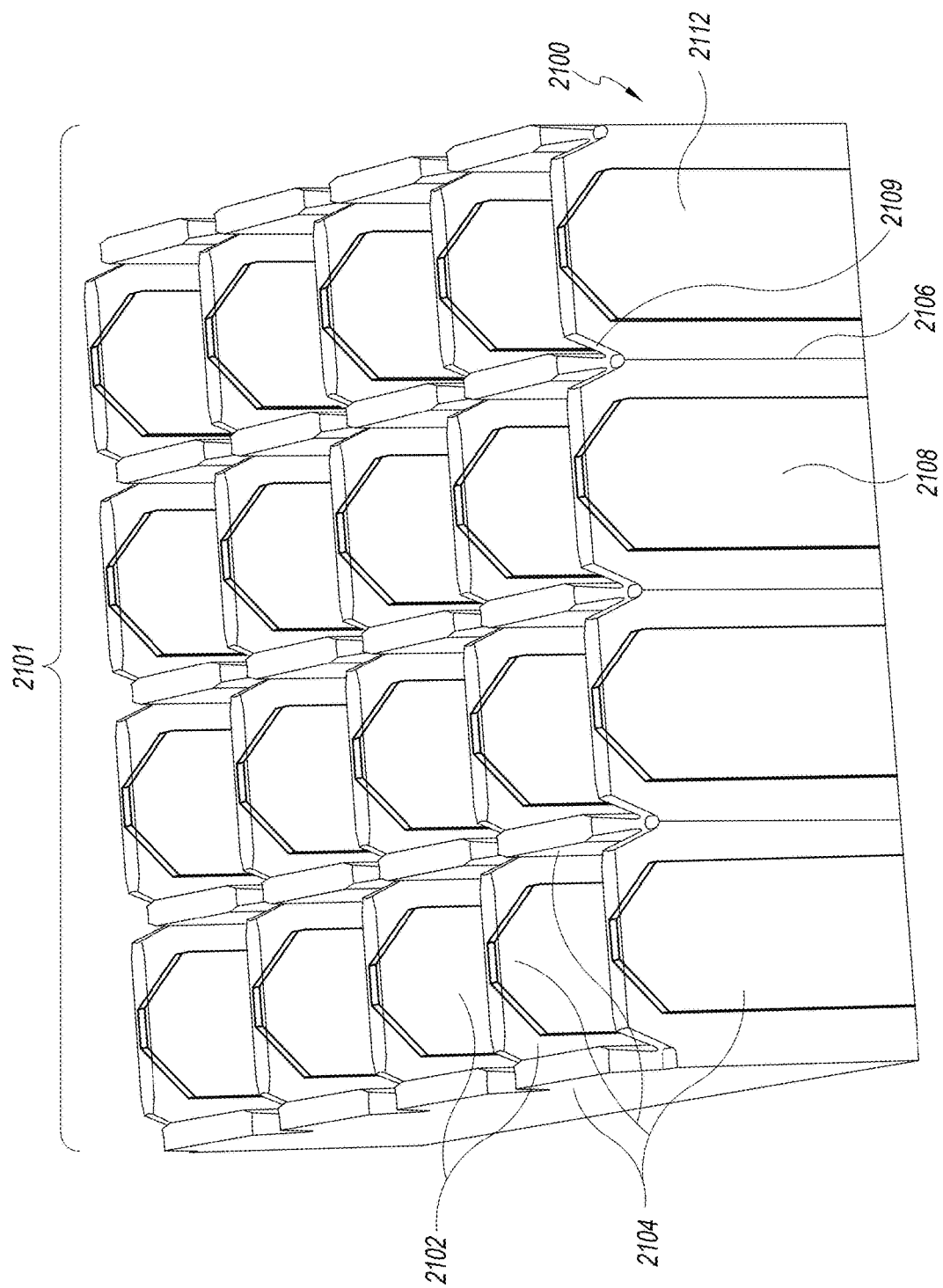

FIG. 21C illustrates an embodiment of a stabilizing structure 2100 with similar features as the other embodiments described previously. In this embodiment, the stabilizing structure 2100 comprises an insert 2112 described in greater detail below in FIG. 22F.

Figure 21D:
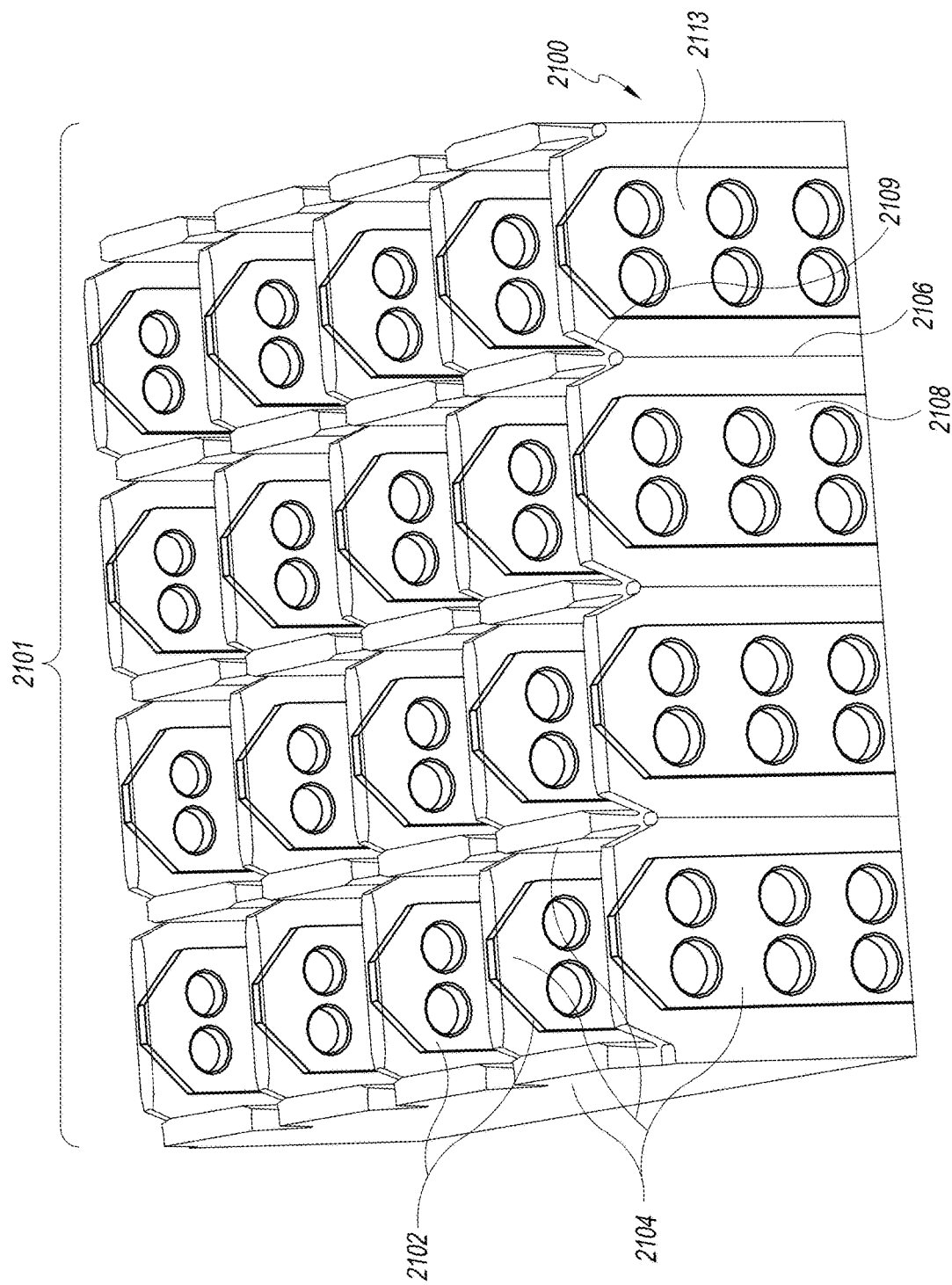
Figure 21E:
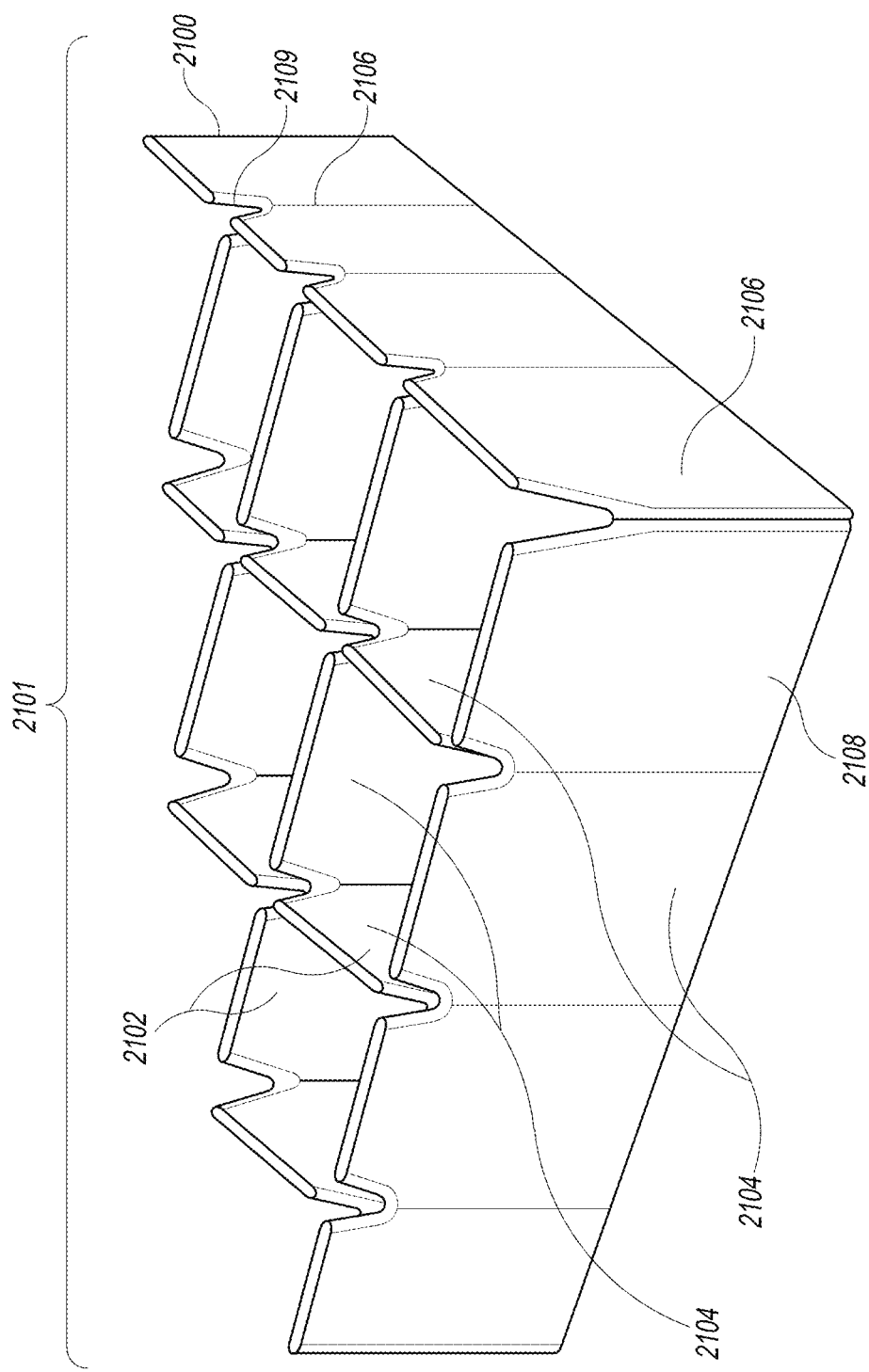

Similarly, FIG. 21D illustrates an embodiment of a stabilizing structure 2100 comprising an insert 2113 described in greater detail below in FIG. 22D. FIG. 21E illustrates an embodiment of a stabilizing structure 2100 comprising an insert 2114 described in greater detail in relation to FIG. 22A.

In the preceding embodiments of stabilizing structures 2100 comprising various inserts 2110, 2111, 2112, 2113, 2114, and 2115, it will of course be understood that embodiments of the stabilizing structure 2100 does not need to contain only one type of insert. Likewise, each cell 2102 or wall 2104 may comprise one or more different types of inserts, or no inserts at all. Varying the different inserts and other properties of the cells 2102 and walls 2104 may thus permit the stabilizing structure 2100 to be tailored to the appropriate wound type so as to effect optimal wound closure and/or treatment.

FIGS. 22A-F illustrate examples of different inserts that may be used as part of a stabilizing structure 2100. Preferably, these inserts may be placed, molded into, or formed as part of a wall 2104 in a stabilizing structure 2100 (e.g., of the types illustrated above in FIG. 21A-E). Various modifications may be made, as described below, that may improve or alter characteristics of the inserts.

Turning now to FIG. 22A, the embodiment of the insert 2114 illustrated here is approximately rectangular in shape, and is adapted to be inserted or formed into one or more of the walls 2104 of an embodiment of the stabilizing structure 2100. In some embodiments, one or more of the inserts 2114 may have a height greater than the width, and the wall 2104 may have a height of at least about 1mm, at least about 5mm, at least about 10mm, at least about 15mm, at least about 20mm, at least about 25mm, at least about 30mm, at least about 35mm, at least about 40mm, at least about 50mm, at least about 75mm, at least about 100mm, at least about 150mm, at least about 200mm, at least about 250mm, at least about 300mm, at least about 350mm, at least about 400mm, or more than 400mm, particularly in extremely obese patients. Preferably, in average patients, the heights may range from about 10mm to 40mm. These measurements may apply to any stabilizing structure described in this section or elsewhere in this specification.

In some embodiments of any stabilizing structure described in this section or elsewhere in this specification, the width may be between about 1mm to 30mm, 2mm to 25mm, 4mm to 20mm, 6mm to 18mm, 8mm to 16mm, or 10mm to 14 mm, preferably about 10.8mm. These measurements may apply to any stabilizing structure described in this section or elsewhere in this specification.

The insert 2114 is preferably thin but with enough structural strength to resist collapse, and in some embodiments of any stabilizing structure described in this section or elsewhere in this specification, the thickness may be at least about 0.01mm to 10mm, 0.2mm to 8mm, 0.4mm to 6mm, 0.5mm to 4mm, 0.75mm to 3mm, or 1-2mm. These measurements may apply to any stabilizing structure described in this section or elsewhere in this specification.

In some embodiments of any stabilizing structure described in this section or elsewhere in this specification, multiple discrete stabilizing structures may be stacked on top of one another to form the wound closure device, to extend the height of the device to any of the dimensions described in this section or elsewhere in this specification (including the dimensions provided for the inserts above). The stacking of multiple stabilizing structures may allow the clinician to have further flexibility in their treatment strategies.

FIG. 22B illustrates an embodiment of the insert 2110 with a generally rectangular configuration, but provided with two notches 2201 cut diagonally across a top end of the insert 2100. The notches 2201 may facilitate clearance of the insert 2100 from any notches 2109 that may be provided in the walls 2104. Further, the notches 2201 may also aid in the insertion of the insert 2100 into the cavity 2108 of the wall 2104. The notches 2201 may also be helpful in conjunction with the notches 2109 in further defining a channel or other opening for fluid to be transmitted or transferred between and through each cell 2102. The notches 2201 may also aid in ensuring that the entire stabilizing structure is able to more easily collapse.

FIG. 22C illustrates an embodiment of an insert 2115 provided with two notches 2201 as well as a horizontal lip 2203. The horizontal lip 2203 may aid in inserting the insert 2115 into the cavity 2108 of the wall 2104, or may aid in fixing the wall 2104 around the insert 2115 when the wall is molded around it. The horizontal lip 2203 may be beneficial in effectively reducing the bulk of the insert at one end of the wall 2104, and in conjunction with a softer material used in the wall 2104, may thereby increase comfort due to the correspondingly greater amount of wall material. In some embodiments, the horizontal lip 2203 and/or notches 2201 may be present on both ends of the insert 2115 or other inserts described in this section or elsewhere in this specification. In some embodiments, the horizontal lip 2203 is approximately half the thickness of the overall insert 2115. For example, the insert 2115 may be between 0.5mm and 4mm in thickness, preferably 2mm. If the insert 2115 measures 2mm in thickness, the thickness of horizontal lip 2203 may be 1mm.

FIG. 22D illustrates an embodiment of the insert 2113, and which is similar to the embodiment used in the stabilizing structure 2100 illustrated in FIG. 21D. This insert 2113 may comprise one or more apertures 2205, which in some embodiments may communicate with one or more holes 2105 that may be formed through one or more walls 2104. In some embodiments, the apertures 2205 are arranged in a 2×3 pattern illustrated here, although other arrangements are possible. Notches 2201 may also be present.

Figure 22F:
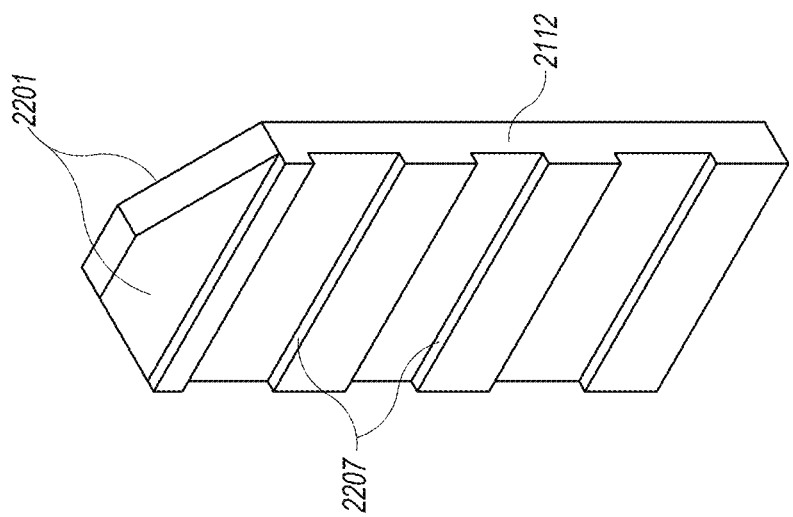
Figure 22E:
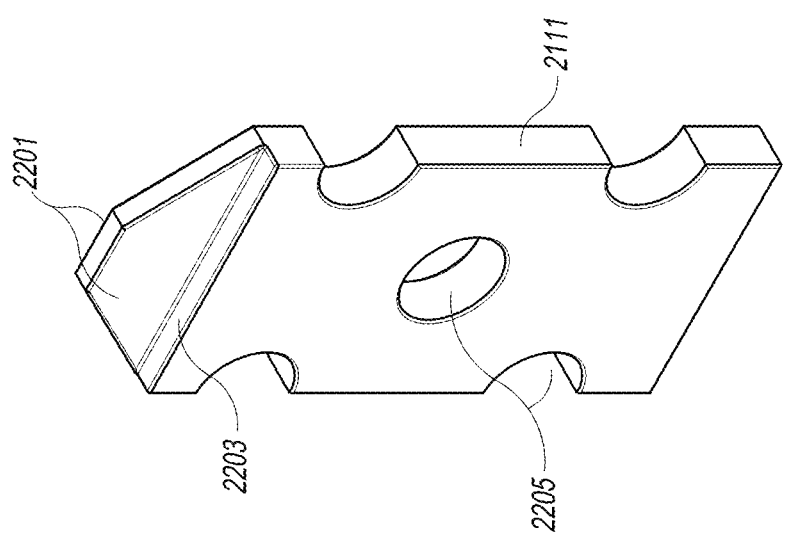

FIG. 22E illustrates an embodiment of the insert 2111, which is similar to the embodiment used in the stabilizing structure 2100 illustrated in FIG. 21B. The insert 2111 preferably comprises two notches 2201. A horizontal lip 2203 may also be provided. Preferably, one or more apertures 2205 may be formed therein. In some embodiments, one or more of the apertures 2205 may extend to the edge of the insert 2111 as illustrated. In some embodiments, the apertures 2205 may be configured to have four apertures arranged around a central aperture, although other configurations are of course possible. In some embodiments, the reduced amount of insert material at the locations of the apertures may be advantageous to provide a greater amount of softer wall material at a hinge point, where this may consequently increase flexibility. In a preferred embodiment, the insert 2111 has a height of 25mm and a width of 10.8mm, with a thickness of 2mm. The first set of apertures may be centered approximately 5mm from the bottom edge of the insert 2111, the central aperture may then be centered approximately 11mm from the bottom, and the top set of apertures may be centered 17mm from the bottom.

FIG. 22F illustrates an embodiment of the insert 2112, which shares some similarities to the embodiment used in the stabilizing structure 2100 illustrated above in FIG. 21C. The insert 2112 preferably may comprise one or more channels 2207 formed therein. Preferably, the one or more channels 2207 are disposed in a horizontal configuration across the width of the insert 2112. While the insert 2112 is preferably configured, like several other embodiments described in this section or elsewhere in this specification, to remain substantially uncompressed in the vertical direction, the inclusion of one or more horizontal channels 2207 may aid in providing additional rigidity in the direction of the plane defined by the cells 2102. In such a case, the rigidity of the one or more walls 2104 may be enhanced, and may thus control the compression of the stabilizing structure 2100 such that any collapse or bending occurs substantially only at the one or more joints 2106.

FIGS. 23A-F illustrate an embodiment of a stabilizing structure 3001 configured to be inserted into a wound. The stabilizing structure 3001 preferably comprises at least one top strip 3002 extending in a first direction (e.g., along an x axis) and at least one bottom strip 3004 extending in a second direction (e.g., along a y axis perpendicular to the x axis), these being preferably arranged into an array comprising multiple strips 3002, 3004. The strips 3002, 3004 are preferably connected together in a movably interlocking configuration, which preferably comprises an interlock mechanism 3006. The strips 3002, 3004 are preferably arranged in an un-collapsed configuration wherein the strips 3002 and 3004 are disposed at angles approximately perpendicular to each other. This arrangement forms a first plane that the stabilizing structure 3001 preferably adopts. Preferably, the stabilizing structure 3001 is more rigid in the direction perpendicular to the plane (i.e., in the vertical direction or along a z axis), and thereby substantially resists compression or deformation in that direction.

Figure 23A:
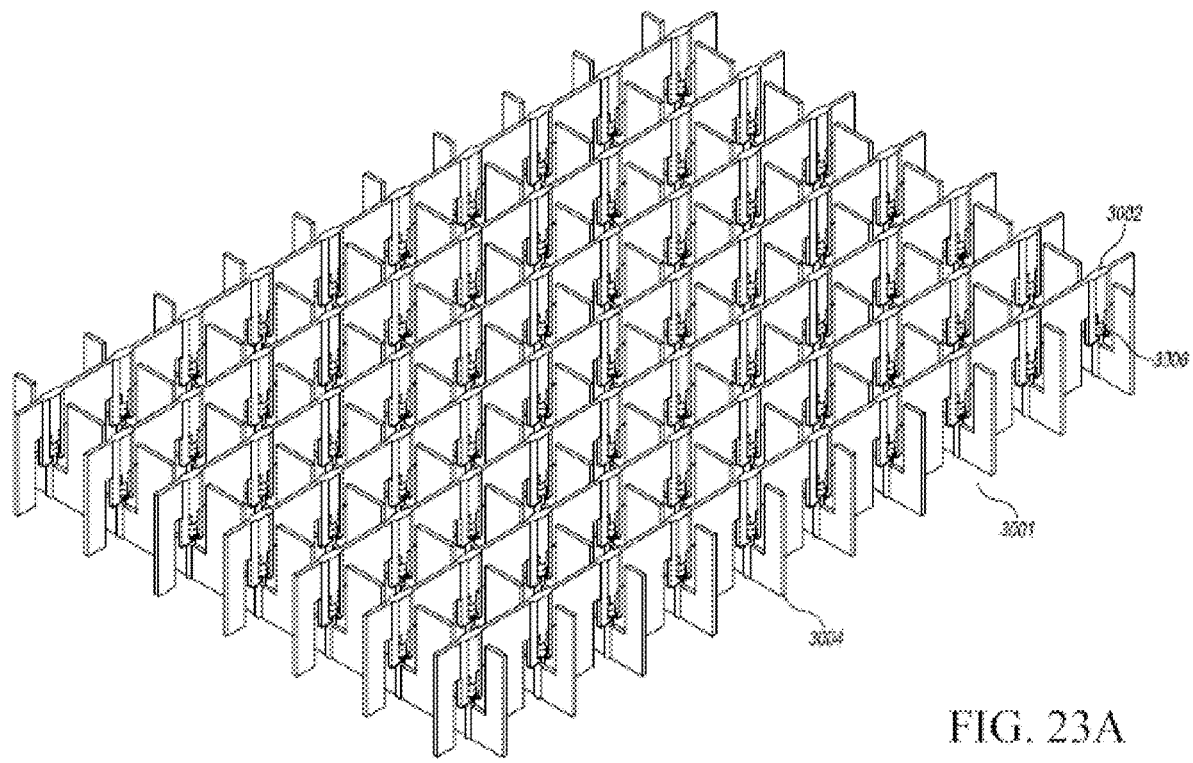
FIGS. 23A-F illustrate multiple views of an embodiment of a stabilizing structure.
Figure 23B:
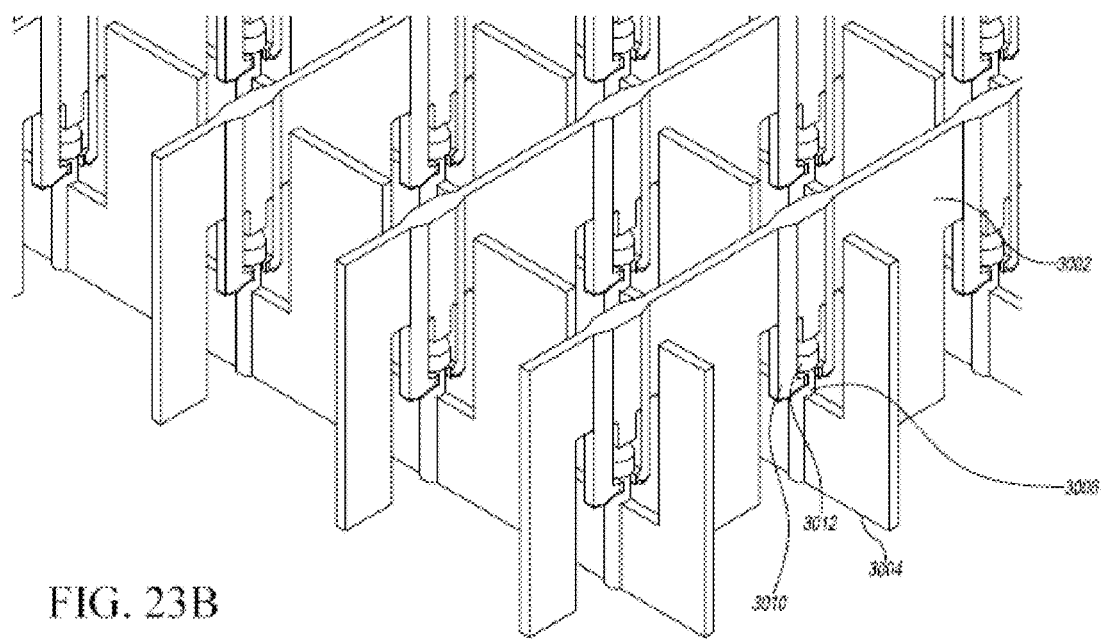
Figure 23C:
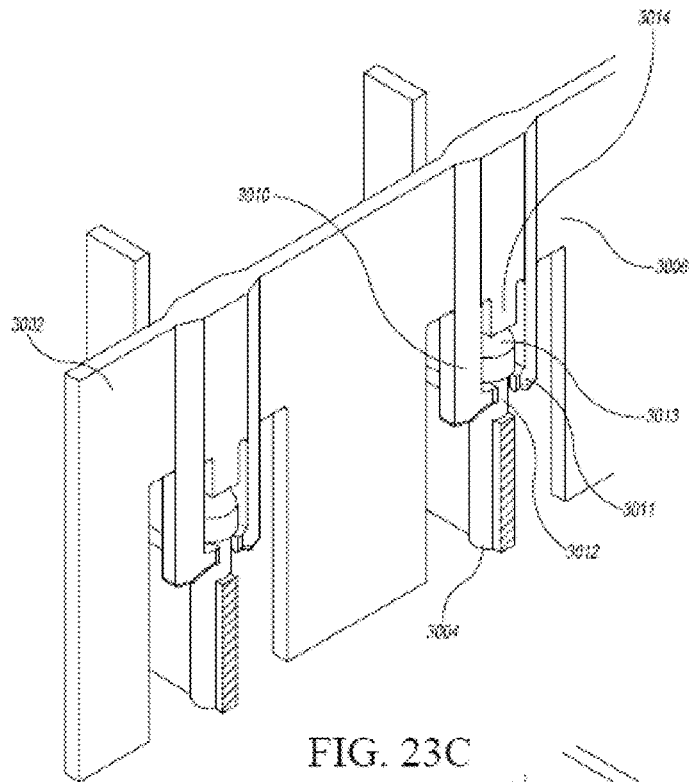
Figure 23D:
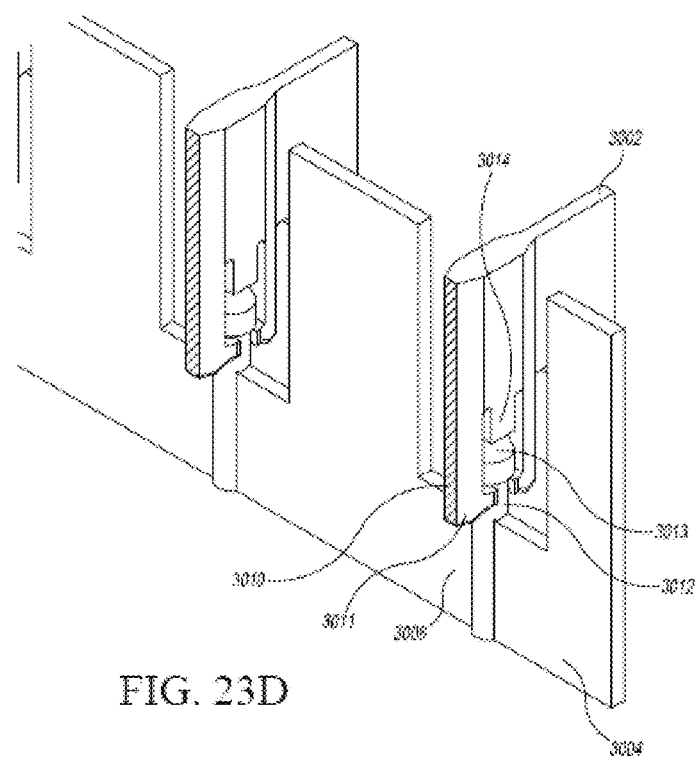
Figure 23E:
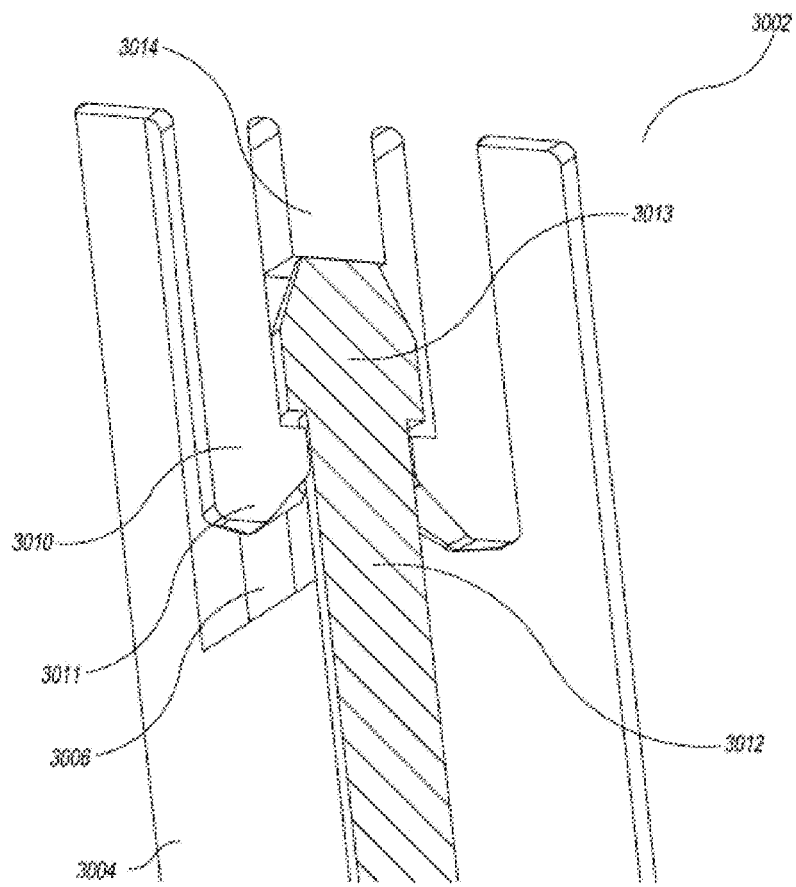
Figure 23F:
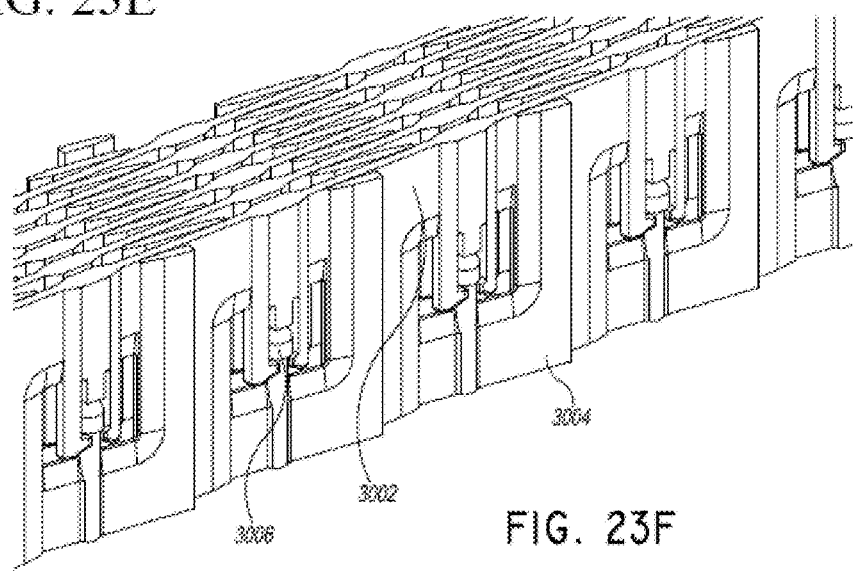

To aid in the closure of a wound, the stabilizing structure 3001 is preferably movable from the substantially un-collapsed configuration to a collapsed configuration, as illustrated in FIG. 23F. This may be beneficial for wound closure and healing, as described previously. In use, negative pressure may apply a closing force across the margins of the wound that the stabilizing structure 3001 is inserted into. As the structure 3001 is preferably configured to be substantially rigid in the vertical direction (i.e., perpendicular to the plane defined by the structure 3001), pressure resulting from atmospheric pressure exerted onto the structure 3001 via the drape is focused substantially downward rather than outward, such that the wound margins are no longer pushed outward as in conventional negative pressure dressings.

Preferably, the structure 3001 adopts a smaller area in the first plane as a result of moving to the compressed configuration. As such, the structure 3001 aids in wound closure by aiding re-approximation of the wound margins. In some embodiments, the stabilizing structures described in this section or elsewhere in this specification are able to reduce their captured volume when in a collapsed configuration (i.e., the volume change between an uncompressed and compressed stabilizing structure) by at least 10%, preferably at least 15%, and even more preferably at least 25%.

FIGS. 23C-E illustrate close-ups of the interlock mechanism 3006. It is to be noted that although reference may be made to various parts of the interlock mechanism 3006 being present on either the top strip 3002 or bottom strip 3004, this description should not be considered as limiting in terms of orientation, and the same interlock mechanism 3006 may be constructed with the top or bottom strips 3002, 3004 reversed.

In a preferred embodiment, the interlock mechanism 3006 preferably comprises two clasps 3010 extending downward from the top strip 3002. Preferably, the clasps 3010 are parallel to each other so as to be on opposite sides of a projection 3012 extending upward from the bottom strip 3004. The clasps 3010 preferably comprise a lip or hook 3011 that may secure themselves under an end 3013 located at the distal end of the projection 3012. In a preferred configuration, the enlarged end 3013 is arranged such that all or a portion of the lip 3011 engages with the enlarged end 3013. The combination of the lip 3011 and enlarged end 3012 may aid in preventing the top strip 3002 from disengaging in a vertical direction away from the bottom strip 3004. In some embodiments, the projection 3012 may abut on the bottom edge of the top strip 3002. In some embodiments, however, and as illustrated here, a stabilizing post 3014 may be present to locate the distal side of the projection 3012 and enlarged end 3013.

FIGS. 24A-D illustrate an embodiment of a stabilizing structure 3201 assembled in a similar manner to the embodiment illustrated above in FIGS. 23A-F. Here, the interlock mechanism 3006 comprises four clasps 3010 surrounding the projection 3012 and the enlarged end 3013 of the projection 3012. Preferably, the clasps 3010 are arranged in a mutually orthogonal configuration, although different orientations are contemplated as well. It will be understood that any number of clasps 3010 may be used to secure the projection 3012, for example three or five clasps 3010.

Figure 24A:
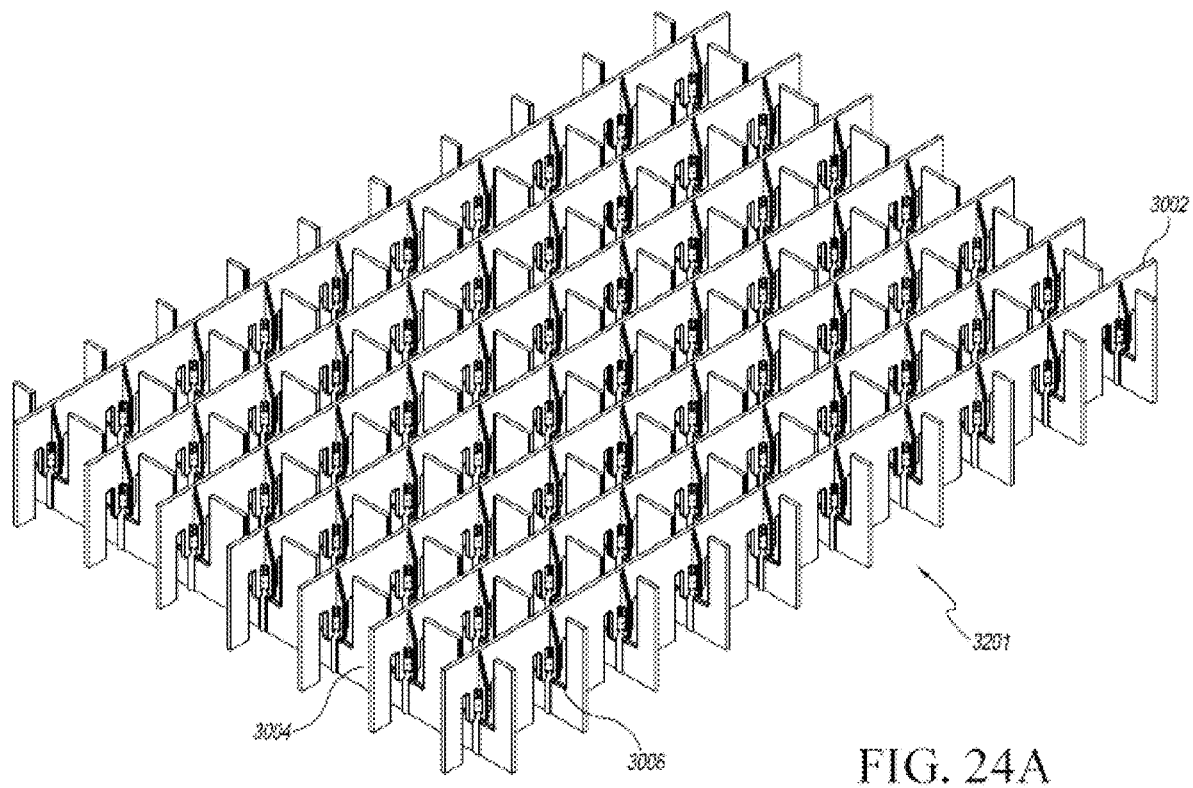
FIGS. 24A-D illustrate multiple views of an embodiment of a stabilizing structure.
Figure 24B:
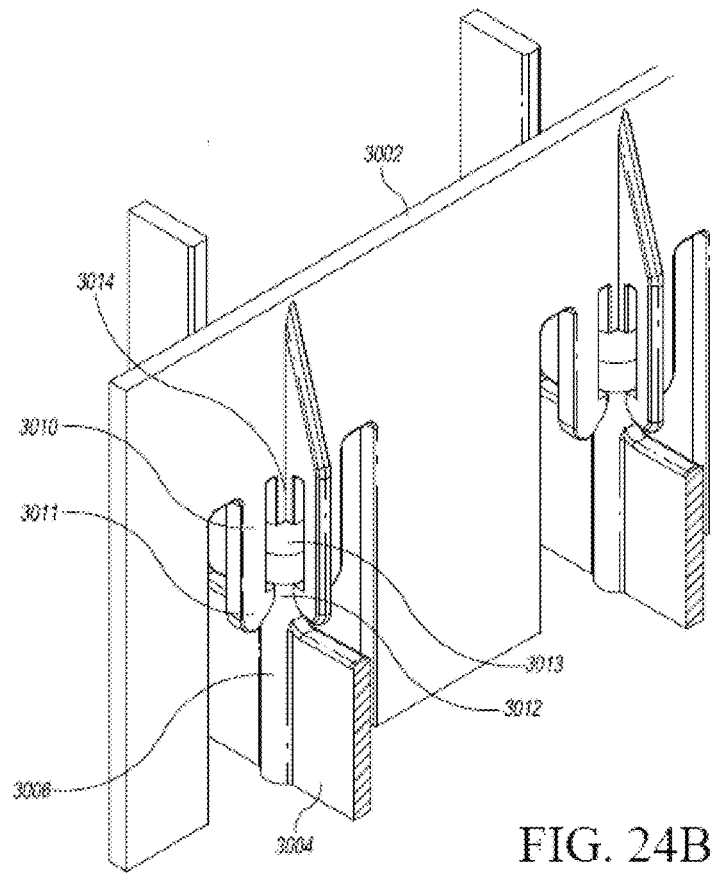
Figure 24C:
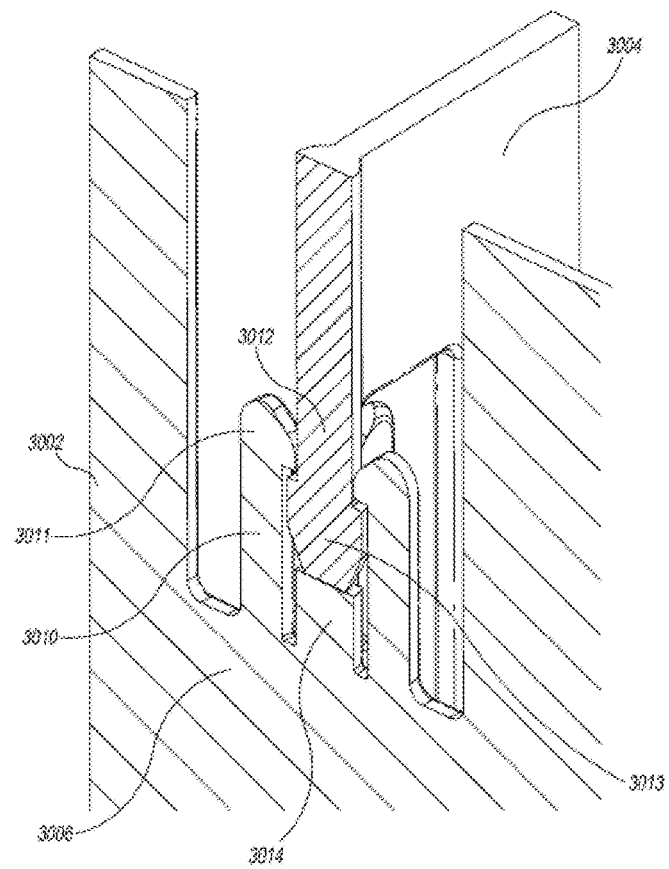
Figure 24D:
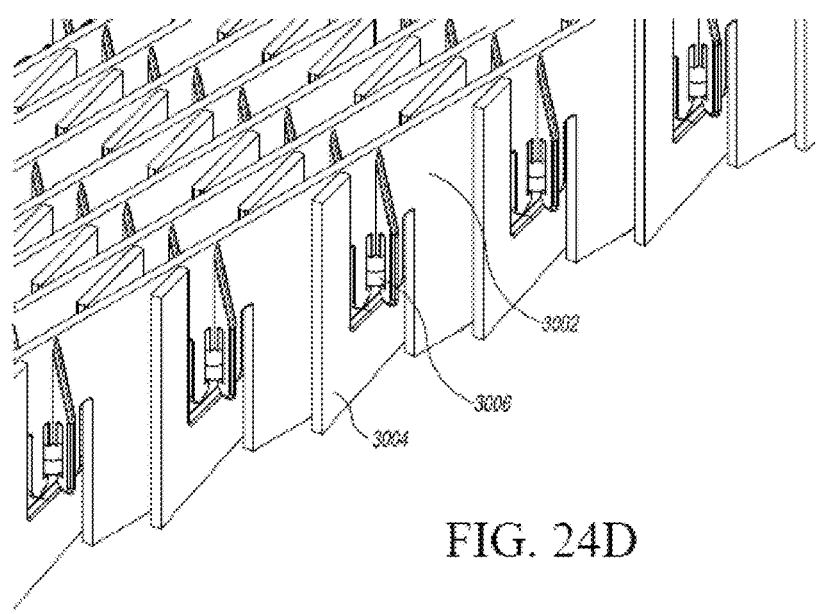

It will be noted that due to the addition of additional clasps 3010 in comparison to the embodiment illustrated in FIGS. 23A-F, the embodiment illustrated here will have a compressed configuration that is slightly larger, as illustrated in FIG. 24D. This may be useful in some situations; for example, some wounds may require a more gradual closure of the wound margins, and the embodiment described here may be well adapted for this purpose. For example, in clinical situations involving compartment syndrome, especially in the abdomen, application of full wound closure may not be appropriate or desirable, as wound closure may cause complications such as excessive pressure on organs and underlying tissue structures and/or reduction of blood flow to distal anatomical structures. Additionally, in some cases a too rapid or complete wound closure may be too painful for a patient. Accordingly, limiting the amount of closure may therefore be beneficial in such types of wounds. Limiting the amount of closure may also be beneficial in cases of compartment syndrome in the lower limbs.

FIGS. 25A-E illustrate an embodiment of a stabilizing structure 3301 comprising an interlock mechanism 3006 arranged in a tubular conformation. In this embodiment, a cup-shaped member 3020 is preferably configured to receive the enlarged end 3013 of the projection 3012. The projection 3012 may extend vertically from the top strip 3002. The cup-shaped member 3020 is preferably cylindrical or tubular in shape, and may extend vertically from the bottom strip 3004, although it will be understood that the cup-shaped member 3020 and projection 3012 may be located on opposite strips.

Preferably, one or more slits 3021 are formed into the cup-shaped member 3020 so as to permit some "give" to permit the projection 3012 to be received into the cup-shaped member. A lip or hook 3022 may also aid in securing the enlarged end 3013 of the projection 3012. A stabilizing post 3014 may also be present to prevent the projection 3012 from extending too deeply into the cup-shaped member 3020.

Figure 25A:
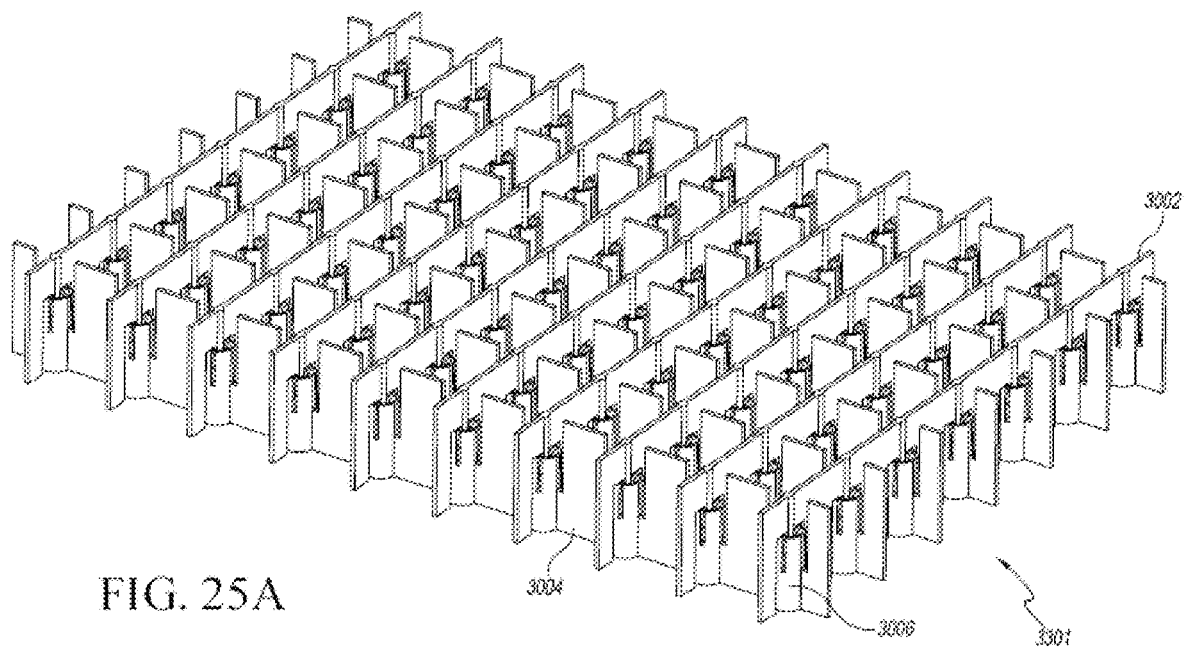
FIGS. 25A-E illustrate multiple views of an embodiment of a stabilizing structure.
Figure 25B:
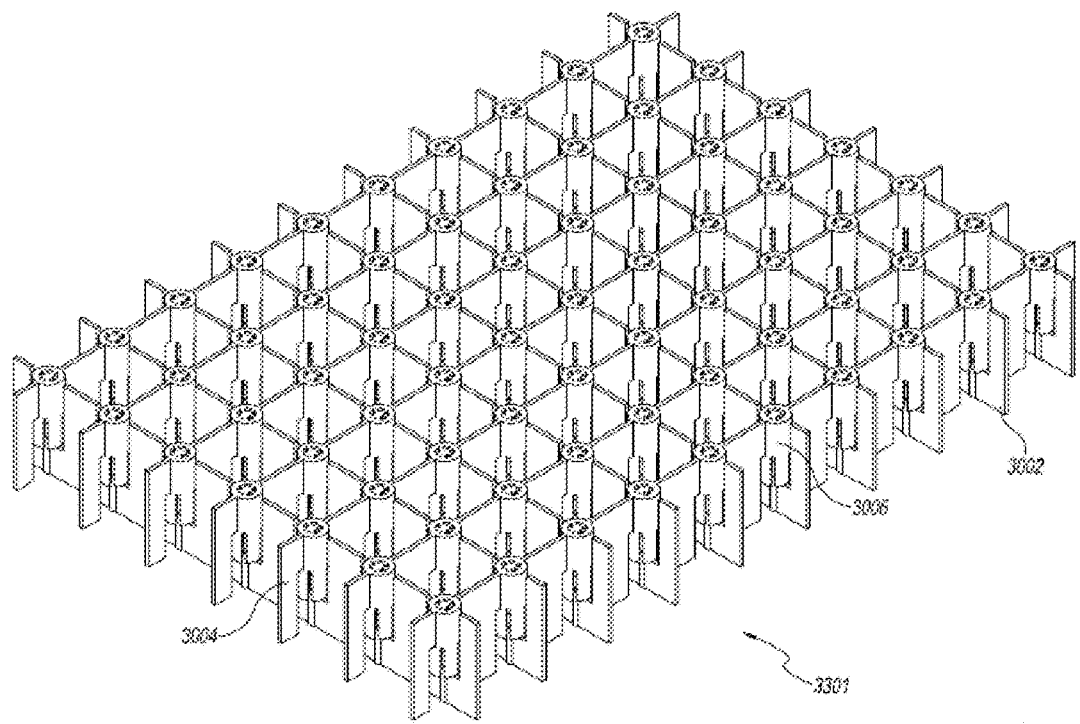
Figure 25C:
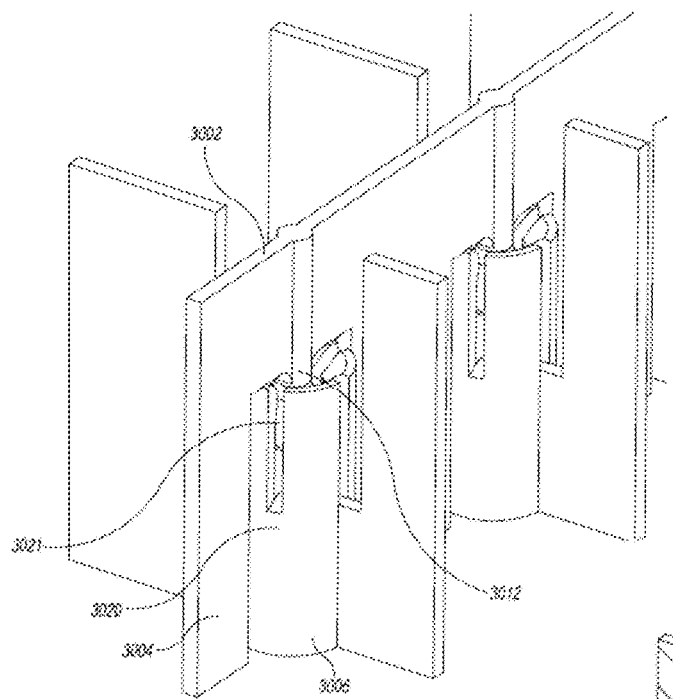
Figure 25D:
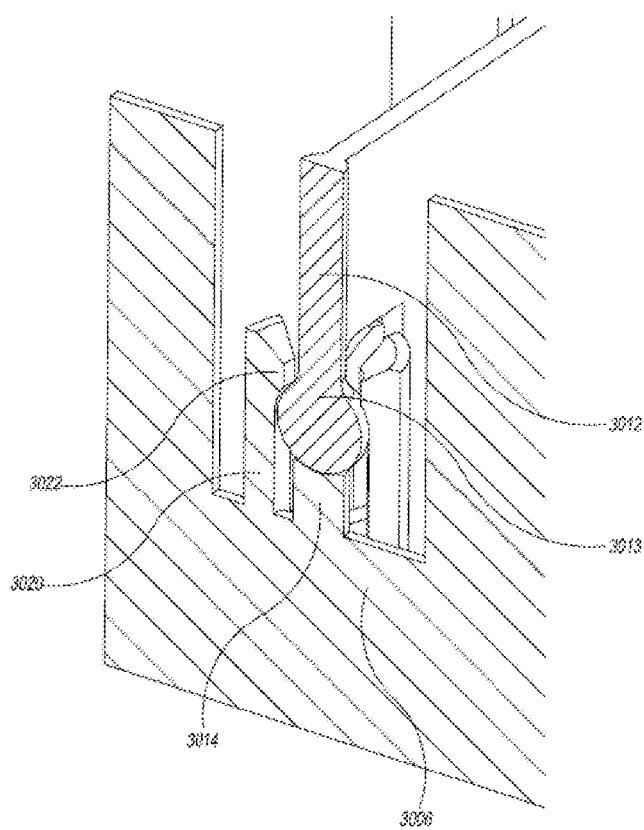
Figure 25E:
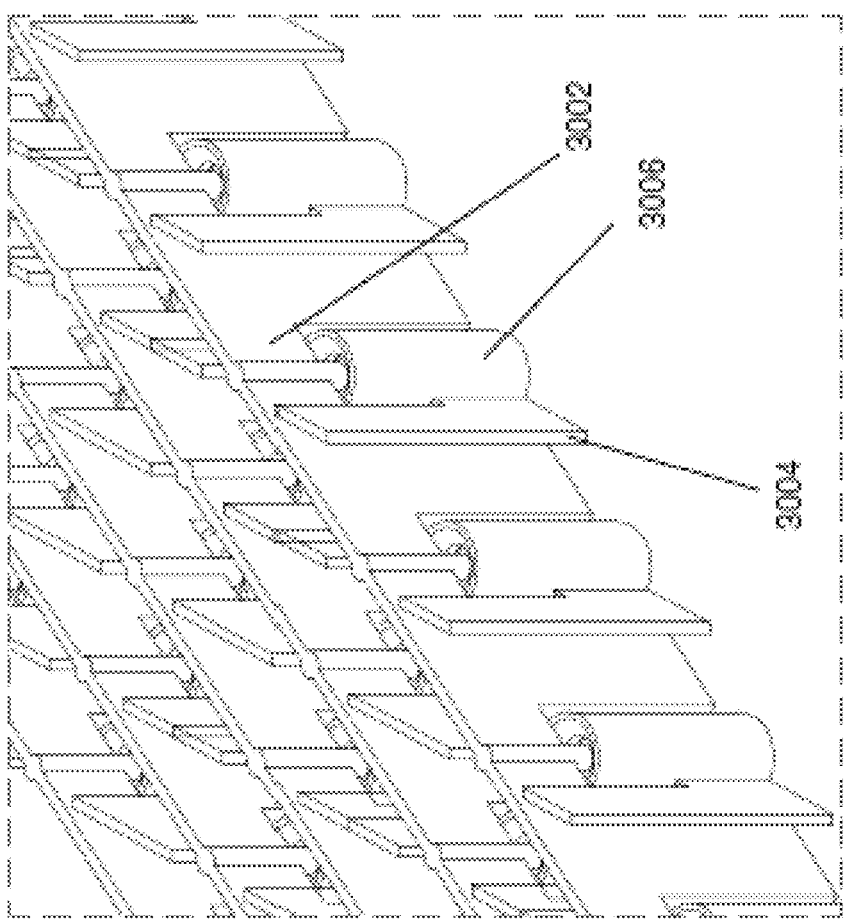

FIG. 25E illustrates a compressed view of an embodiment of the stabilizing structure 3301. Compared to FIG. 23F, this embodiment has a slightly larger compressed configuration.

Figure 26:
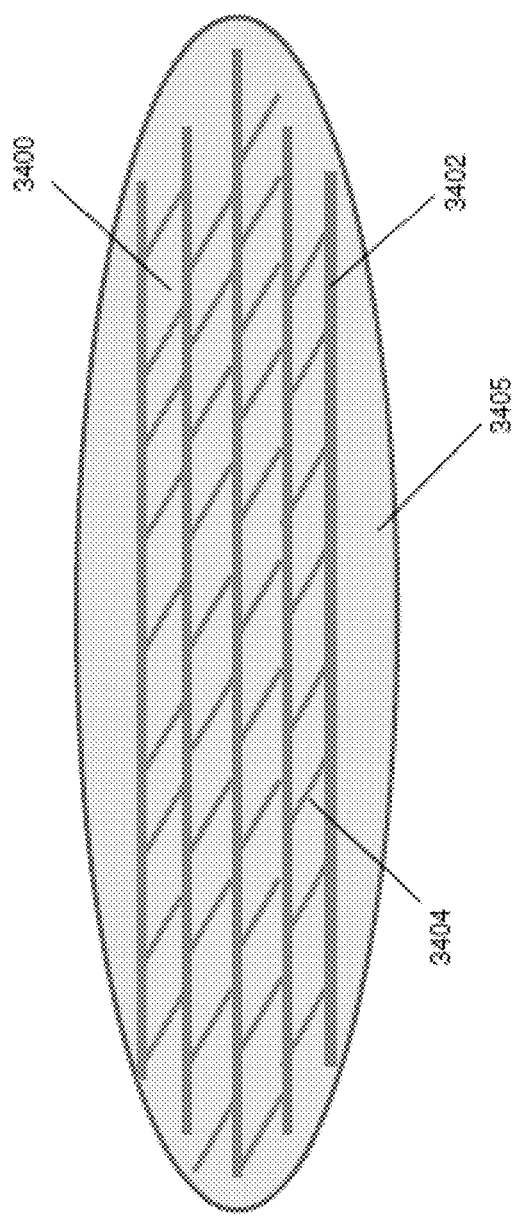
FIG. 26 schematically illustrates an embodiment of a stabilizing structure.

FIG. 26 schematically illustrates an embodiment of a stabilizing structure 3400 configured to be inserted into a wound. Here, the stabilizing structure 3400 is shown inserted into a wound 3405. Preferably, the stabilizing structure 3400 preferably comprises at least one, and more preferably at least two, long strips 3402 whose longitudinal length may be oriented along a longitudinal axis of the wound 3405, or along a direction along which closure is sought. Each of the one or more long strips 3402 are preferably substantially rigid and extend substantially along the entire length of the wound 3405. In a preferred embodiment, the long strip 3402 is continuous and does not have any breaks or hinges along its length. This is in contrast to certain other embodiments described above.

One or more struts 3404 are preferably attached at one or more points to the long strip 3402. Preferably, these struts 3404 are movably attached, for example via a hinge-like attachment or flexible joint, such that these may collapse in a direction perpendicular to a longitudinal length defined by the length of the one or more long strips 3402. In some embodiments, the struts 3404 may be angled at a non-perpendicular angle with respect to the long strip 3402 so as to collapse more readily. In embodiments comprising two or more long strips 3402, the struts 3404 may be hinged between two parallel long strips 3402.

It will be recognized that while these struts 3404 may be configured to collapse along a direction perpendicular to the longitudinal length of the one or more long strips 3402, the struts 3404 are preferably rigid in a vertical direction (i.e., in the direction extending upward from a plane defined by the wound 3405). As such, a combination of the struts 3404 and the long strips 3402 may thus form a stabilizing structure 3400 that is substantially rigid in a vertical direction while being collapsible in a horizontal direction perpendicular to the longitudinal axis of the long strips 3402 (i.e., in the plane of the wound 3405).

Figure 27A:
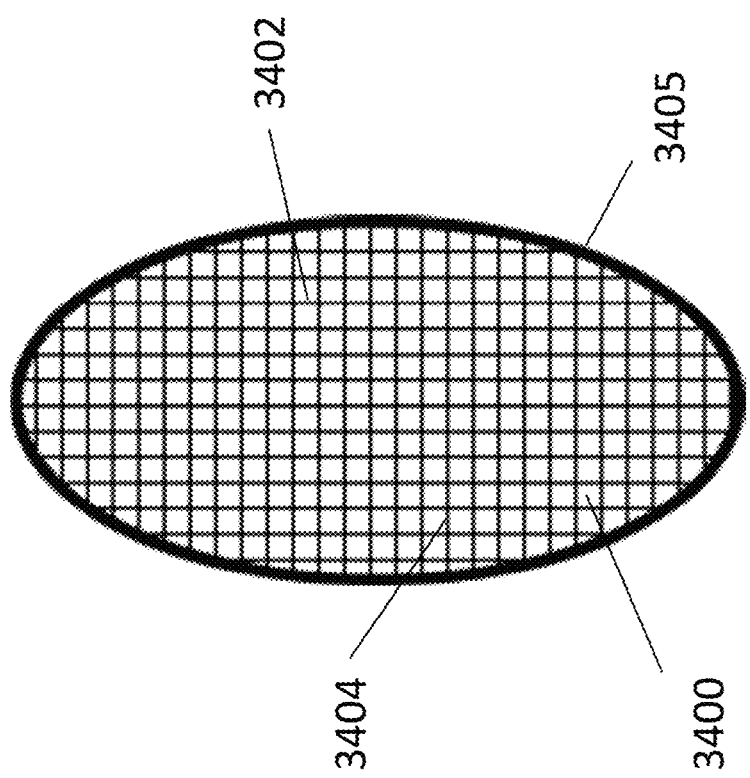
FIG. 27A illustrates a top view of an embodiment of an oval shaped stabilizing structure.

FIG. 27A illustrates a top view of an embodiment of stabilizing structure 3400 cut into an oval shape and inserted into a wound 3405. Preferably, the stabilizing structure 3400 comprises a plurality of elongate strips 3402 whose longitudinal length may be oriented along a longitudinal axis of the wound 3405, or along a direction along which closure is sought. Each of the plurality of elongate strips 3402 is preferably substantially rigid and extends substantially along the entire length of the wound 3405. A plurality of intervening members are positioned between adjacent elongate strips 3402. These intervening members may be struts 3404 as described with respect to FIG. 26, preferably attached at one or more points to the elongate strips 3402. The intervening members may also be portions of elongate strips such as described with respect to FIGS. 23A-25E above, extending perpendicular or at an angle to elongate strips 3402. The stabilizing structure of FIG. 27A may also comprise the embodiments described with respect to FIGS. 21A-22F.

Figure 27B:
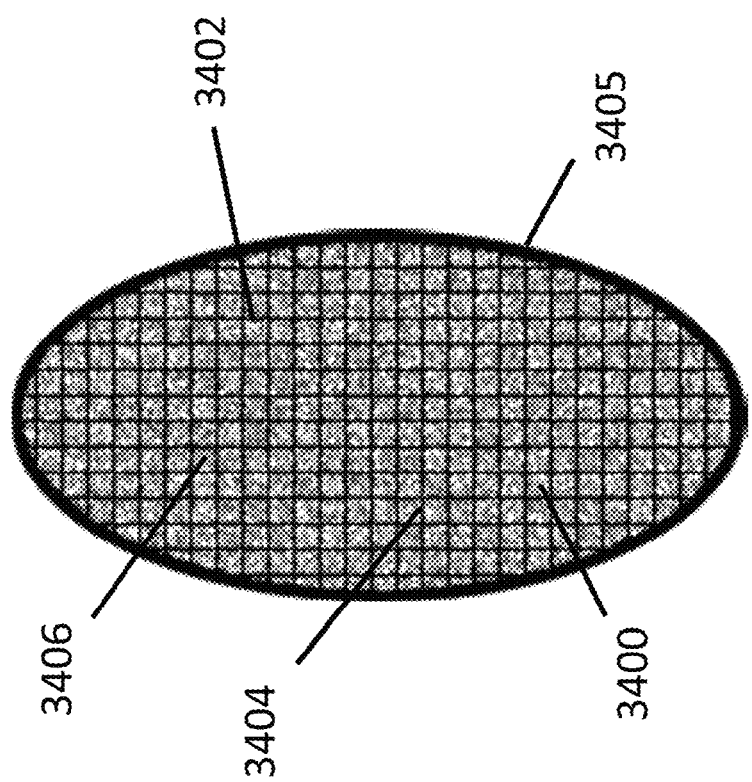
FIG. 27B illustrates a top view of an embodiment of an oval shaped stabilizing structure with foam.

FIG. 27B illustrates a top view of an embodiment of an oval shaped stabilizing structure 3400 inserted into a wound 3405. This embodiment may have the same configuration as described above with respect to FIG. 27A. Additionally, foam 3406 can be inserted between and around the stabilizing structure.

Stabilizing Structures and Wound Closure Devices of FIGS. 28A-31 and 33-35

Figure 28A:
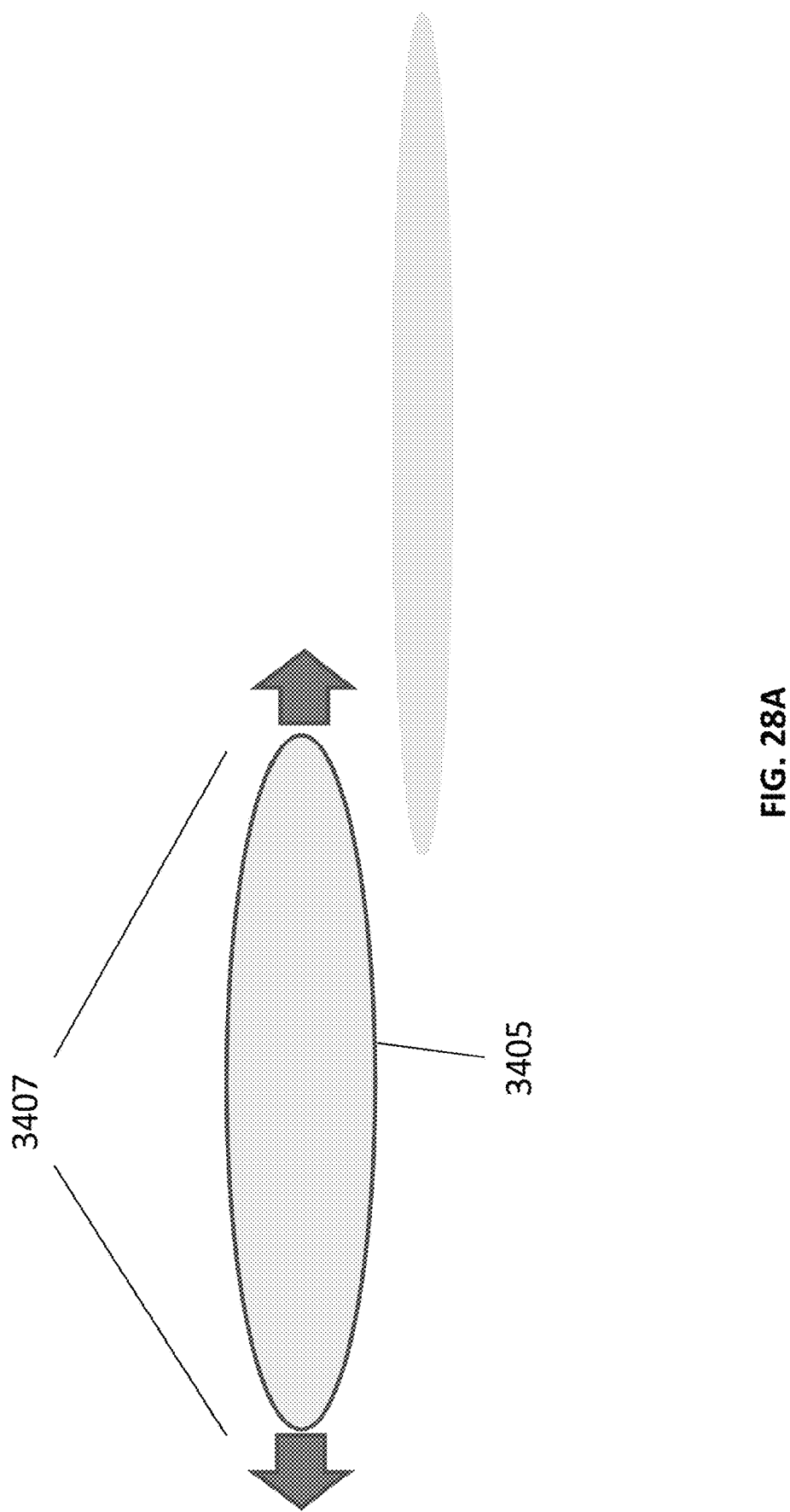
FIGS. 28A-B illustrate embodiments of methods for closing a wound.

FIG. 28A illustrates an embodiment of a method for the closure of a wound using any of the stabilizing structures described in this section or elsewhere in this specification before or as hereafter described, through the application of tension along an axis of wound 3405. In this example, when the wound is viewed from above, tension is applied along the longitundinal axis of the wound, generally represented by arrows 3407. Tension along the longitundinal axis prevents contraction of the wound along the longitudinal axis, however the tension along the longitudinal axis can cause the lateral edges of the wound to be drawn together, promoting wound closure. In some embodiments, additional inward tension can be applied to the lateral edges of the wound, thereby providing additional wound closing force.

Figure 28B:
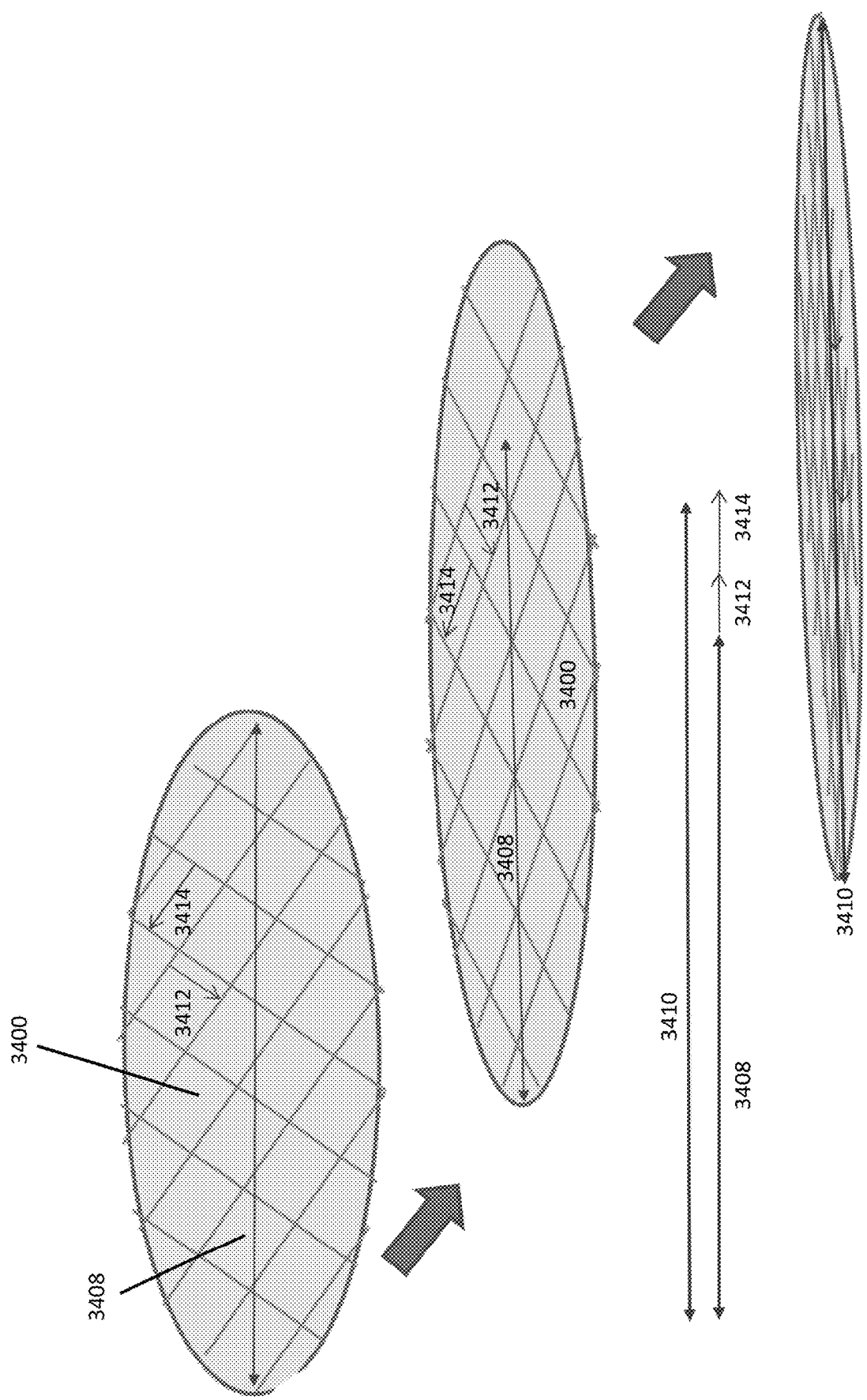

FIG. 28B illustrates an embodiment of a method for the closure of a wound through the use of a stabilizing structure 3400 that collapses and lengthens when a wound is treated under negative pressure. As illustrated, the stabilizing structure 3400 may be cut to an appropriate size to approximate the shape of the wound (e.g., in an oval shape), and the stabilizing structure is placed in the wound 3405. In some embodiments as described above, the stabilizing structure may have a plurality of diamond-shaped cells, and the cells are arranged in the wound in an orientation that causes the cells to be flattened as the lateral edges of the wound come closer together, while becoming longer along the longitudinal axis of the wound. It will be recognized that while this structure is configured to collapse under negative pressure horizontally within the wound in a direction perpendicular to the longitudinal axis of the wound, the structure is substantially rigid in the vertical direction. Line 3408 represents the length of the structure prior to lengthening under negative pressure, while line 3410 represents the final length of the structure after collapsing and lengthening under negative pressure. Lines 3412 and 3414 represent the lengths of particular sections within the stabilizing structure. In certain embodiments, when a wound is treated with application of negative pressure, the structure will collapse inward on one axis, thereby lengthening the structure by some additional amount in another axis that can be the sum of the lengths of lines 3412 and 3414. In some embodiments, the structure can lengthen by amounts other than the sum of lines 3410 and 3412.

In some embodiments, the collapse can occur slowly, thereby applying increasing longitudinal tension over a long period of time. In certain embodiments, the collapse and lengthening of the structure can occur immediately upon application of negative pressure. In further embodiments, the collapse can occur at any rate.

Figure 29A:
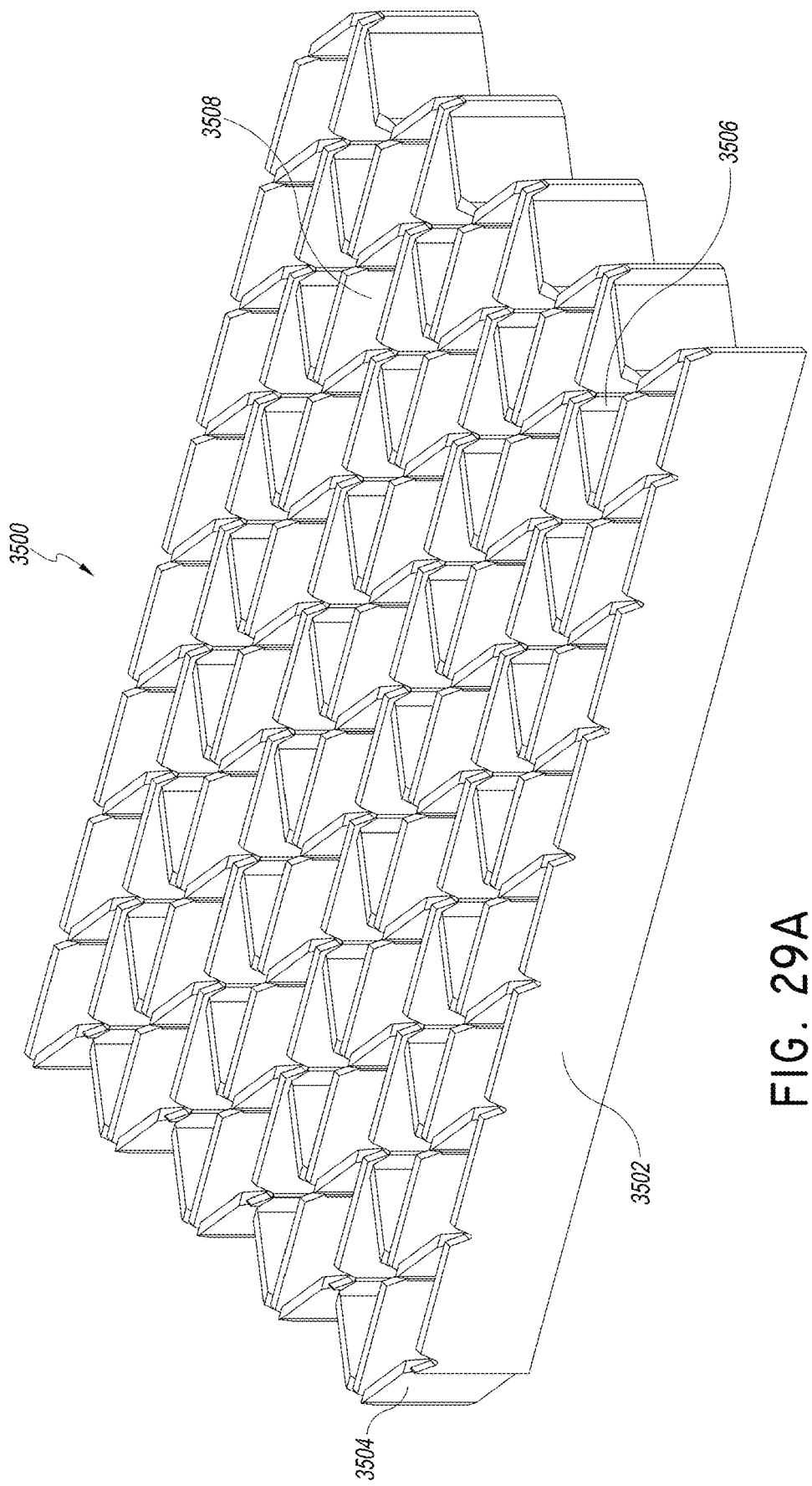
FIGS. 29A-C illustrate multiple views of an embodiment of a stabilizing structure.
Figure 29B:
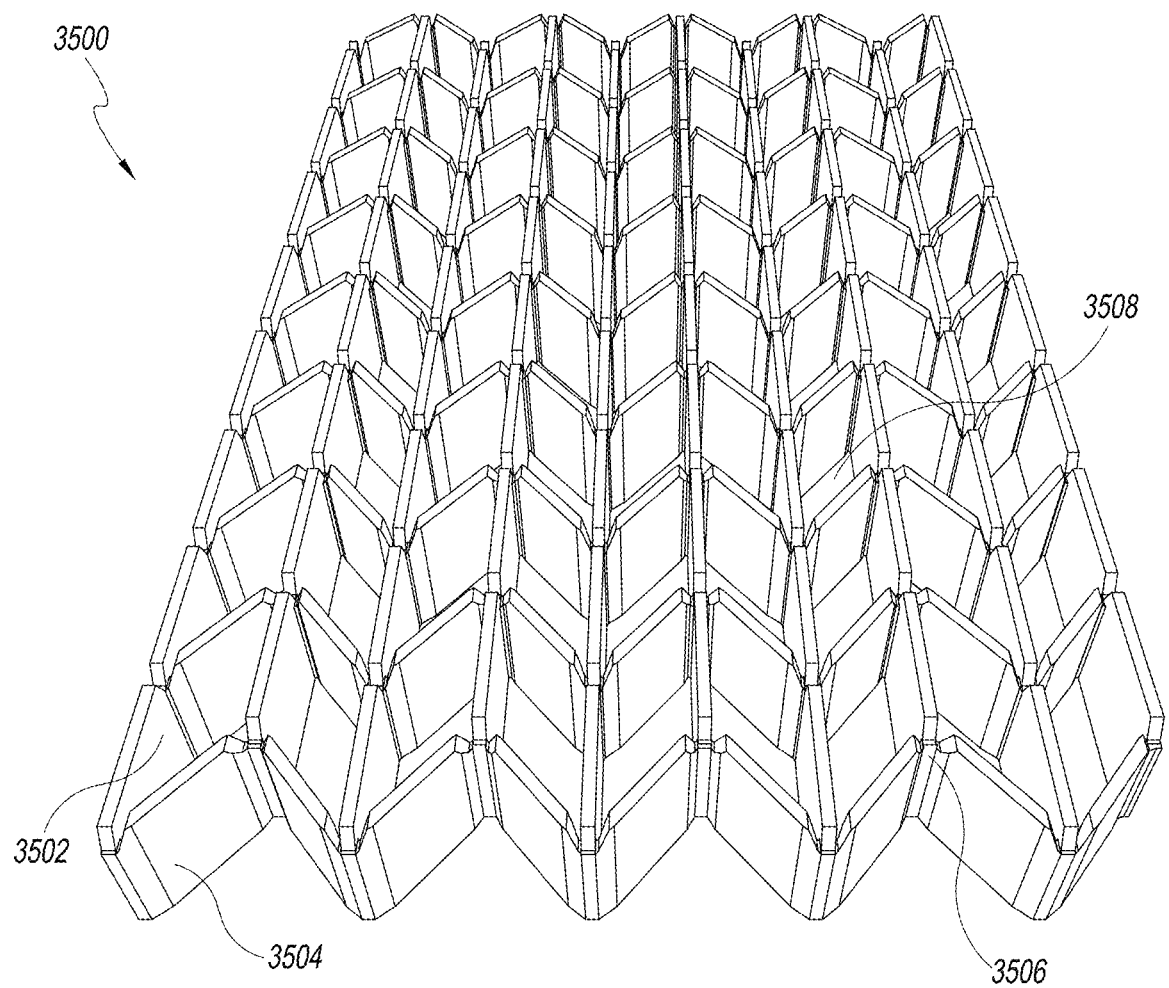
Figure 29C:
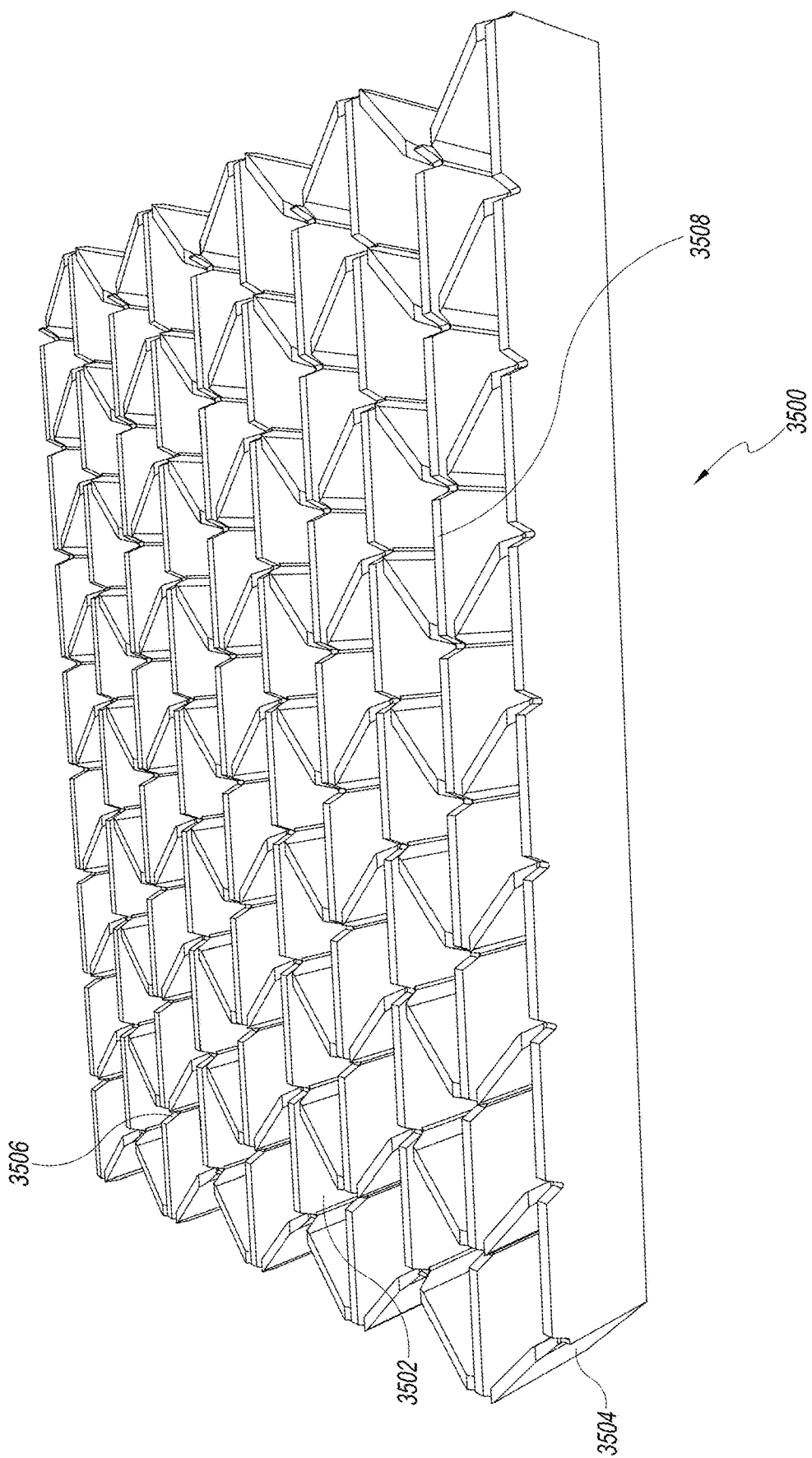

FIGS. 29A-C illustrate another embodiment of a stabilizing structure 3500. The stabilizing structure 3500 comprises a plurality of elongate strips 3502 arranged in parallel, and whose longitudinal length can be aligned with the longitudinal axis of a wound when placed in a wound. The stabilizing structure further comprises a plurality of intervening members 3504 connected to the elongate strips 3502 by a plurality of joints 3506. As illustrated, the plurality of intervening members 3504 between adjacent elongate strips 3502 define a row of cells 3508 between each pair of adjacent elongate strips.

In some embodiments, the elongate strips 3502 are rigid. In certain embodiments, the elongate strips 3502 are semi-rigid. In particular embodiments, the elongate strips 3502 are flexible. In some embodiments, the elongate strips 3502 are compressible. As illustrated in FIGS. 29A-29C, one embodiment comprises a plurality of strips that are rigid in a vertical dimension but also are flexible and capable of bending along their length.

In some embodiments, the intervening members 3504 are rigid. In certain embodiments the intervening members 3504 are semi-rigid. In particular embodiments, the intervening members are flexible. In some embodiments, the intervening members 3504 are compressible. As illustrated in FIG. 29A-29C, one embodiment comprises intervening members in the form of panels equally spaced apart between adjacent strips, to define a plurality of similar-shaped (e.g., diamond-shaped) cells. In other embodiments, the intervening members need not be equally spaced. The intervening members may be attached to the strips by joints 3506 in the form of a hinge (e.g., a living hinge or a more flexible piece of material between the strips and the intervening members).

In some embodiments, the plurality of intervening members 3504 are configured to pivot relative to the elongate strips 3502 and to collapse so as to allow the elongate strips to collapse relative to one another and come closer together. In some embodiments, the joints 3506 are configured to pivot and collapse in only one direction. In certain embodiments, the joints 3506 are configured to pivot and collapse in both directions, comprising a full 180 degrees of rotation relative to the elongate strips 3502. In certain embodiments, when the joints pivot, they pivot completely so as to rest the intervening members 3504 against the elongate strips 3502. In some embodiments, the joints do not pivot completely and the intervening members do not come to rest against the elongate strips 3502.

Preferentially, in certain embodiments, by controlling the direction in which the pivoting occurs, the collapsed length of the stabilizing structure 3500 can be controlled. In particular embodiments, because of the rigidity of the elongate strips, the cells 3508 in a row between adjacent elongate strips are configured to collapse together as the adjacent elongate strips 3502 collapse relative to one another. In some embodiments, one or more rows of cells 3508 between adjacent strips 3502 are configured to collapse in a first direction, and one or more rows of cells between adjacent strips 3502 are configured to collapse in a second direction opposite the first direction. As illustrated in FIGS. 29A-29C, the orientation of cells in adjacent rows alternates so that cells of a first row collapse in a first direction, and cells of a next row collapse in an opposite second direction. Joints 3506 may be configured so that joints 3506 in adjacent rows collapse in different directions.

By configuring the joints 3506 and/or cells of the stabilizing structure to pivot and collapse in preferred directions, the length of the collapsed structure can be modified. The embodiment shown in FIGS. 29A-29C will have a shorter collapsed length than a structure where all the rows of cells 3508 are configured to collapse in the same direction. Thus, the collapsed length of the structure can be controlled depending on the orientation of the cells and the direction in which the intervening members collapse between adjacent rows. In some embodiments as described above with respect to FIGS. 28A-28B, the stabilizing structure preferably lengthens after collapse under negative pressure. In other embodiments, it may be preferred that the stabilizing structure not lengthen after collapse under negative pressure.

In FIGS. 29A-29C, the intervening members 3504 in adjacent rows are generally aligned so that the intervening members connect to the elongate strips at approximately the same location on opposite sides of the strip and share the same joint 3506 location. In other embodiments, the intervening members 3504 between a first elongate strip 3502 and a second elongate strip 3502 are offset relative to intervening members 3504 between the second 3502 and a third adjacent strip 3502. In these embodiments, the intervening members 3504 are staggered such that they do not share the same joint 3506 location.

As shown in FIGS. 29A-29C, the enclosed cell 3508 formed by two intervening members and two sections of the elongate strips is a quadrilateral. In some preferred embodiments, the enclosed shape can be a square, rectangle, diamond, oblong, oval, and/or parallelepiped. In some embodiments, the enclosed shape is a rhomboid. In certain embodiments the enclosed shape is a trapezoid.

In certain preferred embodiments, the joint 3506 may be configured to limit the range of motion of the intervening member 3504, and may be used to prevent the intervening members 3504 from becoming fully perpendicular to the adjacent strips. Thus, the joint may be configured to pre-set the intervening members 3504 in a partially collapsed position. For example, a lip or other portion of material at the joint may be used to limit the angular motion of the intervening members. The lip or other portion of material may also prevent the joint from collapsing completely flat. In some embodiments, the joint may be configured to prevent the intervening members from rotating in 180 degrees along the plane formed by the strips.

In some embodiments, when the stabilizing structure 3500 is placed in a wound, the elongate strips 3502 are positioned generally parallel to the lateral edges of the wound. Preferably, the stabilizing structure is configured in the wound such that the elongate strips are positioned parallel to the longitudinal axis of the wound, as described with respect to FIGS. 28A-28B above. The strips may also bend along their length and bow outwardly to fit within the wound. The stabilizing structure may be cut to an appropriate size to fit the structure in the wound. In other embodiments, the elongate strips 3502 are positioned perpendicular to the edge of the wound, or may not be oriented along any edge of the wound.

In the embodiments of FIGS. 29A-29C, as well as in other embodiments of stabilizing structures described in this section or elsewhere in this specification, the strips can be constructed from a material selected from the group consisting of silicone, polyurethane rigid plastics, semi-rigid plastics, flexible plastic materials, composite materials, biocompatible materials and foam. In some embodiments, the intervening members can be constructed from a material selected from the group consisting of silicone, polyurethane, rigid plastics, semi-rigid plastics, flexible plastic materials, composite materials, biocompatible materials and foam. In some embodiments, the stabilizing structure is surrounded by absorbent materials. In certain embodiments the stabilizing structure is surrounded by non-absorbent materials. In some embodiments the material surrounding the stabilizing structure is foam. In particular embodiments, the spaces between the intervening members 3504 and the elongate strips 3502 are filled with foam.

Figure 30A:
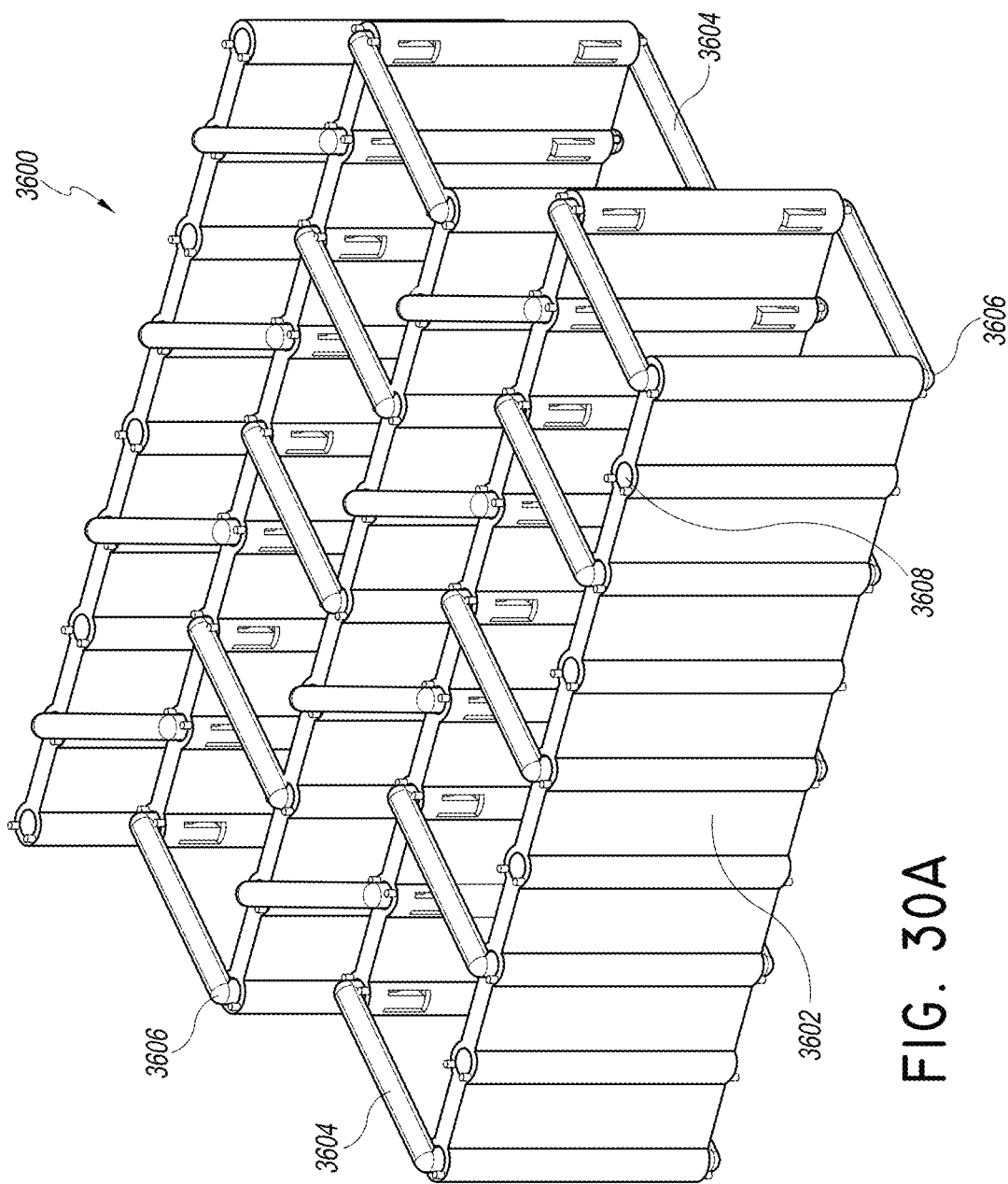
FIGS. 30A-G illustrate multiple views of an embodiment of a stabilizing structure.

FIGS. 30A-G illustrate an embodiment of a stabilizing structure 3600 that is similar to the ones described above in relation to FIGS. 29A-C and FIG. 28B. As illustrated in FIG. 30A, in some embodiments, the stabilizing structure 3600 comprises a plurality of elongate strips 3602 connected by a plurality of intervening members 3604 at a plurality of joints 3606. As illustrated in FIGS. 30A-G, the plurality of intervening members comprise a plurality of bars 3604 connecting adjacent elongate strips and connected to the elongate strips at upper and lower joint locations. The plurality of joints in one embodiment comprise a plurality of pins 3606 connected to the bars and received in upper and lower vertical openings in the strips 3602. Other types of joints are also contemplated, including ball joints. The bars are preferably equally spaced within a row between adjacent elongate strips, and may be offset or staggered in an adjacent row, such that in an adjacent row, the bars connect to the elongate strip at a location between the bars of the first row. In other embodiments, the intervening member can comprise a wire or other elongate structure configured to extend between adjacent elongate strips.

Figure 30B:
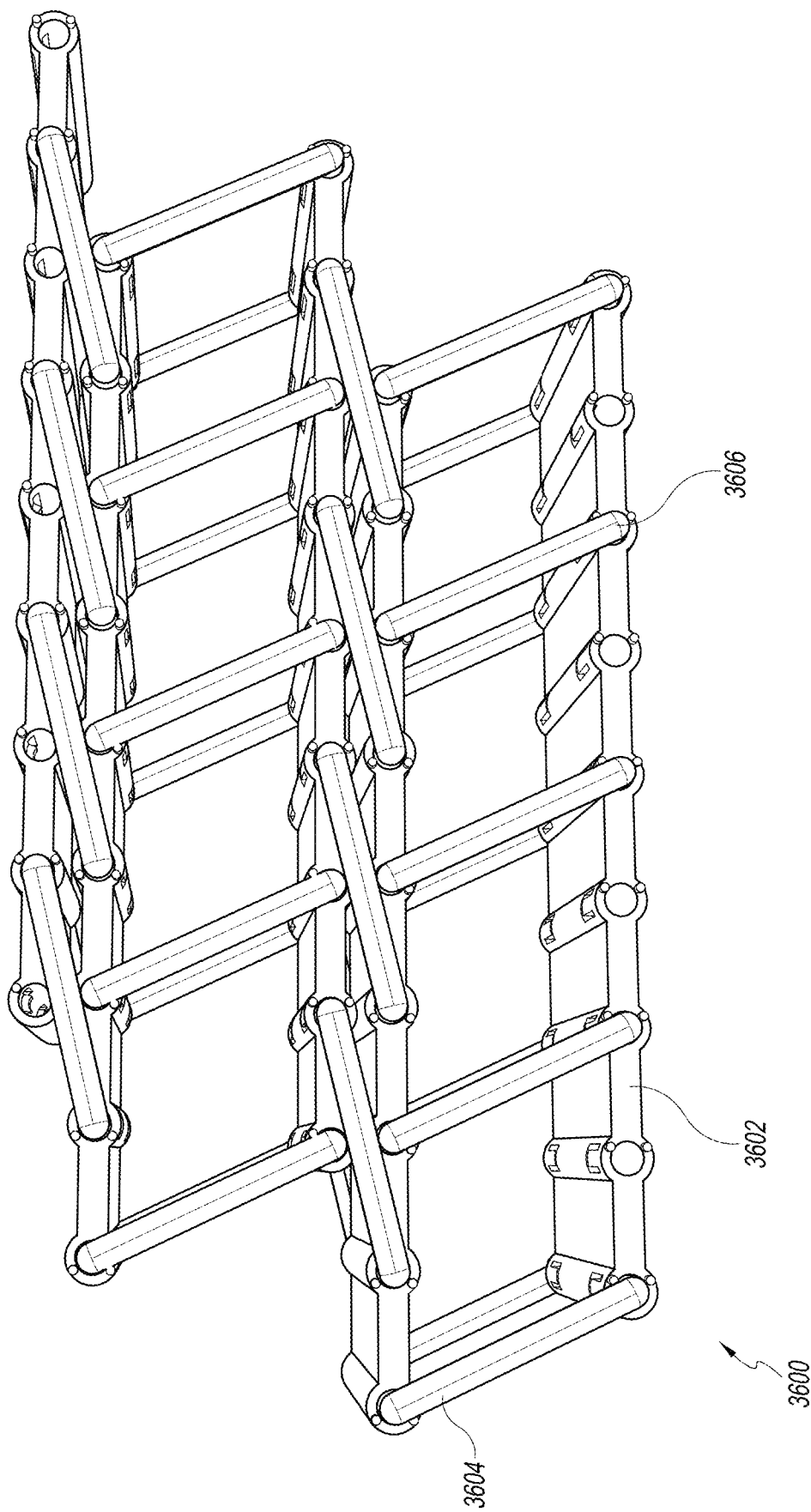
Figure 30C:
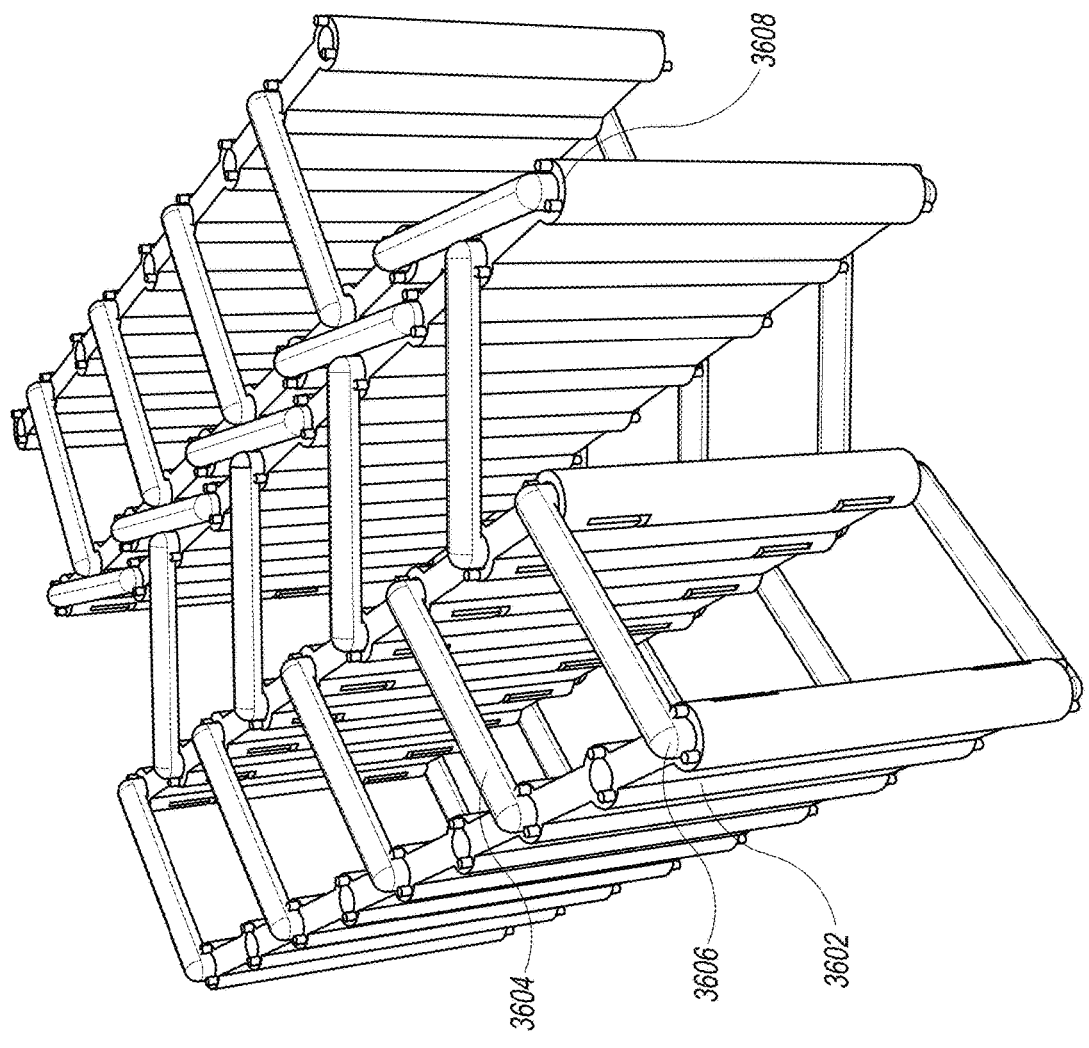
Figure 30D:
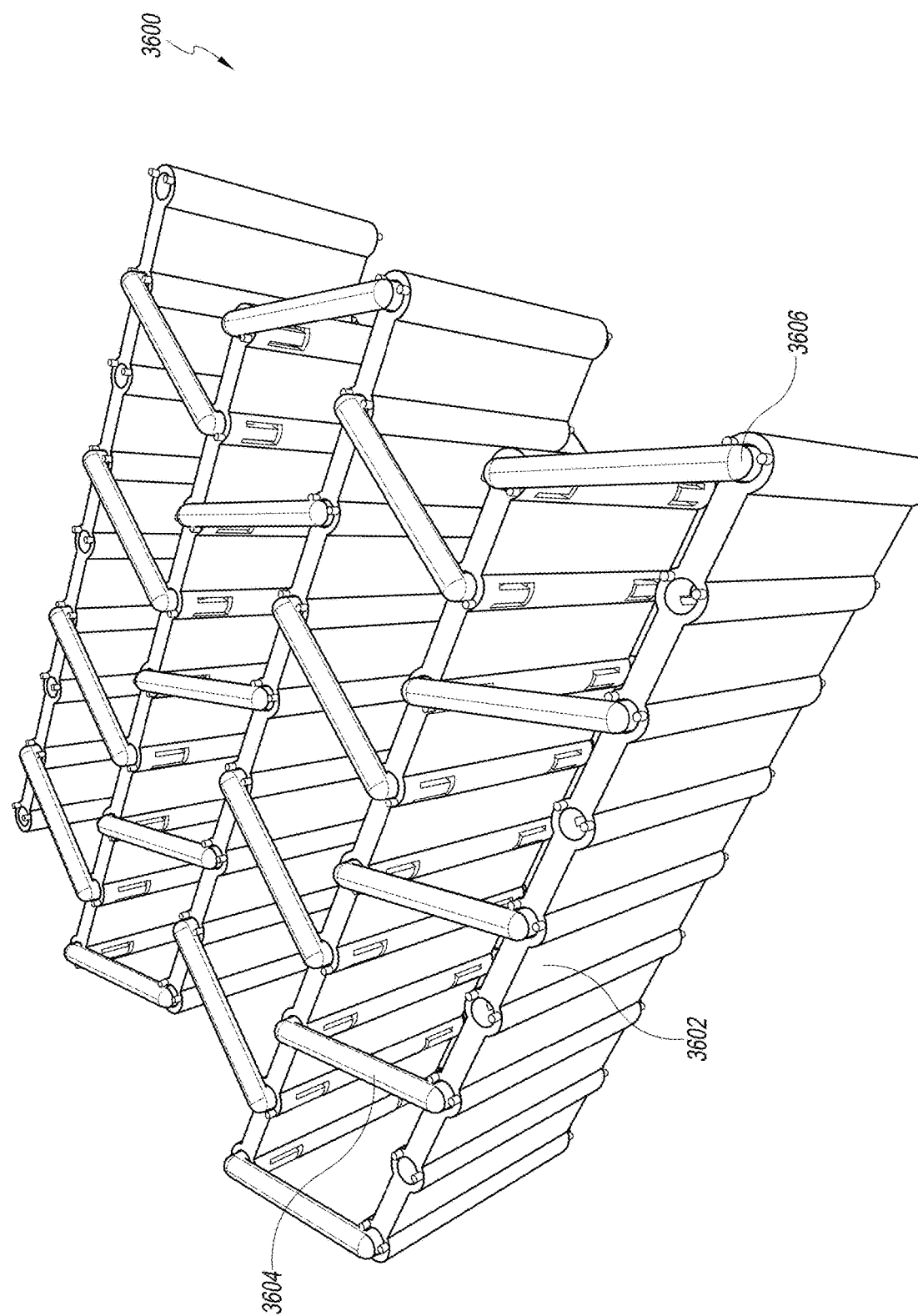

Preferably, as illustrated in the top view of FIG. 30B and the front view of FIG. 30C, in certain embodiments the pins cause the bars to protrude above the vertical top and the vertical bottom of the elongate strips 3602. In other embodiments, the bars 3604 may be connected to the elongate strips so that they are located flush with the vertical top and vertical bottom of the elongate strips 3602. In further other embodiments, the bars 3604 may be connected so that they are located below the vertical top of the elongate strips 3602 and above the vertical bottom of the elongate strip.

As illustrated in FIGS. 30A and 30C, the joints 3606 can preferably comprise a plurality of stops 3608 configured to limit the rotation of the bars relative to the strips. The stops may protrude vertically from the strips to limit the movement of the bars. For example, these stops may be used to prevent the bars from becoming fully perpendicular with respect to the adjacent strips, and may be used to provide a preferential direction of collapse to adjacent rows. As shown in FIG. 30A, a first row may have bars angled in a first direction, and a second row may have bars angled in a second direction. In some embodiments, there are two stops per bar on a given strip, to restrict motion in two directions. In other embodiments, there is one stop or three or more stops per bar on a given strip.

Figure 30E:
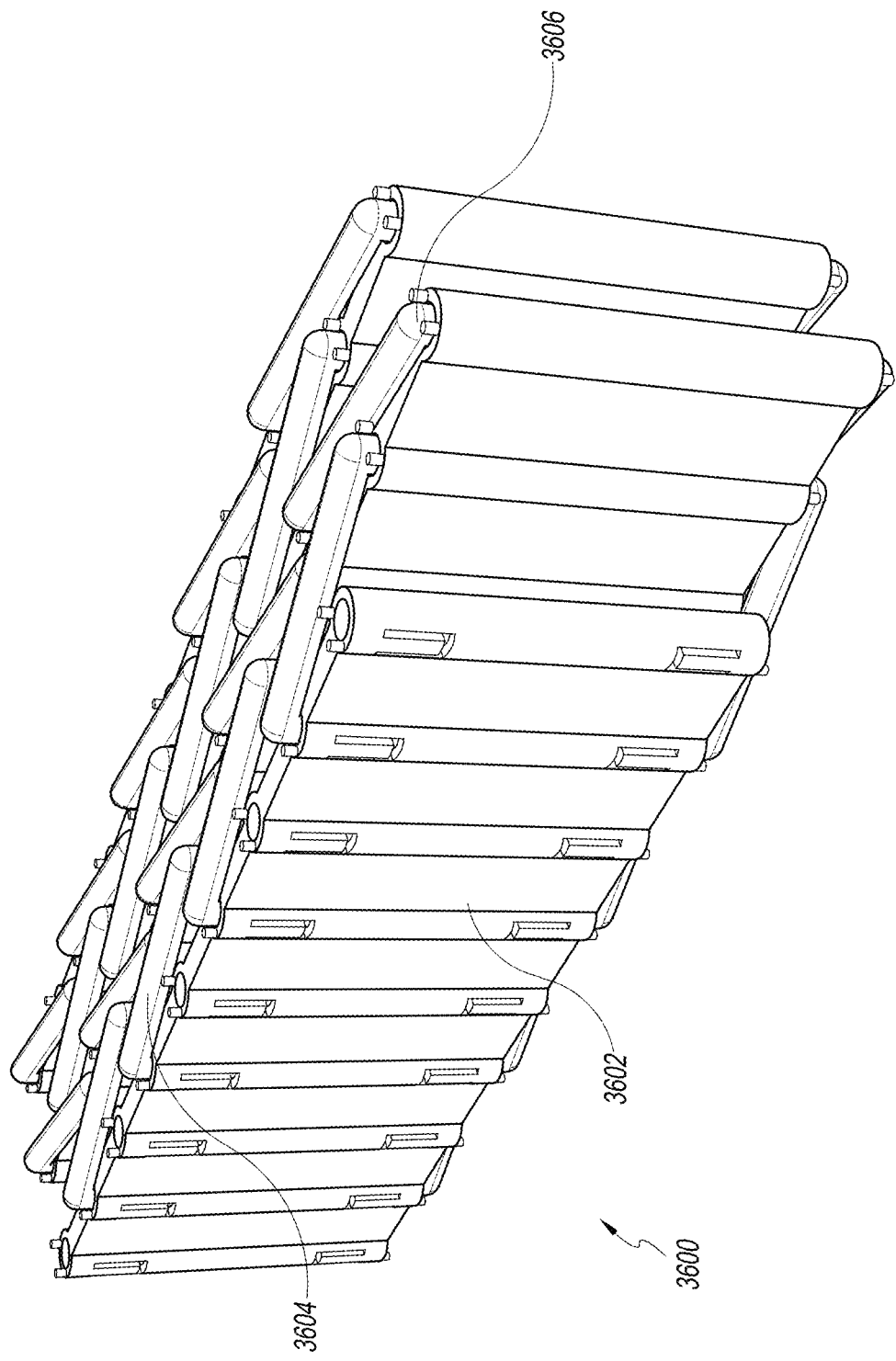
Figure 30F:
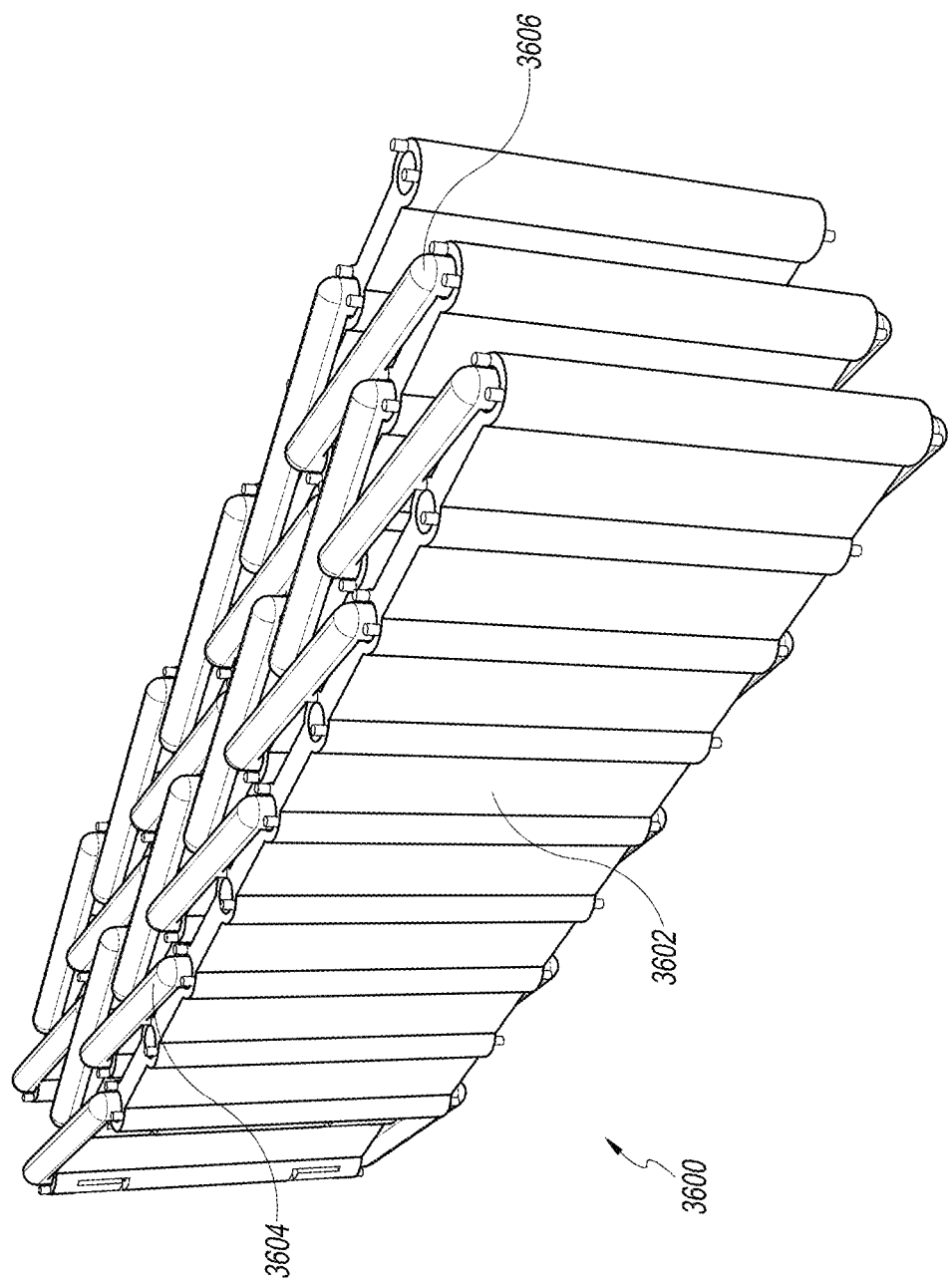
Figure 30G:
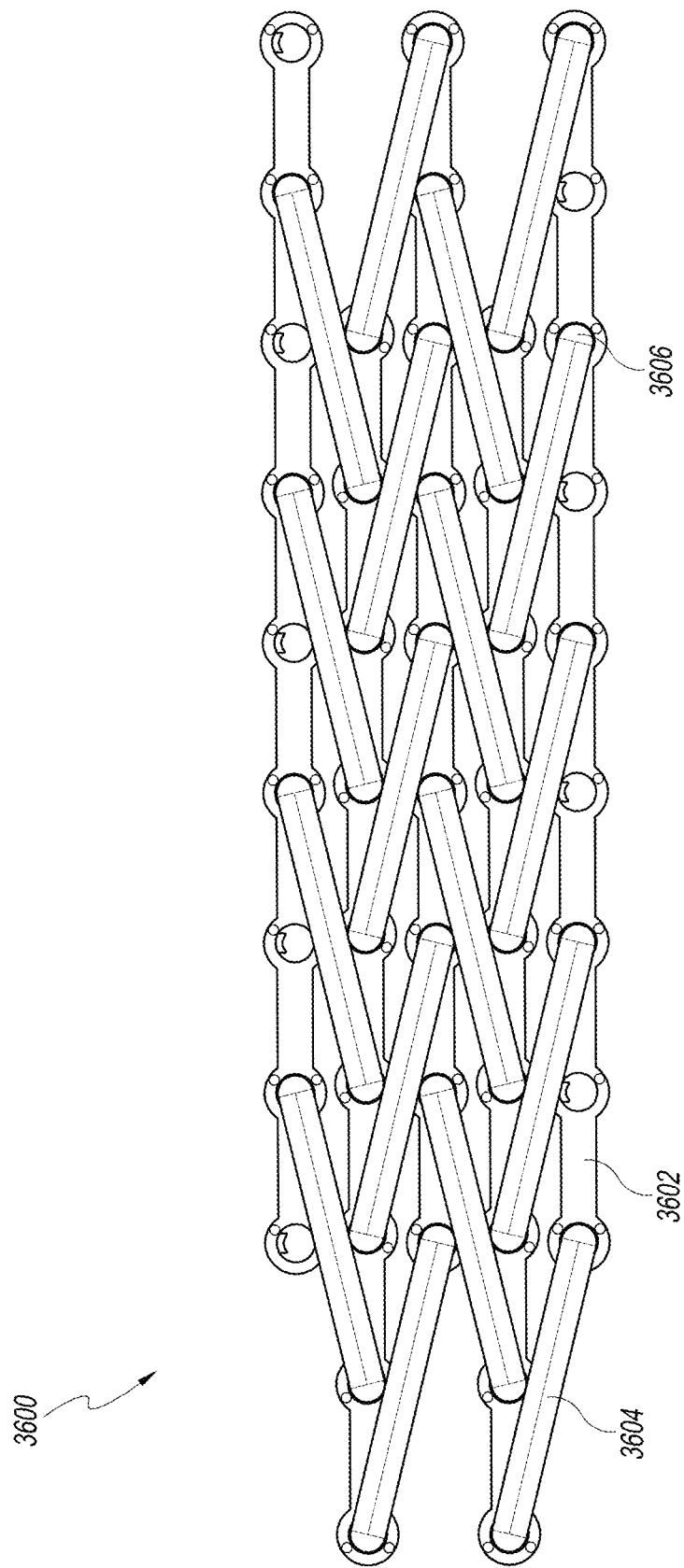

FIGS. 30E-G illustrate the stabilizing structure 3600 in a collapsed configuration. Similar to the structures of FIGS. 29A-C and FIG. 28B, the structure 3600 may be positioned in a wound in an orientation configured to collapse in a direction perpendicular to the longitudinal axis of the wound. As described above, the stabilizing structure may be surrounded by or filled with absorbent material such as foam. In one embodiment, because the vertical space between the upper and lower bars of the structure 3600 are open (as best shown in FIG. 30C), elongate blocks of foam or other compressible material may be placed in between adjacent strips to provide a desired compressibility as the structure collapses.

Figure 31:
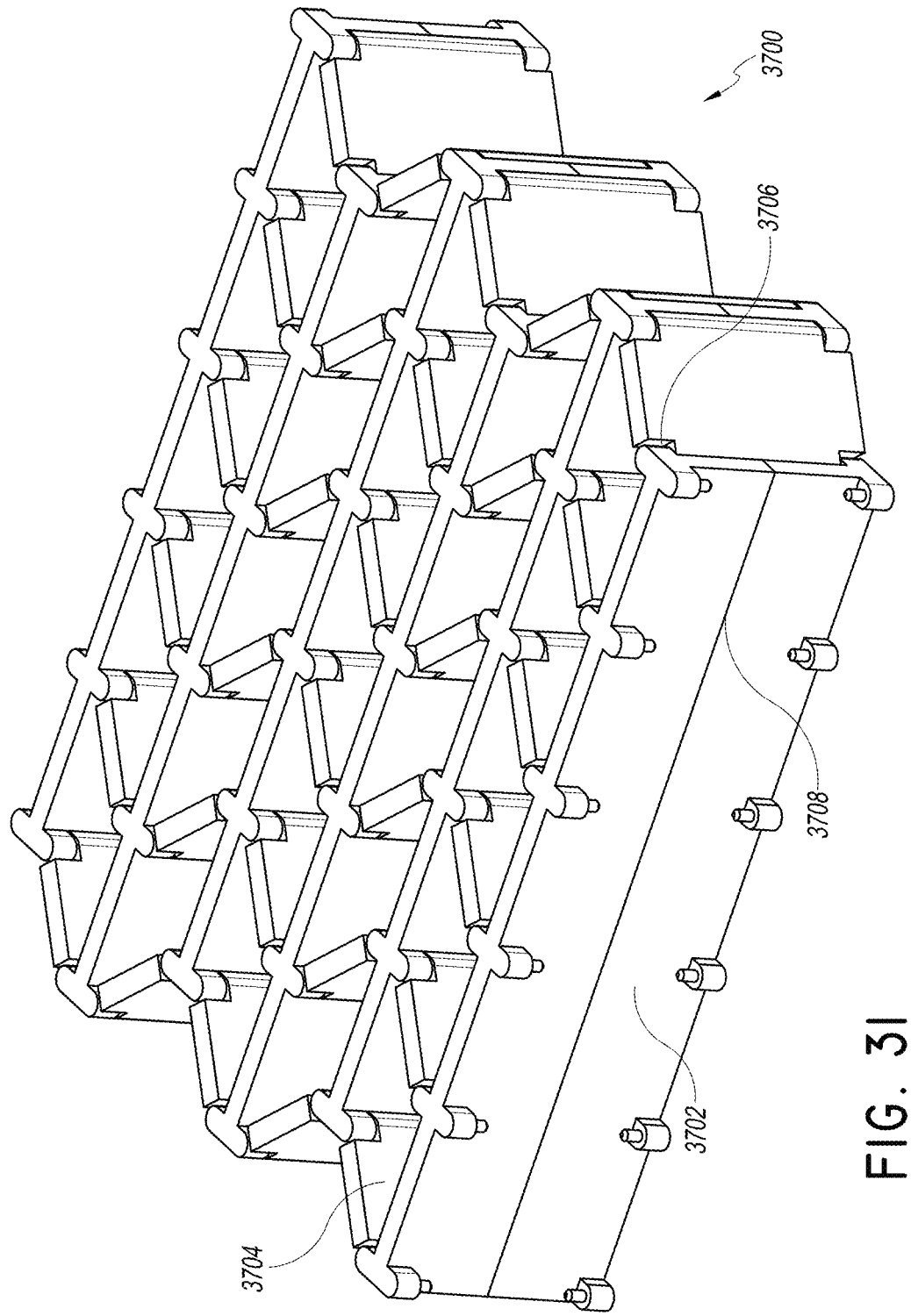
FIG. 31 illustrates one embodiment of a hinged stabilizing structure for closing a wound.

FIG. 31 illustrates an embodiment of a stabilizing structure 3700 that is similar to the structures described above in relation to FIG. 28B, FIGS. 29A-C and FIGS. 30A-G. In certain embodiments, the stabilizing structure 3700 can collapse in any manner described above. The elongate strip 3702 as illustrated is formed in two halves, and can be separated along line 3708. The intervening members 3704 can be in the form of panels as described above. The joints 3706 on the upper half of an elongate strip may comprise pins located on opposite sides of the strip extending downward from the top of the upper half of the strip. The joints 3706 on the lower half of an elongate strip may comprise pins located on opposite sides of the strip extending upward from the bottom of the lower half of the strip. These pins may engage vertical openings located at the four corners of the intervening member 3704. As the upper and lower halves are brought together, the pins may engage the openings in the panels. The upper and lower halves may be secured by any number of mechanisms, such as with adhesive and mechanical connections.

In the FIG. 31 embodiment, with the ability to separate the two halves of 3702 along line 3708, intervening members 3704 may be easily removed or replaced. In some embodiments, only some of the intervening members 3704 are removed. In certain embodiments, alternating intervening members 3704 are removed. In certain preferred embodiments, intervening members are removed in a preferential manner so as to allow the stabilizing structure 3700 to collapse in a controlled manner most appropriate for a particular wound. For example, the joints 3706 may have variable levels of resistance to rotation, thus allowing for control over the collapse of the structure by adding or removing the intervening members 3704. Additionally, stops such as those described in relation to FIG. 30A, could be incorporated into the structure or any other structure described in this section or elsewhere in this specification to further control collapse. In some embodiments, the intervening members are replaced or removed to maximize the collapsed length of the structure 3700. In certain embodiments, intervening members are replaced or removed to minimize the collapsed length of structure 3700. In some embodiments, intervening members are replaced or removed to attain a desired length for the collapsed structure.

Figure 33:
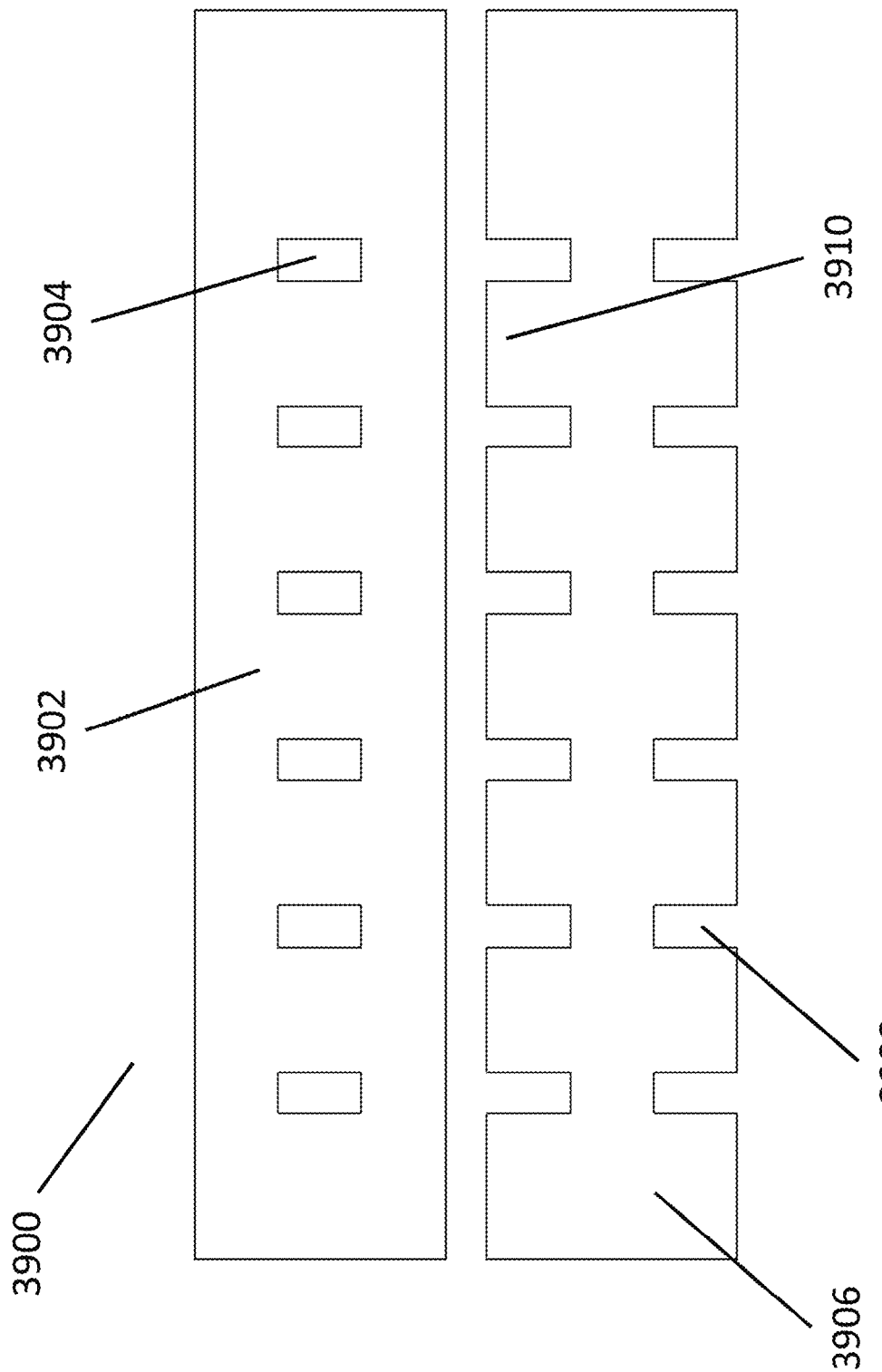
FIG. 33 illustrates one embodiment of a stabilizing structure for a wound.

FIG. 33 illustrates another embodiment of elongate strips 3900 that may be used to form a stabilizing structure, similar to that described in FIGS. 8A-D. The first strip 3902 illustrated in the upper portion of FIG. 33 may be an elongate strip having a plurality of spaced apart openings 3904 extending along a central axis of the strip. The second strip 3906 illustrated in the lower portion of FIG. 33 may have a plurality of spaced apart notches 3908 extending from the upper and lower edges of the second strip and separate by a middle portion. A plurality of the first strips 3902 and a plurality of the second strips 3906 can be assembled into a stabilizing structure similar to what is shown in FIGS. 8A, 8C and 8D, wherein the plurality of first strips 3902 are arranged in parallel to each other, and the plurality of second strips 3906 are arranged in parallel to each other. The plurality of first 3902 and second strips 3906 engage one another by the middle portions 3910 of the second strips positioned through the openings 3904 in the first strips, to place the plurality of first strips at an angle to the plurality of second strips. This structure is configured to collapse in a horizontal plane while remaining rigid in the vertical plane.

Figure 34:
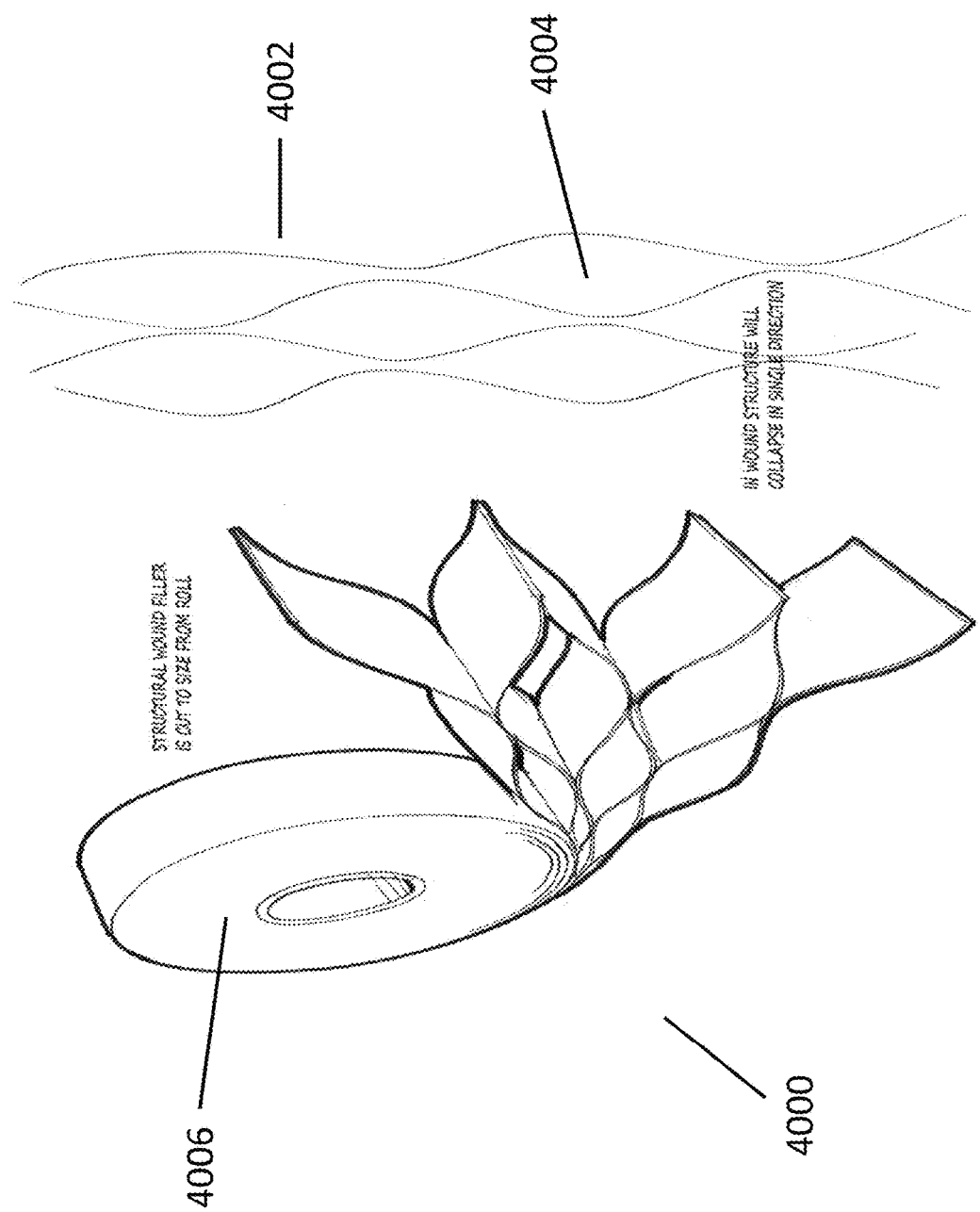
FIG. 34 illustrates an embodiment of a stabilizing structure for a wound cut from a roll.

FIG. 34 illustrates an embodiment of a stabilizing structure 4000 similar to the embodiment of FIG. 13 described above. A plurality of longitudinal strips 4002 can be provided each in the form of a wavy strip that, when joined face-to-face, form one or more circular or ovoid cells 4004. The entire structure can be collapsed into a substantially flat configuration, and can be contained within a roll 4006. To use the stabilizing structure, a portion of the structure can be unrolled and cut at a desired length. Preferably, as the stabilizing structure is unrolled it expands to its natural, deployed configuration. It will be appreciated that other embodiments of the stabilizing structure, and not just embodiments using the wavy strips of FIG. 13, may be assembled into a rolled configuration.

Figure 35:
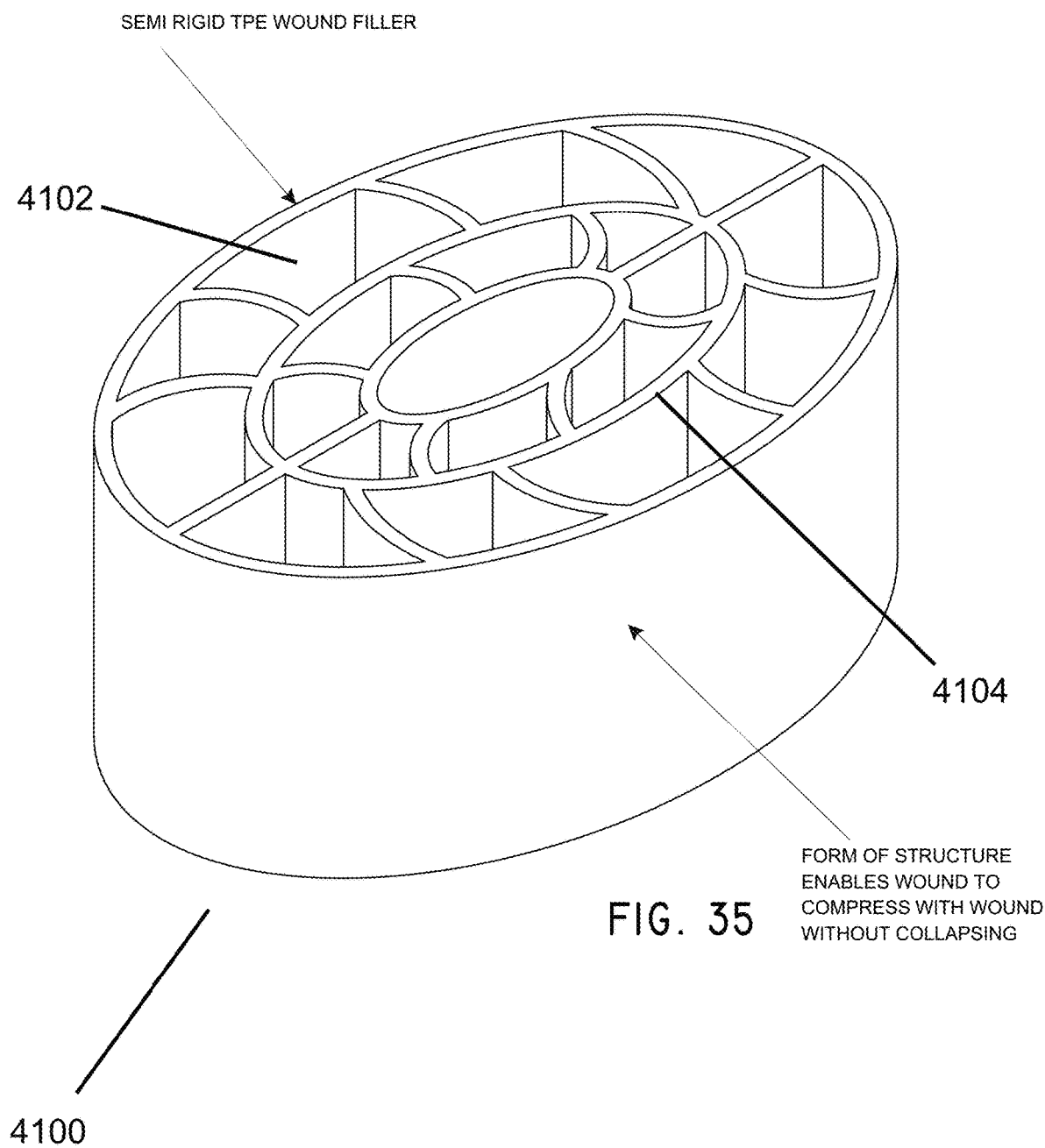
FIG. 35 illustrates an embodiment of a stabilizing structure having an oval shape.

FIG. 35 illustrates another embodiment of a stabilizing structure. In this embodiment, the stabilizing structure 4100 has an elongate, preferably oval shape, wherein cells 4102 within the oval shape have a plurality of cells arranged in a plurality of concentric rings 4104. In the embodiment illustrated, a central oval cell is surrounded by two oval-shaped rings. Other embodiments can include more than two oval-shaped rings.

Stabilizing Structures and Wound Closure Devices of FIGS. 36A-44

FIGS. 36A-F illustrate embodiments of a stabilizing structure 4200 that are similar to the embodiments described above in relation to FIGS. 29A-32. The stabilizing structure may comprise a plurality of elongate strips 4202 arranged in parallel, whose longitudinal length can be aligned with the longitudinal axis when placed in a wound. The stabilizing structure can further comprise a plurality of intervening members 4204 connected to the elongate strips 4202 via joints 4206. In certain embodiments, the stabilizing structure 4200 can collapse in any manner described in this section or elsewhere in this specification with or without the application of negative pressure. For example, the stabilizing structure may collapse significantly more in one plane than in another plane. In some embodiments, the stabilizing structure can be comprised of any materials described in this section or elsewhere in this specification, including: flexible plastics such as silicone, polyurethane, rigid plastics such as polyvinyl chloride, semi-rigid plastics, semi-flexible plastics, biocompatible materials, composite materials, metals, and foam.

The stabilizing structure 4200 and all stabilizing structures and wound closure devices described in this section or elsewhere in this specification can collapse on a variety of timescales in a dynamic fashion. In certain embodiments, the majority of the collapse may occur within the first few minutes upon application of negative pressure. However, after the initial collapse, the stabilizing structure or wound closure device may continue to collapse at a much slower rate, thereby applying increasing longitudinal tension over a long period of time and drawing the edges of the wound closer together. By slowly drawing the wound edges closer together over time, the stabilizing structure or wound closure device allows the surrounding healing tissue to remodel synergistically with the closure of the device or stabilizing structure. Slow, dynamic wound closure may allow the surrounding tissue to heal at an accelerated rate, because the collapsing structure or device slowly brings the edges of the wound closer together without stressing the newly formed or weakened tissue too quickly.

In some embodiments, the stabilizing structures described in this section or elsewhere in this specification can placed into a wound for a period of time and then removed or replaced with another stabilizing structure. For example, a stabilizing structure could be inserted into a wound for a period of time, promoting closure of the wound by drawing the edges closer together. After a period of time has passed, the stabilizing structure can be replaced by a stabilizing structure of a different size or collapsibility, for example a stabilizing structure of a smaller size or decreased density. This process could be repeated over and over, thereby continuously drawing the edges of the wound together over time and allowing for continuing repair and remodeling of the surrounding tissue.

In some embodiments, the stabilizing structure is configured to remain in the wound for at least about less than 1 hour, at least about 1 hour, at least about 2 hours, at least about 4 hours, at least about 6 hours, at least about 8 hours, at least about 12 hours, at least about 24 hours, at least about 2 days, at least about 4 days, at least about 6 days, at least about 1 week, at least about 2 weeks, at least about 3 weeks, or more than 3 weeks.

In certain embodiments, up to 90% of the collapse of the stabilizing structure or wound closure device may occur within the first few minutes upon application of negative pressure, while the remaining 10% of the collapse may occur slowly over a period of many minutes, hours, days, weeks, or months. In other embodiments, up to about 80% of the collapse, up to about 70%, up to about 60%, up to about 50%, up to about 40%, up to about 30%, up to about 20%, up to about 10%, or about 0% of the collapse will occur immediately within the first few minutes upon application of negative pressure while the remainder of the collapse occurs at a much slower rate such as over the course of many minutes, hours, days weeks, or months. In other embodiments, the stabilizing structure can collapse at a variable rate.

In some embodiments, the entirety of the collapse occurs at a slowed rate, while in other embodiments the entirety of the collapse occurs almost immediately within the first few minutes. In further embodiments, the collapse can occur at any rate and the rate can vary over time. In certain embodiments, the rate of collapse can be altered in a variable fashion by adding and/or removing portions of the structure or by controlling the application of negative pressure and irrigant fluid.

Figure 36A:
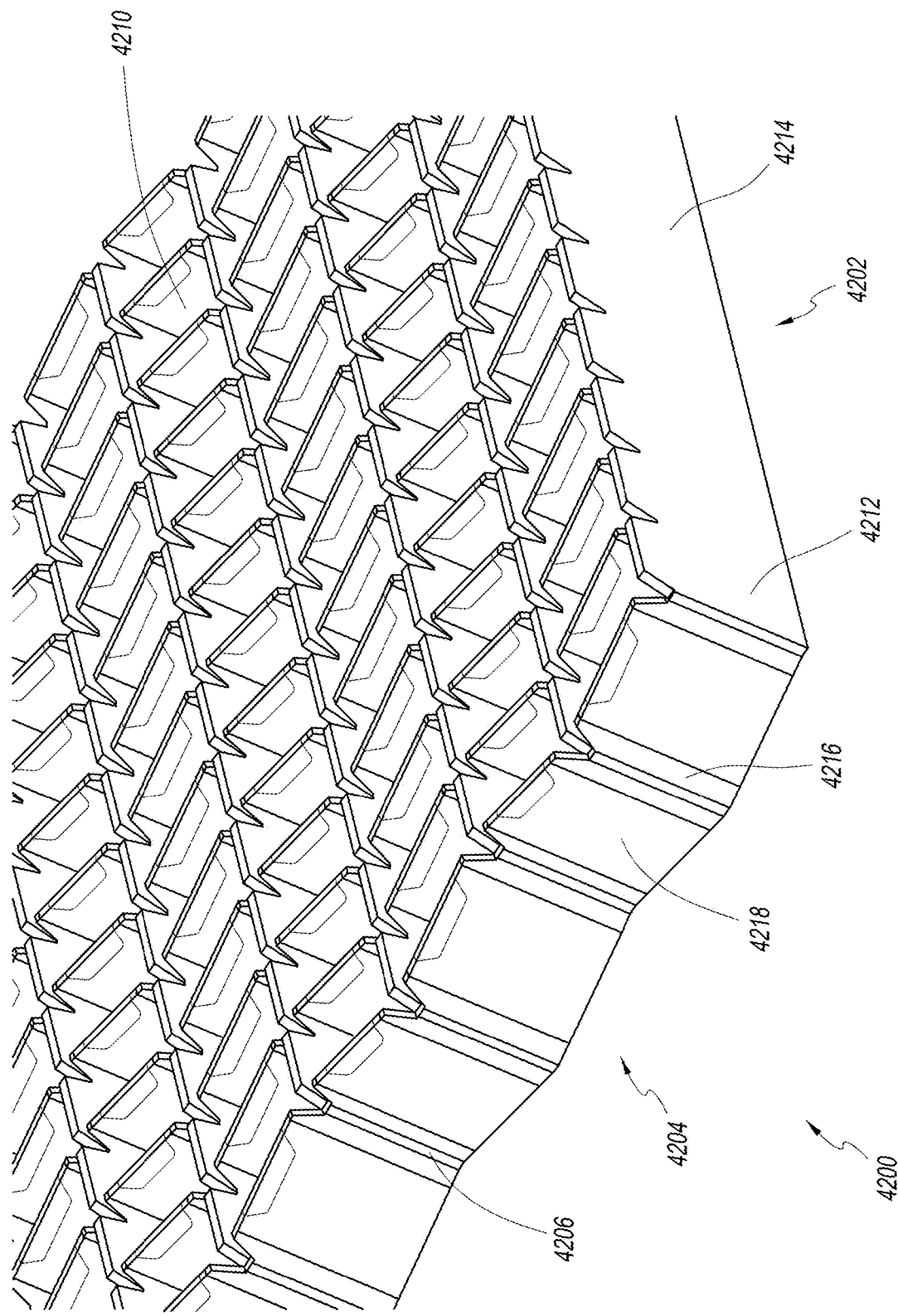
Figure 36B:
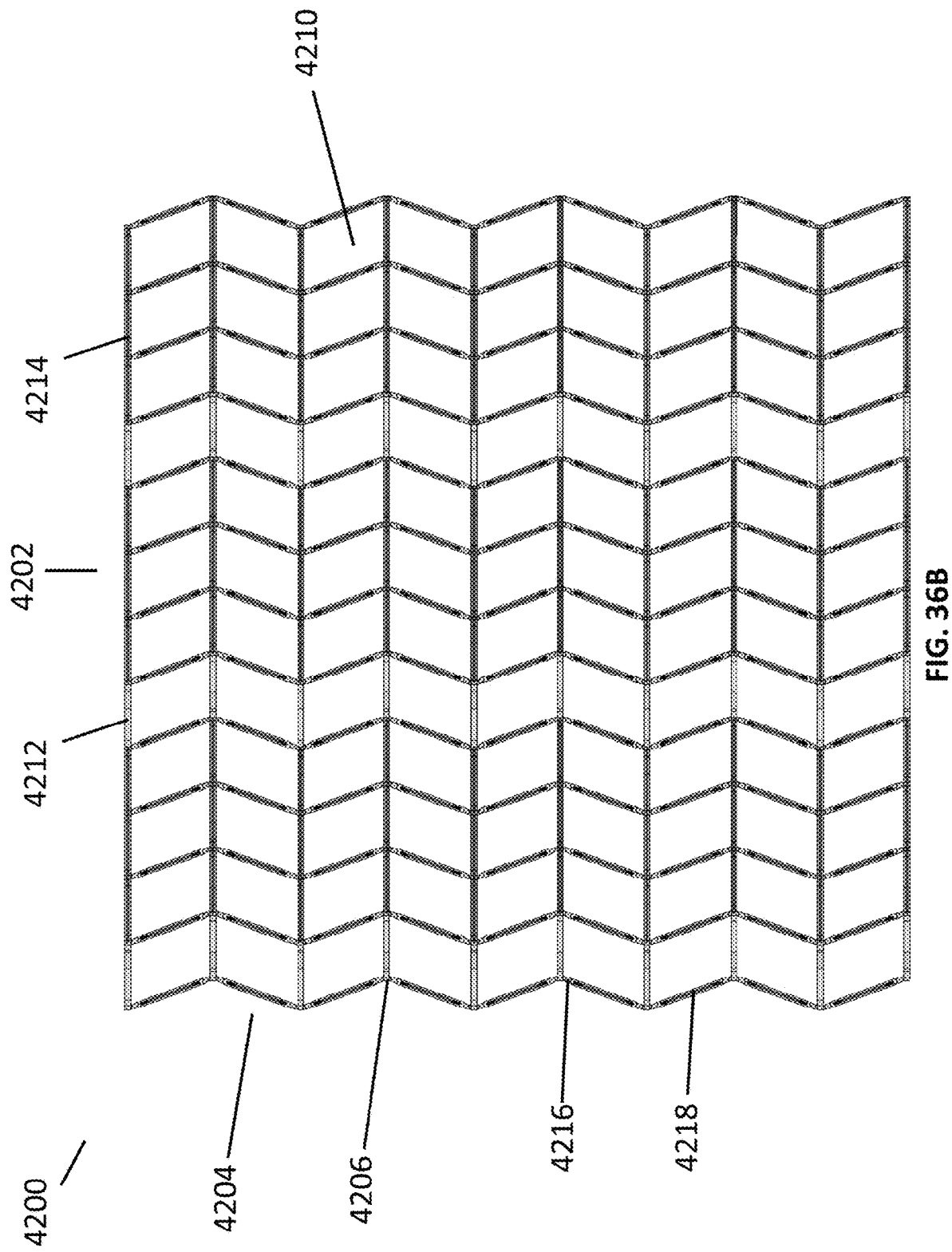

As illustrated in the perspective view of FIG. 36A and the top view of FIG. 36B, the intersection of the intervening members 4204 and the elongate strips 4202 may define a plurality of cells 4210. In certain embodiments, the cells 4210 may be of any of the shapes and sizes described in this section or elsewhere in this specification, such as those described in relation to FIGS. 29A-29C. For instance, a cell may be in the shape of a square, a diamond, an oblong, an oval, and/or a parallelepiped.

The joints 4206 are configured to allow the intervening members 4204 to collapse, similar to the joints described in FIGS. 29A-C and FIG. 31. The joints 4206 can be configured to allow the intervening members to collapse in any manner as described in this section or elsewhere in this specification in relation to other embodiments, such as those described in relation to FIGS. 29A-C. For example, the joints 4206 may be configured to allow or preferentially cause a first row of intervening members 4204 to collapse in one direction, while allowing or preferentially causing an adjacent row to collapse in another direction.

The elongate strips 4202 may comprise alternating flexing segments 4212 and supporting segments 4214. In a preferred embodiment, the flexing segments 4212 can be constructed from a flexible or semi-flexible material such as silicone and/or polyurethane. However, any flexible or semi-flexible material may be suitable. The flexing segments 4212 can flex in any direction, allowing the stabilizing structure to collapse more readily in any direction, but particularly in the horizontal plane. In a preferred embodiment, the supporting segments 4214 can be constructed from a rigid or semi-rigid material such as polyvinyl chloride (PVC). However, any rigid or semi-rigid material may be suitable. In the embodiment illustrated, the elongate strips 4202 comprise elongate strips of a first material such as silicone and/or polyurethane, with a plurality of elongate inserts of a second, more rigid material 4214 embedded into the first material. Thus, the flexing segments 4212 are the areas in the elongate strips 4202 where the more rigid inserts are not located.

As illustrated in FIGS. 36A-D, the supporting segments 4214 may be larger than the flexing segments 4212. In one embodiment, the supporting segments 4214 can be approximately three times as large as the flexing segments 4212 (such as by spanning three cells 4210). In other embodiments, the supporting segments 4214 may be the same size as the flexing segments 4212. In further embodiments, the flexing segments 4212 can be larger than the supporting segments 4214. Alternatively, the lengths and widths of the individual segments of the elongate strips 4202 can be variable. For example, the height of the supporting segments 4214 can be reduced, such that they do not extend from approximately the top to approximately the bottom of the stabilizing structure 4200. In some embodiments a smaller supporting segment could encompass approximately half the height of the elongate strip 4202. In certain embodiments, the supporting segment 4214 could be located in the upper or in the lower portion of the elongate strip. Such embodiments may be accomplished by utilizing an insert of a second material that has a smaller height than the height of the first material forming the elongate strip 4202.

In some embodiments, the supporting segment does not alternate with the flexing segment 4212 and instead, the elongate strips 4202 are comprised entirely of supporting segments 4214 (e.g., a silicone strip or other material with an embedded more rigid insert extending the entire length thereof, or simply a more rigid material by itself). Alternatively, the entirety of the elongate strip 4202 can be comprised only of flexing segments 4212 (e.g., a strip made only of silicone or other more flexible material).

The elongate strips 4202 may be manufactured from a female mold that may further encompass the entire stabilizing structure 4200. The supporting segments 4214 can be inserted into the female mold, followed by an injection of a flexible polymer such as silicone and/or polyurethane to encase the supporting segments 4214 within the flexible polymer frame. The supporting segments 4214 can be inserted into the mold in any desired manner or quantity, allowing for many potential variations of the stabilizing device.

In further embodiments, the supporting segments 4214 are insertable and/or removable from the elongate strips 4202, and may be inserted and/or removed to alter the collapsibility of the stabilizing structure 4200. Supporting segments 4214 can be inserted and/or removed from the stabilizing structure 4200 after it has been placed in a wound to variably control the collapse of the stabilizing structure

4200. In such embodiments, the elongate strips 4202 may form pockets that are open from one side (e.g., from the top) to allow insertion and removal of the supporting segments 4214.

Figure 36C:
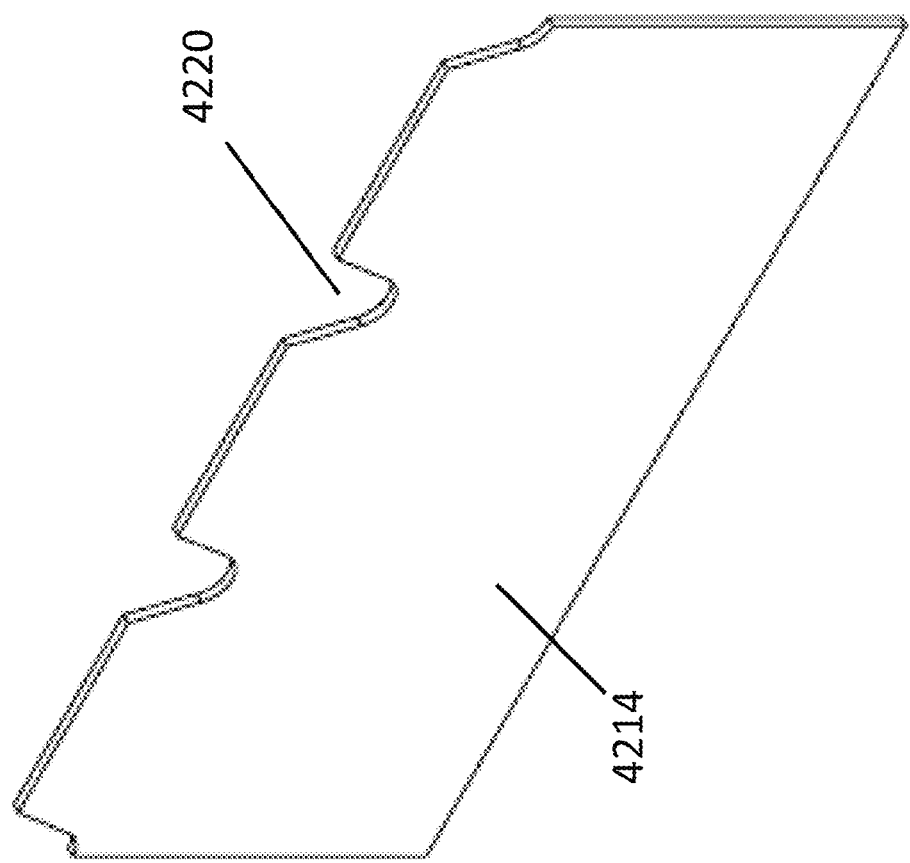
Figure 36D:
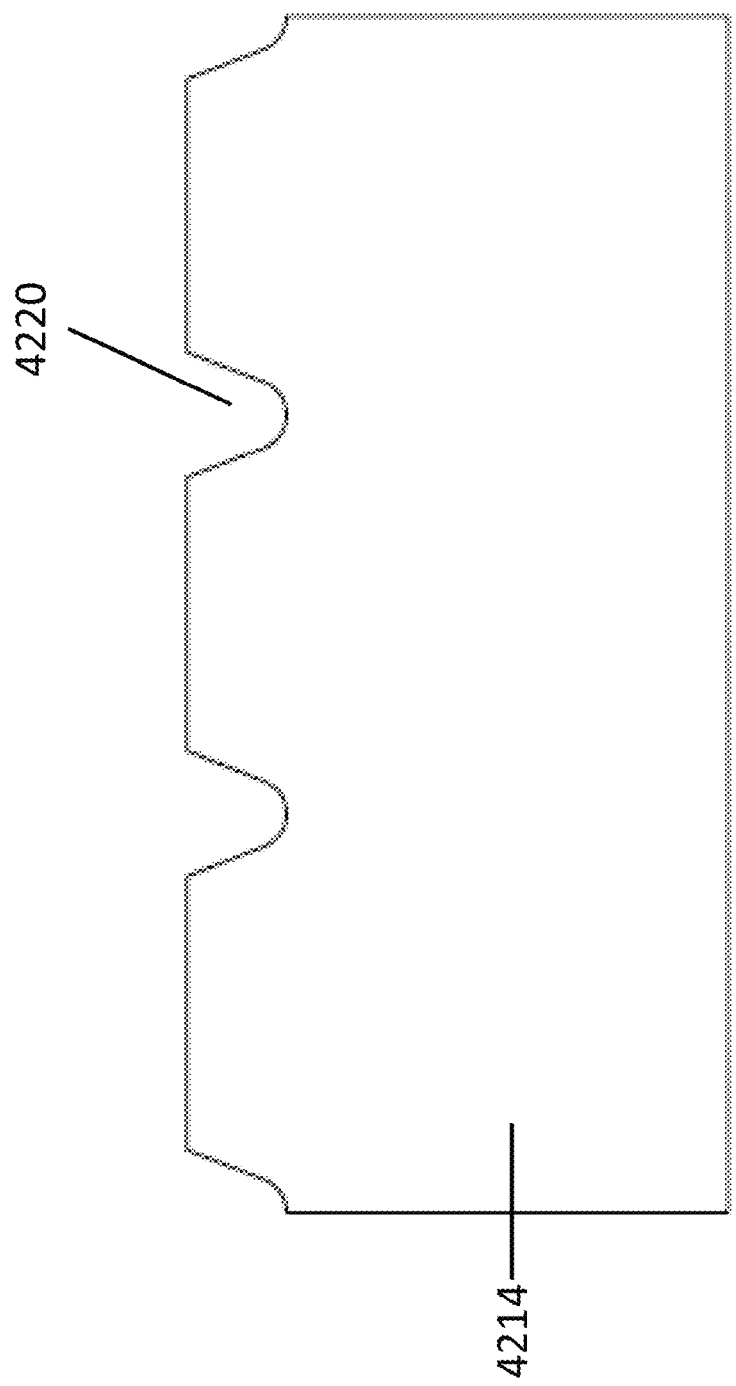

FIGS. 36C-D illustrate in greater detail an embodiment of an individual supporting segment 4214. The supporting member 4214 may be a flat, plate-like structure having a rectangular shape, with a length greater than its height, and two parallel surfaces. The supporting segment can comprise at least one notch 4220, preferably located on the upper edge of the supporting segment. In other embodiments, the notch or notches can be located on the bottom or the sides of the supporting segment. In further embodiments, the top notch could have a corresponding bottom notch. In certain embodiments, the notch could be configured so as to allow tearing of the supporting segment in a transecting line across the supporting segment. The notch or notches 4220 may advantageously provide flexibility to the structure. The notches 4220 may allow the stabilizing structure to flex more easily in the horizontal plane or in the vertical plane. The notches 4220 may further allow the stabilizing structure to twist in multiple planes. The notches 4220 may also improve fluid flow within the stabilizing structure 4200. In some embodiments, the supporting segment does not contain a notch and the uppermost edge is flat. The notch 4220 can be located at other locations on the supporting segment, for example the bottom edge or the sides. The shape of the notch can be a rounded triangle as in FIGS. 36C-D or any other similar shape.

Figure 36F:
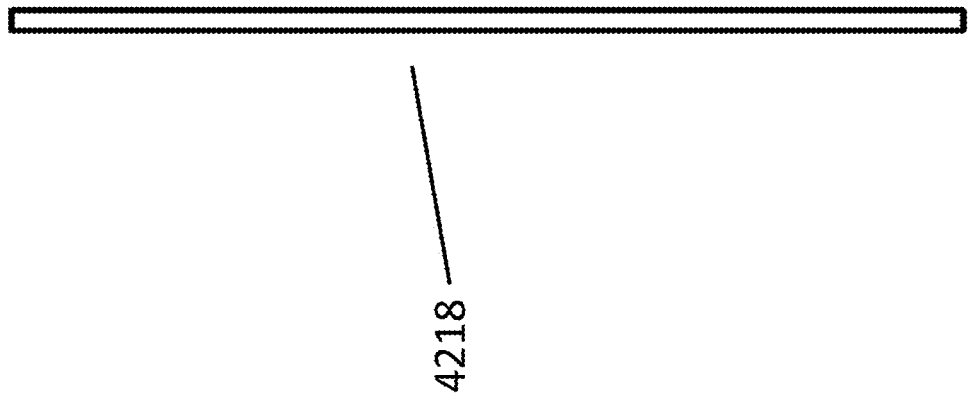
Figure 37A:
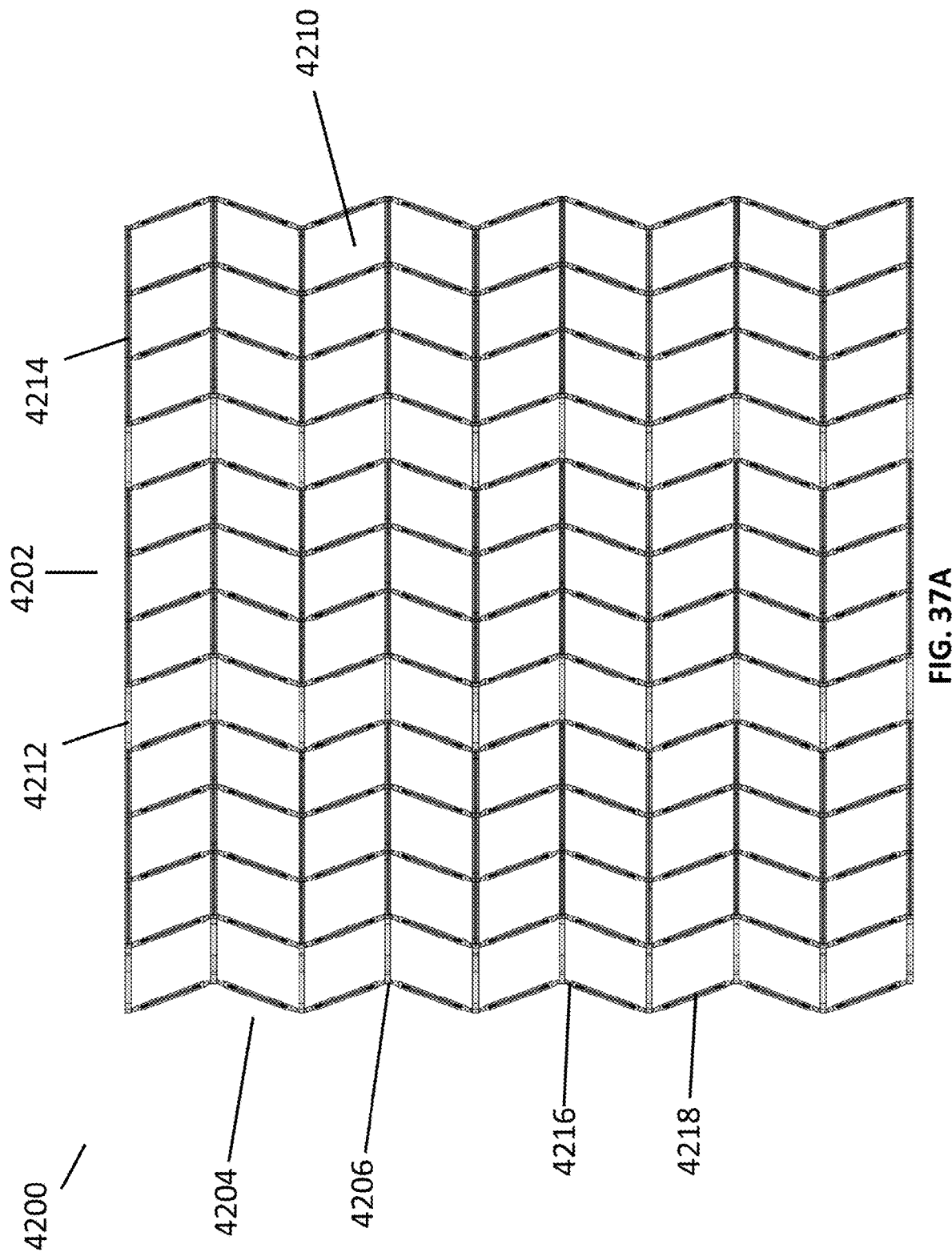
FIG. 37A-D illustrate multiple views of an embodiment of a stabilizing structure comprising openings for fluid passage.
Figure 37B:
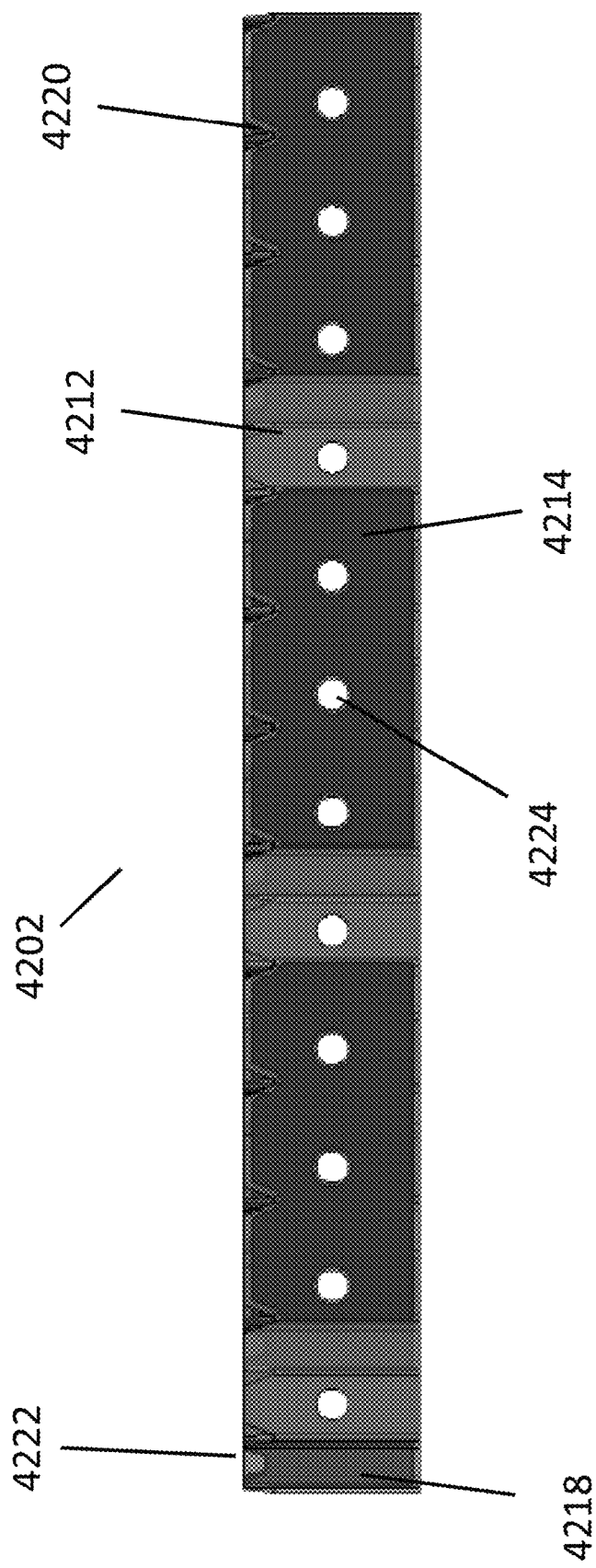
Figure 37C:
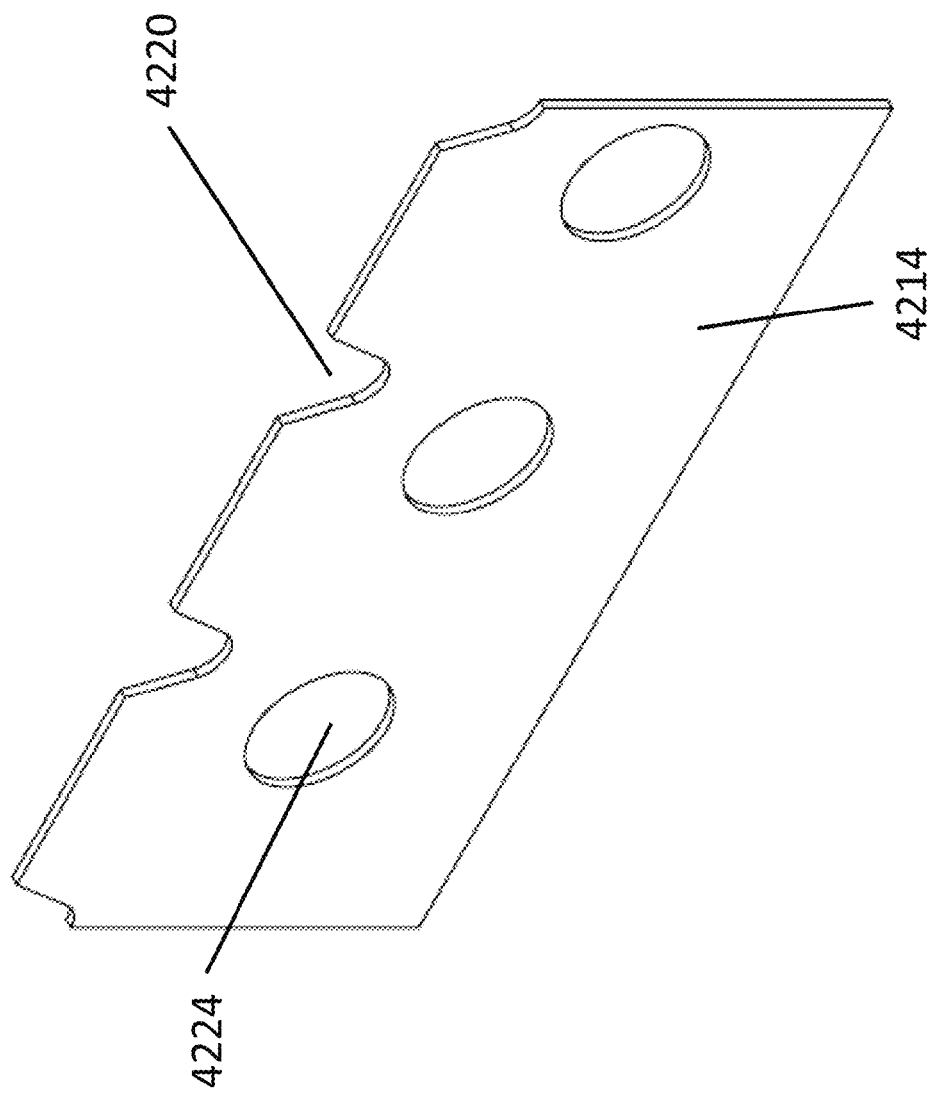
Figure 37D:
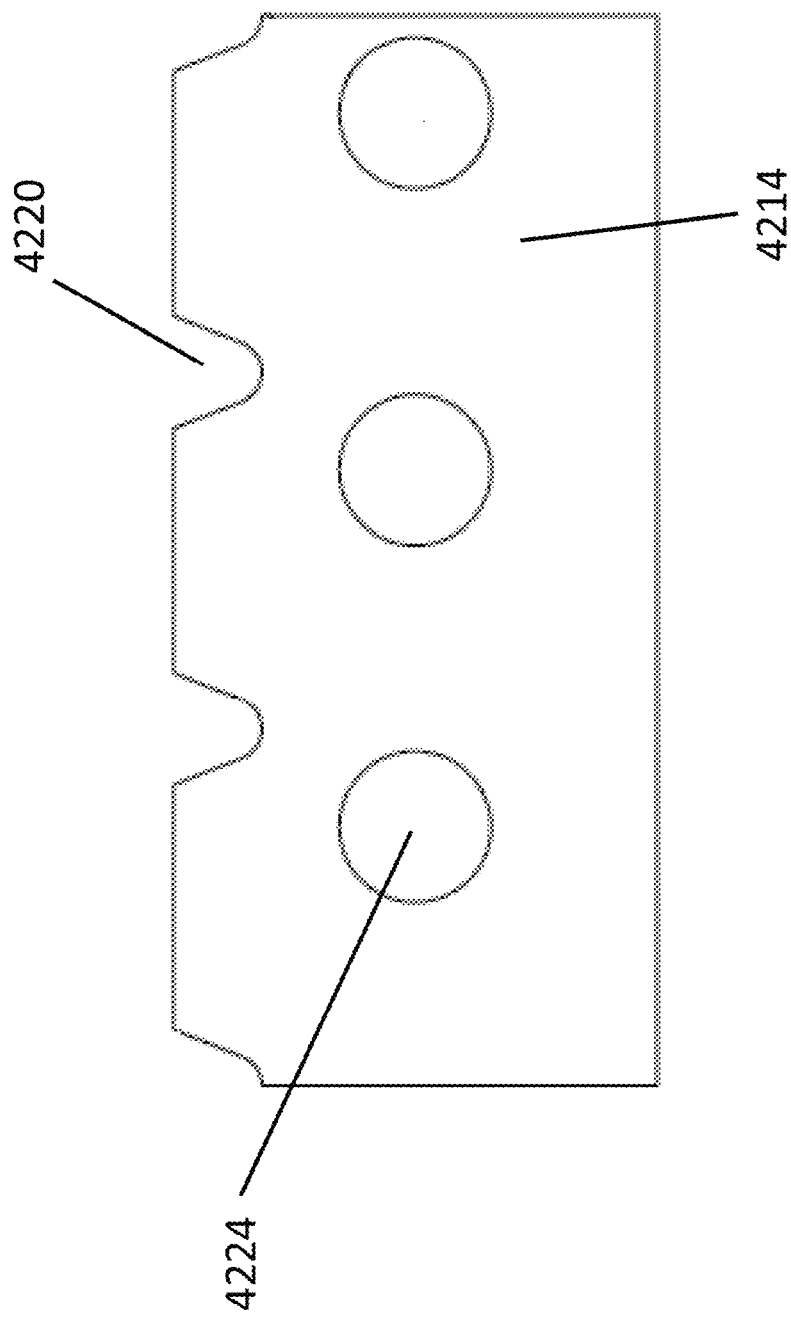

The intervening members 4204 in some embodiments may comprise a first material 4216 with an embedded insert 4218 made of a more rigid material. One embodiment of the embedded insert is illustrated in FIGS. 36E-F. In certain embodiments, the insert 4218 is placed within a female mold and a flexible polymer such as silicone and/or polyurethane is injected around the insert to entomb the insert 4218 within a flexible polymer frame. The inserts 4218 can be inserted into the mold in any desired manner or quantity, allowing for many potential variations of the stabilizing device. In other embodiments, the first material 4216 may be in the form of a sleeve configured to receive the insert 4218. Further, the sleeve 4216 may be configured to allow for the removal of an insert 4218, such as by providing an opening in the top of the sleeve. In a preferred embodiment, the first material 4216 is constructed from a flexible or semi-flexible material such as silicone and/or polyurethane. However, any flexible or semi-flexible material may be suitable. In a preferred embodiment, the insert 4218 is constructed from a rigid or semi-rigid material such as polyvinyl chloride. However, any rigid or semi-rigid material may be suitable.

FIG. 36E illustrates a front view of insert 4218, while FIG. 36F illustrates a side view of insert 4218. The insert in one embodiment may be a flat, plate-like structure having a rectangular shape, with a height greater than its width, and two parallel surfaces. The insert can comprise an indent 4222. The indent is preferably located at the upper portion of the insert, however, the indent 4222 can be positioned on either side of the insert, or on the bottom. The indent 4222 can be configured such that it aids in allowing fluid to flow through the stabilizing structure by providing a flow path. The indent 4222 can improve flexibility of the stabilizing structure 4200 and be configured to allow for a more efficient collapse of the stabilizing structure 4200.

In some embodiments, the stabilizing structure 4200 of FIGS. 36A-B can be configured to include perforations or detachable sections that allow portions of the device to separate from the remainder of the device. For example, perforations may be incorporated into the joints 4206 between various cells contained within the stabilizing structure 4200, allowing for the removal of individual rows or cells to alter the shape of the stabilizing structure 4200. In some embodiments, as described above in relation to FIGS. 36C-D, the sections may be detached along perforations or lines in the elongate strips corresponding to the notches 4220.

In some embodiments, the inserts 4218 may be entombed within first material 4216 in a variable number of intervening members 4204 to control the shape and collapse of the stabilizing structure 4200. In other embodiments, the inserts 4218 may be inserted directly into sleeves comprised of first material 4216 within the intervening members 4204 to control the shape and collapse of the stabilizing structure 4200.

For example, the inserts 4218 can be present in at least about 5% of the intervening members, at least about 10% of the intervening members, at least about 15% of the intervening members, at least about 20% of the intervening members, at least about 25% of the intervening members, at least about 30% of the intervening members, at least about 35% of the intervening members, at least about 40% of the intervening members, at least about 45% of the intervening members, at least about 50% of the intervening members, at least about 55% of the intervening members, at least about 60% of the intervening members, at least about 65% of the intervening members, at least about 70% of the intervening members, at least about 75% of the intervening members, at least about 80% of the intervening members, at least about 85% of the intervening members, at least about 90% of the intervening members, at least about 95% of the intervening members, or about 100% of the intervening members.

In certain embodiments, a variable number of supporting segments 4214 may be entombed within elongate strips 4202 to control the collapsibility of the stabilizing structure 4200. In other embodiments, a variable number of supporting segments may be inserted into a pocket contained within the elongate strips 4202 to control the collapsibility of the stabilizing structure. For example, the supporting segments 4214 can be present in at least about 5% of the total length of the elongate strips, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the total length of the elongate strips.

In certain embodiments, the inserts 4218 or supporting segments 4214 may be inserted and/or removed over time to variably control the collapse of the stabilizing structure 4200. For example, although initially all the available sleeves 4216 of the stabilizing structure may contain an insert, after the initial placement of the stabilizing structure in a wound, additional inserts 4218 may be removed over time, thus causing the stabilizing structure 4200 to collapse even further. Inserts can also be added to the stabilizing structure after it is inserted into a wound, thereby decreasing the collapsibility of the stabilizing structure 4200. Thus, the addition and/or removal of the inserts 4216 or supporting segments 4214 allows for variable control of the collapse of the stabilizing structure 4200. In similar fashion, supporting segments 4214 can be inserted and removed from the elongated strips over time to provide variable control over the collapse of the stabilizing structure 4200.

In certain embodiments of the stabilizing structures described in this section or elsewhere in this specification, such as in stabilizing structure 4200 as described in FIG. 36A, the flexibility of various sections of the stabilizing structure is enhanced by thinning of that section. For example, in certain embodiments, rather than using a flexible material for a flexing segment 4212 of elongate strip 4202, instead the flexing segment 4212 can be constructed of a similar material to that used to construct supporting segment 4214. In this embodiment, since supporting segment 4212 is thicker than flexing segment 4212 it will not flex to the degree of flexion that may be experienced by flexing segment 4212. In certain embodiments, the entire stabilizing structure 4200 may be constructed from a single rigid or semi-rigid material, but made to have different rigid and flexible portions by thinning certain areas of the stabilizing structure 4200. In further embodiments, the joints 4206 may be thinned to allow for greater flexibility as compared to the surrounding sections. In certain embodiments, thinning of a section of the stabilizing structure 4200, may allow the thinner portion to be more readily detached from the structure.

As described above in relation to FIGS. 11A-16B and applicable to all stabilizing structures or wound closure devices described in this section or elsewhere in the specification, a soft polymer could be molded over the entire stabilizing structure 4200 to soften the feel of the device, thereby protecting the surrounding organs and/or other tissues. In other embodiments, the soft polymer could be molded only over the bottom portion of the stabilizing device 4200, while in some embodiments the softer polymer can be molded over the top and/or the sides of the device. In some embodiments, the soft polymer could be molded over particular edges of the stabilizing structure 4200, such as those on the bottom, sides, and/or top. In certain embodiments, the soft polymer could be molded over any side or combination of sides of the stabilizing structure 4200. The soft polymer may act like a softened rim surrounding the hard edges of the stabilizing structure 4200.

FIGS. 37A-D illustrate multiple views of another embodiment of the stabilizing structure 4200, similar to the stabilizing structures depicted in FIGS. 29A-C and 36A-E. As in the stabilizing structure embodiment depicted in FIGS. 36A-F, the stabilizing structure 4200 comprises elongate strips 4202 and intervening members 4204. The elongate strips 4202 may comprise openings 4224 configured to allow the passage of fluid through the elongate strips 4202. To construct the openings, holes or other shapes may be punched directly through the elongate strips 4202. In the embodiment illustrated and as further shown in FIGS. 37C and 37D, the elongate strips 4202 further comprise more rigid inserts 4214 as described above. In such embodiments, the openings 4224 may be punched through the rigid inserts 4214 in locations of the strip where the inserts are located, as well as through flexing segments 4212 where the inserts are not located. The openings can be configured to evenly distribute fluid throughout the stabilizing device and/or direct fluid flow along a particular passage or direction. In other embodiments, the intervening members comprise openings, similar to the openings described in relation to the elongate strips.

Figure 38B:
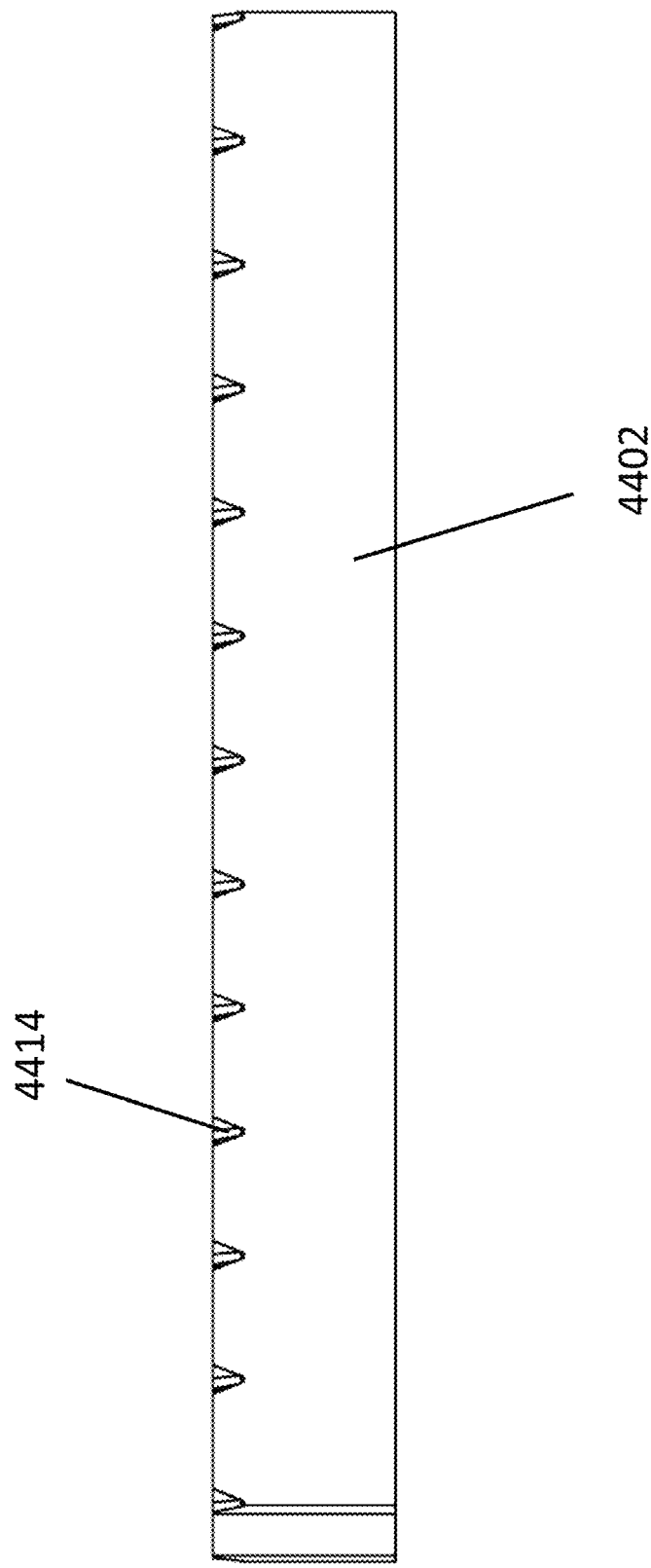

FIGS. 38A-B illustrate embodiments of a stabilizing structure 4400, with functional and structural elements similar to the embodiments of the stabilizing structure depicted in FIGS. 36A-F. Similar to the other stabilizing structures described previously, the stabilizing structure 4400 comprises elongate strips 4402 and intervening members 4404. The elongate strip 4402 may be a single unitary strip with no differing flexing segments or support segments. In certain embodiments, the elongate strip 4402 can be comprised entirely of rigid or semi-rigid materials such as polyvinyl chloride. In other embodiments, the elongate strip 4402 may be comprised entirely of flexible or semi-flexible material such as silicone and/or polyurethane. Similar to the embodiments described in FIGS. 36A-F, stabilizing structure 4400 may collapse in any manner described in this section or elsewhere in this specification within any timescale described in this section or elsewhere in this specification.

Figure 38C:
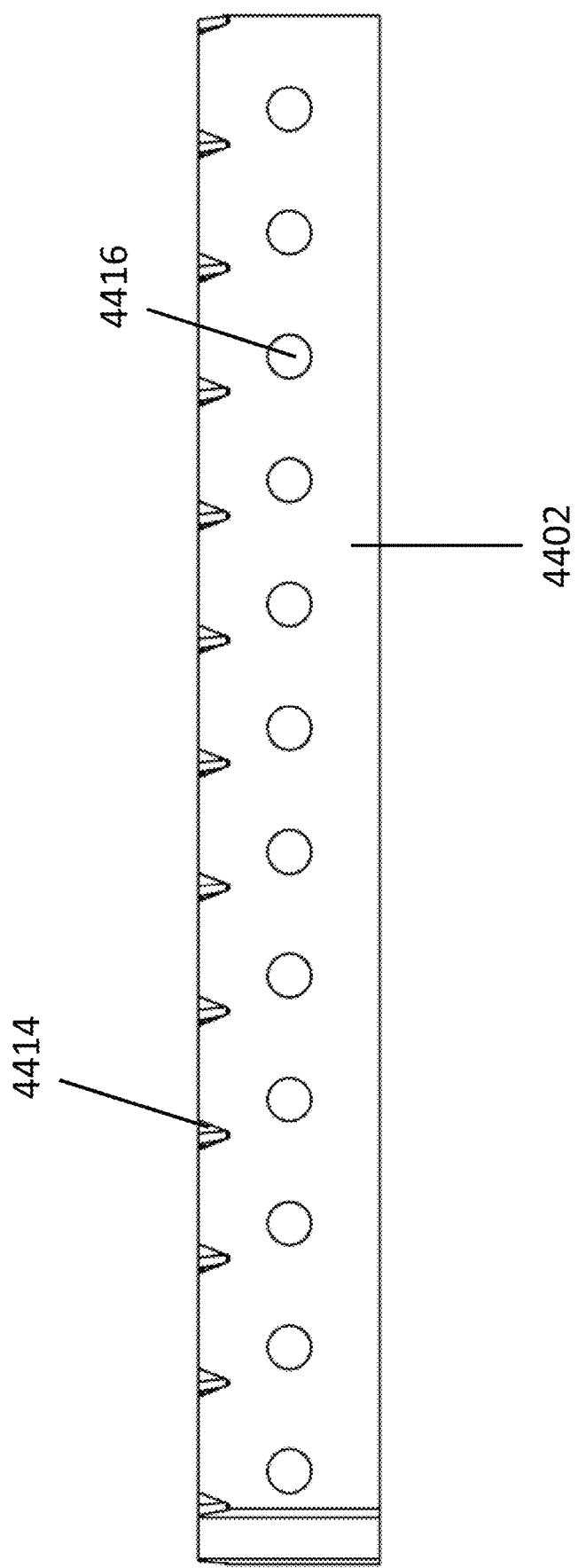

FIGS. 38C depict an embodiment of herein the elongate strips 4402 comprise openings 4416 to allow the passage of fluid similar to the passage of fluid described in FIGS. 37A-E.

Figure 39A:
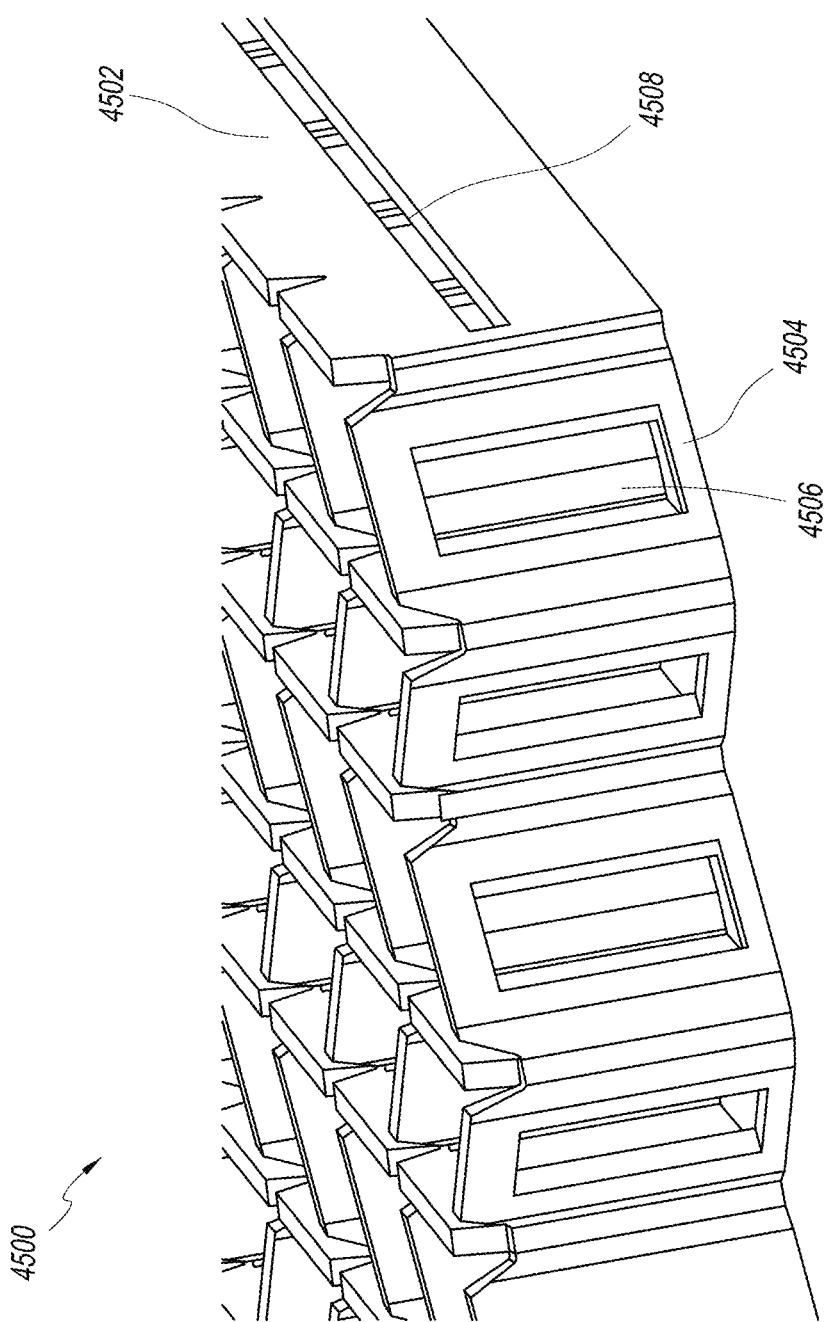
FIG. 39A-B illustrate multiple embodiments of a stabilizing structure comprising windows.
Figure 39B:
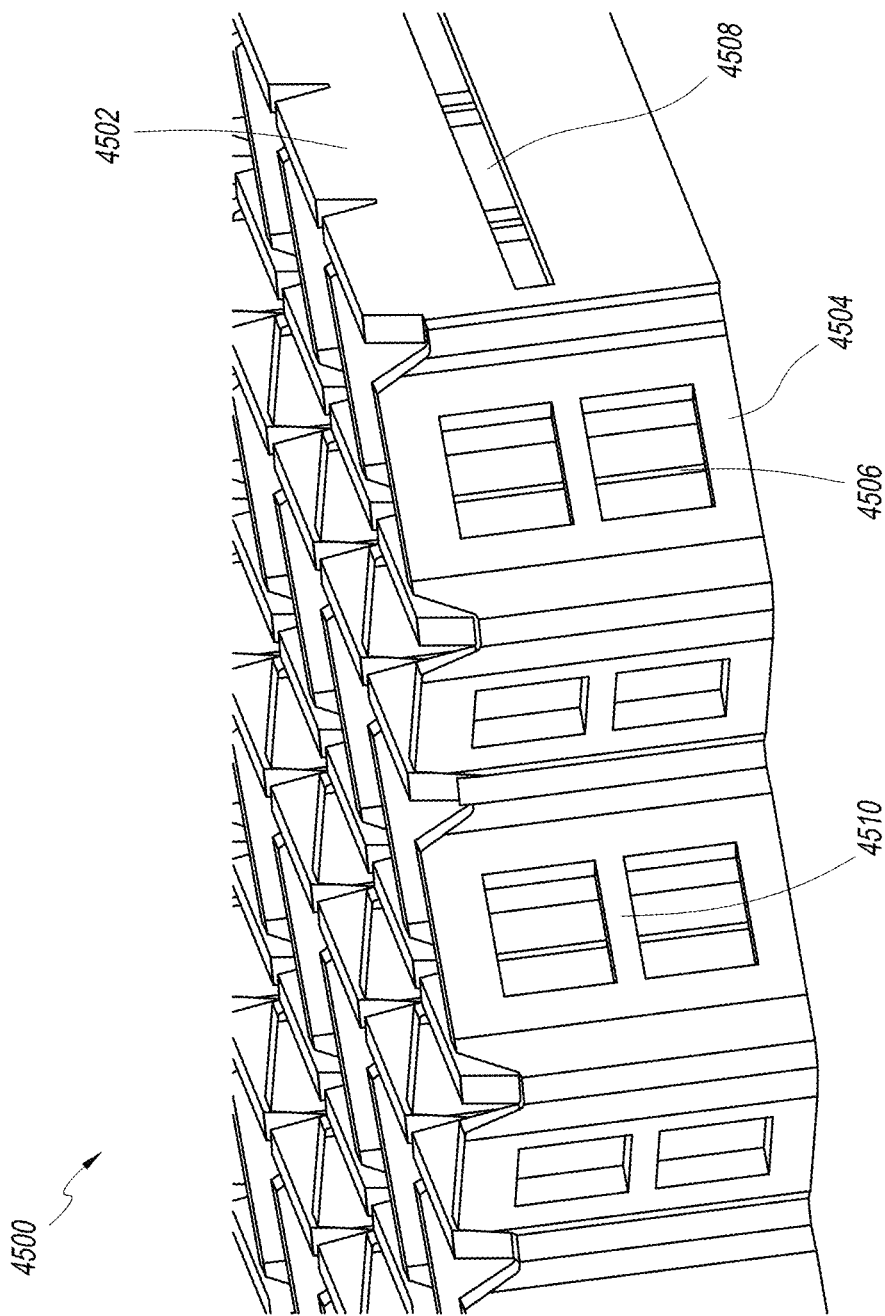

FIGS. 39A-B illustrate embodiments of stabilizing structure 4500 that are similar to the stabilizing structures described above in relation to FIGS. 29A-32. Stabilizing structure 4500 comprises elongate strips 4502 and intervening members 4504. Intervening members 4504 can further comprise windows 4506, configured to allow the passage of fluid. In some embodiments, all intervening members 4504 may comprise windows 4506, however in other embodiments only the horizontally outermost intervening members 4504 comprise windows 4506, while the inner intervening members are similar to other embodiments described in this section or elsewhere in this specification.

In certain embodiments, at least about 5% of the intervening members comprise windows, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the intervening members.

The elongate strip 4502 may further comprise a gap 4508, configured to allow the passage of fluid. The gap may extend nearly the entire length of the elongate strips 4502 or extend only a portion of the length of the elongate strip 4502.

FIG. 39B illustrates an embodiment of a stabilizing structure 4500, where the windows 4506 further comprise bars 4510. In certain embodiments, at least about 5% of the windows comprise bars, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of the windows.

Figure 40:
FIG. 40 is a photograph of one embodiment of a foam layer with fingers.
Figure 41:
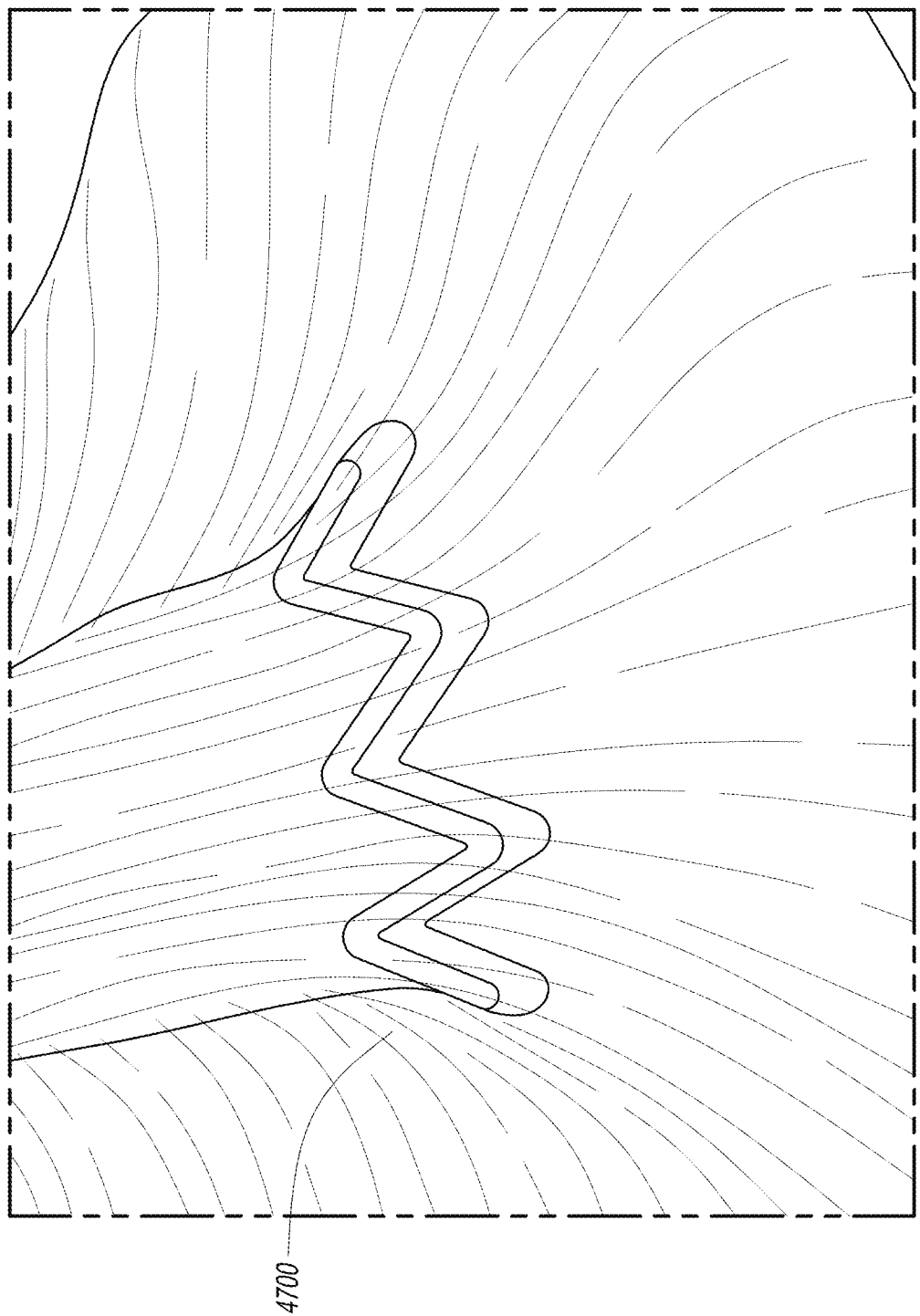
FIG. 41 is a photograph of an experiment to determine the efficacy of certain embodiments of wound closure devices.

FIG. 40 is a photograph of an embodiment of a foam layer 4600 that may be used in combination with any of the stabilizing structures or wound closure devices described in this section or elsewhere in this specification. As described above, the foam layer 4600 may be located above or below the stabilizing structure or wound closure device. In some embodiments, the foam layer 4600 is located both above and below the stabilizing structure or wound closure device. The foam layer 4600 can surround the perimeter of the stabilizing structure or wound closure device or completely surround the entirety of the stabilizing structure or wound closure device. The foam layer 4600 can be constructed from absorbent materials, materials configured to distribute fluid, or both.

The foam layer 4600 further comprises fingers 4602, that can extend from the foam layer into the stabilizing structure or closure device. For example, the fingers 4602 may extend into and around the gaps or cells depicted in the stabilizing structures of FIGS. 29A-40B. The fingers 4602 may also extend around the outside of the perimeter of the stabilizing structure. In some embodiments, the fingers 4602 from one foam layer 4600 may extend through the interior or around the outside of the stabilizing structure to meet the fingers 4602 from a second foam layer 4600.

In some embodiments, the foam layer 4600 can have perforations or pre-cuts to allow portions of the foam layer 4600 to be easily torn away to shape the foam for a particular wound. In some embodiments, the fingers 4602 can extend at least about 1mm from the surface of the foam layer, at least about 3mm from the surface of the foam layer, at least about 5mm from the surface of the foam layer, at least about 7.5mm from the surface of the foam layer, at least about 10mm from the surface of the foam layer, at least about 12.5mm from the surface of the foam layer, at least about 25mm from the surface of the foam layer, at least about 17.5mm from the surface of the foam layer, at least about 20mm from the surface of the foam layer, at least about 25mm from the surface of the foam layer, or more than 25mm.

FIG. 41A is a photograph of a non-limiting experiment involving an embodiment of the stabilizing structures 4700 described in the preceding examples, particularly those described in FIGS. 29A-C and FIGS. 36A-F. In this non-limiting experiment, the stabilizing structure has been inserted into a cadaveric wound, then sealed with a drape and connected to a source of negative pressure as described previously.

In other embodiments, the stabilizing structure is rounded at the edges to fit more closely within the shape of the wound. The stabilizing structure may be cut or bent to a desired shape. For example, the stabilizing structure may be made into the shape of an oval to better fit into wounds shaped like an oval. Further, as described in this section or elsewhere in this specification, in some embodiments the stabilizing structure may have perforations or preformed cuts, allowing portions of the stabilizing structure to be torn away to create a desired shape.

Figure 42A:
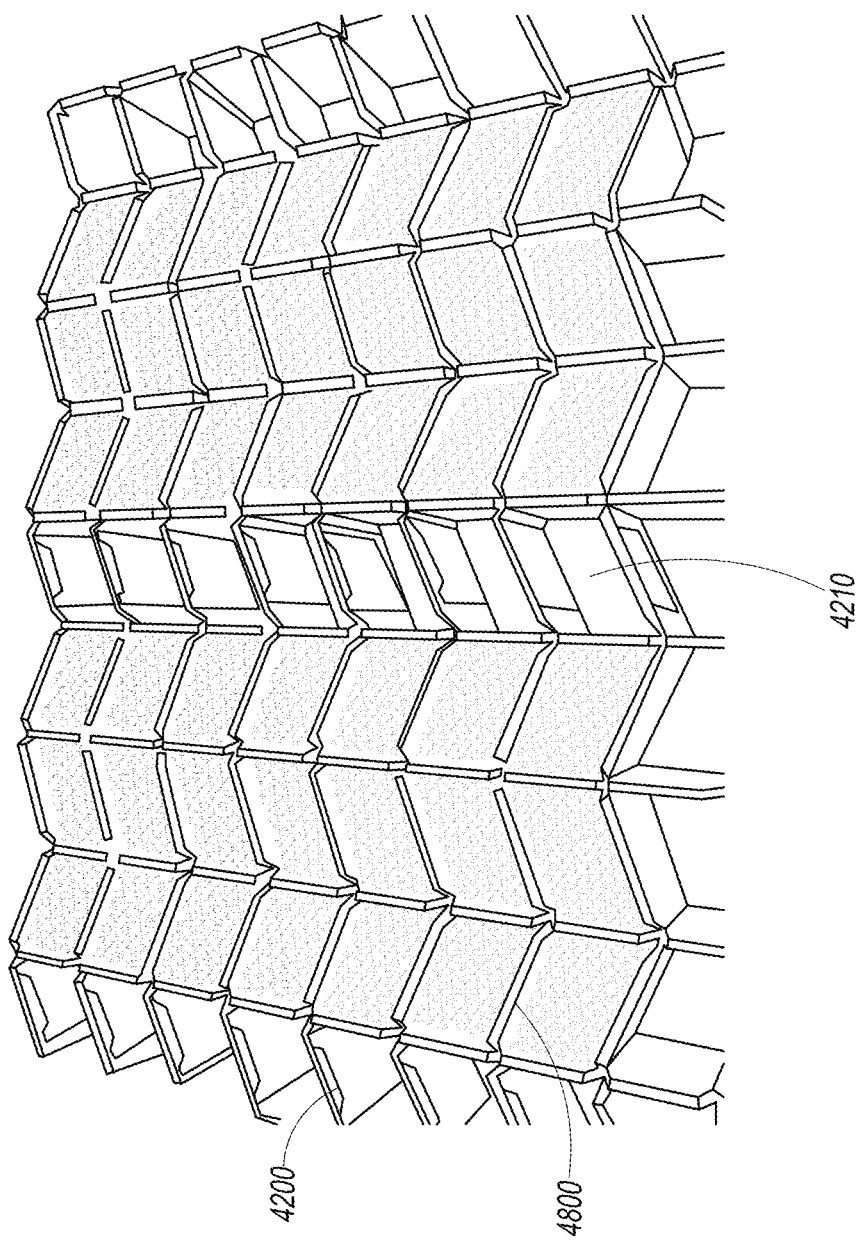
FIG. 42A-C are photographs of various embodiments of a stabilizing structure comprising foam inserts
Figure 42B:
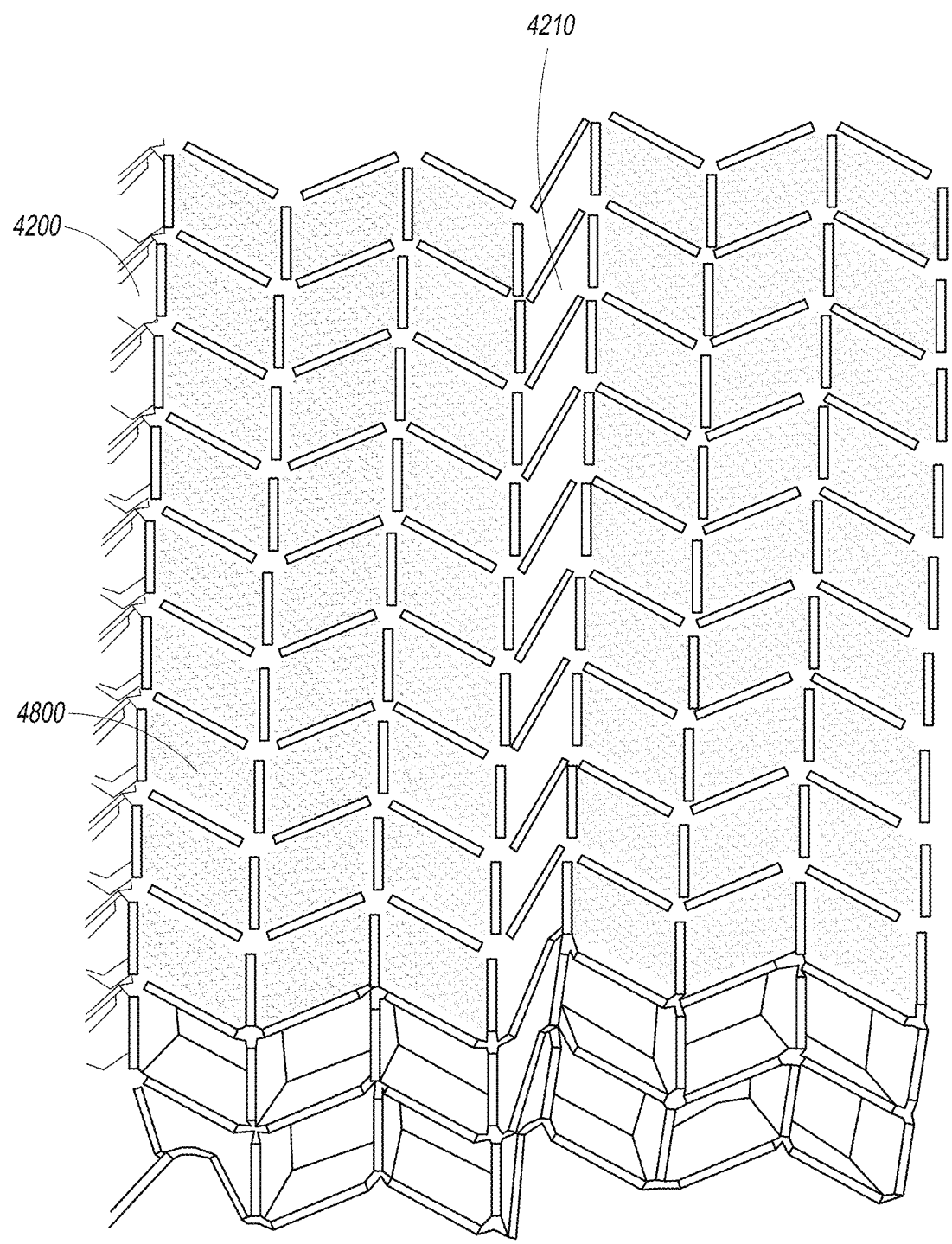
Figure 42C:
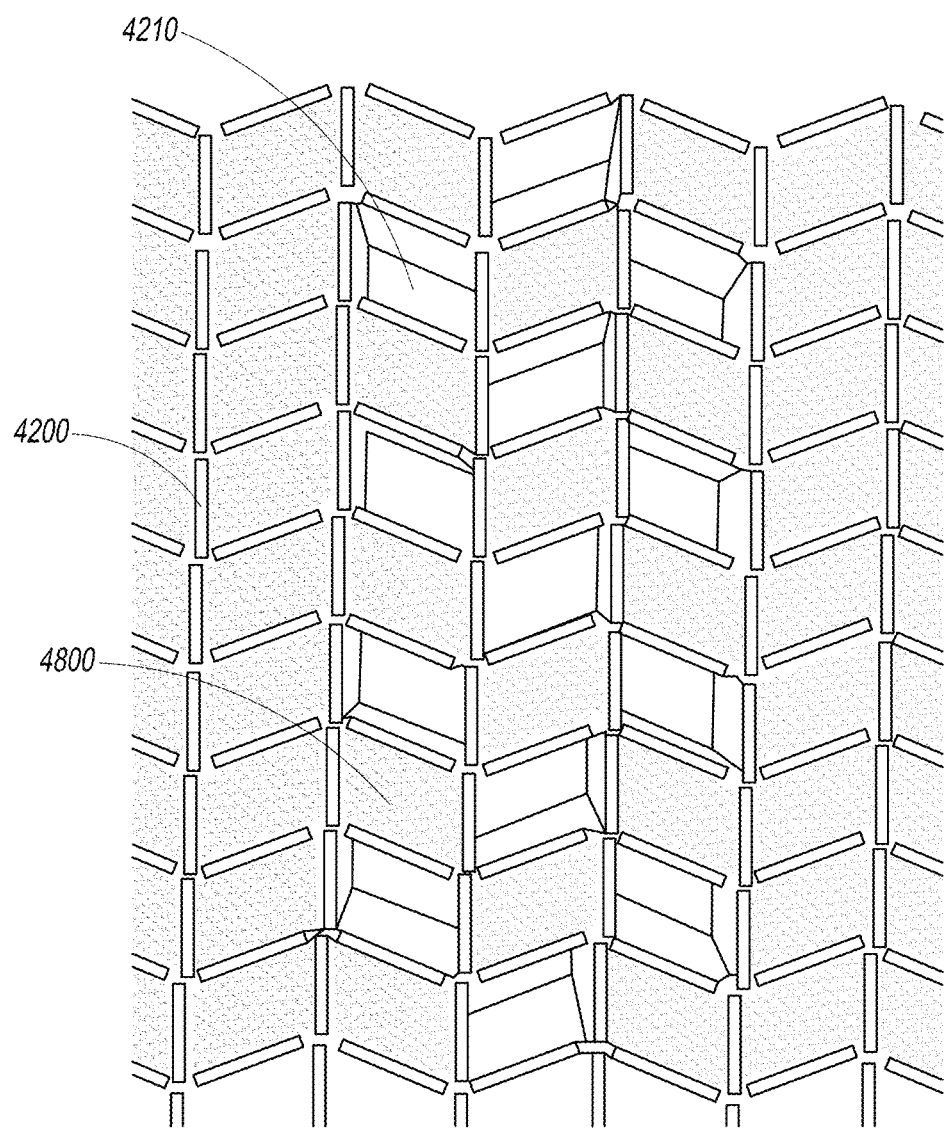

FIGS. 42A-C are photographs of embodiments of stabilizing structure 4200, similar to those embodiments of a stabilizing structure described in relation to FIGS. 36A-39B, further comprising foam inserts 4800. The inserts 4800 may be constructed from any material described in this section or elsewhere in this specification, including flexible foams, semi-flexible foams, semi-rigid foams, and rigid foams and other porous or compressible materials. The stiffness of the foam inserts 4800 can be used to control the collapse of stabilizing structure 4200. For example, stiffer foams may impede the collapse of the stabilizing structure 4200, while flexible foams may allow the stabilizing structure to collapse more quickly and easily. Varying the flexibility/stiffness of the foams allows the structure to collapse at any rate as described in this section or elsewhere in this specification. In some embodiments, the overall density of the stabilizing structure and/or wound closure device may be altered by increasing or reducing the amount of foam within the structure 4200. By reducing the overall density, the structure will be more readily collapsible. Thus, the use of a lower density structure with less foam may allow for greater wound closure as such a structure is more readily collapsible. Conversely, the use of a higher density structure with more foam may be less collapsible. In other embodiments, the foam inserts only comprise a portion of the individual cells 4210.

In some embodiments, the foams may be configured to degrade or dissolve over time, thereby allowing foam inserts to prop the stabilizing structure open initially, before later degrading or dissolving in a controlled manner to control the rate of collapse of the stabilizing structure. In further embodiments, the foam inserts may be impregnated with biologically active materials that may promote wound healing. For example, the biologically active materials may be anti-inflammatory molecules, growth factors, or anti-microbials.

FIG. 42A is a photographic perspective view of the stabilizing structure 4200 in an open state whereby the cells 4210 that do not contain foam are not collapsed. FIG. 42B is a photographic of the top of stabilizing structure 4200 wherein the cells 4210 are in a collapsed state. FIG. 42C is a photograph of a top view of the stabilizing structure 4200 wherein some of the rows have alternating cells filled with foam inserts 4800 or without foam inserts 4210. In some embodiments, the foam inserts can be inserted into at least about 5% of the cells, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, at least about 95%, or about 100% of cells.

Figure 43:
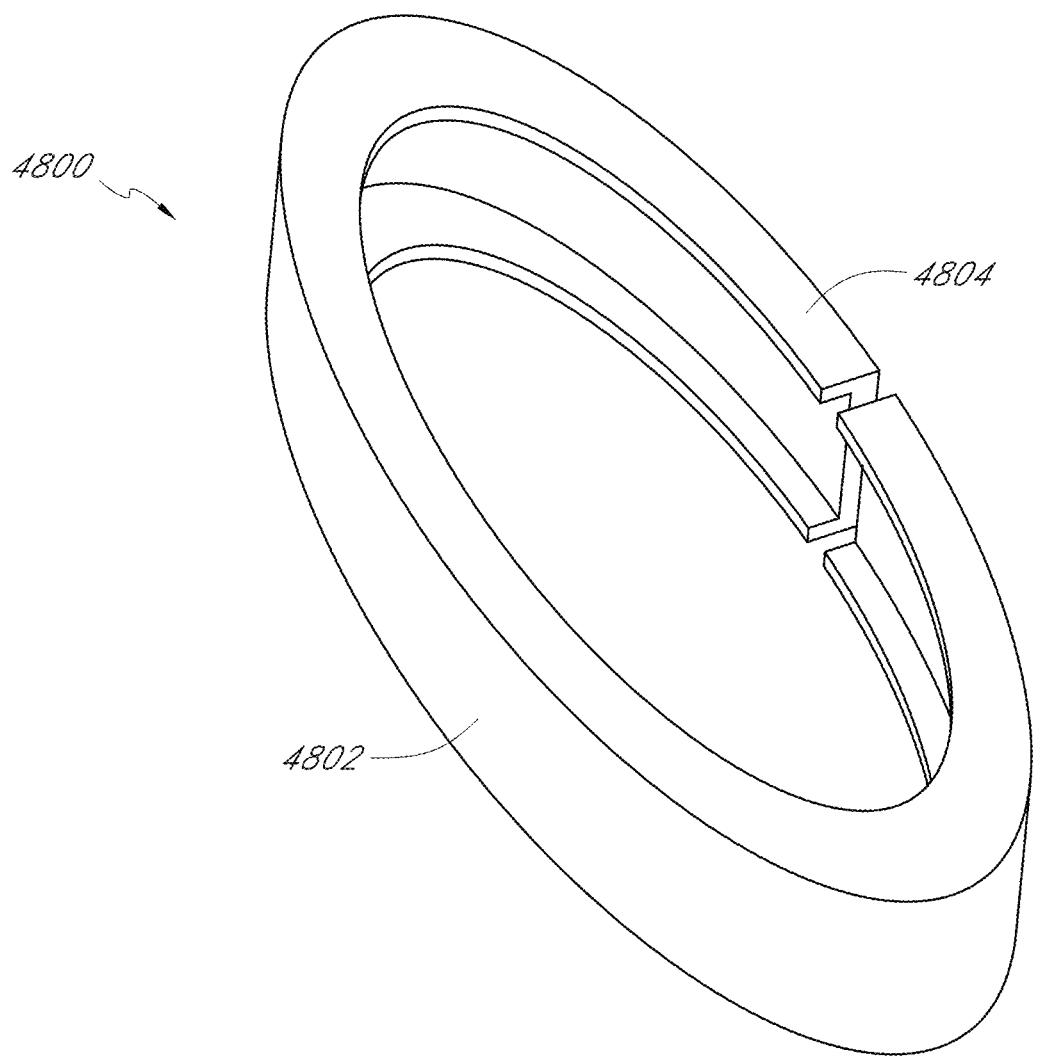
FIG. 43 illustrates an embodiment of a ring that can surround a stabilizing structure.

FIG. 43 illustrates an embodiment of a ring 4800 that may surround the stabilizing structures as described in this section or elsewhere in this specification. The ring 4800 can comprise a layer of tissue anchors 4802 configured to grip the surrounding edges of a wound. For example, the tissue anchors can be hooks, barbs, prongs, or other structures such as those described in relation to FIG. 3A-D, that serve to attach to the tissue of a wound. In certain embodiments, the tissue anchors comprise hook and loop fasteners such as those used in Velcro technologies. In certain embodiments, the ring 4800 can be comprised of foam, such as those described previously or the ring can be comprised of a combination of a foam layer and a tissue anchor layer 4802. A lip 4804 may extend inward from the ring 4800 and serve to overlap the top and/or the bottom of a stabilizing structure as described in this section or elsewhere in this specification, thereby securing the ring 4800 around the stabilizing structure.

Figure 44:
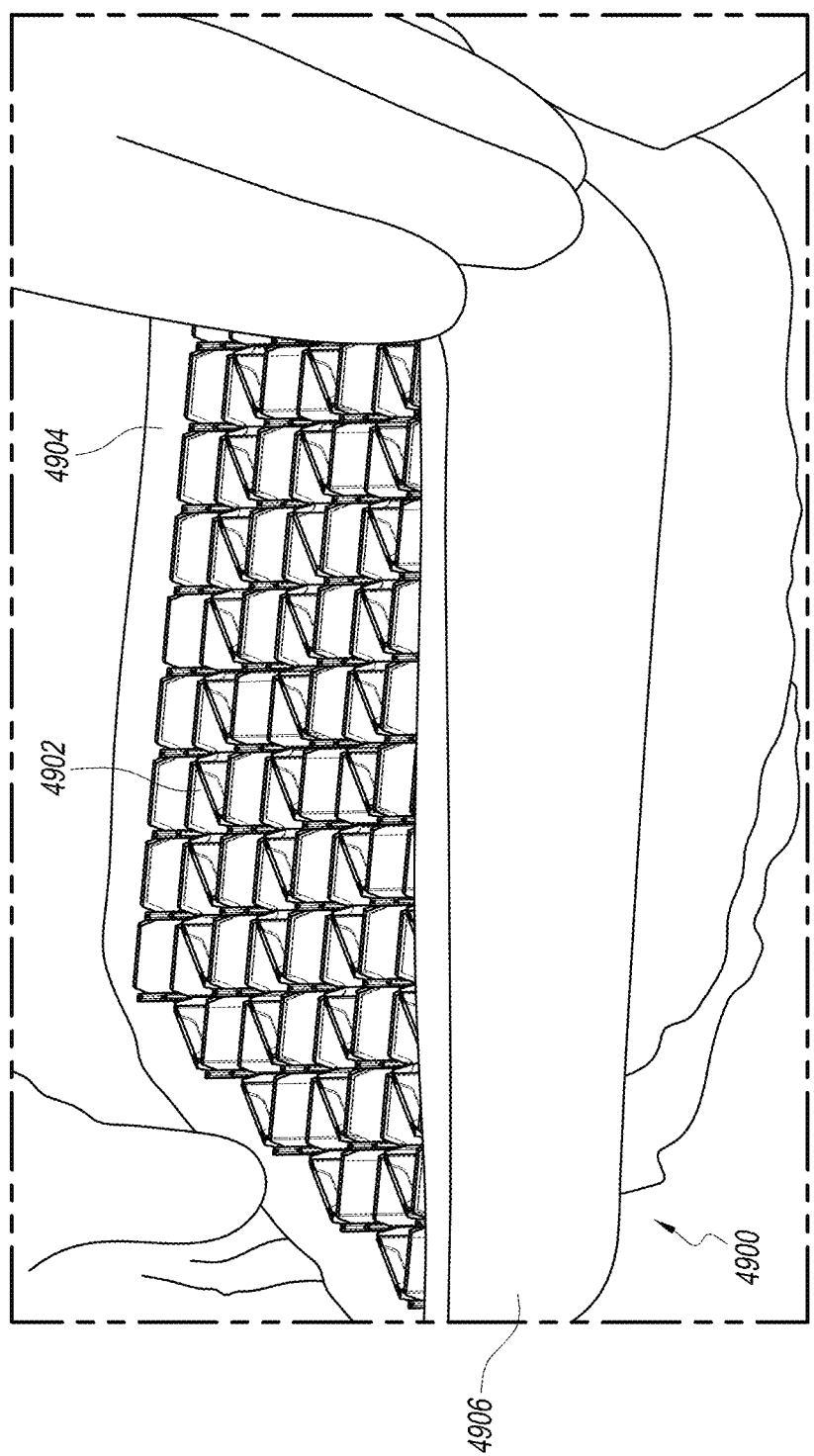
FIG. 44 illustrates an embodiment of a stabilizing structure with a surrounding ring and foam layer.

FIG. 44 is a photograph of a wound closure device 4900 comprising a stabilizing structure 4902 such as those described in this section or elsewhere in this specification, a foam layer 4904 such as those described in this section or elsewhere in this specification, and a ring 4906 comprising tissue anchors similar to the ring depicted in FIG. 43. In some embodiments, the wound closure device 4900 may be placed in a wound and sealed with a drape. Similar to the embodiments illustrated in FIGS. 29A-C and FIGS. 36A-F, the stabilizing structure 4902 can collapse in any manner described in this section or elsewhere in this specification.

The stabilizing structures and/or wound closure devices described in this section or elsewhere in this specification may be used in conjunction with methods or systems for the closure of a wound. In some embodiments of methods of use for closure of a wound, one or more of the stabilizing structures or wound closure devices of any of the embodiments described in this section or elsewhere in this specification is placed into a wound. In some embodiments, an organ protection layer may be provided in the wound before placement of the stabilizing structure. In certain embodiments, foam or other porous material may be placed in the wound along with the stabilizing structure or wound closure device, either below, above, or surrounding the stabilizing structure or wound closure device. Foam or other porous material may also surround the perimeter of the stabilizing structure or wound closure device. The stabilizing structure or wound closure device may be configured to collapse in any manner as described in this section or elsewhere in this specification, for example by having a particular size and shape, or by comprising a certain volume of foam or other porous material within the cells of the structure. The stabilizing structure or wound closure device may further be altered in any manner described in this section or elsewhere in this specification so as to better accommodate the shape of the wound. After placement in the wound, the stabilizing structure or wound closure device can be sealed by a fluid-tight drape. The fluid-tight drape can comprise a port configured for the application of negative pressure. A source of negative pressure may then be connected to the port and negative pressure may be applied to the wound. The stabilizing structure or wound closure device may be replaced over time by stabilizing structures or wound closure devices of various shapes and sizes as desired to best promote wound healing.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

While certain embodiments have been described, these embodiments have been presented by way of example only, and are not intended to limit the scope of protection. Indeed, the novel methods and systems described in this section or elsewhere in this specification may be embodied in a variety of other forms. Furthermore, various omissions, substitutions and changes in the form of the methods and systems described in this section or elsewhere in this specification may be made. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure.

Although the present disclosure includes certain embodiments, examples and applications, it will be understood by those skilled in the art that the present disclosure extends beyond the specifically disclosed embodiments to other alternative embodiments and/or uses and obvious modifications and equivalents thereof, including embodiments which do not provide all of the features and advantages set forth in this section or elsewhere in this specification. Accordingly, the scope of the present disclosure is not intended to be limited by the specific disclosures of preferred embodiments in this section or elsewhere in this specification, and may be defined by claims as presented in this section or elsewhere in this specification or as presented in the future.

What is claimed is:

1. A wound closure apparatus, comprising:
a stabilizing structure, comprising a plurality of cells provided side-by-side in a plane, each cell defined by a plurality of planar walls, each cell having a top end and a bottom end with an opening extending through the top end and the bottom end in a direction perpendicular to the plane;
wherein the stabilizing structure is configured to collapse more within the plane than along the direction perpendicular to the plane;
separate foam layers provided above, below, or on both upper and lower regions of the stabilizing structure, the foam layers comprising a plurality of fingers that extend into the cells of the stabilizing structure to a position between adjoining planar walls of cells wherein the adjoining walls rotate during collapse of the stabilizing structure; and
wherein the fingers are conically shaped.

2. The stabilizing structure of claim 1, wherein the foam layers further comprise:
a base within a horizontal plane;
wherein the plurality of fingers extend in a vertical direction perpendicular to the horizontal plane, the fingers comprising a bottom incorporated into the base of the foam layer and a top opposite the base; and
wherein the bottom of the fingers have a larger diameter than the top of the fingers.

3. The stabilizing structure of claim 1, wherein the foam layers further comprise a plurality of connecting sections that connect the fingers.

4. The stabilizing structure of claim 1, wherein the foam layers comprise a plurality of depressions.

5. The stabilizing structure of claim 1 wherein the stabilizing structure has an oval outer shape in the plane.

6. The stabilizing structure of claim 1 wherein the stabilizing structure comprises a flexible material.

7. The stabilizing structure of claim 6 wherein the flexible material comprises a silicone material or a polyurethane material.

8. The stabilizing structure of claim 1 wherein one or more cells have a diamond shape.

9. The stabilizing structure of claim 1 wherein the foam layers comprise an open cell foam such that fluid passes through the open cell foam upon application of negative pressure to a wound in which the stabilizing structure is positioned.

10. The stabilizing structure of claim 1 wherein the foam layers have varying flexibility.

11. The stabilizing structure of claim 1 wherein the fingers extend at least 1 mm from the foam layer into the cells of the stabilizing structure.

12. A wound closure apparatus, comprising:
a stabilizing structure, comprising a plurality of cells provided side-by-side in a plane, each cell defined by a plurality of planar walls, each cell having a top end and a bottom end with an opening extending through the top end and the bottom end in a direction perpendicular to the plane wherein the stabilizing structure has a length direction and a width direction and an outer surface having an oval shape;
wherein the stabilizing structure is configured to collapse more within the plane than along the direction perpendicular to the plane;

separate foam layers provided above, below, or on both upper and lower regions of the stabilizing structure, the foam layers comprising a plurality of fingers that extend into the cells of the stabilizing structure to a position between adjoining planar walls of cells wherein the adjoining walls rotate in the plane during collapse of the stabilizing structure upon application of negative pressure; and wherein the fingers are conically shaped.

13. The stabilizing structure of claim 12, wherein the foam layers further comprise:

a base within a horizontal plane;

wherein the plurality of fingers extend in a vertical direction perpendicular to the horizontal plane, the fingers comprising a bottom incorporated into the base of the foam layer and a top opposite the base; and wherein the bottom of the fingers have a larger diameter than the top of the fingers.

14. The stabilizing structure of claim 12, wherein the foam layers further comprise a plurality of connecting sections that connect the fingers.

15. The stabilizing structure of claim 12, wherein the foam layers comprise a plurality of depressions.

16. The stabilizing structure of claim 12 wherein the oval shape of the stabilizing structure is longer in the length direction than the width direction such that the stabilizing structure preferentially collapses in the width direction.

17. The stabilizing structure of claim 12 wherein the stabilizing structure comprises a flexible material.

18. The stabilizing structure of claim 17 wherein the flexible material comprises a silicone material or a polyurethane material.

19. The stabilizing structure of claim 12 wherein one or more cells have a diamond shape.

20. The stabilizing structure of claim 12 wherein the foam layers comprise an open cell foam such that fluid passes through the open cell foam upon application of negative pressure to a wound in which the stabilizing structure is positioned.

21. The stabilizing structure of claim 12 wherein the foam layers have varying flexibility.

22. The stabilizing structure of claim 12 wherein the fingers extend at least 1 mm from the foam layer into the cells of the stabilizing structure.

* * * * *